(12) United States Patent
Widdowson

(10) Patent No.: US 10,702,521 B2
(45) Date of Patent: Jul. 7, 2020

(54) METHODS FOR TREATING NEISSERIA GONORRHOEAE INFECTION WITH SUBSTITUTED 1,2-DIHYDRO-2A,5,8A-TRIAZAACENAPHTHYLENE-3,8-DIONES

(71) Applicant: GlaxoSmithKline Intellectual Property Development Limited, Brentford, Middlesex (GB)

(72) Inventor: Katherine Louisa Widdowson, San Diego, CA (US)

(73) Assignee: GlaxoSmithKline Intellectual Property Development Limited (GB)

(*) Notice: Subject to any disclaimer, the term of this patent is extended or adjusted under 35 U.S.C. 154(b) by 0 days.

(21) Appl. No.: 15/505,715

(22) PCT Filed: Aug. 20, 2015

(86) PCT No.: PCT/IB2015/056325
§ 371 (c)(1),
(2) Date: Feb. 22, 2017

(87) PCT Pub. No.: WO2016/027249
PCT Pub. Date: Feb. 25, 2016

(65) Prior Publication Data
US 2017/0304301 A1    Oct. 26, 2017

Related U.S. Application Data

(60) Provisional application No. 62/040,488, filed on Aug. 22, 2014.

(51) Int. Cl.
| | | |
|---|---|---|
| A61K 31/4745 | (2006.01) | |
| A61K 31/4985 | (2006.01) | |
| C07D 471/16 | (2006.01) | |
| C07D 487/06 | (2006.01) | |
| A61K 31/538 | (2006.01) | |
| A61K 31/5383 | (2006.01) | |
| A61K 31/542 | (2006.01) | |
| A61K 31/554 | (2006.01) | |
| A61K 31/5415 | (2006.01) | |
| A61K 31/4375 | (2006.01) | |
| A61K 31/4545 | (2006.01) | |
| A61K 31/4725 | (2006.01) | |
| A61K 31/5377 | (2006.01) | |

(52) U.S. Cl.
CPC ...... *A61K 31/4985* (2013.01); *A61K 31/4375* (2013.01); *A61K 31/4545* (2013.01); *A61K 31/4725* (2013.01); *A61K 31/538* (2013.01); *A61K 31/5377* (2013.01); *A61K 31/5383* (2013.01); *A61K 31/542* (2013.01); *A61K 31/5415* (2013.01); *A61K 31/554* (2013.01)

(58) Field of Classification Search
CPC ............ C07D 487/06; C07D 471/16; A61K 31/4745; A61K 31/4985
USPC ............ 544/345; 514/250, 294; 546/94
See application file for complete search history.

(56) References Cited

U.S. PATENT DOCUMENTS 8,389,524 B2 * 3/2013 Davies ............... C07D 471/16
514/250

FOREIGN PATENT DOCUMENTS

| EP | 0624376 | * | 3/2000 |
|---|---|---|---|
| WO | WO 2008/128942 A1 | | 10/2008 |
| WO | WO 2009/141398 A1 | | 11/2009 |
| WO | WO 2010/043714 A1 | | 4/2010 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Hackam, et al. JAMA, 296(14), 2006, 1731-1732.*
"A Dose-Ranging Study Evaluating the Efficacy, Safety, and Tolerability of GSK2140944 in the Treatment of Uncomplicated Urogenital Gonorrhea Caused by Neisseria Gonorrhoeae", ClinicalTrials NCT02294682, Nov. 18, 2014, pp. 1-5, XP002748885, Retrieved from the Internet: URL:https://clinicaltrials.gov/archive/NCT (2014).
Ross et al., "Determination of Disk Diffusion and MIC Quality Control Guidelines for GSK2140944, a Novel Bacterial Type II Topoisomerase Inhibitor Antimicrobial Agent", *Journal of Clinical Microbiology*, vol. 52, No. 7, pp. 2629-2632 (2014).

(Continued)

*Primary Examiner* — Douglas M Willis
(74) *Attorney, Agent, or Firm* — Hao Yin

(57) ABSTRACT

The present invention relates to methods for treating *Neisseria Gonorrhoeae* infection which comprises administering to a subject in need thereof novel 1,2-dihydro-2a,5,8a-triazaacenaphthylene-3,8-dione compounds:

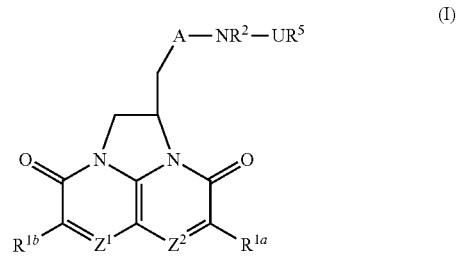

or pharmaceutically acceptable salts thereof and/or corresponding pharmaceutical compositions.

12 Claims, No Drawings

(56) References Cited

OTHER PUBLICATIONS

Ison et al., "Drift in Susceptibility of Neisseria gonorrhoeae to Ciprofloxacin and Emergence of Therapeutic Failure", *Antimicrobial Agents and Chemotherapy*, vol. 42, No. 11, pp. 2919-2922 (1998).
Flamm et al., "In Vitro Evaluation of ABT-719, A Novel DNA Gyrase Inhibitor", *Antimicrobial Agents and Chemotherapy*, vol. 39, No. 4, pp. 964-970 (1995).
Mitsuyama, Junichi, Basis of Quinolone Antibiotics, *Journal of Japanese Pharmacology*, vol. 130, No. 4, pp. 287-293 (2007)—Translation.

* cited by examiner

METHODS FOR TREATING NEISSERIA GONORRHOEAE INFECTION WITH SUBSTITUTED 1,2-DIHYDRO-2A,5,8A-TRIAZAACENAPHTHYLENE-3,8-DIONES

This application is a 371 of International Application No. PCT/IB2015/056325, filed 20 Aug. 2015, which claims benefit of U.S. Provisional Application No. 62/040,488, filed 22 Aug. 2014.

STATEMENT REGARDING FEDERALLY SPONSORED RESEARCH

This Invention Was Made With Government Support Under The United States Of America Department Of Health And Human Services Assistant Secretary For Preparedness And Response, Biomedical Advanced Research and Development Authority (BARDA), within the Office of the Assistant Secretary for Preparedness and Response in the U.S. Department of Health and Human Services, Agreement No.: HHSO100201300011C and under the Agreement No. HDTRA1-07-9-0002 awarded by the Defense Threat Reduction Agency. The Government may have certain rights in the invention.

FIELD OF THE PRESENT INVENTION

The present invention relates to methods for treating *Neisseria gonorrhoeae* infection which comprises administering to a subject in need thereof novel Tricyclic nitrogen containing compounds and corresponding pharmaceutical compositions as described herein.

BACKGROUND OF THE PRESENT INVENTION

Gonorrhea is the second most prevalent bacterial sexually transmitted infection globally and remains an important clinical and public health problem throughout the world. Gonococcal infections following sexual and perinatal transmission are a major source of morbidity worldwide [Barry, 2009]. Infections can involve cervicitis, proctitis, urethritis, pelvic inflammatory disease, epididymitis, orchitis, prostatitis, conjunctivitis, pharyngitis and other disseminated gonococcal diseases.

*Neisseria gonorrhoeae*, also known as gonococci (plural), GC (an abbreviation) or gonococcus (singular), is a species of Gram-negative coffee bean-shaped diplococci bacteria responsible for the sexually transmitted infection gonorrhea. [1]

Complications include infertility, ectopic pregnancy, chronic pelvic pain, adverse outcomes of pregnancy, and increased susceptibility to and transmission of human immunodeficiency virus [Workowski, 2008; Barry, 2009].

Infections due to *Chlamydia trachomatis* and *Neisseria gonorrhoeae* can cause cervicitis, urethritis, proctitis, and pelvic inflammatory disease (PID), and their complications can significantly compromise a woman's reproductive functioning. These infections are a leading preventable cause of involuntary infertility and ectopic pregnancy and can influence pregnancy outcomes ranging from low birth weight, prematurity, fetal demise, and congenital infection. Chlamydial and gonococcal infections can also increase susceptibility to and facilitate transmission of HIV. Kimberly Workowski. 2013 American College of Physicians, Annals of Internal Medicine, In the Clinic.

A variety of antimicrobial agents have been used over the years for the treatment of gonorrhea; however, effective treatment options for gonorrhea have diminished rapidly because of the emergence and worldwide spread of antimicrobial resistance to many drugs previously used or considered first line, i.e., penicillins, narrow-spectrum cephalosporins, tetracyclines, macrolides, and fluoroquinolones [Workowski, 2008; Barry, 2009].

The current Centers for Disease Control and Prevention (CDC) recommended treatment regimen for uncomplicated gonorrhea is combination therapy with a single intramuscular dose of ceftriaxone plus either a single dose of azithromycin or a 7-day regimen of doxycycline [CDC, 2012]. While the CDC guidelines may help delay the emergence of cephalosporin-resistant gonorrhea, they are not able to eliminate this impending threat.

Therefore, the CDC has urged scientists and private-sector drug developers to prioritize the identification and study of new, effective antibiotic treatment options for gonorrhea [CDC, 2013].

WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2006002047, WO2006014580, WO2006010040, WO2006017326, WO2006012396, WO2006017468, WO2006020561, WO2006081179, WO2006081264, WO2006081289, WO2006081178, WO2006081182, WO01/25227, WO02/40474, WO02/07572, WO2004024712, WO2004024713, WO2004035569, WO2004087647, WO2004089947, WO2005016916, WO2005097781, WO2006010831, WO2006021448, WO2006032466, WO2006038172, WO2006046552, WO06099884, WO06126171, WO06137485, WO06105289, WO06125974, WO06134378, WO07016610, WO07081597, WO07071936, WO07115947, WO07118130, WO07122258, WO08006648, WO08003690 and WO08009700 disclose quinoline, naphthyridine, morpholine, cyclohexane, piperidine and piperazine derivatives having antibacterial activity. WO2004104000 discloses tricyclic condensed ring compounds capable of selectively acting on cannabinoid receptors. WO2003048081, WO2003048158 and US2003232804 disclose glycinamides as Factor Xa inhibitors.

SUMMARY OF THE PRESENT INVENTION

In general, the present invention relates to methods for treating *Neisseria gonorrhoeae* infection which comprises administering to a subject in need thereof novel Tricyclic nitrogen containing compounds and corresponding pharmaceutical compositions as described herein.

DETAILED DESCRIPTION OF THE PRESENT INVENTION

Compounds

In general, the present invention relates to methods for treating *Neisseria gonorrhoeae* infection which comprises administering to a subject in need thereof novel Tricyclic nitrogen containing compounds and corresponding pharmaceutical compositions as described herein.

In particular, the present invention provides for use of a compound of formula (I) or a pharmaceutically acceptable salt and/or N-oxide thereof:

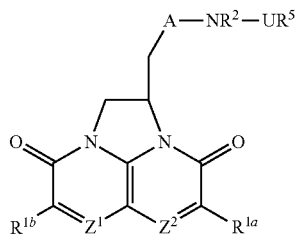

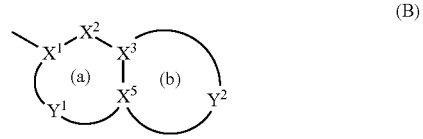

wherein:
$Z^1$ and $Z^2$ are independently selected from CH and N;
$R^{1a}$ and $R^{1b}$ are independently selected from hydrogen; halogen; cyano; $(C_{1-6})$alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted$(C_{1-6})$alkyl; $(C_{1-6})$alkoxy-substituted$(C_{1-6})$alkyl; hydroxy $(C_{1-6})$alkyl; an amino group optionally N-substituted by one or two $(C_{1-6})$alkyl, formyl, $(C_{1-6})$alkylcarbonyl or $(C_{1-6})$alkylsulphonyl groups; and aminocarbonyl wherein the amino group is optionally substituted by $(C_{1-4})$alkyl;
provided that $R^{1a}$ and $R^{1b}$ are H when $Z^2$ or $Z^1$ is N, respectively;
$R^2$ is hydrogen, or $(C_{1-4})$alkyl, or together with $R^6$ forms Y as defined below; A is a group (i):

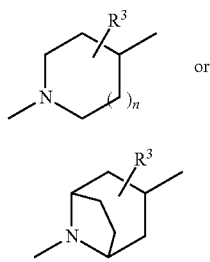

in which: $R^3$ is as defined for $R^{1a}$ and $R^{1b}$ or is oxo and n is 1 or 2:
or A is a group (ii)

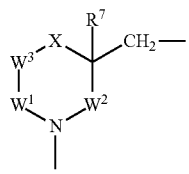

$W^1$, $W^2$ and $W^3$ are $CR^4R^8$
or $W^2$ and $W^3$ are $CR^4R^8$ and $W^1$ represents a bond between $W^3$ and N.
X is O, $CR^4R^8$, or $NR^6$;
one $R^4$ is as defined for $R^{1a}$ and $R^{1b}$ and the remainder and $R^8$ are hydrogen or one $R^4$ and $R^8$ are together oxo and the remainder are hydrogen;
$R^6$ is hydrogen or $(C_{1-6})$alkyl; or together with $R^2$ forms Y; $R^7$ is hydrogen; halogen; hydroxy optionally substituted with $(C_{1-6})$alkyl; or $(C_{1-6})$alkyl;
Y is $CR^4R^8CH_2$; $CH_2CR^4R^8$; (C=O); $CR^4R^8$; $CR^4R^8$(C=O); or (C=O)$CR^4R^8$;
or when X is $CR^4R^8$, $R^8$ and $R^7$ together represent a bond;

U is selected from CO, and $CH_2$ and
$R^5$ is an optionally substituted bicyclic carbocyclic or heterocyclic ring system (B):

containing up to four heteroatoms in each ring in which
at least one of rings (a) and (b) is aromatic;
$X^1$ is C or N when part of an aromatic ring, or $CR^{14}$ when part of a non-aromatic ring;
$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
$X^3$ and $X^5$ are independently N or C;
$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring;
$Y^2$ is a 2 to 6 atom linker group, each atom of $Y^2$ being independently selected from N, $NR^{13}$, O, $S(O)_x$, CO, $CR^{14}$ when part of an aromatic or non-aromatic ring or may additionally be $CR^{14}R^{15}$ when part of a non aromatic ring;
each of $R^{14}$ and $R^{15}$ is independently selected from: H; $(C_{1-4})$alkylthio; halo; carboxy$(C_{1-4})$alkyl; $(C_{1-4})$alkyl; $(C_{1-4})$alkoxycarbonyl; $(C_{1-4})$alkylcarbonyl; $(C_{1-4})$ alkoxy $(C_{1-4})$alkyl; hydroxy; hydroxy$(C_{1-4})$alkyl; $(C_{1-4})$alkoxy; nitro; cyano; carboxy; amino or aminocarbonyl optionally mono- or di-substituted by $(C_{1-4})$ alkyl; or
$R^{14}$ and $R^{15}$ may together represent oxo;
each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; $(C_{1-4})$ alkoxycarbonyl; $(C_{1-4})$alkylcarbonyl; $(C_{1-6})$alkylsulphonyl; aminocarbonyl wherein the amino group is optionally mono or disubstituted by $(C_{1-4})$alkyl; and
each x is independently 0, 1 or 2.

The invention also provides a pharmaceutical composition comprising a compound of formula (I), or a pharmaceutically acceptable salt and/or N-oxide thereof, and a pharmaceutically acceptable carrier.

In one aspect one of $Z^1$ and $Z^2$ is CH or N and the other is CH.

In particular aspects:
(i) $Z^1$ and $Z^2$ are both CH;
(ii) $Z^1$ is N and $Z^2$ is CH;
(iii) $Z^1$ is CH and $Z^2$ is N.

In a particular aspect $R^{1a}$ and $R^{1b}$ are independently hydrogen, $(C_{1-4})$alkoxy, $(C_{1-4})$alkylthio, $(C_{1-4})$alkyl, cyano, carboxy, hydroxymethyl or halogen; more particularly hydrogen, methoxy, methyl, cyano, or halogen.

In particular embodiments $R^{1a}$ and $R^{1b}$ are hydrogen.

In a particular aspect $R^2$ is hydrogen.

Particular examples of $R^3$ include hydrogen; optionally substituted hydroxy; optionally substituted amino; halogen; $(C_{1-4})$ alkyl; 1-hydroxy-$(C_{1-4})$ alkyl; optionally substituted aminocarbonyl. More particular $R^3$ groups are hydrogen; $CONH_2$; 1-hydroxyalkyl e.g. $CH_2OH$; optionally substituted hydroxy e.g. methoxy; optionally substituted amino; and halogen, in particular fluoro. Most particularly R³ is hydrogen, hydroxy or fluoro.

In a particular aspect, when A is (ia), n is 1. In a further aspect R³ is in the 3- or 4-position. In a more particular aspect, A is (ia), n is 1 and R³ is in the 3-position, and more particularly is cis to the NR² group. In particular embodiments, A is a group (ia) in which n is 1 and R³ is hydrogen or hydroxy. More particularly where A is 3-hydroxy-piperidin-4-yl the configuration is (3R,4S) or (3S,4R). Alternatively and more particularly where A is piperidin-4-yl the configuration is (3R,4S).

In an alternative more particular aspect, when A is (ia), n is 1, R³ is in the 4-position and is methyl.

In a particular aspect, when A is (ii), X is CR⁴R⁸ and R⁸ is H and R⁴ is H or OH and more particularly OH is trans to R⁷. In a further aspect W¹ is a bond. In another aspect R⁷ is H. In an additional aspect W¹ is a bond, W² and W³ are both CH₂ and R⁷ is H. Where A is 4-hydroxypyrrolidin-3-ylmethyl, in a particular aspect the configuration is (3S,4S). Where A is pyrrolidin-3-ylmethyl, in a particular aspect the configuration is 3S.

In a particular aspect, when A is (ii), X is O, R⁷ is H and W¹, W² and W³ are each CH₂.

In certain embodiments U is CH₂.

In certain embodiments R⁵ is an aromatic heterocyclic ring (B) having 8-11 ring atoms including 2-4 heteroatoms of which at least one is N or NR¹³ in which, in particular embodiments, Y² contains 2-3 heteroatoms, one of which is S and 1-2 are N, with one N bonded to X³.

In alternative embodiments the heterocyclic ring (B) has ring (a) aromatic selected from optionally substituted benzo, pyrido, pyridazino and pyrimidino and ring (b) non aromatic and Y² has 3-5 atoms, more particularly 4 atoms, including at least one heteroatom, with O, S, CH₂ or NR¹³ bonded to X⁵ where R¹³ is other than hydrogen, and either NHCO bonded via N to X³, or O, S, CH₂ or NH bonded to X³. In a particular aspect the ring (a) contains aromatic nitrogen, and more particularly ring (a) is pyridine or pyrazine. Examples of rings (B) include optionally substituted:
(a) And (b) Aromatic
1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, naphthalen-2-yl, 1,3-dioxo-isoindol-2yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-6-yl, pyrido[1,2-a]pyrimidin-4-one-3-yl (4-oxo-4H-pyrido[1,2-a]pyrimidin-3-yl), benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimdin-4-one-2-yl (4-oxo-4H-pyrido[1,2-a]pyrimidin-2-yl), quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, thiazolo[4,5-b]pyridin-5-yl, [1,2,3]thiadiazolo[5,4-b]pyridin-6-yl, 2H-isoquinolin-1-one-3-yl (1-oxo-1,2-dihydro-isoquinolin-3-yl), [1,2,3]thiadiazolo[5,4-b]pyridine-6-yl

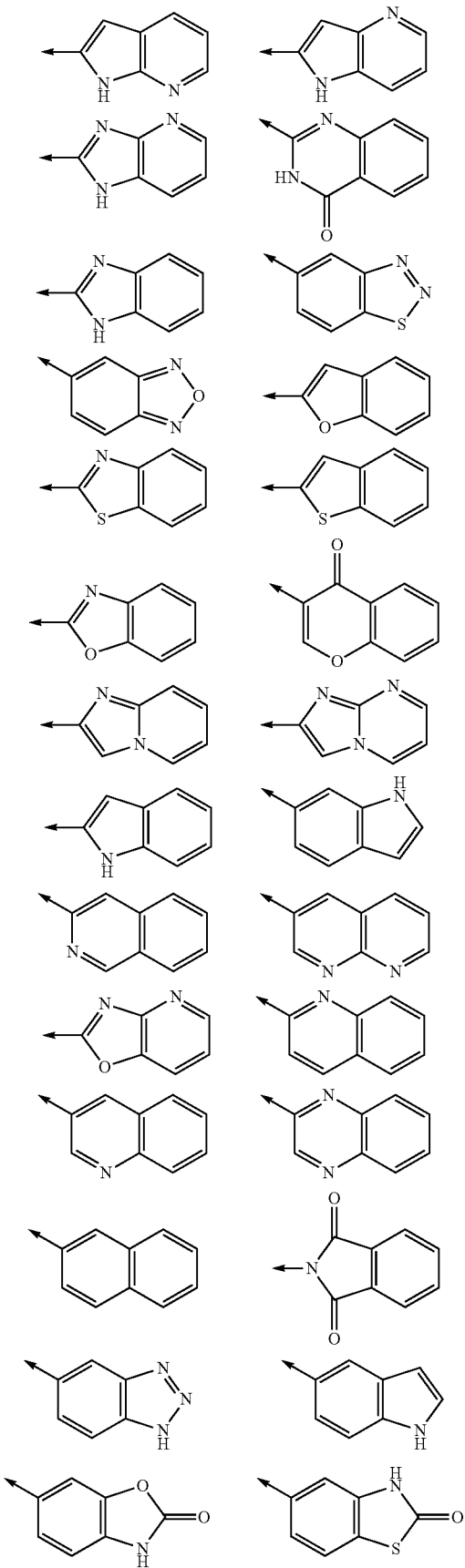

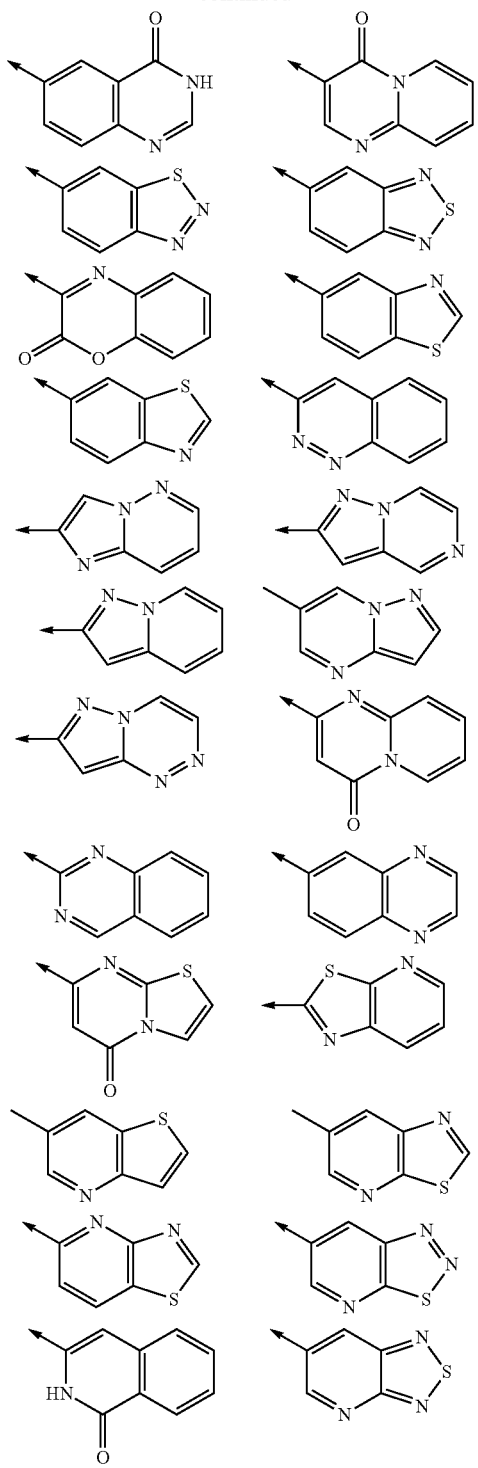
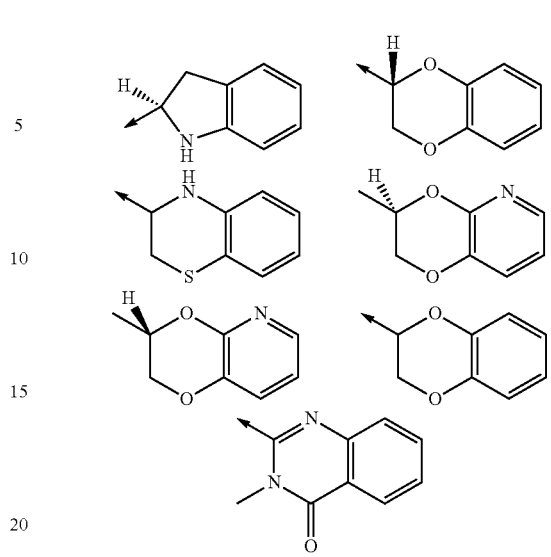

→ is the point of attachment
(b) Is Non Aromatic 1,1,3-trioxo-1,2,3,4-tetrahydrol 1⁶-benzo[1,4] thiazin-6-yl, benzo[1,3]dioxol-5-yl, 2,3-dihydro-benzo[1,4]dioxin-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl (1,2,3,4-tetrahydro-[1,8]naphthyridin-7-yl), 2-oxo-3,4-dihydro-1H-[1,8]naphthyridin-6-yl, 6-oxo-6,7-dihydro-5H-pyridazino[3,4-b][1,4]thiazin-3-yl (6-oxo-6,7-dihydro-5H-8-thia-1,2,5-triaza-naphthalen-3-yl), 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6,7-dihydro-[1,4]dioxino[2,3-d]pyrimidin-2-yl, [1,3]oxathiolo[5,4-c]pyridin-6-yl, 3,4-dihydro-2H-pyrano[2,3-c]pyridin-6-yl, 2,3-dihydro[1,4]oxathiino[2,3-c]pyridin-7-yl, 6,7-dihydro[1,4]dioxino[2,3-c]pyridazin-3-yl, 5,6,7,8-tetrahydroisoquinolin-3-yl, 6,7-dihydro-5H-cyclopenta[c]pyridin-3-yl, 1,3-dihydrofuro[3,4-c]pyridin-6-yl, 3,4-dihydro-2H-[1,4]oxathiepino[2,3-c]pyridin-8-yl, [1,3]oxathiolo[4,5-c]pyridin-6-yl, 6,7-dihydro[1,4]oxathiino[2,3-c]pyridazin-3-yl, 6,7-dihydro-5H-pyrano[2,3-c]pyridazin-3-yl, 5,6-dihydrofuro[2,3-c]pyridazin-3-yl, 2,3-dihydrofuro[2,3-c]pyridin-5-yl, 2-substituted 1H-pyrimido[5,4-b][1,4]oxazin-7(6H)-one, 2-substituted 5,6-dihydropyrido[2,3-d]pyrimidin-7(1H)-one, 7-substituted 2H-chromen-2-one, 7-substituted 2H-pyrano[2,3-b]pyridin-2-one, 2-substituted 6,7-dihydro-5H-pyrano[2,3-d]pyrimidine, 8-substitited 2H-pyrido[1,2-a]pyrimidin-2-one, 2,3-dihydro-1-benzofuran-5-yl, 1H-pyrimido[5,4-b][1,4]thiazin-7(6H)-one-2-yl, 3,4-dihydro-2H-chromen-7-yl, 2,3-dihydro-1-benzofuran-6-yl, 3,4-dihydro-2H-chromen-6-yl, 3,4-dihydro-2H-pyrido[3,2-b][1,4]oxazine-6-yl, 3,4-dihydro-2H-pyrido[3,2-b][1,4]thiazine-6-yl, 6,7-dihydro-5H-thieno[3,2-b]pyran-2-yl, 2,3,4,5-tetrahydro-1,5-benzothiazepine-7-yl.
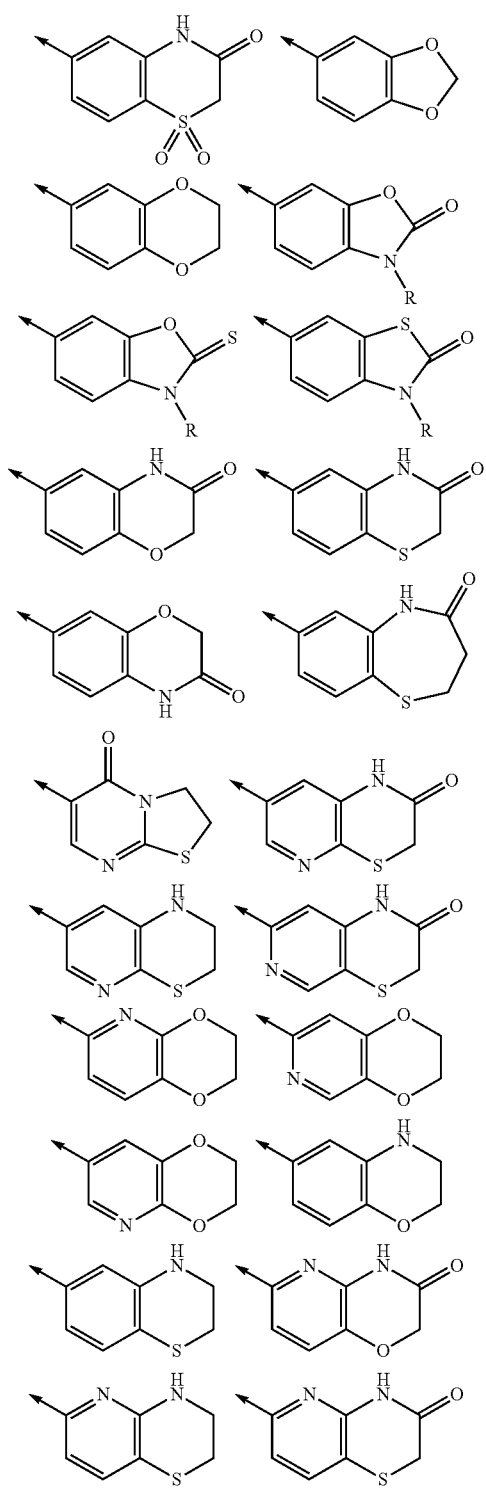
-continued
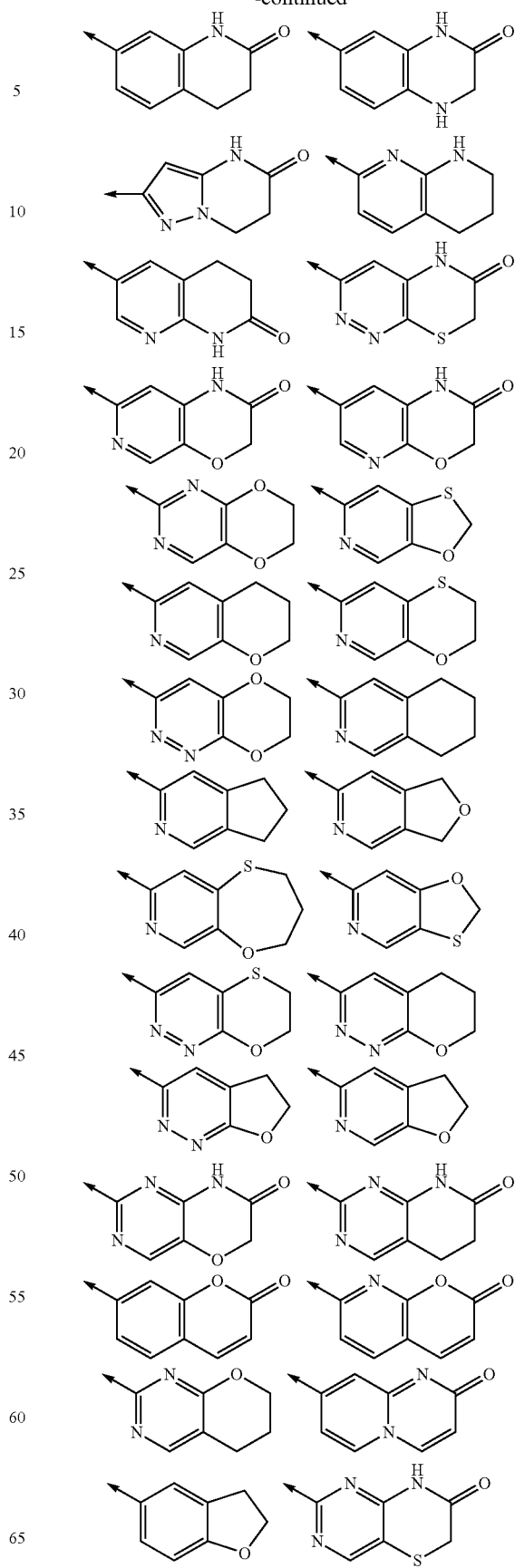

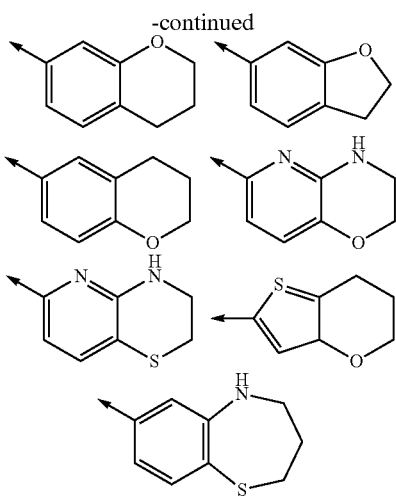

where R is an optional substituent
→ is the point of attachment

In some embodiments $R^{13}$ is H if in ring (a) or in addition $(C_{1-4})$alkyl such as methyl or isopropyl when in ring (b). More particularly, in ring (b) $R^{13}$ is H when $NR^{13}$ is bonded to $X^3$ and $(C_{1-4})$alkyl when $NR^{13}$ is bonded to $X^5$.

In further embodiments $R^{14}$ and $R^{15}$ are independently selected from hydrogen, halo, hydroxy, $(C_{1-4})$ alkyl, $(C_{1-4})$ alkoxy, nitro and cyano. More particularly $R^{15}$ is hydrogen.

More particularly each $R^{14}$ is selected from hydrogen, chloro, fluoro, hydroxy, methyl, methoxy, nitro and cyano. Still more particularly $R^{14}$ is selected from hydrogen, fluorine or nitro.

Most particularly $R^{14}$ and $R^{15}$ are each H.

Particular groups $R^5$ include:
[1,2,3]thiadiazolo[5,4-b]pyridin-6-yl
1H-pyrrolo[2,3-b]pyridin-2-yl
2,3-dihydro-[1,4]dioxino[2,3-b]pyridin-6-yl
2,3-dihydro-[1,4]dioxino[2,3-b]pyridin-7-yl
2,3-dihydro-[1,4]dioxino[2,3-c]pyridin-7-yl
2,3-dihydro-benzo[1,4]dioxin-6-yl
2-oxo-2,3-dihydro-1H-pyrido[2,3-b][1,4]oxazin-7-yl
2-oxo-2,3-dihydro-1H-pyrido[2,3-b][1,4]thiazin-7-yl
3,4-dihydro-2H-benzo[1,4]oxazin-6-yl
3-methyl-2-oxo-2,3-dihydro-benzooxazol-6-yl
3-oxo-3,4-dihydro-2H-benzo[1,4]oxazin-6-yl
3-oxo-3,4-dihydro-2H-pyrido[3,2-b][1,4]oxazin-6-yl
3-oxo-3,4-dihydro-2H-benzo[1,4]thiazin-6-yl (4H-benzo[1,4] thiazin-3-one-6-yl)
4-oxo-4H-pyrido[1,2-a]pyrimidin-2-yl
6-nitro-benzo[1,3]dioxol-5-yl
7-fluoro-3-oxo-3,4-dihydro-2H-benzo[1,4]oxazin-6-yl
8-hydroxy-1-oxo-1,2-dihydro-isoquinolin-3-yl
8-hydroxyquinolin-2-yl
benzo[1,2,3]thiadiazol-5-yl
benzo[1,2,5]thiadiazol-5-yl
benzothiazol-5-yl
thiazolo-[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-chloro-3-oxo-3,4-dihydro-2H-pyrido[3,2-b][1,4]oxazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl
[1,3]oxathiolo[5,4-c]pyridin-6-yl
3,4-dihydro-2H-pyrano[2,3-c]pyridin-6-yl
5-carbonitro-2,3-dihydro-1,4-benzodioxin-7-yl
2,3-dihydro[1,4]oxathiino[2,3-c]pyridin-7-yl
6,7-dihydro[1,4]dioxino[2,3-c]pyridazin-3-yl
5,6,7,8-tetrahydroisoquinolin-3-yl
6,7-dihydro-5H-cyclopenta[c]pyridin-3-yl
1,3-dihydrofuro[3,4-c]pyridin-6-yl
6-fluoro-2,3-dihydro-1,4-benzodioxin-7-yl
3,4-dihydro-2H-[1,4]oxathiepino[2,3-c]pyridin-8-yl,
[1,3]oxathiolo[4,5-c]pyridine-6-yl
2,3-dihydro-1-benzofuran-5-yl
6,7-dihydro[1,4]oxathiino[2,3-c]pyridazin-3-yl
6,7-dihydro-5H-pyrano[2,3-c]pyridazin-3-yl
5,6-dihydrofuro[2,3-c]pyridazin-3-yl
2-substituted 1H-pyrimido[5,4-b][1,4]oxazin-7(6H)-one
2-substituted 4-chloro-1H-pyrimido[5,4-b][1,4]oxazin-7(6H)-one
2-substituted 5,6-dihydropyrido[2,3-d]pyrimidin-7(1H)-one
2-substituted 4-chloro-5,6-dihydropyrido[2,3-d]pyrimidin-7(1H)-one
2-substituted 4-methyl-5,6-dihydropyrido[2,3-d]pyrimidin-7(1H)-one
2-substituted 4-methyloxy-5,6-dihydropyrido[2,3-d]pyrimidin-7(1H)-one
7-substituted 2H-chromen-2-one
7-substituted 2H-pyrano[2,3-b]pyridin-2-one
4-chloro-6,7-dihydro-5H-pyrano[2,3-d]pyrimidin-2-yl
8-substituted 2H-pyrido[1,2-a]pyrimidin-2-one
6,7-dihydro-5H-pyrano[2,3-d]pyrimidin-2-yl)
5-chloro-1-benzothiophen-2-yl
6-chloro-1-benzothiophen-2-yl
1-benzothiophen-5-yl
1-methyl-1H-1,2,3-benzotriazol-6-yl
imidazo[2,1-b][1,3]thiazol-6-yl
4-methyl-3,4-dihydro-2H-1,4-benzoxazin-7-yl
1-methy-1H-indol-2-yl
1H-pyrimido[5,4-b][1,4]thiazin-7(6H)-one-2-yl
[1,2,5]thiadiazolo[3,4-b]pyridine-6-yl
4-fluoro-1H-benzimidazol-2-yl
3,4-dihydro-2H-chromen-7-yl
2,3-dihydro-1-benzofuran-6-yl
3,4-dihydro-2H-chromen-6-yl
6-chloro-2,3-dihydro-1,4-benzodioxin-7-yl
7-chloro-3,4-dihydro-2H-pyrido[3,2-b][1,4]oxazine-6-yl
7-chloro-3,4-dihydro-2H-pyrido[3,2-b][1,4]thiazine-6-yl
3,4-dihydro-2H-pyrido[3,2-b][1,4]thiazin-6-yl
5-fluoro-2,3-dihydro-1,4-benzodioxin-7-yl
5-fluoro-2,3-dihydro-1,4-benzodioxin-6-yl
8-fluoro-2H-1,4-benzoxazin-3 (4H)-one-6-yl
8-fluoro-3,4-dihydro-2H-1,4-benzoxazin-6-yl
7,8-difluoro-3,4-dihydro-2H-1,4-benzoxazin-6-yl
6,7-dihydro-5H-thieno[3,2-b]pyran-2-yl
5-methyl-2,3-dihydro-1,4-benzodioxin-7-yl
4-oxo-2,3,4,5-tetrahydro-1,5-benzothiazepin-7-yl
3,4-dihydro-2H-1,4-benzothiazine-6-yl
2,3,4,5-tetrahydro-1,5-benzothiazepine-7-yl
7-fluoro-3,4-dihydro-2H-1,4-benzoxazine-6-yl

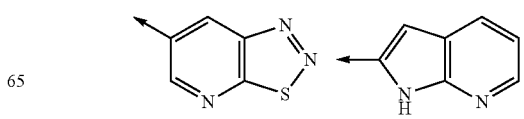

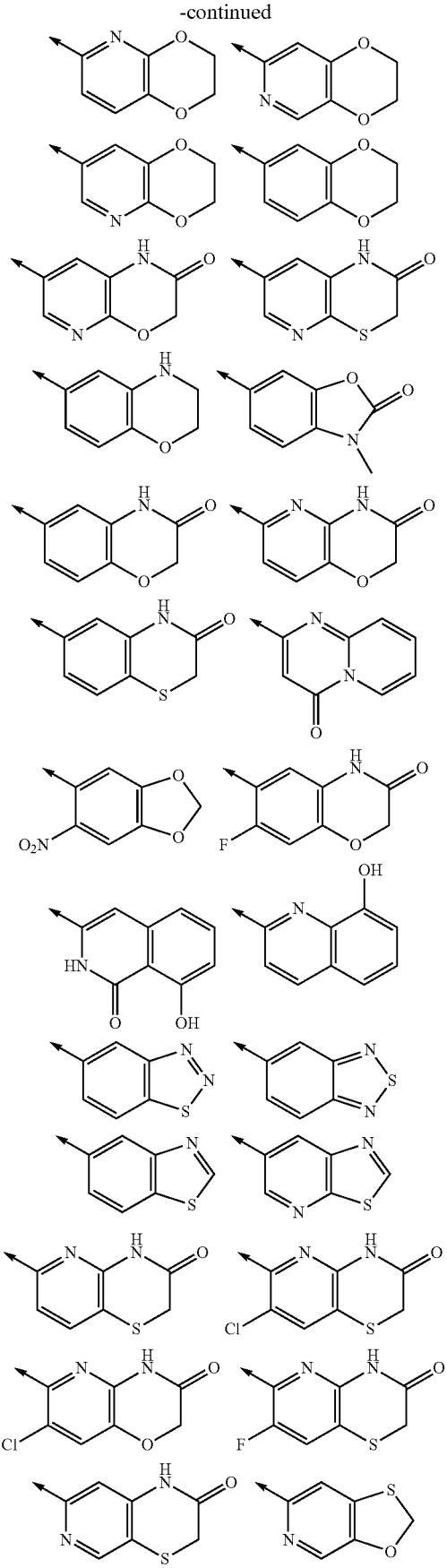
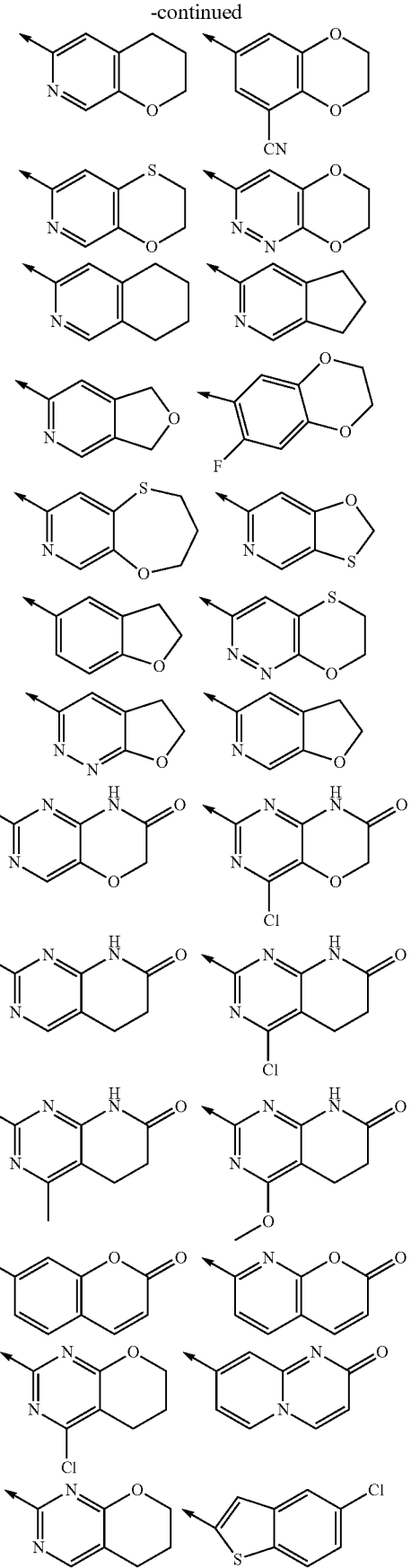

-continued

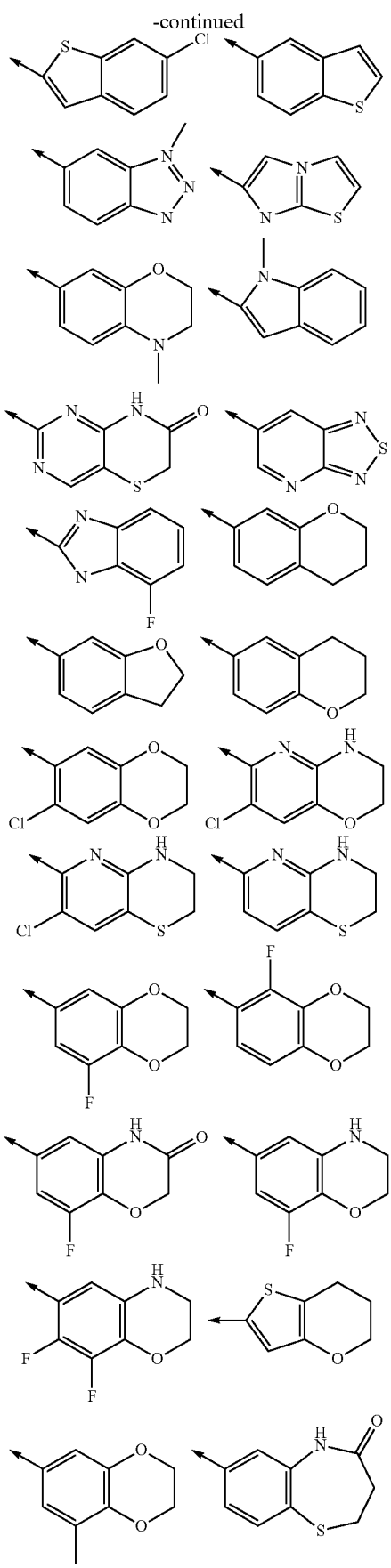

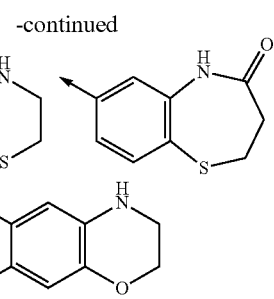

-continued

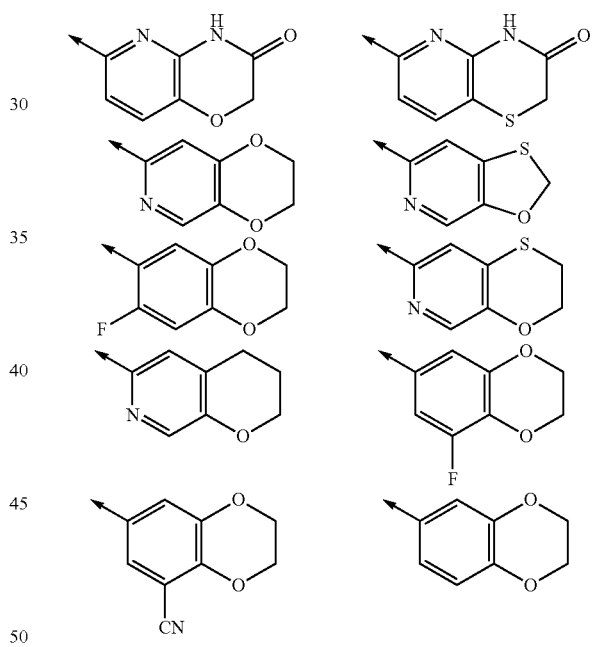

→ is the point of attachment
especially
3-oxo-3,4-dihydro-2H-pyrido[3,2-b][1,4]oxazin-6-yl
3-oxo-3,4-dihydro-2H-pyrido[3,2-b][1,4]thiazin-6-yl
2,3-dihydro-[1,4]dioxino[2,3-c]pyridin-7-yl
[1,3]oxathiolo[5,4-c]pyridin-6-yl
6-fluoro-2,3-dihydro-1,4-benzodioxin-7-yl
2,3-dihydro[1,4]oxathiino[2,3-c]pyridin-7-yl
3,4-dihydro-2H-pyrano[2,3-c]pyridin-6-yl
5-fluoro-2,3-dihydro-1,4-benzodioxin-7-yl
5-carbonitro-2,3-dihydro-1,4-benzodioxin-7-yl
2,3-dihydro-benzo[1,4]dioxin-6-yl → is the point of attachment Definitions When used herein, the term "alkyl" includes groups having straight and branched chains, for instance, and as appropriate, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo.
Haloalkyl moieties include 1-3 halogen atoms.

Compounds within the invention contain a heterocyclyl group and may occur in two or more tautomeric forms depending on the nature of the heterocyclyl group; all such tautomeric forms are included within the scope of the invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Furthermore, it will be understood that phrases such as "a compound of formula (I) or a pharmaceutically acceptable salt or N-oxide thereof" are intended to encompass the compound of formula (I), an N-oxide of formula (I), a pharmaceutically acceptable salt of the compound of formula (I), a solvate of formula (I), or any pharmaceutically acceptable combination of these. Thus by way of non-limiting example used here for illustrative purpose, "a compound of formula (I) or a pharmaceutically acceptable salt thereof" may include a pharmaceutically acceptable salt of a compound of formula (I) that is further present as a solvate.

Since the compounds of formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10% of a compound of the formula (I) or pharmaceutically acceptable salt and/or N-oxide thereof.

Particular compounds according to the invention include those mentioned in the examples and their pharmaceutically acceptable N-oxides, salts and solvates.

Pharmaceutically acceptable salts of the above-mentioned compounds of formula (I) include the acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. The invention extends to all such derivatives.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes enantiomers and diastereoisomers at the attachment point of $NR^2$ and $R^3$. The different isomeric forms may be separated or resolved one from the other by conventional methods, or any given isomer may be obtained by conventional synthetic methods or by stereospecific or asymmetric syntheses. Certain compounds of formula (I) may also exist in polymorphic forms and the invention includes such polymorphic forms.

Processes for Making Compounds Used in Present Invention

The compounds according to the present invention or pharmaceutically acceptable salts thereof, are prepared using conventional organic syntheses.

Suitable synthetic routes are depicted below in the following general reaction schemes. The skilled artisan will appreciate that if a substituent described herein is not compatible with the synthetic methods described herein, the substituent may be protected with a suitable protecting group that is stable to the reaction conditions. The protecting group may be removed at an necessary or suitable point in the reaction sequence to provide a desired intermediate or target compound.

Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

In a further aspect of the invention there is provided a process for preparing compounds of formula (I) where $Z^2$ is nitrogen, and pharmaceutically acceptable salts and/or N-oxides thereof, which process comprises reacting a compound of formula (IIA):

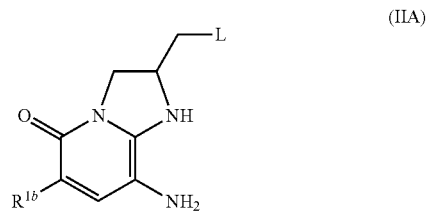

(IIA)

in which L is a leaving group or $-A(Q^1)(Q^2)$, where $Q^1$ and $Q^2$ are both attached to the same carbon atom on A, $Q^1$ is H and $Q^2$ is $N(R^{20})R^{2'}$ or $Q^1$ and $Q^2$ together form ethylenedioxy or oxo, $R^{20}$ is $UR^5$ or a group convertible thereto and $R^{2'}$ is $R^2$ or a group convertible thereto, A, $R^{1b}$, $R^2$, U and $R^5$, are as defined in formula (I), with (i) ethyl bromoacetate followed by cyclisation and oxidation or (ii) ethyl oxoacetate followed by cyclisation, to give a compound of formula (IIIA):

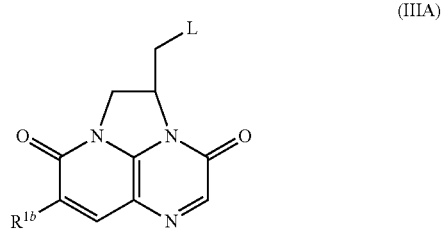

(IIIA)

and thereafter optionally or as necessary converting L to $-A-NR^2-UR^5$, interconverting any variable groups, and/or forming a pharmaceutically acceptable salt and/or N-oxide thereof.

The reaction variant (i) is a selective alkylation with ethyl bromoacetate under basic conditions (such as potassium carbonate) (see Yoshizawa, H. et al., Heterocycles (2004), 63(8), 1757-1763 for an example of this selectivity in the alkylation of 2,3-diaminopyridines), thermal cyclisation under strong basic conditions (such as potassium t-butoxide) and then oxidation with manganese dioxide under conventional conditions (see for examples Smith, M. B.; March, J. M. Advanced Organic Chemistry, Wiley-Interscience 2001).

The reaction variant (ii) may be carried out in toluene and the cyclisation effected under strongly basic conditions (such as potassium t-butoxide).

L may be a hydroxy group which can be oxidised to the aldehyde by conventional means such as 1,1,1-tris-(acetyloxy)-1,1-dihydro-1,2-benziodooxol-3-(1H)-one for reductive alkylation with HA-N($R^{20}$)$R^{2'}$ under conventional conditions (see for examples Smith, M. B.; March, J. M. Advanced Organic Chemistry, Wiley-Interscience 2001).

Alternatively L may be bromo which can be alkylated with HA-N($R^{20}$)$R^{2'}$ under conventional conditions.

Where $Q^1$ and $Q^2$ together form ethylenedioxy the ketal may be converted to the ketone ($Q^1$ and $Q^2$ together form oxo) by conventional acid hydrolysis treatment with eg aqueous HCl or trifluoroacetic acid and the conversion to $NR^2UR^5$ by conventional reductive alkylation with amine NH$R^{2'}R^{20}$ (see for example Nudelman, A., et al, Tetrahedron 60 (2004) 1731-1748) and subsequent conversion to the required substituted amine, or directly with NH$R^2UR^5$, such as with sodium triacetoxyborohydride in dichloromethane/methanol.

Conveniently one of $R^{20}$ and $R^{2'}$ is an N-protecting group, such as such as t-butoxycarbonyl, benzyloxycarbonyl or 9-fluorenylmethyloxycarbonyl. This may be removed by several methods well known to those skilled in the art (for examples see "Protective Groups in Organic Synthesis, T. W. Greene and P. G. M. Wuts, Wiley-Interscience, 1999), for example conventional acid hydrolysis with, for example trifluoroacetic acid or hydrochloric acid. The invention further provides compounds of formula (IIIA) in which L is -A-N($R^{20}$)$R^{2'}$ and $R^{20}$ is hydrogen.

The free amine of formula (IIIA) in which $R^{20}$ is hydrogen may be converted to $NR^2UR^5$ by conventional means such as amide formation with an acyl derivative $R^5$COW, for compounds where U is CO or, where U is CH$_2$, by alkylation with an alkyl halide $R^5$CH$_2$-halide in the presence of base, acylation/reduction with an acyl derivative $R^5$COW or reductive alkylation with an aldehyde $R^5$CHO under conventional conditions (see for examples Smith, M. B.; March, J. M. Advanced Organic Chemistry, Wiley-Interscience 2001). The appropriate reagents containing the required $R^5$ group are known compounds or may be prepared analogously to known compounds, see for example WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO06002047, WO06014580, WO06010040, WO06017326, WO06012396, WO06017468, WO06020561, WO2004/035569, WO2004/089947, WO2003082835, WO06002047, WO06014580, WO06010040, WO06017326, WO06012396, WO06017468, WO06020561, WO06132739, WO06134378, WO06137485, WO06081179, WO06081264, WO06081289, WO06081178, WO06081182, WO07016610, WO07081597, WO07071936, WO07115947, WO07118130, WO07122258, WO08006648, WO08003690, WO08009700, WO2007067511 and EP0559285.

Where $R^5$ contains an NH group, this may be protected with a suitable N-protecting group such as t-butoxycarbonyl, benzyloxycarbonyl or 9-fluorenylmethyloxycarbonyl during the coupling of the $R^5$ derivative with the free amine of formula (IIB). The protecting group may be removed by conventional methods, such as by treatment with trifluoroacetic acid.

In a further aspect of the invention there is provided a process for preparing compounds of formula (I) where $Z^1$ is nitrogen, and pharmaceutically acceptable salts and/or N-oxides thereof, which process comprises reacting a compound of formula (IIB):

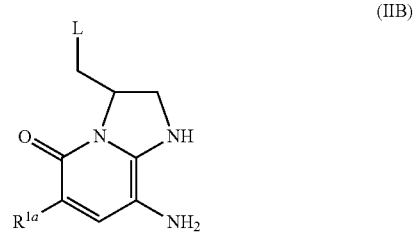

(IIB)

in which L is a leaving group or -A($Q^1$)($Q^2$), where $Q^1$ and $Q^2$ are both attached to the same carbon atom on A, $Q^1$ is H and $Q^2$ is N($R^{20}$)$R^{2'}$ or $Q^1$ and $Q^2$ together form ethylenedioxy or oxo, $R^{20}$ is $UR^5$ or a group convertible thereto and $R^{2'}$ is $R^2$ or a group convertible thereto, A, $R^{1a}$, $R^2$, U and $R^5$, are as defined in formula (I), with (i) ethyl bromoacetate followed by cyclisation and oxidation or (ii) ethyl oxoacetate followed by cyclisation, to give a compound of formula (IIIB):

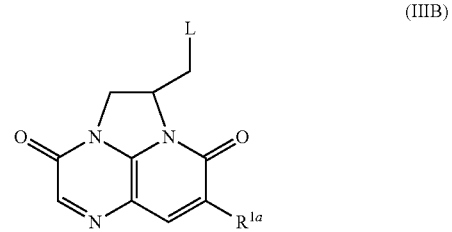

(IIIB)

and thereafter optionally or as necessary converting L to -A-NR$^2$—UR$^5$, interconverting any variable groups, and/or forming a pharmaceutically acceptable salt and/or N-oxide thereof.

The reaction and subsequent transformations is carried out as for the preparation of compounds of formula (IIIA).

The invention further provides compounds of formula (IIIB) in which L is -A-N($R^{20}$)$R^{2'}$ and $R^{20}$ is hydrogen.

Compounds of formula (IIB) (L=-A($Q^1$)($Q^2$)) may be prepared by Scheme 1:

Scheme 1

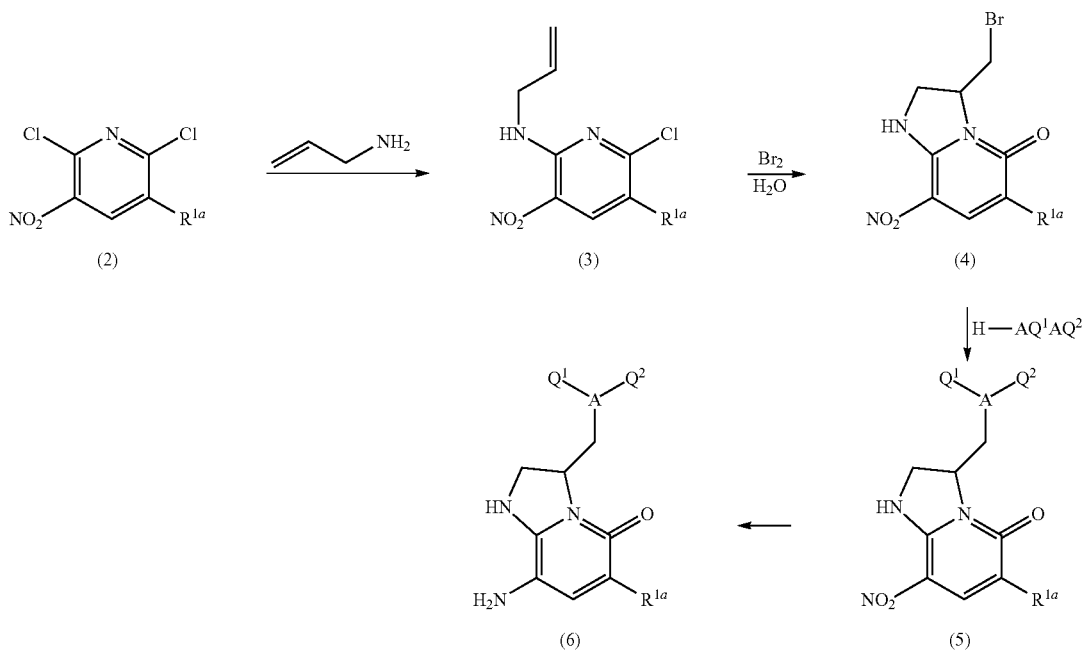

Chloropyridine (2) can be reacted with allylamine to give (3) which can then be cyclised with bromine generating pyridone (4) after a hydrolytic workup (see Schmid, S et al, Synthesis, 2005 (18), 3107). Displacement with H-A(Q¹)(Q²) gives (5) and hydrogenation of (5) over Pd/C can give amine (6).

Compounds of formula (IIIA) may be prepared by Scheme 2 utilising compounds of formula (IVA):

(IVA)

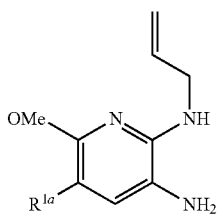

The starting material may be prepared by reduction of compound (3) from Scheme 1 with sodium methoxide and then reduction with tin (II) chloride or sodium dithionite. Cyclisation of (IVA) with propiolate esters gives (19) (Scheme 2) (see Kalyanam, N. et al, Indian Journal of Chemistry, Section B: Organic Chemistry Including Medicinal Chemistry (1992), 31B(7), 415-420). Standard protection to give (20) then cyclisation with bromine (see Schmid, S et al, Synthesis, 2005 (18), 3107) may then access bromomethyl analogue (21) which may be deprotected with TFA to (22) and oxidised with hydrogen peroxide or manganese (II) oxide to give (23) (see Sakata, G., Heterocycles (1985), 23(1), 143-51).

Scheme 2

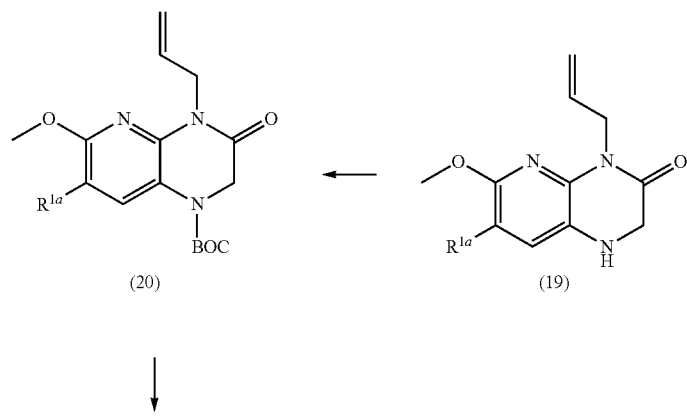

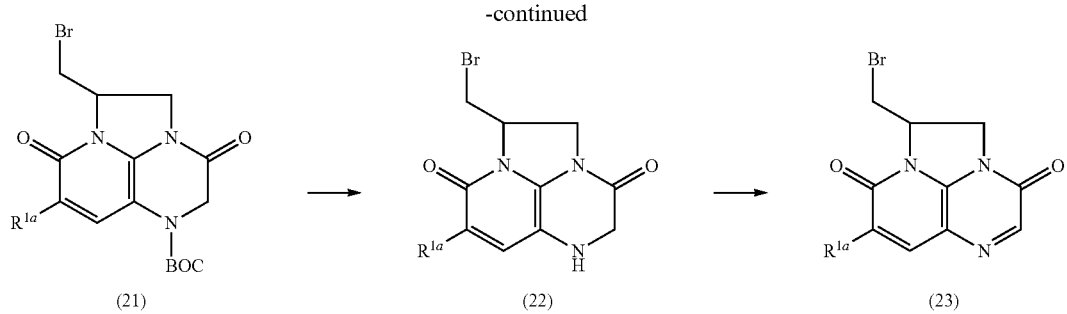

Compounds of formula (I) in which $Z^1$ and $Z^2$ are both CH may be prepared by Scheme 3:

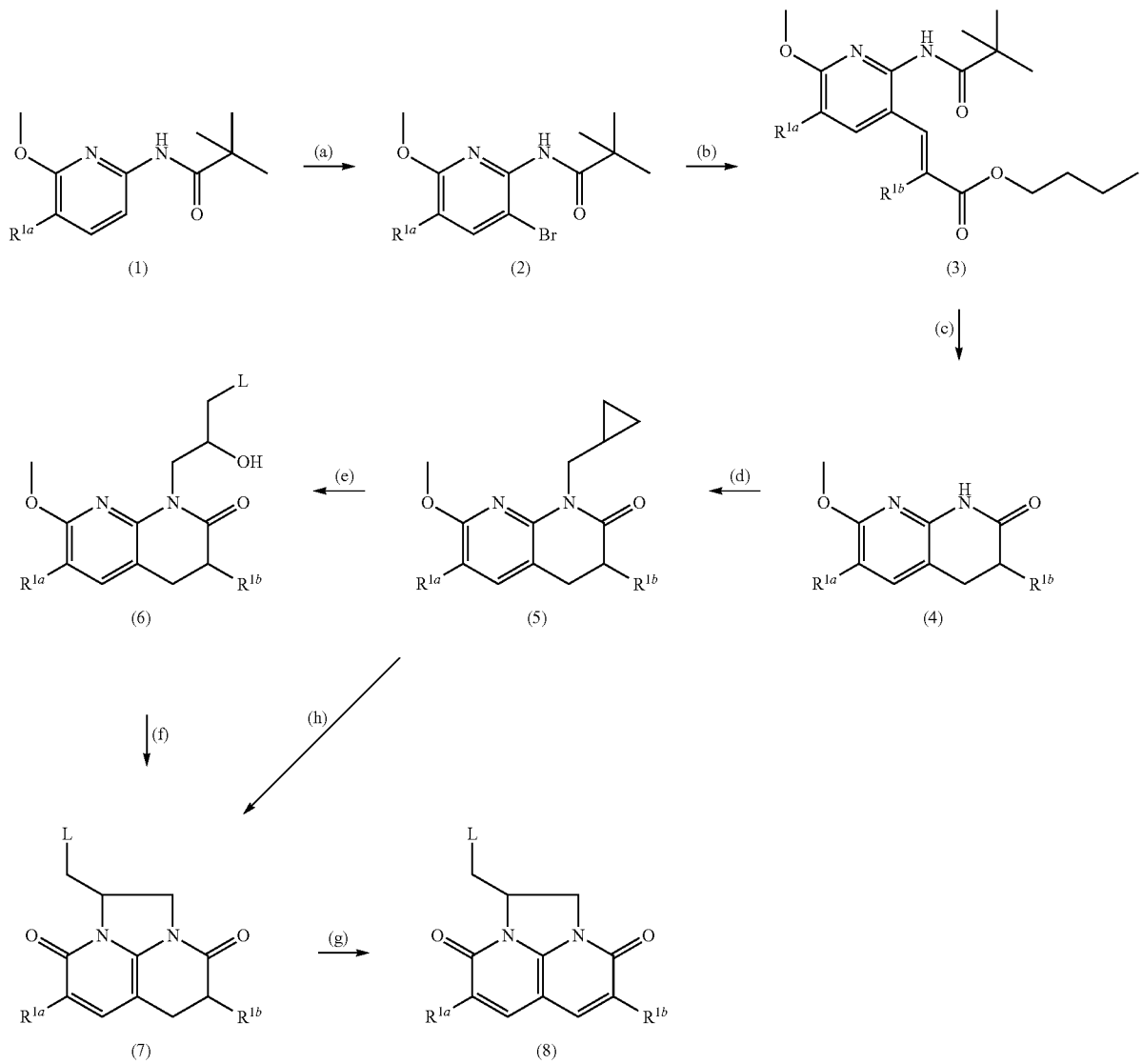

L is ——A(Q¹)(Q²)

(a) n-butyl lithium, dibromoethane (b) tris(dibenzylideneacetone)dipalladium(0), N,N-dicyclohexylmethylamine, bis(tri-t-butylphosphine)palladium(0), butyl acrylate (c) hydrogen, palladium/charcoal followed by acid treatment (HCl) (d) see text (e) amine H——A(Q¹)(Q²), heat (f) methylsulphonic anhydride, triethylamine then KI (g) 2,3-dichloro-5,6-dicyano-1,4-benzoquinone (h) i) DMF, heat, ii) methanesulphonyl chloride, triethylamine, iii) amineH——A(Q¹)(Q²), heat.

Metallation of (1) (commercially available) with n-butyl lithium followed by bromination with dibromoethane affords bromopyridine derivative (2) (see Zhichkin, P. et al, Synlett (2006), (3), 379-382 for examples of this type of metallation chemistry). Heck reaction of (2) using palladium catalysis (see Sydorenko, N, et al, Organic & Biomolecular Chemistry (2005), 3(11), 2140-2144 for an example of this type of catalysis in a Heck reaction) gives acryate (3). Hydrogenation of the double bond of (3) followed by acid treatment to remove the pivalate residue and effect lactamisation yields the bicyclic lactam (4). Conversion to the epoxide (5) can be effected in a number of ways—reaction with epichlorohydrin under basic conditions affords racemic epoxide. Reaction with (commercially available) R or S-glycidyl nosylate ((2R)- or (2S)-2-oxiranylmethyl 3-nitrobenzenesulfonate) or (2R)- or (2S)-2-oxiranylmethyl 4-methylbenzenesulfonate, with base eg sodium hydride or potassium t-butoxide, gives the corresponding chiral epoxides. Alternatively, allylation with allyl bromide under basic conditions affords the corresponding N-allyl material which can be epoxidised under standard achiral or chiral conditions to give the corresponding achiral or chiral epoxides. The epoxide(s) (5) may be opened with amine H-A($Q^1$)($Q^2$) such as 1,1-dimethylethyl 4-piperidinylcarbamate by heating in DMF to afford (6) which can then be cyclised with methanesulphonic anhydride to give (7). Alternatively, the epoxide (5) may be opened and cyclised directly with heating, to afford (7) (L=OH). Oxidation to (8) may be carried out by oxidation with 2,3-dichloro-5,6-dicyano-1,4-benzoquinone (DDQ). Subsequent conversion to compounds of formula (I) may be carried out as generally described herein. In particular, conversion of L to A($Q^1$)($Q^2$) may be carried out on (7) or (8). As a further variation to Scheme 3, epoxide (5) may be prepared from (2) by first introducing a suitable epoxide precursor group (—$CH_2$—CHOH—$CH_2$OH, protected as a cyclic ester) before carrying out the steps (b) and (c).

The invention further provides compounds of formula (8) from Scheme 3 in which L is -A-N($R^{20}$)$R^{2'}$ and $R^{20}$ is hydrogen.

Compounds of formula (I) in which $Z^2$ is N may alternatively be prepared by Scheme 4:

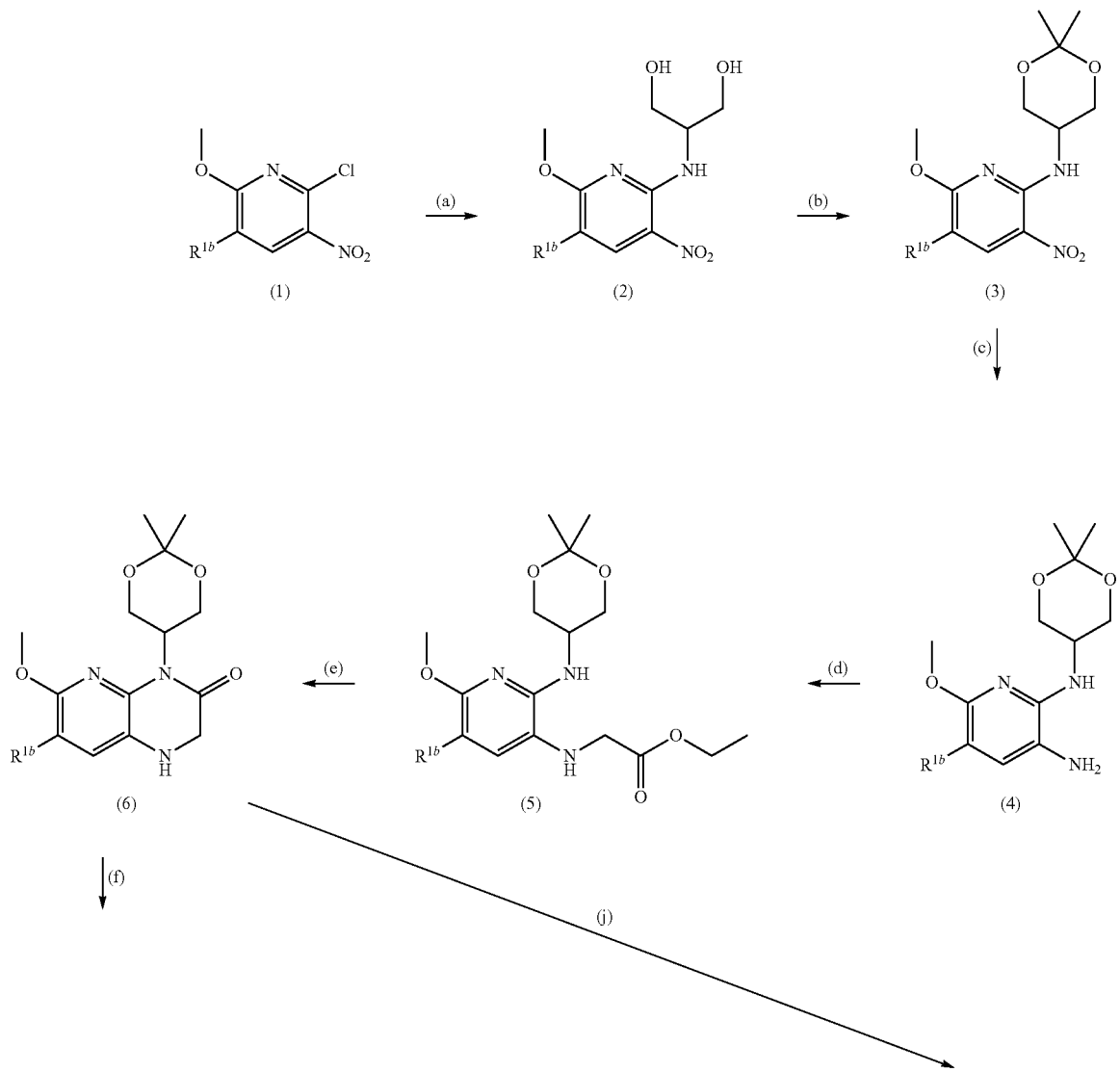

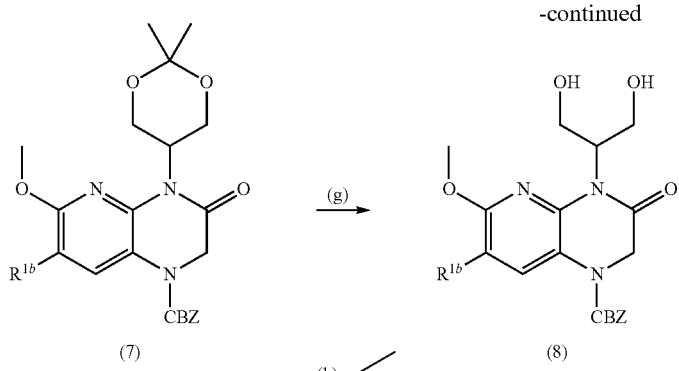

(7)

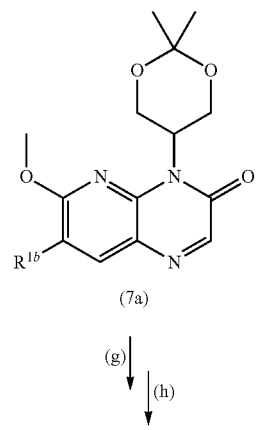

(7a)

(8)

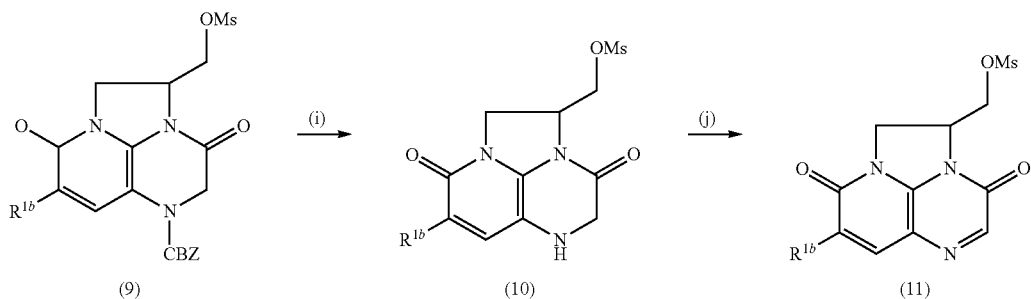

(9)            (10)            (11)

(a) 2-amino-1,3-propanediol (b) dimethoxpropane, p-toluenesulfonic acid (c) hydrogen, palladium/charcoal (d) ethyl bromoacetate, potassium carbonate (e) sodium hydride (f) Benzyl chloroformate (g) Aqueous acid (h) Methane sulphonic anhydride (i) Hydrogen, palladium/charcoal (j) MnO2

(a) 2-amino-1,3-propanediol (b) dimethoxypropane, p-toluenesulfonic acid (c) hydrogen, palladium/charcoal (d) ethyl bromoacetate, potassium carbonate (e) sodium hydride (f) Benzyl chloroformate (g) Aqueous acid (h) Methane sulphonic anhydride (i) Hydrogen, palladium/charcoal (j) MnO$_2$ Reaction of nitropyridine (1) with 2-amino-1,3-propanediol affords diol (2) which is protected as acetal (3). Reduction of the nitro group gives amine (4) which is alkylated to yield ester (5). Cyclisation can be effected with sodium hydride to give (6). This is protected with a carboxybenzyl (CBz) group (7) then cleaved to give the diol (8). Cyclisation with methanesulphonic anhydride affords the mesylate (9), then hydrogenolysis of the CBz group (10) and subsequent oxidation with manganese(II)oxide gives the key dione intermediate mesylate (11). The order of steps may be changed to go via (7a). The mesylate (11) may be converted to the compound of formula (I) as generally described herein.

Chiral compounds of formula (I) in which $Z^2$ is N may alternatively be prepared by Scheme 4a:

Scheme 4a

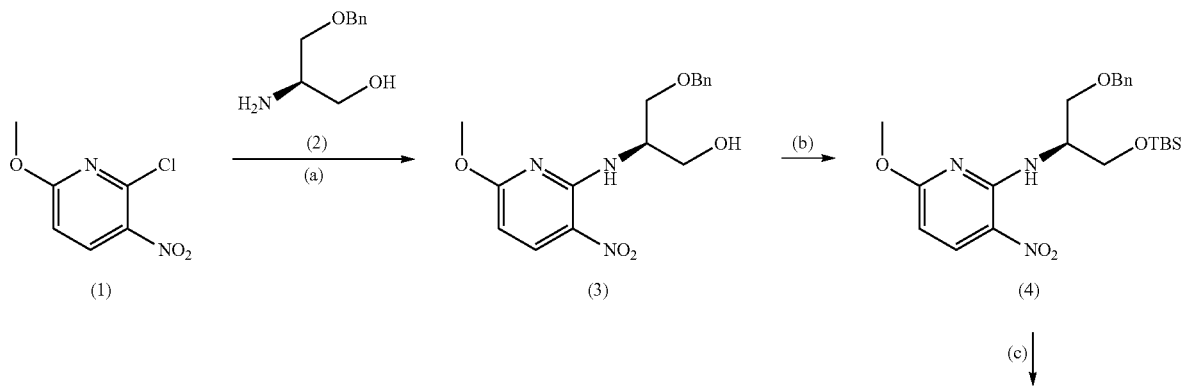

(1)            (3)            (4)

-continued

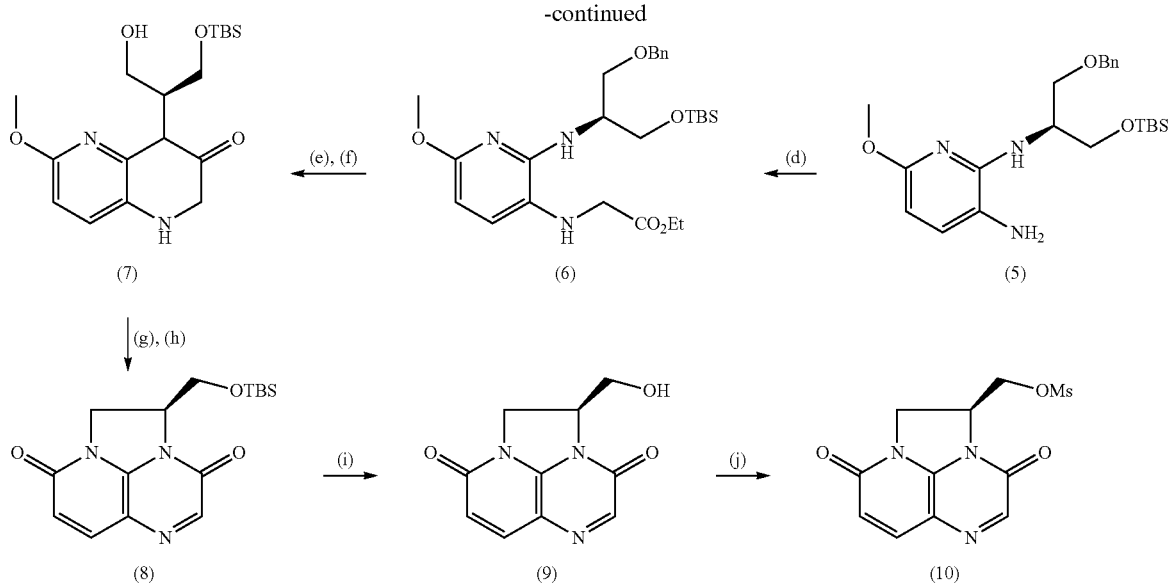

Bn = benzyl
(a) EtOH, reflux, (b) TBS—Cl, (c) Zinc, acetic acid, (d) ethyl bromoacetate, potasium carbonate (e) NaH, (f) hydrogen, palladium/charcoal, (g) MnO, (h) methanesulfonic anhydride
(i) TFA, (j) methanesulfonic anhydride Reaction of nitropyridine (1) with chiral amine (2) gives intermediate (3). Protection of (3) with tert-butyl-dimethyl-silylchloride gives (4). Reduction of the nitro group gives amine (5), which is alkylated to yield ester (6). Cyclisation of (6) can be effected with sodium hydride and then treatment with hydrogen over a palladium/charcoal catalyst gives intermediate (7). Oxidation with manganese(II)oxide and treatment with methanesulfonic anhydride gives (8). This intermediate can be deprotected with TFA to give (9) and reacted with methanesulfonic anhydride to give (10). The mesylate (10) formed may then be converted to the compound of formula (I) as generally described herein.

Compounds of formula (I) in which $Z^1$ is N may alternatively be prepared by Scheme 5:

Scheme 5

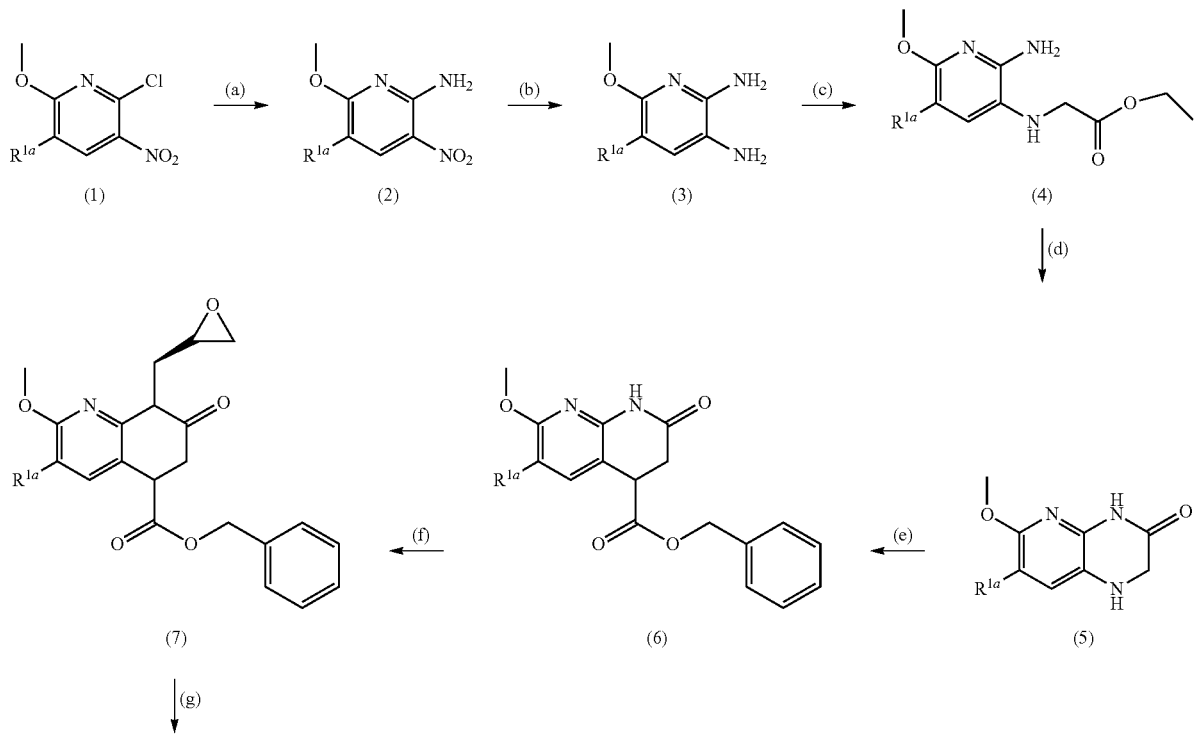

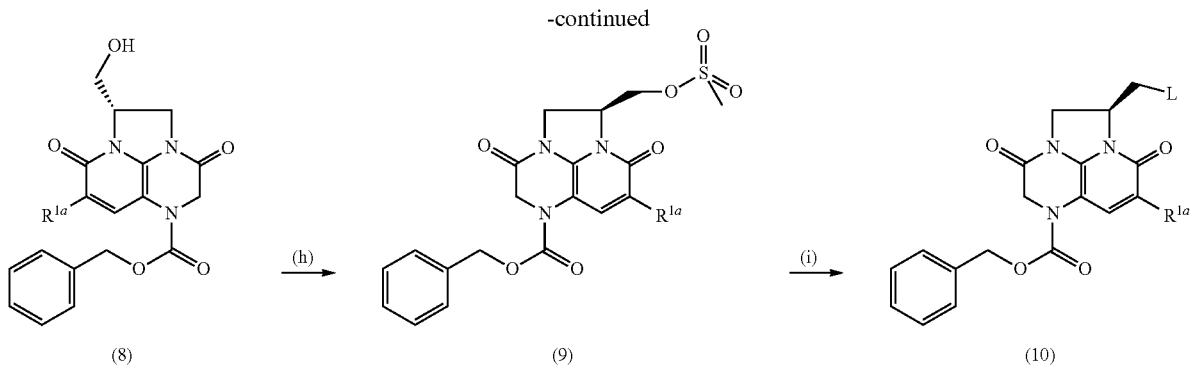

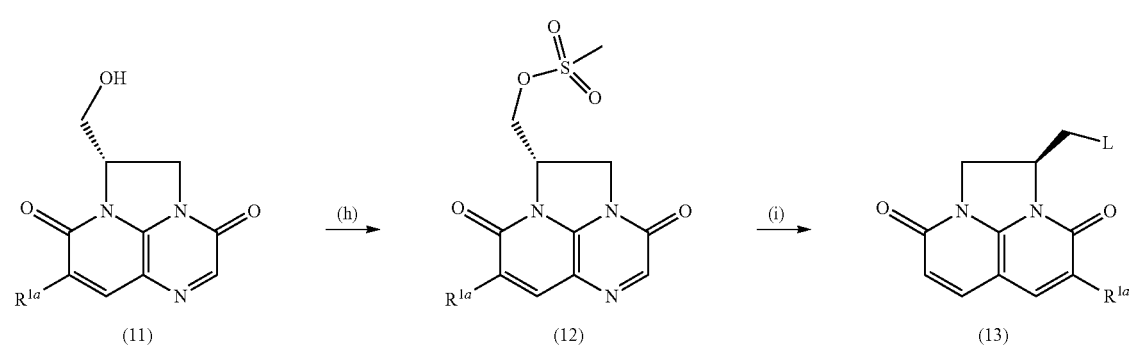

L is —A(Q¹)(Q²)

(a) NH₃/MeOH (b) hydrogen, palladium/charcoal (c) ethyl bromoacetate, potassium carbonate (d) potassium tert-butoxide (e) CBzCl (f) NaH, (S)-glycidyl nosylate (g) DMF, heat (h) methanesulfonyl chloride (i) amine H—A(Q¹)(Q²), heat (j) hydrogen, palladium/charcoal then MnO₂

Reaction of nitropyridine (1) with ammonia affords nitropyridine (2) which is reduced to bis-aniline (3). Alkyation with ethyl bromoacetate followed by cyclisation with potassium tert-butoxide gives (5). This is protected with a carboxybenzyl group to give (6) which can then be reacted with (commercially available) S-glycidyl nosylate ((2S)-2-oxiranylmethyl 3-nitrobenzenesulfonate) to give (7). Cyclisation under thermal conditions gives (8). Mesylation, displacement with an appropriate amine, hydrogenolysis of the CBz group (10) and subsequent oxidation with manganese(II) oxide gives (13). Alternatively hydrogenolysis of the CBz group (10) and subsequent oxidation with manganese(II) oxide, followed by mesylation and displacement with an appropriate amine also gives (13). This may be converted to the compound of formula (I) as generally described herein.

Compounds of formula (I) in which $Z^1$ and $Z^2$ are both N may be prepared by Scheme 6:

Scheme 6

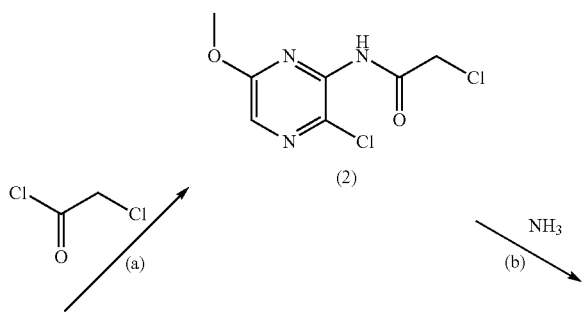

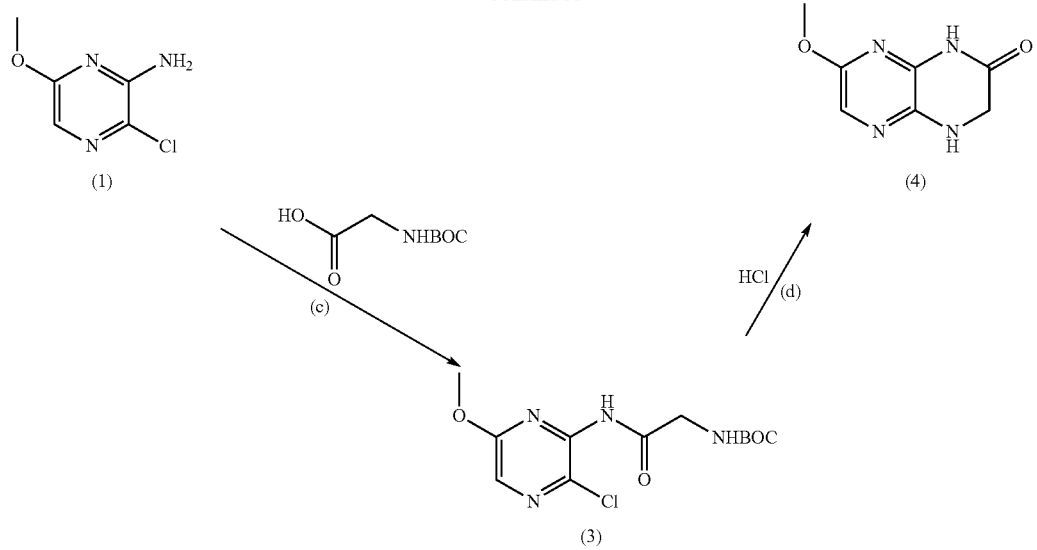

(a) chloroacetyl chloride (b) ammonia (c) Boc-glycine (d) HCl

Compound (1) (Bioorganic & Medicinal Chemistry Letters (2005), 15(24), 5446-5449) is converted to (2) by acylation with chloroacetyl chloride followed by treatment with ammonia to give (4). Alternatively (1) may be converted to (3) by coupling with Boc-glycine followed by acidic deprotection to give (4). Compound (4) may then be converted to a compound of formula (I) by analogy with the conversion of compound (5) of Scheme 5.

Interconversions of $R^{1a}$, $R^{1b}$, $R^2$, A and $R^5$ are conventional. In compounds which contain an optionally protected hydroxy group, suitable conventional hydroxy protecting groups which may be removed without disrupting the remainder of the molecule include acyl and alkylsilyl groups. N-protecting groups are removed by conventional methods.

Interconversion of $R^{1a}$ and $R^{1b}$ groups may be carried out conventionally, on compounds of formula (I). For example $R^{1a}$ or $R^{1b}$ methoxy is convertible to $R^{1a}$ or $R^{1b}$ hydroxy by treatment with lithium and diphenylphosphine (general method described in Ireland et al, J. Amer. Chem. Soc., 1973, 7829) or HBr. Alkylation of the hydroxy group with a suitable alkyl derivative bearing a leaving group such as halide, yields $R^{1a}$ or $R^{1b}$ substituted alkoxy. $R^{1a}$ or $R^{1b}$ halo such as bromo may be converted to cyano by treatment with copper (I) cyanide in N,N-dimethylformamide. $R^{1a}$ or $R^{1b}$ carboxy may be obtained by conventional hydrolysis of $R^{1a}$ or $R^{1b}$ cyano, and the carboxy converted to hydroxymethyl by conventional reduction.

Compounds of formula HA-N($R^{20}$)$R^{2'}$ are known compounds or may be prepared analogously to known compounds, see for example WO2004/035569, WO2004/089947, WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2003082835, WO2002026723, WO06002047 and WO06014580, WO06134378, WO06137485, WO07016610, WO07081597, WO07071936, WO07115947, WO07118130, WO07122258, WO08006648, WO08003690 and WO08009700.

Further details for the preparation of compounds of formula (I) are found in the examples.

Pharmaceutical Compositions And Formulations

The antibacterial compounds according to the invention may be formulated for administration in any convenient way for use in human or veterinary medicine, by analogy with other antibacterials/antitubercular compounds.

The pharmaceutical compositions of the invention may be formulated for administration by any route and include those in a form adapted for oral, topical or parenteral use and may be used for the treatment of bacterial infection including tuberculosis in mammals including humans.

The compositions may be in the form of tablets, capsules, powders, granules, lozenges, suppositories, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

Moreover, the quantity of the compound or composition of the present invention administered will vary depending on the patient and the mode of administration and can be any effective amount.

Treatment regimen for the administration of the compounds and/or compositions of the present invention can also be determined readily by those with ordinary skill in art.

The quantity of the compound and/or composition of the present invention administered may vary over a wide range to provide in a unit dosage an effective amount based upon the body weight of the patient per day to achieve the desired effect.

The compositions may contain from 0.1% by weight, preferably from 10-60% by weight, of the active material, depending on the method of administration. Where the compositions comprise dosage units, each unit will preferably contain from 50-1000 mg of the active ingredient.

The dosage as employed for adult human treatment will preferably range from 100 to 3000 mg per day, for instance 1500 mg per day depending on the route and frequency of administration. Such a dosage corresponds to about 1.5 to about 50 mg/kg per day. Suitably the dosage is from 5 to 30 mg/kg per day.

In particular, a composition of the present invention is presented as a unit dose and taken preferably from 1 to 5 times daily, most preferably once daily to achieve the desired effect.

Conventional administration methods may be suitable for use in the present invention.

Depending upon the treatment being effected, the compounds, and/or or compositions of the present invention can be administered orally, intravascularly, intraperitoneally, subcutaneously, intramuscularly or topically. Preferably, the composition is adapted for oral administration.

The compounds and/or compositions prepared according to the present invention can be used to treat warm blooded animals, such as mammals, which include humans.

The compound of formula (I) may be the sole therapeutic agent in the compositions of the invention or a combination with other antibacterials including antitubercular compounds. If the other antibacterial is a β-lactam then a β-lactamase inhibitor may also be employed.

Compounds of formula (I) may be used in the treatment of bacterial infections caused by a wide range of organisms including both Gram-negative and Gram-positive organisms, such as upper and/or lower respiratory tract infections, skin and soft tissue infections and/or urinary tract infections. Compounds of formula (I) may be also used in the treatment of tuberculosis caused by *Mycobacterium tuberculosis*. Some compounds of formula (I) may be active against more than one organism. This may be determined by the methods described herein.

Treatment Methods

The present invention relates to methods for treating *Neisseria gonorrhoeae* infection which comprises administering to a subject in need thereof novel Tricyclic nitrogen containing compounds and corresponding pharmaceutical compositions as described herein.

In one aspect the present invention relates to a method for treating *Neisseria gonorrhoeae* infection which comprises administering to a subject in need thereof an effective amount of a compound of Formula (I):

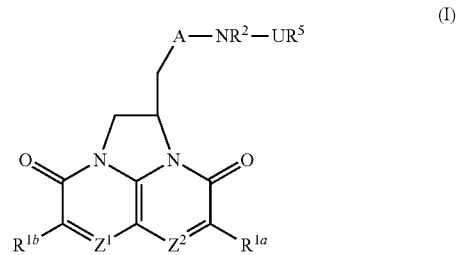

where:

$Z^1$ and $Z^2$ are independently selected from CH and N;

$R^{1a}$ and $R^{1b}$ are independently selected from hydrogen; halogen; cyano; $(C_{1-6})$alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted$(C_{1-6})$alkyl; $(C_{1-6})$alkoxy-substituted$(C_{1-6})$alkyl; hydroxy $(C_{1-6})$alkyl; an amino group optionally N-substituted by one or two $(C_{1-6})$alkyl, formyl, $(C_{1-6})$alkylcarbonyl or $(C_{1-6})$alkylsulphonyl groups; and aminocarbonyl wherein the amino group is optionally substituted by $(C_{1-4})$alkyl;

provided that $R^{1a}$ and $R^{1b}$ are H when $Z^2$ or $Z^1$ is N, respectively;

$R^2$ is hydrogen, or $(C_{1-4})$alkyl, or together with $R^6$ forms Y as defined below;

A is a group (i):

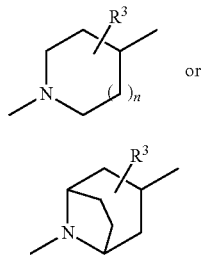

in which: $R^3$ is as defined for $R^{1a}$ and $R^{1b}$ or is oxo and n is 1 or 2: or A is a group (ii)

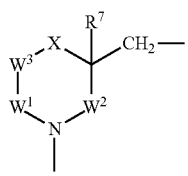

$W^1$, $W^2$ and $W^3$ are $CR^4R^8$ or $W^2$ and $W^3$ are $CR^4R^8$ and $W^1$ represents a bond between $W^3$ and N.

X is O, $CR^4R^8$, or $NR^6$;

one $R^4$ is as defined for $R^{1a}$ and $R^{1b}$ and the remainder and $R^8$ are hydrogen or one $R^4$ and $R^8$ are together oxo and the remainder are hydrogen;

$R^6$ is hydrogen or $(C_{1-6})$alkyl; or together with $R^2$ forms Y;

$R^7$ is hydrogen; halogen; hydroxy optionally substituted with $(C_{1-6})$alkyl; or $(C_{1-6})$alkyl;

Y is $CR^4R^8CH_2$; $CH_2CR^4R^8$; (C=O); $CR^4R^8$; $CR^4R^8$(C=O); or (C=O)$CR^4R^8$;

or when X is $CR^4R^8$, $R^8$ and $R^7$ together represent a bond;

U is selected from CO, and $CH_2$ and $R^5$ is an optionally substituted bicyclic carbocyclic or heterocyclic ring system (B):

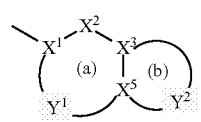

containing up to four heteroatoms in each ring in which
at least one of rings (a) and (b) is aromatic;

$X^1$ is C or N when part of an aromatic ring, or $CR^{14}$ when part of a non-aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring;

$Y^2$ is a 2 to 6 atom linker group, each atom of $Y^2$ being independently selected from N, $NR^{13}$, O, $S(O)_x$, CO, $CR^{14}$ when part of an aromatic or non-aromatic ring or may additionally be $CR^{14}R^{15}$ when part of a non aromatic ring;

each of $R^{14}$ and $R^{15}$ is independently selected from: H; $(C_{1-4})$alkylthio; halo; carboxy$(C_{1-4})$alkyl; $(C_{1-4})$alkyl; $(C_{1-4})$alkoxycarbonyl; $(C_{1-4})$alkylcarbonyl; $(C_{1-4})$alkoxy$(C_{1-4})$alkyl; hydroxy; hydroxy$(C_{1-4})$alkyl; $(C_{1-4})$alkoxy; nitro; cyano; carboxy; amino or aminocarbonyl optionally mono- or di-substituted by $(C_{1-4})$alkyl; or $R^{14}$ and $R^{15}$ may together represent oxo;

each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; $(C_{1-4})$alkoxycarbonyl; $(C_{1-4})$alkylcarbonyl; $(C_{1-6})$alkylsulphonyl; aminocarbonyl wherein the amino group is optionally mono or disubstituted by $(C_{1-4})$alkyl; and each x is independently 0, 1 or 2; or a pharmaceutically acceptable salt thereof.

In another aspect, the present invention relates to a method, where in the compound of Formula I:
(i) $Z^1$ and $Z^2$ are both CH;
(ii) $Z^1$ is N and $Z^2$ is CH; or
(iii) $Z^1$ is CH and $Z^2$ is N.

In another aspect, the present invention relates to a method, where $R^{1a}$ is hydrogen and $R^{1b}$ is hydrogen as defined for compound of Formula I.

In another aspect, the present invention relates to a method, wherein in the compound of Formula I:
A is (ia), n is 1 and $R^3$ is H or hydroxy in the 3-position;
A is (ii), X is $CR^4R^8$ and $R^8$ is H and $R^4$ is H or OH; or
A is (ii), X is O, $R^7$ is H and $W^1$, $W^2$ and $W^3$ are each $CH_2$.

In another aspect, the present invention relates to a method, where A is piperidin-4-yl or pyrrolidin-4-ylmethyl as defined for compound of Formula I.

In another aspect, the present invention relates to a method, wherein U is $CH_2$ as defined for compound of Formula I.

In another aspect, the present invention relates to a method, where in the compound of Formula I: $R^5$ is an aromatic heterocyclic ring (B) having 8-11 ring atoms including 2-4 heteroatoms of which at least one is N or $NR^{13}$ in which $Y^2$ contains 2-3 heteroatoms, one of which is S and 1-2 are N, with one N bonded to $X^3$, or the heterocyclic ring (B) has ring (a) aromatic selected from optionally substituted benzo, pyrido, pyridazino and pyrimidino and ring (b) non aromatic and $Y^2$ has 3-5 atoms, including at least one heteroatom, with O, S, $CH_2$ or $NR^{13}$ bonded to $X^5$ where $R^{13}$ is other than hydrogen, and either NHCO bonded via N to $X^3$, or O, S, $CH_2$ or NH bonded to $X^3$.

In another aspect, the present invention relates to a method, where in the compound of Formula I:
$R^5$ is selected from:
3-oxo-3,4-dihydro-2H-pyrido[3,2-b][1,4]oxazin-6-yl;
3-oxo-3,4-dihydro-2H-pyrido[3,2-b][1,4]thiazin-6-yl;
2,3-dihydro-[1,4]dioxino[2,3-c]pyridin-7-yl;
[1,3]oxathiolo[5,4-c]pyridin-6-yl;
6-fluoro-2,3-dihydro-1,4-benzodioxin-7-yl;
2,3-dihydro[1,4]oxathiino[2,3-c]pyridin-7-yl;
3,4-dihydro-2H-pyrano[2,3-c]pyridin-6-yl;
5-fluoro-2,3-dihydro-1,4-benzodioxin-7-yl;
5-carbonitro-2,3-dihydro-1,4-benzodioxin-7-yl; or
2,3-dihydro-benzo[1,4]dioxin-6-yl.

In another aspect, the present invention relates to a method, wherein in the compound of Formula I: A is selected from:

1-({4-[(2,3-Dihydro[1,4]dioxino[2,3-c]pyridin-7-ylmethyl)
amino]-1-piperidinyl}methyl)-1,2-dihydro-3H,8H-2a,5,
8a-triazaacenaphthylene-3,8-dione;
1-({4-[([1,3]Oxathiolo[5,4-c]pyridin-6-ylmethyl)amino]-1-
piperidinyl}methyl)-1,2-dihydro-4H,9H-imidazo[1,2,3-
ij]-1,8-naphthyridine-4,9-dione;
1-({4-[(2,3-Dihydro[1,4]dioxino[2,3-c]pyridin-7-ylmethyl)
amino]-1-piperidinyl}methyl)-1,2-dihydro-4H,9H-imi-
dazo[1,2,3-ij]-1,8-naphthyridine-4,9-dione;
1-({4-[(2,3-Dihydro[1,4]dioxino[2,3-c]pyridin-7-ylmethyl)
amino]-1-piperidinyl}methyl)-1,2-dihydro-4H,9H-imi-
dazo[1,2,3-ij]-1,8-naphthyridine-4,9-dione;
(1R)-1-({4-[([1,3]Oxathiolo[5,4-c]pyridin-6-ylmethyl)
amino]-1-piperidinyl}methyl)-1,2-dihydro-4H,9H-imi-
dazo[1,2,3-ij]-1,8-naphthyridine-4,9-dione;
(1R)-1-({4-[(2,3-Dihydro[1,4]oxathiino[2,3-c]pyridin-7-yl-
methyl)amino]-1-piperidinyl}methyl)-1,2-dihydro-4H,
9H-imidazo[1,2,3-ij]-1,8-naphthyridine-4,9-dione;
(1R)-1-({4-[(5,6,7,8-Tetrahydro-3-isoquinolinylmethyl)
amino]-1-piperidinyl}methyl)-1,2-dihydro-4H,9H-imi-
dazo[1,2,3-ij]-1,8-naphthyridine-4,9-dione;
(1R)-1-({4-[(6,7-Dihydro-5H-cyclopenta[c]pyridin-3-ylm-
ethyl)amino]-1-piperidinyl}methyl)-1,2-dihydro-4H,9H-
imidazo[1,2,3-ij]-1,8-naphthyridine-4,9-dione;
(1R)-1-({4-[(1,3-Dihydrofuro[3,4-c]pyridin-6-ylmethyl)
amino]-1-piperidinyl}methyl)-1,2-dihydro-4H,9H-imi-
dazo[1,2,3-ij]-1,8-naphthyridine-4,9-dione;
(1R)-1-({4-[(3,4-Dihydro-2H-pyrano[2,3-c]pyridin-6-ylm-
ethyl)amino]-1-piperidinyl}methyl)-1,2-dihydro-4H,9H-
imidazo[1,2,3-ij]-1,8-naphthyridine-4,9-dione;
7-[({1-[(4,9-Dioxo-1,2-dihydro-4H,9H-imidazo[1,2,3-ij]-1,
8-naphthyridin-1-yl)methyl]-4-piperidinyl}amino)
methyl]-2,3-dihydro-1,4-benzodioxin-5-carbonitrile;
1-(4-{[(3-Oxo-3,4-dihydro-2H-1,4-benzothiazin-6-yl)
methyl]amino}-1-piperidinyl)methyl]-1,2-dihydro-4H,
9H-imidazo[1,2,3-ij]-1,8-naphthyridine-4,9-dione;
(1R)-1-({4-[([1,3]Oxathiolo[5,4-c]pyridin-6-ylmethyl)
amino]-1-piperidinyl}methyl)-1,2-dihydro-3H,8H-2a,5,
8a-triazaacenaphthylene-3,8-dione;
(1R)-1-({4-[(2,3-Dihydro[1,4]oxathiino[2,3-c]pyridin-7-yl-
methyl)amino]-1-piperidinyl}methyl)-1,2-dihydro-3H,
8H-2a,5,8a-triazaacenaphthylene-3,8-dione;
(1R)-1-({4-[(2,3-Dihydro[1,4]dioxino[2,3-c]pyridin-7-ylm-
ethyl)amino]-1-piperidinyl}methyl)-1,2-dihydro-3H,8H-
2a,5,8a-triazaacenaphthylene-3,8-dione;
(2R)-2-({4-[([1,3]Oxathiolo[5,4-c]pyridin-6-ylmethyl)
amino]-1-piperidinyl}methyl)-1,2-dihydro-3H,8H-2a,5,
8a-triazaacenaphthylene-3,8-dione;
(2S)-2-({4-[([1,3]Oxathiolo[5,4-c]pyridin-6-ylmethyl)
amino]-1-piperidinyl}methyl)-1,2-dihydro-3H,8H-2a,5,
8a-triazaacenaphthylene-3,8-dione;
2-({4-[(1,3]Oxathiolo[5,4-c]pyridin-6-ylmethyl)amino]-1-
piperidinyl}methyl)-1,2-dihydro-3H,8H-2a,5,8a-triaz-
aacenaphthylene-3,8-dione;
(2R)-2-({4-[(2,3-Dihydro[1,4]oxathiino[2,3-c]pyridin-7-yl-
methyl)amino]-1-piperidinyl}methyl)-1,2-dihydro-3H,
8H-2a,5,8a-triazaacenaphthylene-3,8-dione;
2-({4-[(2,3-Dihydro[1,4]oxathiino[2,3-c]pyridin-7-ylm-
ethyl)amino]-1-piperidinyl}methyl)-1,2-dihydro-3H,8H-
2a,5,8a-triazaacenaphthylene-3,8-dione;
(2S)-2-({4-[(2,3-Dihydro[1,4]oxathiino[2,3-c]pyridin-7-yl-
methyl)amino]-1-piperidinyl}methyl)-1,2-dihydro-3H,
8H-2a,5,8a-triazaacenaphthylene-3,8-dione;
2-({4-[(2,3-Dihydro[1,4]dioxino[2,3-c]pyridin-7-ylmethyl)
amino]-1-piperidinyl}methyl)-1,2-dihydro-3H,8H-2a,5,
8a-triazaacenaphthylene-3,8-dione;
(1R)-1-({4-[(2,3-Dihydro[1,4]oxathiino[2,3-c]pyridin-7-yl-
methyl)amino]-4-methyl-1-piperidinyl}methyl)-1,2-di-
hydro-4H,9H-imidazo[1,2,3-ij]-1,8-naphthyridine-4,9-di-
one;
(1R)-1-({4-Methyl-4-[([1,3]oxathiolo[5,4-c]pyridin-6-ylm-
ethyl)amino]-1-piperidinyl}methyl)-1,2-dihydro-4H,9H-
imidazo[1,2,3-ij]-1,8-naphthyridine-4,9-dione;
(2R)-2-({4-[(2,1,3-Benzothiadiazol-5-ylmethyl)amino]-1-
piperidinyl}methyl)-1,2-dihydro-3H,8H-2a,5,8a-triaz-
aacenaphthylene-3,8-dione;
(2R)-2-[(4-{[(7-Fluoro-2,3-dihydro-1,4-benzodioxin-6-yl)
methyl]amino}-1-piperidinyl)methyl]-1,2-dihydro-3H,
8H-2a,5,8a-triazaacenaphthylene-3,8-dione;
(2R)-2-({4-[(3,4-Dihydro-2H-[1,4]oxathiepino[2,3-c]pyri-
din-8-ylmethyl)amino]-1-piperidinyl}methyl)-1,2-di-
hydro-3H,8H-2a,5,8a-triazaacenaphthylene-3,8-dione;
(2R)-2-({4-[([1,3]Oxathiolo[4,5-c]pyridin-6-ylmethyl)
amino]-1-piperidinyl}methyl)-1,2-dihydro-3H,8H-2a,5,
8a-triazaacenaphthylene-3,8-dione;
(2R)-2-[(4-{[(3-Oxo-3,4-dihydro-2H-pyrido[3,2-b][1,4]thi-
azin-6-yl)methyl]amino}-1-piperidinyl)methyl]-1,2-di-
hydro-3H,8H-2a,5,8a-triazaacenaphthylene-3,8-dione;
(1R)-1-({4-[(2,3-Dihydro-1,4-benzodioxin-6-ylmethyl)
amino]-1-piperidinyl}methyl)-1,2-dihydro-4H,9H-imi-
dazo[1,2,3-ij]-1,8-naphthyridine-4,9-dione;
(1R)-1-[(4-{[(8-Fluoro-2,3-dihydro-1,4-benzodioxin-6-yl)
methyl]amino}-1-piperidinyl)methyl]-1,2-dihydro-4H,
9H-imidazo[1,2,3-ij]-1,8-naphthyridine-4,9-dione;
(1R)-1-[(4-{[(7-Chloro-3-oxo-3,4-dihydro-2H-pyrido[3,2-
b][1,4]oxazin-6-yl)methyl]amino}-1-piperidinyl)
methyl]-1,2-dihydro-4H,9H-imidazo[1,2,3-ij]-1,8-naph-
thyridine-4,9-dione;
(1R)-1-[(4-{[(4-Chloro-7-oxo-6,7-dihydro-1H-pyrimido[5,
4-b][1,4]oxazin-2-yl)methyl]amino}-1-piperidinyl)
methyl]-1,2-dihydro-4H,9H-imidazo[1,2,3-ij]-1,8-naph-
thyridine-4,9-dione;
(1R)-1-[(4-{[(7-Oxo-6,7-dihydro-1H-pyrimido[5,4-b][1,4]
thiazin-2-yl)methyl]amino}-1-piperidinyl)methyl]-1,2-
dihydro-4H,9H-imidazo[1,2,3-ij]-1,8-naphthyridine-4,9-
dione;
(1R)-1-({4-[(1,2,3-Benzothiadiazol-5-ylmethyl)amino]-1-
piperidinyl}methyl)-1,2-dihydro-4H,9H-imidazo[1,2,3-
ij]-1,8-naphthyridine-4,9-dione;
(1R)-1-({4-[(2,3-Dihydro-1-benzofuran-5-ylmethyl)
amino]-1-piperidinyl}methyl)-1,2-dihydro-4H,9H-imi-
dazo[1,2,3-ij]-1,8-naphthyridine-4,9-dione;
(1R)-1-({4-[(3,4-Dihydro-2H-pyrano[2,3-c]pyridin-6-ylm-
ethyl)amino]-1-piperidinyl}methyl)-1,2-dihydro-3H,
8H-2a,5,8a-triazaacenaphthylene-3,8-dione;
(1R)-1-({4-[(2,3-Dihydrofuro[2,3-c]pyridin-5-ylmethyl)
amino]-1-piperidinyl}methyl)-1,2-dihydro-3H,8H-2a,5,
8a-triazaacenaphthylene-3,8-dione;
(2R)-2-({4-[(3,4-Dihydro-2H-pyrano[2,3-c]pyridin-6-ylm-
ethyl)amino]-1-piperidinyl}methyl)-1,2-dihydro-3H,8H-
2a,5,8a-triazaacenaphthylene-3,8-dione;
(2R)-2-({4-[(2,3-Dihydro-1,4-benzodioxin-6-ylmethyl)
amino]-1-piperidinyl}methyl)-1,2-dihydro-3H,8H-2a,5,
8a-triazaacenaphthylene-3,8-dione;
(2R)-2-[(4-{[(8-Fluoro-2,3-dihydro-1,4-benzodioxin-6-yl)
methyl]amino}-1-piperidinyl)methyl]-1,2-dihydro-3H,
8H-2a,5,8a-triazaacenaphthylene-3,8-dione;
7-{[(1-{[(2R)-3,8-Dioxo-1,2-dihydro-3H,8H-2a,5,8a-triaz-
aacenaphthylen-2-yl]methyl}-4-piperidinyl)amino]
methyl}-2,3-dihydro-1,4-benzodioxin-5-carbonitrile;
(2R)-2-({4-[(2,3-Dihydrofuro[2,3-c]pyridin-5-ylmethyl)
amino]-1-piperidinyl}methyl)-1,2-dihydro-3H,8H-2a,5,
8a-triazaacenaphthylene-3,8-dione;

(1R)-1-({4-[(2,3-Dihydro-1,4-benzodioxin-6-ylmethyl) amino]-1-piperidinyl}methyl)-1,2-dihydro-3H,8H-2a,5, 8a-triazaacenaphthylene-3,8-dione;

(1R)-1-({4-[([1,2,5]Thiadiazolo[3,4-b]pyridin-6-ylmethyl) amino]-1-piperidinyl}methyl)-1,2-dihydro-4H,9H-imidazo[1,2,3-ij]-1,8-naphthyridine-4,9-dione;

(1R)-1-[(4-{[(4-Fluoro-1H-benzimidazol-2-yl)methyl] amino}-1-piperidinyl)methyl]-1,2-dihydro-4H,9H-imidazo[1,2,3-ij]-1,8-naphthyridine-4,9-dione;

(1R)-1-[((2S)-2-{[([1,3]Oxathiolo[5,4-c]pyridin-6-ylmethyl)amino]methyl}-4-morpholinyl)methyl]-1,2-dihydro-4H,9H-imidazo[1,2,3-ij]-1,8-naphthyridine-4,9-dione;

(1R)-1-{[(2S)-2-({[(7-Chloro-3-oxo-3,4-dihydro-2H-pyrido[3,2-b][1,4]oxazin-6-yl)methyl]amino}methyl)-4-morpholinyl]methyl}-1,2-dihydro-4H,9H-imidazo[1,2,3-ij]-1,8-naphthyridine-4,9-dione;

(2R)-2-({4-[([1,2,5]Thiadiazolo[3,4-b]pyridin-6-ylmethyl) amino]-1-piperidinyl}methyl)-1,2-dihydro-3H,8H-2a,5, 8a-triazaacenaphthylene-3,8-dione;

(1R)-1-({4-[(3,4-Dihydro-2H-chromen-7-ylmethyl)amino]-1-piperidinyl}methyl)-1,2-dihydro-4H,9H-imidazo[1,2,3-ij]-1,8-naphthyridine-4,9-dione;

(1R)-1-({4-[(2,3-Dihydro-1-benzofuran-6-ylmethyl) amino]-1-piperidinyl}methyl)-1,2-dihydro-4H,9H-imidazo[1,2,3-ij]-1,8-naphthyridine-4,9-dione;

(1R)-1-({4-[(3,4-Dihydro-2H-chromen-6-ylmethyl)amino]-1-piperidinyl}methyl)-1,2-dihydro-4H,9H-imidazo[1,2,3-ij]-1,8-naphthyridine-4,9-dione;

(2R)-2-[(4-{[(5-Fluoro-2,3-dihydro-1,4-benzodioxin-6-yl) methyl]amino}-1-piperidinyl)methyl]-1,2-dihydro-3H, 8H-2a,5,8a-triazaacenaphthylene-3,8-dione;

(1R)-1-{[(2S)-2-({[(7-fluoro-2,3-dihydro-1,4-benzodioxin-6-yl)methyl]amino}methyl)-4-morpholinyl]methyl}-1,2-dihydro-4H,9H-imidazo[1,2,3-ij]-1,8-naphthyridine-4,9-dione;

(1R)-1-[((3S)-3-{[([1,3]Oxathiolo[5,4-c]pyridin-6-ylmethyl)amino]methyl}-1-pyrrolidinyl)methyl]-1,2-dihydro-4H,9H-imidazo[1,2,3-ij]-1,8-naphthyridine-4,9-dione;

7-{[(1-{[(1R)-3,8-Dioxo-1,2-dihydro-3H,8H-2a,5,8a-triazaacenaphthylen-1-yl]methyl}-4-piperidinyl)amino] methyl}-2,3-dihydro-1,4-benzodioxin-5-carbonitrile;

(1R)-1-[(4-{[(7-Fluoro-2,3-dihydro-1,4-benzodioxin-6-yl) methyl]amino}-1-piperidinyl)methyl]-1,2-dihydro-3H, 8H-2a,5,8a-triazaacenaphthylene-3,8-dione;

(1R)-1-[(4-{[(8-Fluoro-2,3-dihydro-1,4-benzodioxin-6-yl) methyl]amino}-1-piperidinyl)methyl]-1,2-dihydro-3H, 8H-2a,5,8a-triazaacenaphthylene-3,8-dione;

(1R)-1-[(4-{[(2-Oxo-2H-chromen-7-yl)methyl]amino}-1-piperidinyl)methyl]-1,2-dihydro-4H,9H-imidazo[1,2,3-ij]-1,8-naphthyridine-4,9-dione;

(1R)-1-[(4-{[(2-oxo-2H-chromen-7-yl)methyl]amino}-1-piperidinyl)methyl]-1,2-dihydro-4H,9H-imidazo[1,2,3-ij]-1,8-naphthyridine-4,9-dione;

(1R)-1-[(4-{[(2-oxo-2H-chromen-7-yl)methyl]amino}-1-piperidinyl)methyl]-1,2-dihydro-4H,9H-imidazo[1,2,3-ij]-1,8-naphthyridine-4,9-dione;

(1R)-1-({4-[(3,4-dihydro-2H-pyrido[3,2-b][1,4]thiazin-6-ylmethyl)amino]-1-piperidinyl}methyl)-1,2-dihydro-4H, 9H-imidazo[1,2,3-ij]-1,8-naphthyridine-4,9-dione;

or 1-[(4-{[(3-Oxo-3,4-dihydro-2H-1,4-benzothiazin-6-yl) methyl]amino}-1-piperidinyl)methyl]-1,2-dihydro-4H, 9H-imidazo[1,2,3-ij]-1,8-naphthyridine-4,9-dione;

or a free base of a compound of Table 1;
or a pharmaceutically acceptable salt thereof.

In another aspect, the present invention relates to a method for treating *Neisseria gonorrhoeae* infection which comprises administering to a subject in need thereof a pharmaceutical composition which comprises an effective amount of a compound of Formula (I):

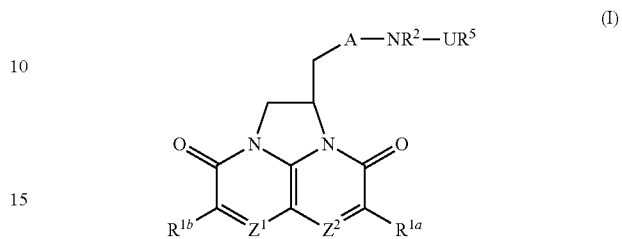

wherein substituents A, $R^{1a}$, $R^{1b}$, $R^2$, $R^5$, $Z^1$ and $Z^2$ are as defined in claim 1; and pharmaceutically acceptable excipient(s).

In another aspect, the present invention relates to a method for treating *Neisseria gonorrhoeae* infection which comprises administering to a subject in need thereof an effective amount of a compound of:

Formula (IIIA):

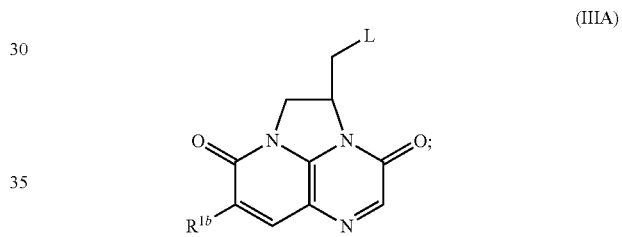

Formula (IIIB):

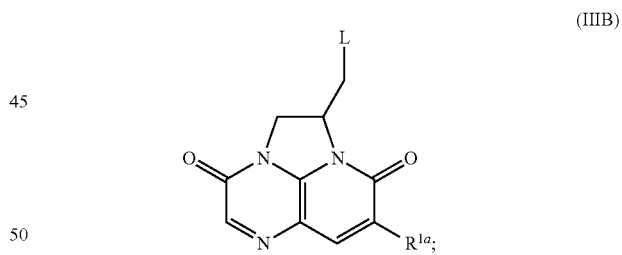

or
Formula (8):

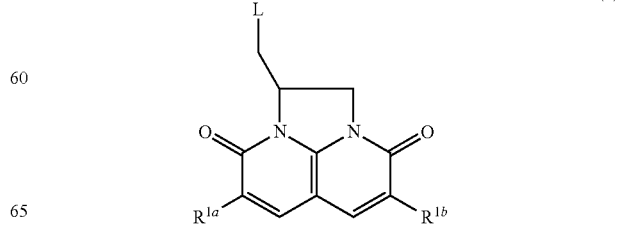

in which L is -A-N($R^{20}$)$R^{2'}$ and $R^{20}$ is hydrogen, $R^{2'}$ is $R^2$ or a group convertible thereto and A, $R^2$, $R^{1a}$ and $R^{1b}$ are as defined in claim 1.

In another aspect, the present invention relates to a method for treating *Neisseria gonorrhoeae* infection which comprises administering to a subject in need thereof a pharmaceutical composition comprising an effective amount of a compound of:

Formula (IIIA):

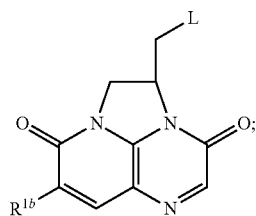

(IIIA)

Formula (IIIB):

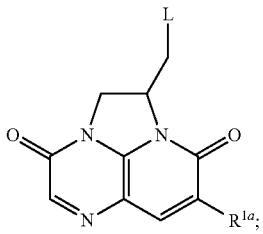

(IIIB)

Formula (8):

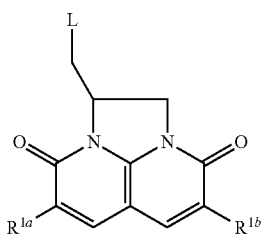

(8)

in which L is -A-N($R^{20}$)$R^{2'}$ and $R^{20}$ is hydrogen, $R^{2'}$ is $R^2$ or a group convertible thereto and A, $R^2$, $R^{1a}$ and $R^{1b}$ are as defined in claim 1; and pharmaceutically acceptable excipient(s).

In another aspect, the present invention relates to a method for treating *Neisseria gonorrhoeae* infection which comprises administering to a subject in need thereof an effective amount of a compound as shown below:

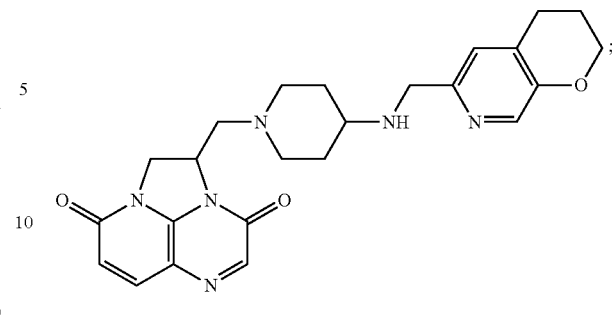

a pharmaceutically acceptable salt thereof.

In another aspect, the present invention relates to a method for treating *Neisseria gonorrhoeae* infection which comprises administering to a subject in need thereof an effective amount of a compound as shown below:

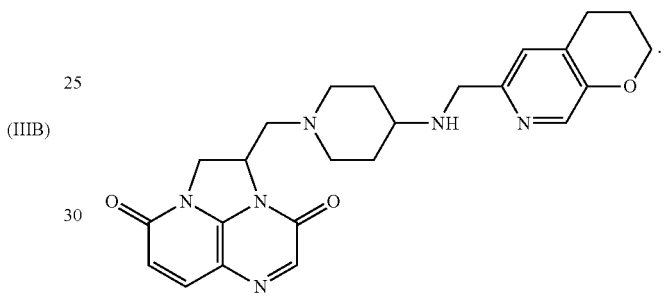

In another aspect, the present invention relates to a method for treating *Neisseria gonorrhoeae* infection which comprises administering to a subject in need thereof a pharmaceutical composition which comprises:

a compound:

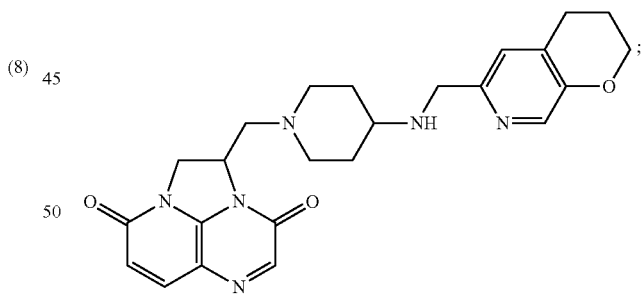

a pharmaceutically acceptable salt thereof; and pharmaceutically acceptable excipient(s).

In another aspect, the present invention relates to a method for treating *Neisseria gonorrhoeae* infection which comprises administering to a subject in need thereof an effective amount of a compound (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione:

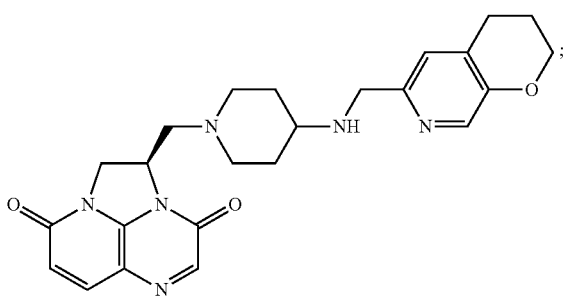 [SMILES: O=c1ccc2ncc(=O)n3c2n1C[C@H]3CN1CCC(NCc2cc3c(cn2)OCCC3)CC1]

a pharmaceutically acceptable salt thereof.

In another aspect, the present invention relates to a method for treating *Neisseria gonorrhoeae* infection which comprises administering to a subject in need thereof an effective amount of a compound (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione:

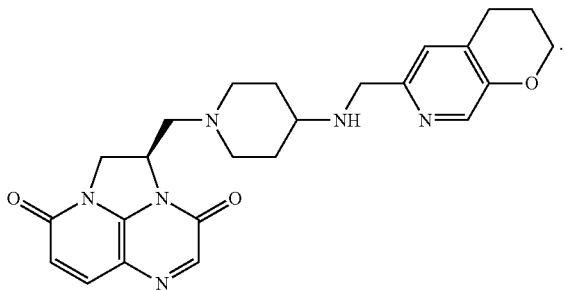 [SMILES: O=c1ccc2ncc(=O)n3c2n1C[C@H]3CN1CCC(NCc2cc3c(cn2)OCCC3)CC1]

In another aspect, the present invention relates to a method for treating *Neisseria gonorrhoeae* infection which comprises administering to a subject in need thereof a pharmaceutical composition which comprises:

a compound (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione:

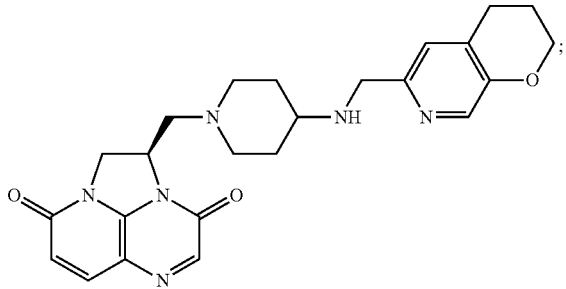 [SMILES: O=c1ccc2ncc(=O)n3c2n1C[C@H]3CN1CCC(NCc2cc3c(cn2)OCCC3)CC1]

or a pharmaceutically acceptable salt thereof; and pharmaceutically acceptable excipient(s).

The Examples set forth below are illustrative of the present invention and are not intended to limit, in any way, the scope of the present invention.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The following examples illustrate the preparation of certain compounds of Formula (I) and the activity of certain compounds of Formula (I) against various bacterial organisms including *Neisseria gonorrhoeae*.

EXAMPLES AND EXPERIMENTAL

General

Abbreviations in the Examples

MS=mass spectrum
ES=Electrospray mass spectroscopy
LCMS/LC-MS=Liquid chromatography mass spectroscopy
HPLC=high performance liquid chromatography
rt=room temperature
Rf=retention factor Certain reagents are also abbreviated herein. TFA refers to trifluoroacetic acid, THF refers to tetrahydrofuran, Pd/C refers to palladium on carbon catalyst, DCM refers to dichloromethane, MeOH refers to methanol, DMF refers to dimethylformamide, EtOAc refers to ethylacetate, DDQ refers to 2,3-dichloro-5,6-dicyano-1,4-benzoquinone, NaBH(OAc)$_3$ refers to sodium triacetoxyborohydride, Pd$_2$(dba)$_3$ refers to tris(dibenzylideneacetone)dipalladium (0).

Proton nuclear magnetic resonance ($^1$H NMR) spectra were recorded at 400 or 250 MHz, and chemical shifts are reported in parts per million (ppm) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, td=triplet of doublets, app=apparent, br=broad. J indicates the NMR coupling constant measured in Hertz. CDCl$_3$ is deuteriochloroform and CD$_3$OD is tetradeuteriomethanol. Mass spectra were obtained using electrospray (ES) ionization techniques. All temperatures are reported in degrees Celsius.

MP-carbonate refers to macroporous triethylammonium methylpolystyrene carbonate (Argonaut Technologies). Amberlyst®A21 is a weakly basic, macroreticular resin with alkyl amine functionality, ®Registered trademark of Rohm & Haas Co.

AD mix alpha is prepared by mixing potassium osmate (K$_2$OsO$_4$.2H$_2$O) (0.52 g), (3a,9R,3'''a,4'''b,9'''R)-9,9'-[1,4-phthalazinediylbis(oxy)]bis[6'-(methyloxy)-10,11-dihydrocinchonan] [(DHQ)$_2$PHAL] (5.52 g), then adding potassium ferricyanide [K$_3$Fe(CN)$_6$] (700 g) and powdered potassium carbonate (294 g). This mixture is stirred in a blender for 30 minutes. This provides approximately 1 kg of AD mix alpha, which is commercially available from Aldrich. See K. Barry Sharpless et al, J. Org. Chem., 1992, 57 (10), 2771. AD mix beta is the corresponding mixture prepared with (9S,9'''S)-9,9'-[1,4-phthalazinediylbis(oxy)]bis[6'-(methyloxy)-10,11-dihydrocinchonan][(DHQD)$_2$PHAL]. Where AD mix alpha/beta is referred to, this is a 1:1 mixture of the alpha and beta mix.

Celite® is a filter aid composed of acid-washed diatomaceous silica, and is a trademark of Manville Corp., Denver, Colo.

SCX Cartridge is an ion exchange column containing strong cation exchange resin (benzene sulfonic acid) supplied by Varian, USA.

Chiralpak IA and Chiralpak AS-H are polysaccharide based chiral HPLC columns (Chiral Technologies Inc.). Chiralpak AS-H column comprise amylose tris [(S)-alpha-methylbenzylcarbamate) coated onto 5 µm silica. Chiralpak IA column comprise silica for preparative column (5 µm particle size, 21 mm ID×250 mm L) immobilized with Amylose tris (3,5-dimethylphenylcarbamate). Chiralpak AD and AD-H columns comprise silica for preparative columns (5 µm particle size AD-H and 10 µm particle size AD, 21 mm ID×250 mm L; 20 µM particle size AD, 101 mm ID×250 mm L) coated with Amylose tris (3,5-dimethylphenylcarbamate) (Chiral Technologies USA). Measured retention times are dependent on the precise conditions of the chromatographic procedures. Where quoted below in the Examples they are indicative of the order of elution. Kromasil 5 micron C-18 column (21 mm×250 mm) comprises octadecylsilane chemically bonded to 5 micron porous silica gel.

As will be understood by the skilled chemist, references to preparations carried out in a similar manner to, or by the general method of, other preparations, may encompass variations in routine parameters such as time, temperature, workup conditions, minor changes in reagent amounts etc.

Reactions involving metal hydrides including lithium hydride, lithium aluminium hydride, di-isobutylaluminium hydride, sodium hydride, sodium borohydride and sodium triacetoxyborohydride are carried out under argon or other inert gas.

Example 1 1-({4-[(2,3-Dihydro[1,4]dioxino[2,3-c]pyridin-7-ylmethyl)amino]-1-piperidinyl}methyl)-1,2-dihydro-3H,8H-2a,5,8a-triazaacenaphthylene-3,8-dione dihydrochloride

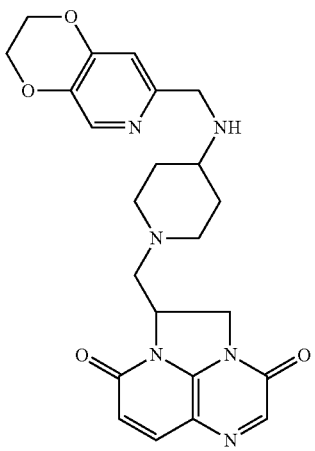 [SMILES: O=c1cnc2ccc(=O)n3c2n1CC3CN1CCC(NCc2cc3c(cn2)OCCO3)CC1]

(a) 6-Chloro-3-nitro-N-2-propen-1-yl-2-pyridinamine

This was prepared by a modification of the method of Schmid, S., et al, Synthesis (2005), (18), 3107-3118. A solution of 2,6-dichloro-3-nitropyridine (8.0 g, 41.45 mmol) in anhydrous dichloromethane (180 ml) was cooled to −15° C., under argon. Triethylamine (6.0 ml, 43 mmol) was added and then allylamine (3.23 ml, 43 mmol) was added in small portions over 3 hours, keeping the temperature at −15° C. The reaction mixture was stirred overnight during which time it warmed to room temperature. The reaction mixture was washed with 0.2M aqueous citric acid (100 ml), saturated aqueous NaHCO$_3$ solution (100 ml), passed through a hydrophobic frit and evaporated to a yellow oil which was purified by chromatography on silica eluting with a 0 to 50% ethyl acetate in hexane giving a yellow solid (7.49 g, 85%).

$C_8H_8ClN_3O_2$ requires 213, MS (ES+) m/z 214, 216 (MH$^+$).

(b) 3-(Bromomethyl)-8-nitro-2,3-dihydroimidazo[1,2-a]pyridin-5(1H)-one

This was prepared by a modification of the method of Schmid, S., et al, Synthesis (2005), (18), 3107-3118. A solution of 6-chloro-3-nitro-N-2-propen-1-yl-2-pyridinamine (20 g, 93.6 mmol) in chlorobenzene (500 ml) was treated with a solution containing bromine (4.75 ml, 92.7 mmol) in chlorobenzene (100 ml), dropwise over 4.5 hours, keeping T<26° C. with cooling when required. The thick suspension was stirred at room temperature for 18 hours and diluted with hexane (200 ml) and then the reaction mixture was then pored into hexane (1000 ml). After 15 minutes the orange precipitate was collected by filtration and washed with hexane (250 ml) to give 26.6 g of an orange solid (3-(bromomethyl)-5-chloro-8-nitro-2,3-dihydroimidazo[1,2-a]pyridin-1-ium bromide). This intermediate was added, over 45 minutes, to a rapidly stirred mixture of saturated aqueous NaHCO$_3$ solution (1000 ml) and ethyl acetate (500 ml). The bright red mixture was stirred for 1 hour, diluted with ethyl acetate (200 ml) and the layers were separated. The aqueous layer was washed with ethyl acetate (200 ml) and the organic extracts were combined, dried (anhydrous sodium sulphate), filtered and evaporated to give the product as a brown solid (18.3 g, contains 40% 6-bromo-3-(bromomethyl)-8-nitro-2,3-dihydroimidazo[1,2-a]pyridin-5(1H)-one).

$C_8H_8BrN_3O_3$ requires 273, MS (ES+) m/z 274, 276 (MH$^+$).

(c) 1,1-Dimethylethyl {1-[(8-nitro-5-oxo-1,2,3,5-tetrahydroimidazo[1,2-a]pyridin-3-yl)methyl]-4-piperidinyl}carbamate A suspension of a 3:2 mixture of 3-(bromomethyl)-8-nitro-2,3-dihydroimidazo[1,2-a]pyridin-5(1H)-one and 6-bromo-3-(bromomethyl)-8-nitro-2,3-dihydroimidazo[1,2-a]pyridin-5(1H)-one (18.2 g) was treated with 1,1-dimethylethyl 4-piperidinylcarbamate (26.6 g, 132.8 mmole) in acetonitrile (900 ml) then pyridine (10.7 ml, 132 mmol). The mixture was heated at 60° C. under argon for 17 hours and then heated at 70° C. for 2 hours, cooled and evaporated to about half the volume. The thick yellow precipitate was removed by filtration and washed well with diethyl ether. The filtrate was evaporated to dryness and the residue partitioned between chloroform (500 ml) and water (200 ml). The undissolved material was removed by filtration and washed with chloroform (100 ml). The layers in the filtrate were separated and the aqueous layer was washed with chloroform (200 ml). The combined organic extracts were passed through a hydrophobic frit and evaporated to a dark yellow gum which was chromatographed eluting with 0 to 100% ethyl acetate in hexane then 0 to 30% methanol in ethyl acetate to give a yellow solid (10.98 g).

$C_{18}H_{27}N_5O_5$ requires 393, MS (ES+) m/z 394 (MH$^+$).

(d) 1,1-Dimethylethyl {1-[(3,8-dioxo-1,2,5a,8b-tetrahydro-3H,8H-2a,5,8a-triazaacenaphthylen-1-yl)methyl]-4-piperidinyl}carbonate A suspension of 1,1-dimethylethyl {1-[(8-nitro-5-oxo-1,2,3,5-tetrahydroimidazo[1,2-a]pyridin-3-yl)methyl]-4-piperidinyl}carbamate (2.0 g, 5.08 mmol) and anhydrous potassium carbonate (700 mg, 5.06 mmol) in absolute alcohol (150 ml) was hydrogenated at atmospheric pressure in the presence of 10% Pd on C (1 g) for 4 hours. The reaction was filtered through Keiselguhr, washed through with ethanol (100 ml) and the dark purple mixture was reacted immediately by treating with anhydrous potassium carbonate (1.4 g, 10 mmol) and ethyl bromoacetate (550 ul, 4.95 mmol) and stirred at room temperature for 20 hours and then heated at 60° C. for 30 minutes. After 45 minutes a further 0.25 ml of ethyl bromacetate was added and heated at 60° C. for 1.5 hours. 0.25 ml of ethyl bromacetate was added and the reaction was again heated at 60° C. for 1. hour. The reaction was filtered through Keiselguhr and evaporated to dryness. The mixture was azeotroped with chloroform and then chromatographed eluting with 0 to 100% ethyl acetate in hexane and then with 0 to 20% methanol in ethyl acetate. A second purification eluting with 0 to 50% methanol in ethyl acetate gave a dark gum (37 mg, 1.6%).

$C_{20}H_{27}N_5O_2$ requires 401, MS (ES+) m/z 402 (MH$^+$).

(e) 1-[(4-Amino-1-piperidinyl)methyl]-1,2,5a,8b-tetrahydro-3H,8H-2a,5,8a-triazaacenaphthylene-3,8-dione A solution of 1,1-dimethylethyl {1-[(3,8-dioxo-1,2,5a,8b-tetrahydro-3H,8H-2a,5,8a-triazaacenaphthylen-1-yl)methyl]-4-piperidinyl}carbamate (37 mg, 0.092 mmol) in anhydrous dichloromethane (2 ml) was treated with TFA (1 ml) and stirred at room temperature for 1 hour, evaporated to dryness, mixed with anhydrous dichloromethane and evaporated to a dark gum. This gum was dissolved in 1:1 dichloromethane:methanol (10 ml) and treated with MP-carbonate resin (600 mg) and stirred for 1.5 hours. The reaction was filtered and the resin was washed with 1:1 dichloromethane:methanol (30 ml) and the filtrate was evaporated to dryness. Purification on a 5 g SCX column eluting with a methanol to 2N methanolic ammonia gradient gave the product as a gum. Further evaporation from diethyl ether gave the product as a brown solid (22.8 mg, 82%).

$C_{15}H_{19}N_5O_2$ requires 301, MS (ES+) m/z 302 (MH$^+$).

(f) Title Compound

A solution of 1-[(4-amino-1-piperidinyl)methyl]-1,2,5a,8b-tetrahydro-3H,8H-2a,5,8a-triazaacenaphthylene-3,8-dione (22.8 mg, 0.0757 mmol) in anhydrous dichloromethane (3 ml) and anhydrous methanol (0.6 ml) was treated with 2,3-dihydro[1,4]dioxino[2,3-c]pyridine-7-carbaldehyde (12.5 mg, 0.076 mmol) (for a synthesis see WO2004058144 Example 2(c) or WO03/087098 Example 19(d)) and stirred, under argon, for 15 minutes and then treated with sodium triacetoxyborohydride (48 mg, 0.226 mmol) and stirred at room temperature for 17 hours. The reaction was then treated with a further portion of 2,3-dihydro[1,4]dioxino[2,3-c]pyridine-7-carbaldehyde (2 mg) and sodium triacetoxyborohydride (10 mg) and the mixture was stirred for 4 hours, treated with saturated aqueous NaHCO$_3$ solution (1 ml) and stirred for 10 minutes. The layers were separated and the aqueous layer was washed with 9:1 dichloromethane:methanol (2×10 ml). The combined organic extracts were passed through a hydrophobic frit and evaporated to a brown gum which was chromatographed eluting with 0 to 30% methanol in dichloromethane to give the free base of the title compound as a yellow gum (20.6 mg, 60%).

$C_{23}H_{26}N_6O_4$ requires 450, MS (ES+) m/z 451 (MH$^+$).

$^1$H NMR (250 MHz) δ(CDCl$_3$) 1.38-1.54 (2H, m), 1.83-1.93 (2H, m), 2.19-2.36 (2H, m), 2.54-2.73 (3H, m), 2.93-2.98 (1H, m), 3.09-3.15 (1H, m), 3.85 (2H, s), 4.26-4.61 (6H, m), 4.96-5.05 (1H, m), 6.33 (1H, d), 6.82 (1H, s), 7.76 (1H, d), 7.87 (1H, s) and 8.10 (1H, s)

The free base of the title compound was dissolved in anhydrous dichloromethane (2 ml) and anhydrous methanol (0.5 ml) and treated with 1M HCl in diethyl ether (0.5 ml). Diethyl ether was added (5 ml) and the suspension was cooled. After centrifuging the solvent was removed and the solid was dried to give the title compound as a brown solid (23.5 mg).

$C_{23}H_{26}N_6O_4$ requires 450, MS (ES+) m/z 451 (MH$^+$).

Example 2 1-({4-[([1,3]Oxathiolo[5,4-c]pyridin-6-ylmethyl)amino]-1-piperidinyl}methyl)-1,2-dihydro-4H,9H-imidazo[1,2,3-ij]-1,8-naphthyridine-4,9-dione hydrochloride

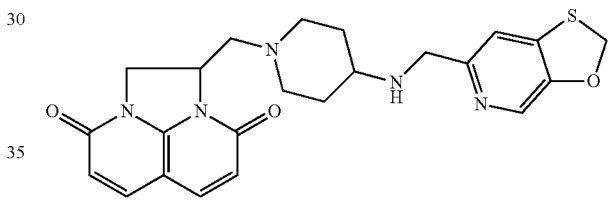

(a) N-(6-Chloro-2-pyridinyl)-2,2-dimethylpropanamide

A solution of 6-chloro-2-pyridinamine (13.776 g, 107 mmol) in toluene (100 ml) and triethylamine (16.28 ml, 118 mmol) at 50° C. under argon was treated with 2,2-dimethylpropanoyl chloride (13.81 ml, 112 mmol). The reaction was then stirred at 50° C. for 4 h and then at rt for 18 h. 2M HCl (200 ml) was then added and the mixture was extracted with diethyl ether (3×500 ml). The organic extracts were dried (MgSO$_4$), filtered and evaporated to give the product as a brown solid (21.005 g, 92%).

MS (ES+) m/z 213/215 (MH$^+$).

(b) N-(3-Bromo-6-chloro-2-pyridinyl)-2,2-dimethylpropanamide

A solution of N-(6-chloro-2-pyridinyl)-2,2-dimethylpropanamide (4.83 g, 22.7 mmol) in THF (40 ml) at −78° C. under argon was treated with n-butyl lithium (20 ml, 2.5M in Hexanes, 50 mmol) over 10 min and then allowed warm to 0° C., stirred at 0° C. for 3 h and then recooled to −78° C. The reaction was then treated dropwise with dibromoethane (2.057 ml, 23.9 mmol) and the reaction was allowed warm to rt and stirred at rt for 0.5 h. The reaction was then treated with water (5 ml), stirred at rt for 5 min, treated with more water (500 ml) and extracted with diethyl ether (3×500 ml). The organic extracts were dried (MgSO$_4$), filtered, evaporated and the residue chromatographed (0-25% ethyl acetate:Hexane) to give the product as a yellow solid (3.489 g, 53%).

MS (ES+) m/z 291/293/295 (MH+).

(c) N-(3-Bromo-6-chloro-2-pyridinyl)-2,2-dimethyl-N-2-propen-1-ylpropanamide A solution of N-(3-bromo-6-chloro-2-pyridinyl)-2,2-dimethylpropanamide (2.305 g, 7.907 mmol) in DMF (40 ml) at 0° C. under argon was treated with sodium hydride (0.696 g, 17.395 mmol) and then allowed warm to rt over 0.25 h, stirred at rt for 0.25 h and then treated with allyl iodide (1.61 ml, 17.395 mmol) and stirred at rt for 1 h. The reaction was then treated with water (10 ml), concentrated to approximately 5 ml, treated with more water (200 ml) and extracted with DCM (3×200 ml). The organic extracts were dried (MgSO$_4$), filtered, evaporated and the residue chromatographed (0-20% ethyl acetate:Hexane) to give the product as a yellow oil which solidified to an off white solid (5.324 g, 67%).

MS (ES+) m/z 331/333/335 (MH+).

(d) N-[3-Bromo-6-(methyloxy)-2-pyridinyl]-2,2-dimethyl-N-2-propen-1-ylpropanamide A solution of N-(3-bromo-6-chloro-2-pyridinyl)-2,2-dimethyl-N-2-propen-1-ylpropanamide (12.388 g, 37.370 mmol) in methanol (100 ml) at rt under argon was treated with sodium methoxide solution (25% w/v in methanol, 17.76 g, 82.212 mmol) and then heated at reflux for 42 h. The reaction was then cooled, treated with water (500 ml), and extracted with diethyl ether (3×200 ml). The organic extracts were dried (MgSO$_4$), and evaporated to give the product (10.918 g, 89%).

MS (ES+) m/z 327/329 (MH+).

(e) N-[3-Bromo-6-(methyloxy)-2-pyridinyl]-N-(2,3-dihydroxypropyl)-2,2-dimethylpropanamide A solution of N-[3-bromo-6-(methyloxy)-2-pyridinyl]-2,2-dimethyl-N-2-propen-1-ylpropanamide (1.246 g, 3.81 mmol) in tert-butanol (40 ml) at rt under argon was treated with water (40 ml) and then with AD-mix a (2.86 g) and AD-mix 3 (2.86 g) and stirred at rt for 18 h. The reaction was then treated with saturated aqueous sodium sulfite (40 ml), stirred for 10 min, extracted with 20% methanol/DCM (3×100 ml). The organic extracts were dried (MgSO$_4$), and evaporated to give the crude product (1.728 g, 126%) containing residual tert-butanol.

MS (ES+) m/z 361/363 (MH+).

(f) N-[3-Bromo-6-(methyloxy)-2-pyridinyl]-2,2-dimethyl-N-[(2-oxo-1,3-dioxolan-4-yl)methyl]propanamide A solution of N-[3-bromo-6-(methyloxy)-2-pyridinyl]-N-(2,3-dihydroxypropyl)-2,2-dimethylpropanamide (7.628 g, 21.130 mmol) in DCM (100 ml) and pyridine (3.407 ml, 42.26 mmol) at −78° C. under argon was treated with a solution of triphosgene (6.27 g, 21.130 mmol) in DCM (20 ml) over 5 min and the reaction was then allowed warm to rt and stirred at rt for 30 min. The reaction was then carefully treated with saturated sodium bicarbonate solution (200 ml), extracted with DCM (3×200 ml). The organic extracts were dried (MgSO$_4$), and evaporated and chromatographed (0-50% ethyl acetate:Hexane) to give the product as a white solid (5.722 g, 70%).

MS (ES+) m/z 387/389 (MH+).

(g) Butyl (2E)-3-[2-{(2,2-dimethylpropanoyl)[(2-oxo-1,3-dioxolan-4-yl)methyl]amino}-6-(methyloxy)-3-pyridinyl]-2-propenoate A mixture of N-[3-bromo-6-(methyloxy)-2-pyridinyl]-2,2-dimethyl-N-[(2-oxo-1,3-dioxolan-4-yl)methyl]propanamide (5.722 g, 14.722 mmol), Pd(PtBu$_3$)$_2$(151 mg, 0.296 mmol), Pd$_2$(dba)$_3$ (135 mg, 0.149 mmol), in 1,4-dioxane (40 ml) was treated with N,N'-dicyclohexylmethylamine (3.48 ml, 16.265 mmol) and n-butyl acrylate (2.54 ml, 17.743 mmol) and the mixture was then heated at 80° C. for 1 h. The reaction was then cooled, treated with water (200 ml), extracted with DCM (3×200 ml). The organic extracts were dried (MgSO$_4$), and evaporated and chromatographed (0-50% ethyl acetate:Hexane) to give the product as a yellow oil (6.156 g, 96%).

MS (ES+) m/z 435 (MH+).

(h) Butyl 3-[2-{(2,2-dimethylpropanoyl) [(2-oxo-1,3-dioxolan-4-yl)methyl]amino}-6-(methyloxy)-3-pyridinyl]propanoate A solution of butyl (2E)-3-[2-{(2,2-dimethylpropanoyl) [(2-oxo-1,3-dioxolan-4-yl)methyl]amino}-6-(methyloxy)-3-pyridinyl]-2-propenoate (6.156 g, 14.184 mmol) in ethanol (200 ml) was treated with palladium on carbon (10% paste, 1.23 g) and the mixture was then stirred at rt under 1 atmosphere of hydrogen for 18 h. The reaction mixture was then filtered through a thin pad of Celite, eluting with more ethanol (200 ml). The organic filtrate was then evaporated to give the product as a yellow oil (6.065 g, 98%).

MS (ES+) m/z 437 (MH+).

(i) 1-(2,3-Dihydroxypropyl)-7-(methyloxy)-3,4-dihydro-1,8-naphthyridin-2(1H)-one A solution of butyl 3-[2-{(2,2-dimethylpropanoyl) [(2-oxo-1,3-dioxolan-4-yl)methyl]amino}-6-(methyloxy)-3-pyridinyl]propanoate (6.065 g, 13.911 mmol) in methanol (100 ml) was treated with concentrated aqueous HCl (12M, 50 ml) and then heated at reflux for 48 h. The reaction mixture was then concentrated to approximately 50 ml, neutralised with potassium carbonate and extracted with 20% methanol/DCM (3×100 ml). The organic extracts were dried (MgSO$_4$), and evaporated to give the crude product as a yellow oil (2.325 g, 66%).

MS (ES+) m/z 279 (MH+).

(j) 7-(Methyloxy)-1-(2-oxiranylmethyl)-3,4-dihydro-1,8-naphthyridin-2(1H)-one A solution of 1-(2,3-dihydroxypropyl)-7-(methyloxy)-3,4-dihydro-1,8-naphthyridin-2(1H)-one (2.325 g, 9.226 mmol) in DCM (40 ml) and triethylamine (1.915 ml, 13.839 mmol) at 0° C. under argon was treated with methanesulfonyl chloride (0.714 ml, 9.226 mmol) and stirred at 0° C. for 0.5 h. The reaction mixture was then treated with water (100 ml), extracted with DCM (3×100 ml). The organic extracts were dried (MgSO$_4$), and evaporated. The residue was then dissolved in methanol (50 ml) and treated with potassium carbonate (6.366 g, 46.130 mmol) and stirred at rt for 15 min. The reaction mixture was then treated with water (100 ml), extracted with DCM (3×200 ml). The organic extracts were dried (MgSO$_4$), evaporated and chromatographed (0-100% ethyl acetate:Hexane) to give the product as a yellow oil (428 mg, 20%).

MS (ES+) m/z 235 (MH$^+$).

(k) 1,1-Dimethylethyl (1-{2-hydroxy-3-[7-(methyloxy)-2-oxo-3,4-dihydro-1,8-naphthyridin-1 (2H)-yl]propyl}-4-piperidinyl)carbamate A solution of 7-(methyloxy)-1-(2-oxiranylmethyl)-3,4-dihydro-1,8-naphthyridin-2(1H)-one (428 mg, 1.829 mmol) and 1,1-dimethylethyl 4-piperidinylcarbamate (366 mg, 1.829 mmol) in DMF (2 ml) under argon was heated at 120° C. for 1 h. The mixture was then evaporated and chromatographed (0-10% methanol/DCM) to give the product as a yellow oil (301 mg, 38%).

MS (ES+) m/z 435 (MH$^+$).

(l) 1,1-Dimethylethyl {1-[(4,9-dioxo-1,2,8,9-tetrahydro-4H,7H-imidazo[1,2,3-ij]-1,8-naphthyridin-2-yl)methyl]-4-piperidinyl}carbamate A solution of 1,1-dimethylethyl (1-{2-hydroxy-3-[7-(methyloxy)-2-oxo-3,4-dihydro-1,8-naphthyridin-1(2H)-yl]propyl}-4-piperidinyl)carbamate (301 mg, 0.694 mmol) in chloroform (10 ml) and triethylamine (0.24 ml, 1.735 mmol) at rt under argon was treated with methanesulfonic anhydride (242 mg, 1.388 mmol) and heated at reflux for 2 h. The reaction mixture was then evaporated and dissolved in acetonitrile (10 ml), treated with sodium iodide (520 mg, 3.47 mmol) and heated at 80° C. for 0.25 h. The mixture was then cooled, evaporated was then treated with water (200 ml), extracted with 20% methanol/DCM (3×200 ml). The organic extracts were dried (MgSO$_4$), evaporated and chromatographed (0-10% methanol/DCM) to give the product as an orange oil (194 mg, 70%).

MS (ES+) m/z 403 (MH$^+$).

(m) 1,1-Dimethylethyl {1-[(4,9-dioxo-1,2-dihydro-4H,9H-imidazo[1,2,3-ij]-1,8-naphthyridin-1-yl)methyl]-4-piperidinyl}carbamate A solution of 1,1-dimethylethyl {1-[(4,9-dioxo-1,2,8,9-tetrahydro-4H,7H-imidazo[1,2,3-ij]-1,8-naphthyridin-1-yl)methyl]-4-piperidinyl}carbamate (194 mg, 0.0.483 mmol) (301 mg, 0.694 mmol) in 1,4-dioxane (5 ml) was treated with DDQ (164 mg, 0.724 mmol) and stirred at 60° C. for 24 h. Further DDQ (164 mg, 0.724 mmol) was added and the reaction was stirred for a further 2 h. The reaction was then treated with 5% aqueous potassium carbonate (100 ml), extracted with 20% methanol/DCM (3×200 ml). The organic extracts were dried (MgSO$_4$) and evaporated to give the product as an orange oil (159 mg, 82%).

MS (ES+) m/z 401 (MH$^+$).

(n) 1-[(4-Amino-1-piperidinyl)methyl]-1,2-dihydro-4H,9H-imidazo[1,2,3-ij]-1,8-naphthyridine-4,9-dione dihydrochloride A solution of 1,1-dimethylethyl {1-[(4,9-dioxo-1,2-dihydro-4H,9H-imidazo[1,2,3-ij]-1,8-naphthyridin-1-yl)methyl]-4-piperidinyl}carbamate (159 mg, 0.398 mmol) in chloroform (2 ml) and methanol (2 ml) under argon at rt was treated with 4M HCl in 1,4-dioxane (2 ml) and stirred at rt for 0.5 h. The reaction was then dried and evaporated to give the product as a yellow solid (138 mg, 93%).

MS (ES+) m/z 301 (MH$^+$).

(o) Title Compound

A mixture of 1-[(4-amino-1-piperidinyl)methyl]-1,2-dihydro-4H,9H-imidazo[1,2,3-ij]-1,8-naphthyridine-4,9-dione dihydrochloride (49 mg, 0.131 mmol) in DCM (2 ml) and methanol (0.1 ml) under argon at rt was treated with triethylamine (581, 0.419 mmol) and stirred at rt for 0.25 h before addition of [1,3]oxathiolo[5,4-c]pyridine-6-carbaldehyde (for a synthesis see WO2004058144 Example 61) (22 mg, 0.131 mmol). The mixture was then stirred at rt for 1 h before addition of NaBH(OAc)$_3$ (56 mg, 0.262 mmol).

The reaction was stirred at rt for a further 0.5 h before addition of saturated aqueous sodium bicarbonate (20 ml). The mixture was extracted with 20% methanol/DCM (3×100 ml). The organic extracts were dried (MgSO$_4$), evaporated and chromatographed (0-20% methanol/DCM) to give the product as a clear oil (28 mg, 47%).

MS (ES+) m/z 452 (MH$^+$).

δH (CDCl$_3$, 400 MHz) 1.38-1.48 (2H, m), 1.78-1.95 (2H, m), 2.15-2.37 (2H, m) 2.45-2.60 (1H, m), 2.61-2.72 (2H, m), 2.92-3.02 (1H, m), 3.05-3.12 (1H, m), 3.83 (2H, s), 4.32-4.42 (1H, m), 4.52-4.61 (1H, m), 4.96-5.05 (1H, m), 5.74 (2H, s), 6.22-6.32 (2H, m), 7.20 (1H, s), 7.45-7.52 (2H, m), 7.99 (1H, s).

The free base of the title compound in methanol and chloroform was converted to the hydrochloride salt by adding an equivalent of 4M hydrogen chloride in 1,4-dioxane, followed by evaporation to dryness.

Example 3 1-({4-[(2,3-Dihydro[1,4]dioxino[2,3-c]pyridin-7-ylmethyl)amino]-1-piperidinyl}methyl)-1,2-dihydro-4H,9H-imidazo[1,2,3-ij]-1,8-naphthyridine-4,9-dione hydrochloride

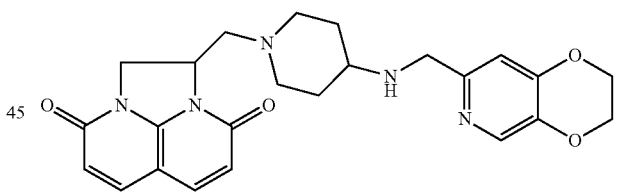

Method A

A mixture of 1-[(4-amino-1-piperidinyl)methyl]-1,2-dihydro-4H,9H-imidazo[1,2,3-ij]-1,8-naphthyridine-4,9-dione dihydrochloride (36 mg, 0.0965 mmol) (for a preparation see Example 2(n) in DCM (2 ml) and methanol (0.1 ml) under argon at rt was treated with triethylamine (43 µl, 0.309 mmol) and stirred at rt for 0.25 h before addition of 2,3-dihydro[1,4]dioxino[2,3-c]pyridine-7-carboxaldehyde (for a synthesis see WO2004058144 Example 2(c) or WO03/087098 Example 19(d))) (16 mg, 0.0965 mmol).

The mixture was then stirred at rt for 1 h before addition of NaBH(OAc)$_3$ (41 mg, 0.193 mmol). The reaction was stirred at rt for a further 0.5 h before addition of saturated aqueous sodium bicarbonate (20 ml). The mixture was extracted with 20% methanol/DCM (3×100 ml). The organic extracts were dried (MgSO$_4$), evaporated and chromatographed (0-20% methanol/DCM) to give the free base of the title compound as a clear oil (24 mg, 55%).

MS (ES+) m/z 450 (MH$^+$).

δH (CDCl$_3$, 400 MHz) 1.30-1.50 (2H, m), 1.80-1.92 (2H, m), 2.19-2.35 (2H, m) 2.49-2.72 (3H, m), 2.92-3.02 (1H, m), 3.07-3.13 (1H, m), 3.81 (2H, s), 4.22-4.51 (5H, m) 4.52-4.60 (1H, m), 4.96-5.04 (1H, m), 6.22-6.32 (2H, m), 6.81 (1H, s), 7.45-7.53 (2H, m), 8.04 (1H, s).

The free base of the title compound in methanol and chloroform was converted to the hydrochloride salt by adding an equivalent of 4M hydrogen chloride in 1,4-dioxane, followed by evaporation to dryness.

Method B (a) 2-Bromo-3-[(phenylmethyl)oxy]propanoic acid

Racemic O-(phenylmethyl)serine (5 g, 25.6 mmol) and potassium bromide (10.7 g, 89.6 mmol) were dissolved in ice-cooled H$_2$SO$_4$ (2.5N) and treated with an solution of sodium nitrite (2.65 g) in water (30 ml) over 50 minutes (keeping the reaction temperature <4° C.). The reaction was then stirred at 0° C. for 45 minutes and then at rt for 1 h, extracted with ethyl acetate (3×100 ml). The combined organic extracts were washed with water, brine, dried (MgSO$_4$), filtered and evaporated to give the product as a yellow oil (6 g, 90%).

MS (ES+) m/z 259/261 (MH$^+$).

(b) Methyl 2-bromo-3-[(phenylmethyl)oxy]propanoate

A solution of 2-bromo-3-[(phenylmethyl)oxy]propanoic acid (6 g, 23.2 mmol) in methanol (40 ml) at rt under argon was treated with thionyl chloride (1.7 ml, 23.2 mmol) and the reaction was then stirred at rt for 3 h and then evaporated to give product as a yellow oil (6.3 g, 99%).

MS (ES+) m/z 273/275 (MH$^+$).

(c) Methyl 2-[4-((2,3-dihydro[1,4]dioxino[2,3-c]pyridin-7-ylmethyl){[(1,1-dimethylethyl)oxy]carbonyl}amino)-1-piperidinyl]-3-[(phenylmethyl)oxy]propanoate A mixture of 1,1-dimethylethyl (2,3-dihydro[1,4]dioxino[2,3-c]pyridin-7-ylmethyl)4-piperidinylcarbamate (1.087 g, 3.11 mmol) (for a synthesis see WO2004/058144 Example 99(h)), methyl 2-bromo-3-[(phenylmethyl)oxy]propanoate (1.0 g, 3.66 mmol) and potassium carbonate (0.860 g, 6.22 mmol) in DMF (50 ml) was heated to 80° C. and stirred under argon for 2.5 h. The solvents were removed under reduced pressure and the residue treated with saturated aqueous sodium bicarbonate. The aqueous was extracted with DCM (5×100 ml) dried MgSO$_4$, filtered and concentrated under reduced pressure. The crude product was chromatographed, eluting with 0-100% EtOAc/40-60 petroleum ether. Appropriate fractions were combined and evaporated under reduced pressure. The residue was then dissolved in DCM (50 ml) and washed with water (20 ml). The organic layer was separated, dried MgSO$_4$ and evaporated under reduced pressure to afford product (618 mg, 35% yield).

MS (ES+) m/z 542 (MH$^+$).

(d) 1,1-Dimethylethyl (2,3-dihydro[1,4]dioxino[2,3-c]pyridin-7-ylmethyl)[1-(2-hydroxy-1-{[(phenylmethyl)oxy]methyl}ethyl)-4-piperidinyl]carbamate A solution of methyl 2-[4-((2,3-dihydro[1,4]dioxino[2,3-c]pyridin-7-ylmethyl) {[(1,1-dimethylethyl)oxy]carbonyl}amino)-1-piperidinyl]-3-[(phenylmethyl)oxy]propanoate (618 mg, 1.141 mmol) in dry THF (8 ml) at −78° C. under Ar was added LiAlH$_4$ (1.312 ml, 1.312 mmol) dropwise. The reaction mixture was allowed to warm to ~−10° C. over 2 h. The mixture was then stirred at 0° C. for 2 h before addition of water (0.1 ml), then sodium hydroxide (0.18 ml, 0.360 mmol) and then water (0.2 ml). The mixture was then stirred for a further 2 h at rt. The resulting mixture was filtered and washed with THF (100 ml). The combined filtrate and washings were evaporated under reduced pressure to afford the product (0.519 g, 89% yield).

MS (ES+) m/z 514 (MH$^+$).

(e) 1,1-Dimethylethyl [1-(2-chloro-1-{[(phenylmethyl)oxy]methyl}ethyl)-4-piperidinyl](2,3-dihydro[1,4]dioxino[2,3-c]pyridin-7-ylmethyl)carbamate A solution of 1,1-dimethylethyl (2,3-dihydro[1,4]dioxino [2,3-c]pyridin-7-ylmethyl)[1-(2-hydroxy-1-{[(phenylmethyl)oxy]methyl}ethyl)-4-piperidinyl]carbamate (150 mg, 0.292 mmol) and triethylamine (0.049 ml, 0.350 mmol), in DCM (5 ml) at 0° C. was treated with methanesulfonyl chloride (0.025 ml, 0.321 mmol). The solution was allowed to warm to room temperature and stirred at this temperature for 1 h. A further 0.2 eq of triethylamine and 0.4 eq of methanesulfonyl chloride was added and the reaction stirred for 30 mins. The reaction mixture was diluted with DCM (20 ml) and treated with water (2 ml). The aqueous layer was extracted again with DCM (50 ml). The organic layers were combined and dried MgSO$_4$, filtered and evaporated under reduced pressure to the crude product (101 mg, 65%), which was used without further purification.

MS (ES+) m/z 532/534 (MH$^+$).

(f) 1,1-Dimethylethyl (2,3-dihydro[1,4]dioxino[2,3-c]pyridin-7-ylmethyl)[1-(2-[7-(methyloxy)-2-oxo-3,4-dihydro-1,8-naphthyridin-1(2H)-yl]-1-{[(phenylmethyl)oxy]methyl}ethyl)-4-piperidinyl]carbamate Method 1: A solution of 1,1-dimethylethyl [1-(2-chloro-1-{[(phenylmethyl)oxy]methyl}ethyl)-4-piperidinyl](2,3-dihydro[1,4]dioxino[2,3-c]pyridin-7-ylmethyl)carbamate (101 mg, 0.190 mmol) in DMF (10 ml) was added dropwise to a solution of the sodium salt of 7-(methyloxy)-3,4-dihydro-1,8-naphthyridin-2(1H)-one (33.8 mg, 0.190 mmol) in DMF) (10 ml) (prepared from addition of sodium hydride (9.11 mg, 0.228 mmol) to 7-(methyloxy)-3,4-dihydro-1,8-naphthyridin-2(1H)-one (33.8 mg, 0.190 mmol) (for a preparation see Example 5(e)) in DMF (10 ml)). The solution was stirred at room temperature overnight under Ar. The reaction was then heated to 60° C. and stirred at this temperature under Ar for 1 h. The reaction was cooled to rt and a further eq of sodium hydride (9.11 mg, 0.228 mmol) was added with stirring under argon. The reaction was stirred at rt for 72 h.

Method 2: A solution of 1,1-dimethylethyl [1-(2-chloro-1-{[(phenylmethyl)oxy]methyl}ethyl)-4-piperidinyl](2,3-dihydro[1,4]dioxino[2,3-c]pyridin-7-ylmethyl)carbamate (343 mg, 0.645 mmol) in DMF (10 ml) was added dropwise to a solution of the sodium salt of 7-(methyloxy)-3,4-dihydro-1,8-naphthyridin-2(1H)-one (138 mg, 0.774 mmol) (prepared from the addition of sodium hydride (60%, 38.7 mg, 0.967 mmol) to 7-(methyloxy)-3,4-dihydro-1,8-naphthyridin-2(1H)-one (138 mg, 0.774 mmol) (for a preparation see Example 5(e)) in DMF (10 ml)). The solution was stirred at room temperature overnight under argon.

The reaction mixtures from Method 1 and Method 2 were combined and the DMF was removed under reduced pressure. The residue was treated with saturated aqueous sodium bicarbonate solution (10 ml) and water (20 ml) and extracted with DCM (3×100 ml). The combined organic layers were dried (MgSO$_4$), filtered and removed under reduced pressure. The crude product was chromatographed, eluting with 0-100% EtOAc/hexane. Appropriate fractions were combined to give two batches of product (batch1: 167 mg, 38%) and (batch2: lower purity, 78 mg, 18%).

MS (ES+) m/z 674 (MH$^+$).

(g) 1,1-Dimethylethyl (2,3-dihydro[1,4]dioxino[2,3-c]pyridin-7-ylmethyl)[1-(2-hydroxy-1-{[7-(methyloxy)-2-oxo-3,4-dihydro-1,8-naphthyridin-1 (2H)-yl]methyl}ethyl)-4-piperidinyl]carbamate A solution of 1,1-dimethylethyl (2,3-dihydro[1,4]dioxino[2,3-c]pyridin-7-ylmethyl) [1-(2-[7-(methyloxy)-2-oxo-3,4-dihydro-1,8-naphthyridin-1(2H)-yl]-1-{[(phenylmethyl)oxy]methyl}ethyl)-4-piperidinyl]carbamate (167 mg, 0.248 mmol) in ethanol (20 ml) was hydrogenated at 1 atmosphere hydrogen pressure for approximately 9 days. The reaction was filtered through Celite and washed with ethanol. The combined filtrate and washings were evaporated under reduced pressure to afford the product (162 mg, 91%).

MS (ES+) m/z 584 (MH$^+$).

(h) 1,1-Dimethylethyl (2,3-dihydro[1,4]dioxino[2,3-c]pyridin-7-ylmethyl){1-[(4,9-dioxo-1,2,8,9-tetrahydro-4H,7H-imidazo[1,2,3-ij]-1,8-naphthyridin-1-yl)methyl]-4-piperidinyl}carbamate A solution of 1,1-dimethylethyl (2,3-dihydro[1,4]dioxino[2,3-c]pyridin-7-ylmethyl)[1-(2-hydroxy-1-{[7-(methyloxy)-2-oxo-3,4-dihydro-1,8-naphthyridin-1(2H)-yl]methyl}ethyl)-4-piperidinyl]carbamate (162 mg, 0.278 mmol) in DCM (10 ml) under argon was cooled to 0° C. and treated with triethylamine (0.046 ml, 0.333 mmol) and methanesulfonyl chloride (0.026 ml, 0.333 mmol). The reaction was allowed to warm to rt and stirred at this temperature for 1 h. A further 1.2 eq of triethylamine (0.046 ml, 0.333 mmol) and methanesulfonyl chloride (0.026 ml, 0.333 mmol) were added and the solution stirred at rt overnight. A further 1.2 eq of triethylamine (0.046 ml, 0.333 mmol) and methanesulfonyl chloride (0.026 ml, 0.333 mmol) were added and the solution heated to 50° C. for 6 h. The solution was cooled to rt, saturated aqueous NaHCO$_3$ (10 ml) was added and the aqueous extracted with 20% MeOH/DCM (3×100 ml). The organic phases were combined, dried MgSO$_4$, filtered and concentrated. The crude product was then chromatographed, eluting with 0-15% MeOH/DCM. Appropriate fractions were combined and evaporated under reduced pressure to afford the product (80 mg, 48%).

MS (ES+) m/z 552 (MH$^+$).

(i) 1,1-Dimethylethyl (2,3-dihydro[1,4]dioxino[2,3-c]pyridin-7-ylmethyl){1-[(4,9-dioxo-1,2-dihydro-4H,9H-imidazo[1,2,3-ij]-1,8-naphthyridin-1-yl)methyl]-4-piperidinyl}carbamate A solution of 1,1-dimethylethyl (2,3-dihydro[1,4]dioxino[2,3-c]pyridin-7-ylmethyl) {1-[(4,9-dioxo-1,2,8,9-tetrahydro-4H,7H-imidazo[1,2,3-ij]-1,8-naphthyridin-1-yl)methyl]-4-piperidinyl}carbamate (80 mg, 0.145 mmol) and DDQ (49.4 mg, 0.218 mmol) in 1,4-dioxane (5 ml) was stirred at 120° C. for 2 h. A further 0.5 eq of DDQ (17 mg) was added and the solution stirred for a further 2 h. The mixture was allowed to cool to rt and was treated with sat NaHCO$_3$ (10 ml). The aqueous layer was extracted with 20% MeOH/DCM (3×100 ml). The organic layers were combined, dried MgSO$_4$, filtered and concentrated to afford the crude product (64 mg, 83%).

MS (ES+) m/z 550 (MH$^+$).

(j) Title Compound

A solution of 1,1-dimethylethyl (2,3-dihydro[1,4]dioxino[2,3-c]pyridin-7-ylmethyl) {1-[(4,9-dioxo-1,2-dihydro-4H,9H-imidazo[1,2,3-ij]-1,8-naphthyridin-1-yl)methyl]-4-piperidinyl}carbamate (64 mg, 0.116 mmol) in DCM (2 ml) and HCl in 1,4-dioxane (0.291 ml, 1.164 mmol) was stirred at rt for 2 h. The solvents were removed under reduced pressure. The crude product was added to an ion exchange column and was eluted with MeOH (20 ml) and then 2M NH$_3$ in MeOH (15 ml) to give the free base of the title compound (34 mg, 65%).

$^1$H NMR and LC-MS identical to product of Example 3A.

The free base of the title product was then converted into the HCl salt by dissolving in DCM (2 ml) and treating with 1 eq 1M HCl in ether. Solvents were removed under reduced pressure to afford the title hydrochloride salt.

Example 4 1-({4-[(2,3-Dihydro[1,4]dioxino[2,3-c]pyridin-7-ylmethyl)amino]-1-piperidinyl}methyl)-1,2-dihydro-4H,9H-imidazo[1,2,3-ij]-1,8-naphthyridine-4,9-dione hydrochloride 1

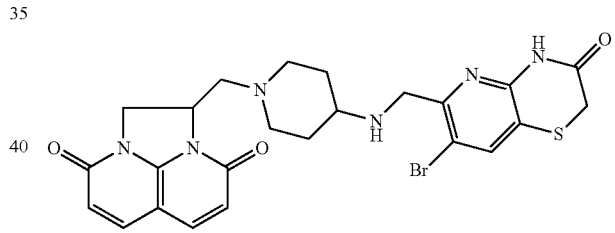

A mixture of 1-[(4-amino-1-piperidinyl)methyl]-1,2-dihydro-4H,9H-imidazo[1,2,3-ij]-1,8-naphthyridine-4,9-dione dihydrochloride (51 mg, 0.136 mmol) (for a preparation see Example 2(n)) in DCM (2 ml) and methanol (0.1 ml) under argon at rt was treated with triethylamine (60 μl, 0.438 mmol) and stirred at rt for 0.25 h before addition of 7-bromo-3-oxo-3,4-dihydro-2H-pyrido[3,2-b][1,4]thiazine-6-carboxaldehyde (for a synthesis, see WO 2002056882 Example 33(e)) (37 mg, 0.136 mmol). The mixture was then stirred at rt for 1 h before addition of NaBH(OAc)$_3$ (86 mg, 0.408 mmol). The reaction was stirred at rt for a further 0.5 h before addition of saturated aqueous sodium bicarbonate (20 ml). The mixture was extracted with 20% methanol/DCM (3×100 ml). The organic extracts were dried (MgSO$_4$), evaporated and chromatographed (0-20% methanol/DCM) to give the free base of the title compound as a clear oil (36 mg, 48%). MS (ES+) m/z 558 (MH$^+$).

δH (CDCl$_3$, 400 MHz) 1.32-1.51 (2H, m), 1.81-2.00 (2H, m), 2.20-2.41 (2H, m) 2.50-2.75 (3H, m), 2.93-3.03 (1H, m), 3.04-3.15 (1H, m), 3.46 (2H, s), 3.98 (2H, s), 4.32-4.41 (1H, m) 4.52-4.61 (1H, m), 4.98-5.04 (1H, m), 6.22-6.32 (2H, m), 7.48-7.51 (2H, m), 7.75 (1H, s).

The free base in methanol and chloroform was converted to the title hydrochloride salt by adding an equivalent of 4M hydrogen chloride in 1,4-dioxane, followed by evaporation to dryness.

Example 5A (1R)-1-({4-[([1,3]Oxathiolo[5,4-c]pyridin-6-ylmethyl)amino]-1-piperidinyl}methyl)-1,2-dihydro-4H,9H-imidazo[1,2,3-ij]-1,8-naphthyridine-4,9-dione hydrochloride

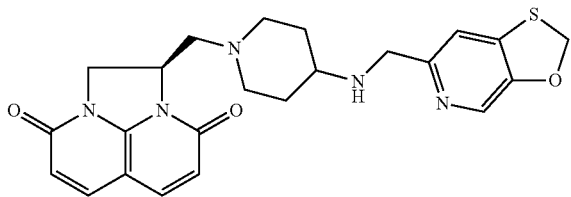 [SMILES: O=c1ccc2ccc(=O)n3c2n1C[C@H]3CN1CCC(NCc2cc3c(cn2)OCS3)CC1]

(a) 2,2-Dimethyl-N-[6-(methyloxy)-2-pyridinyl]propanamide

A suspension of trimethylacetamide (18.08 g, 178.744 mmol), Cs$_2$CO$_3$ (68.823 g, 211.242 mmol), Pd$_2$(dba)$_3$ (1.488 g, 1.625 mmol) and Xantphos (4,5-bis-(diphenylphosphino)-9,9-dimethylxanthene)(1.880 g, 3.249 mmol) in dry, degassed 1,4-dioxane (800 ml) under argon was sonicated for 0.25 h and then treated with 2-chloro-6-(methyloxy)pyridine (19.32 ml, 162.494 mmol). The mixture was then heated at reflux for 24 h. The mixture was evaporated, treated with water (1 L) and extracted 3×DCM (1 L and then 2×500 ml). The organic extracts were dried (MgSO$_4$), evaporated and chromatographed (50-100% DCM/40-60 Petroleum ether then 0-5% methanol/DCM) to give title compound as a yellow solid (25.191 g, 121.111 mmol, 75%). Impure fractions were recolumed (eluting as above) to give more product (4.990 g, 23.990 mmol, 15%).

Total yield of 90%.

MS (ES+) m/z 209 (MH$^+$, 100%).

(b) N-[3-Bromo-6-(methyloxy)-2-pyridinyl]-2,2-dimethylpropanamide

A solution of 2,2-dimethyl-N-[6-(methyloxy)-2-pyridinyl]propanamide (55.011 g, 264.467 mmol) in THF (450 ml) in a three necked 1 L flask with an internal thermometer under argon was cooled to −78° C. and treated with n-butyl lithium (232 ml, 581.847 mmol) over 15 minutes and then allowed to warm to 0° C. and stirred at 0° C. for 7 h. The mixture was then recooled to −78° C. and treated with 1,2-dibromoethane (27.3 ml, 317 mmol) over 10 minutes and then the solution was allowed warm to room temperature and stirred at room temperature for 30 minutes by which time all the solid which had formed dissolved again. Gas was evolved at this stage so a gas bubbler was placed on one of the flasks necks. Water (100 ml) was then carefully added over 10 minutes. Further water (500 ml) was then added and the mixture was extracted with diethyl ether (3×500 ml). The combined organic solvents were then dried (MgSO$_4$), filtered, evaporated to give the crude product. This was then dissolved in warm ethyl acetate (100 ml) and allowed to stand in the freezer overnight. The resultant solid which crystallised out was filtered off, washed with ice-cooled diethyl ether (20 ml) and dried in vacuo to give product as a white solid (45.660 g, 159.011 mmol, 60% yield). The filtrate was evaporated and the residue was chromatographed (0-25% ethyl acetate/40-60 petroleum ether) to give recovered starting material (7.264 g, 34.9 mmol), and product as a white solid (8.038 g, 27.992 mmol, 10% yield). The product from recrystallisation and silica chromatography were identical by NMR and LC-MS and so were combined.

MS (ES+) m/z 287/289 (MH$^+$, 100%).

(c) Butyl (2E)-3-[2-[(2,2-dimethylpropanoyl)amino]-6-(methyloxy)-3-pyridinyl]-2-propenoate A mixture of N-[3-bromo-6-(methyloxy)-2-pyridinyl]-2,2-dimethylpropanamide (78.783 g, 274 mmol), bis(tri-t-butylphosphine)palladium(0) (1 g, 1.957 mmol) and tris(dibenzylideneacetone)dipalladium(0) (0.892 g, 0.974 mmol) in dry, degassed 1,4-dioxane (600 ml) was treated with n-butyl acrylate (47.1 ml, 329 mmol) and dicyclohexylmethylamine (64.5 ml, 302 mmol). The reaction mixture was then heated at 80° C. for 4 h and then at 120° C. for 3 h. The reaction was then evaporated and water (1000 ml) was added and the mixture was extracted with diethyl ether (3×500 ml). The combined organic solvents were then dried (MgSO$_4$), filtered, evaporated to give the crude product. This was then dissolved in DCM (300 ml) and chromatographed (10-30% ethyl acetate:40-60 petroleum ether) and then dried in vacuo to give product as a white solid (87.412 g, 95%).

MS (ES+) m/z 335 (MH$^+$, 100%).

(d) Butyl 3-[2-[(2,2-dimethylpropanoyl)amino]-6-(methyloxy)-3-pyridinyl]propanoate A solution of butyl (2E)-3-[2-[(2,2-dimethylpropanoyl)amino]-6-(methyloxy)-3-pyridinyl]-2-propenoate (43.706 g, 131 mmol) in ethanol (450 ml) under argon at rt was treated with palladium on carbon (5.0 g, 47.0 mmol) and then stirred at rt under 1 atmosphere of hydrogen for 90 h. The reaction mixture was then filtered through a thin pad of Kieselguhr, washing the product through with further ethanol (200 ml). The solvent was then evaporated to give product as a yellow oil (43.549, 99%).

MS (ES+) m/z 337 (MH$^+$, 100%).

(e) 7-(Methyloxy)-3,4-dihydro-1,8-naphthyridin-2(1H)-one

A mixture of butyl 3-[2-[(2,2-dimethylpropanoyl)amino]-6-(methyloxy)-3-pyridinyl]propanoate (86.01 g, 256 mmol) in hydrochloric acid (500 ml, 3000 mmol)(6M aqueous), was heated at 80° C. for 6 h. Reaction was cooled, treated with water (500 ml), transferred to a 5 L conical flask and carefully neutralised with solid potassium carbonate (requires around 250 g)(much effervescence was observed). The mixture was then extracted with 20% MeOH/DCM (3×500 ml). The combined organic solvents were then dried (MgSO$_4$), filtered and evaporated to give the crude product as a yellow solid (35.84 g, 79%).

MS (ES+) m/z 179 (MH$^+$, 100%).

(f) 7-(Methyloxy)-1-[(2R)-2-oxiranylmethyl]-3,4-dihydro-1,8-naphthyridin-2(1H)-one A solution of 7-(methyloxy)-3,4-dihydro-1,8-naphthyridin-2(1H)-one (4.974 g, 27.9 mmol) in DMF (100 ml) at 0° C. under argon was treated with sodium hydride (60%, 1.340 g, 33.5 mmol) and allowed to stir at 0° C. for 20 min. The reaction mixture was then treated with (2S)-2-oxiranylmethyl 3-nitrobenzenesulfonate (7.60 g, 29.3 mmol), stirred at 0° C. and then allowed warm to rt and stirred at rt for 1 h. Water (5 ml) was then added.

Reaction was evaporated, saturated aqueous bicarbonate (500 ml) was then added and the mixture was extracted with DCM (3×500 ml). The combined organic solvents were then dried (MgSO$_4$), filtered and evaporated to give the crude product.

MS (ES+) m/z 235 (MH$^+$, 100%).

(g) (1S)-1-(Hydroxymethyl)-1,2,5,6-tetrahydro-4H, 9H-imidazo[1,2,3-ij]-1,8-naphthyridine-4,9-dione A solution of 7-(methyloxy)-1-[(2R)-2-oxiranylmethyl]-3,4-dihydro-1,8-naphthyridin-2(1H)-one (1.167 g, 4.98 mmol) in DMF (20 ml) under argon was heated to 120° C. for 6 h. Reaction was then evaporated and chromatographed (0-20% methanol/DCM) to give product as an orange solid (339 mg, 31%).

MS (ES+) m/z 221 (MH$^+$, 100%).

Alternatively the reaction can be heated with microwave power at 160° C. for 40 mins.

(h) 1,1-Dimethylethyl (1-{[(2R)-4,9-dioxo-1,2,8,9-tetrahydro-4H,7H-imidazo[1,2,3-ij]-1,8-naphthyridin-2-yl]methyl}-4-piperidinyl)carbamate A solution of (1S)-1-(hydroxymethyl)-1,2,5,6-tetrahydro-4H,9H-imidazo[1,2,3-ij]-1,8-naphthyridine-4,9-dione (1.909 g, 8.67 mmol) in DCM (100 ml) at 0° C. under argon was treated with triethylamine (1.450 ml, 10.40 mmol) and then methanesulfonyl chloride (0.743 ml, 9.54 mmol) and then allowed to warm to rt and stirred at rt for 1 h. The reaction mixture was then treated with saturated aqueous bicarbonate (100 ml) and the mixture was extracted with DCM (2×100 ml). The combined organic solvents were then dried (MgSO$_4$), filtered and evaporated to give the crude intermediate [(2S)-4,9-dioxo-1,2,8,9-tetrahydro-4H,7H-imidazo[1,2,3-ij]-1,8-naphthyridin-2-yl]methyl methanesulfonate. This was dissolved in dry acetonitrile (100 ml) and then treated with pyridine (1.402 ml, 17.34 mmol) and 1,1-dimethylethyl 4-piperidinylcarbamate (3.47 g, 17.34 mmol) and heated at 70° C. for 20 h. After 20 h more 1,1-dimethylethyl 4-piperidinylcarbamate (3.47 g, 17.34 mmol) and pyridine (1.402 ml, 17.34 mmol) were added and the temperature was increased to reflux (heating block 95° C.) and reaction was stirred at this temperature for a further 4 h. The reaction mixture was then evaporated, saturated aqueous NaHCO$_3$ (200 ml) was then added and the mixture was extracted with DCM (3×200 ml). The combined organic solvents were then dried (MgSO$_4$), filtered and evaporated to give the crude product as a brown solid.

MS (ES+) m/z 403 (MH$^+$, 100%).

(i) 1,1-Dimethylethyl (1-{[(1R)-4,9-dioxo-1,2-dihydro-4H,9H-imidazo[1,2,3-ij]-1,8-naphthyridin-1-yl]methyl}-4-piperidinyl)carbamate A solution of 1,1-dimethylethyl (1-{[(2R)-4,9-dioxo-1,2,8,9-tetrahydro-4H,7H-imidazo[1,2,3-ij]-1,8-naphthyridin-2-yl]methyl}-4-piperidinyl)carbamate (5.710 g, 14.19 mmol) in 1,4-dioxane (50 ml) at rt was treated with DDQ (4.83 g, 21.28 mmol) and then heated at 120° C. for 1 h. The reaction was then cooled to rt. The reaction mixture was treated with saturated aqueous K$_2$CO$_3$ (5%, 1000 ml) and extracted with DCM (3×500 ml). The combined organic solvents were then dried (MgSO$_4$), filtered and evaporated to give the crude product as a brown solid. The reaction was repeated using a further portion of carbamate (2.889 g, 7.18 mmol) in 1,4-dioxane (50 ml) with DDQ (2.444 g, 10.77 mmol). The reaction was performed and worked up as above and the combined residues were chromatographed (0-100% ethyl acetate:40-60 Petroleum ether then 0-20% methanol: ethyl acetate) to give the product as a brown solid (1.532 g).

MS (ES+) m/z 401 (MH$^+$, 100%).

(j) (1R)-1-[(4-Amino-1-piperidinyl)methyl]-1,2-dihydro-4H,9H-imidazo[1,2,3-ij]-1,8-naphthyridine-4,9-dione dihydrochloride A solution of 1,1-dimethylethyl (1-{[(1R)-4,9-dioxo-1,2-dihydro-4H,9H-imidazo[1,2,3-ij]-1,8-naphthyridin-1-yl]methyl}-4-piperidinyl)carbamate (1.532 g, 3.83 mmol) in chloroform (20 ml) under argon at rt was treated with 4M HCl in 1,4-dioxane (10 ml, 40.0 mmol) and stirred at rt for 0.25 h. Methanol (20 ml) was then added and reaction was stirred for a further 0.25 h. The reaction was then evaporated and triturated with diethyl ether (20 ml). The solid was then dried in vacuo to give the impure product as a brown solid (1.443 g, 101%).

MS (ES+) m/z 301 (MH$^+$, 100%)

1-[(4-Amino-1-piperidinyl)methyl]-1,2-dihydro-4H,9H-imidazo[1,2,3-ij]-1,8-naphthyridine-4,9-dione dihydrochloride made by this general method (Example 5(a)-(j)) was analyzed via chiral HPLC (Chiralpak AS-H (5 microns) and found to be a single enantiomer, presumed to be R.

(k) Title Compound

A suspension of (1R)-1-[(4-amino-1-piperidinyl)methyl]-1,2-dihydro-4H,9H-imidazo[1,2,3-ij]-1,8-naphthyridine-4, 9-dione dihydrochloride (impure product) (575 mg, 1.540 mmol) in chloroform (20 ml) and methanol (1 ml) at rt under argon was treated with triethylamine (0.644 ml, 4.62 mmol) and stirred at rt for 0.25 h. The solution was then treated with [1,3]oxathiolo[5,4-c]pyridine-6-carbaldehyde (for a synthesis see WO2004058144 Example 61) (258 mg, 1.540 mmol) and stirred for a further 0.5 h. The solution was then treated with NaBH(OAc)$_3$ (979 mg, 4.62 mmol) and stirred at rt for 0.5 h. The reaction was then treated with saturated aqueous NaHCO$_3$ (100 ml) and extracted with 20% methanol/DCM (3×200 ml). The combined organic extracts were dried (MgSO$_4$), filtered, evaporated and chromatographed (0-20% methanol/DCM) to give the free base of the title compound as a light brown solid (574 mg, 1.273 mmol, 83%).

δH (CDCl$_3$, 250 MHz) 1.25-1.45 (2H, m), 1.75-1.95 (2H, m), 2.20-2.45 (2H, m), 2.45-2.55 (1H, m), 2.60-2.75 (2H, m), 2.90-3.00 (1H, m), 3.05-3.15 (1H, dd), 3.85 (2H, s), 4.30-4.40 (1H, m), 4.55-4.65 (1H, m), 4.95-5.05 (1H, m), 5.75 (2H, s), 6.25 (1H, m), 6.30 (1H, m), 7.20 (1H, s), 7.45-7.52 (2H, m), 8.00 (1H, s)

MS (ES+) m/z 452 (MH$^+$).

The free base in DCM/MeOH 2:1 (15 ml) was treated with 1M HCl in diethyl ether and then evaporated to give the title monohydrochloride salt.

Example 5B (1R)-1-({4-[([1,3]Oxathiolo[5,4-c]pyridin-6-ylmethyl)amino]-1-piperidinyl}methyl)-1,2-dihydro-4H,9H-imidazo[1,2,3-ij]-1,8-naphthyridine-4,9-dione benzoate (1R)-1-({4-[([1,3]Oxathiolo[5,4-c]pyridin-6-ylmethyl) amino]-1-piperidinyl}methyl)-1,2-dihydro-4H,9H-imidazo

[1,2,3-ij]-1,8-naphthyridine-4,9-dione was dissolved in methanol and treated with benzoic acid (1 equivalent). Concentration, treatment with diethyl ether and evaporation of the solvents under reduced pressure gave the product as the benzoate salt.

Example 5C (1R)-1-({4-[([1,3]Oxathiolo[5,4-c]pyridin-6-ylmethyl)amino]-1-piperidinyl}methyl)-1,2-dihydro-4H,9H-imidazo[1,2,3-ij]-1,8-naphthyridine-4,9-dione di-trifluoroacetate (1R)-1-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione hydrochloride in eluent [10% MeCN in water (containing 0.1% TFA)] was applied to a preparative reverse phase HPLC column. Product-containing fractions were combined, concentrated and concentrate lyophilized. The product was isolated as a sticky white foam following desiccation (weekend) over $P_2O_5$.

Example 6A (1R)-1-({4-[(2,3-Dihydro[1,4]oxathiino[2,3-c]pyridin-7-ylmethyl)amino]-1-piperidinyl}methyl)-1,2-dihydro-4H,9H-imidazo[1,2,3-ij]-1,8-naphthyridine-4,9-dione hydrochloride

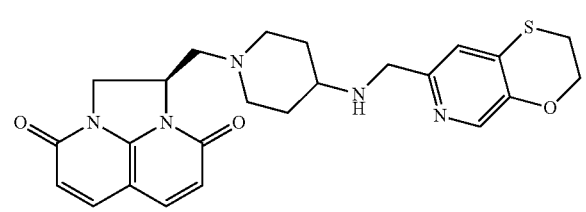 [SMILES: O=c1ccc2ccc(=O)n3c2n1C[C@H]3CN1CCC(NCc2cc3c(cn2)OCCS3)CC1]

A suspension of (1R)-1-[(4-amino-1-piperidinyl)methyl]-1,2-dihydro-4H,9H-imidazo[1,2,3-ij]-1,8-naphthyridine-4,9-dione dihydrochloride (511 mg, 1.369 mmol) (for a preparation see Example 5(j)) in chloroform (20 ml) and methanol (1 ml) at rt under argon was treated with triethylamine (0.572 ml, 4.11 mmol) and stirred at rt for 0.25 h. The solution was then treated with 2,3-dihydro[1,4]oxathiino[2,3-c]pyridine-7-carbaldehyde (for a synthesis see WO2004058144, Example 60) (248 mg, 1.369 mmol) and stirred for a further 0.5 h. The solution was then treated with NaBH(OAc)$_3$ (870 mg, 4.11 mmol) and stirred at rt for 0.5 h. The reaction was then treated with saturated aqueous NaHCO$_3$ (100 ml) and extracted with 20% methanol/DCM (3×200 ml). The combined organic extracts were dried (MgSO$_4$), filtered, evaporated and chromatographed (0-20% methanol/DCM) to give the free base of the title compound as a light brown solid (499 mg, 78%).

MS (ES+) m/z 466 (MH$^+$).

δH (CDCl$_3$, 250 MHz) 1.21-1.48 (2H, m), 1.72-1.92 (2H, m), 2.12-2.39 (2H, m) 2.41-2.78 (3H, m), 2.89-3.22 (4H, m), 3.78 (2H, s), 4.28-4.48 (3H, m) 4.50-4.61 (1H, m), 4.96-5.04 (1H, m), 6.19-6.32 (2H, m), 7.01 (1H, s), 7.42-7.53 (2H, m), 8.00 (1H, s).

The free base in DCM/MeOH 2:1 (15 ml) was treated with one equivalent of 1M HCl in diethyl ether and then evaporated to give the title monohydrochloride salt.

Example 6B (1R)-1-({4-[(2,3-Dihydro[1,4]oxathiino[2,3-c]pyridin-7-ylmethyl)amino]-1-piperidinyl}methyl)-1,2-dihydro-4H,9H-imidazo[1,2,3-ij]-1,8-naphthyridine-4,9-dione hydrochloride (1R)-1-({4-[(2,3-Dihydro[1,4]oxathiino[2,3-c]pyridin-7-ylmethyl)amino]-1-piperidinyl}methyl)-1,2-dihydro-4H,9H-imidazo[1,2,3-ij]-1,8-naphthyridine-4,9-dione was dissolved in methanol and treated with benzoic acid (1 equivalent). Evaporation of the solvents under reduced pressure gave the product as the benzoate salt.

Example 6C (1R)-1-({4-[(2,3-Dihydro[1,4]oxathiino[2,3-c]pyridin-7-ylmethyl)amino]-1-piperidinyl}methyl)-1,2-dihydro-4H,9H-imidazo[1,2,3-ij]-1,8-naphthyridine-4,9-dione ditrifluoroacetate (1R)-1-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione hydrochloride was applied to a preparative reverse phase HPLC column in a mixture of 10% MeCN in water containing 0.1% TFA. Product-containing fractions were combined, concentrated and concentrate lyophilized. The product (bis-TFA salt) was isolated as a white solid following desiccation over $P_2O_5$.

Example 7 (1R)-1-({4-[(5,6,7,8-Tetrahydro-3-isoquinolinylmethyl)amino]-1-piperidinyl}methyl)-1,2-dihydro-4H,9H-imidazo[1,2,3-ij]-1,8-naphthyridine-4,9-dione hydrochloride

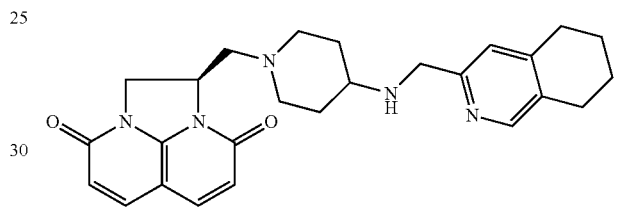

(a) Ethyl 5,6,7,8-tetrahydro-3-isoquinolinecarboxylate

A solution of 1,7-octadiyne (4.00 ml, 30.1 mmol) and ethyl cyanoformate (2.95 ml, 30.1 mmol) in dry degassed 1,4-dioxane (500 ml) under argon at rt was treated with cyclopentadienyl-Cobalt(I)-dicarbonyl (0.814 g, 4.52 mmol) and then heated at reflux for 18 h. Reaction was then evaporated, treated with toluene (100 ml), re-evaporated, dissolved in DCM (100 ml), filtered through a short pad of Kieselguhr, eluting with DCM, organic extracts evaporated, chromatographed (0-100% DCM:40-60 Petroleum ether then 0-10% methanol/DCM) to give product as an impure brown oil (1.27 g, 21%).

MS (ES+) m/z 206 (MH$^+$).

(b) 5,6,7,8-Tetrahydro-3-isoquinolinylmethanol

A solution of ethyl 5,6,7,8-tetrahydro-3-isoquinolinecarboxylate (1.27 g, 6.19 mmol) in THF (50 ml) at −78° C. under argon was treated with LiAlH$_4$ (IM solution in THF, 6.19 ml, 6.19 mmol) and allowed warm to rt. After 10 min at rt, water (1 ml), 2M aq NaOH (1 ml) and water (1 ml) were sequentially added and the mixture stirred at rt for 0.5 h. The mixture was then filtered through a short pad of Kieselguhr, eluting with THF (50 ml), organic extracts were then evaporated, chromatographed (0-20% methanol/DCM) to give product as an orange oil (0.572 g, 57%).

MS (ES+) m/z 164 (MH$^+$).

(c) 5,6,7,8-Tetrahydro-3-isoquinolinecarbaldehyde

A solution of 5,6,7,8-tetrahydro-3-isoquinolinylmethanol (572 mg, 3.50 mmol) in (DCM) (10 ml) at rt under argon was treated with manganese dioxide (3.047 g, 35.0 mmol) and then stirred at rt for 2 h. The reaction mixture was then filtered through a thin pad of Kieselguhr, eluting with DCM (50 ml), the organic extracts were evaporated to give the crude product as a brown oil (435 mg, 77%).

MS (ES+) m/z 162 (MH+).

(d) Title Compound

A suspension of (1R)-1-[(4-amino-1-piperidinyl)methyl]-1,2-dihydro-4H,9H-imidazo[1,2,3-ij]-1,8-naphthyridine-4,9-dione dihydrochloride (87 mg, 0.233 mmol) (for a preparation see Example 5(j)) in chloroform (5 ml) and methanol (0.2 ml) at rt under argon was treated with triethylamine (97 al, 0.699 mmol) and stirred at rt for 0.25 h. The solution was then treated with 5,6,7,8-tetrahydro-3-isoquinolinecarbaldehyde (37.6 mg, 0.233 mmol) and stirred for a further 0.5 h. The solution was then treated with NaBH(OAc)$_3$ (148 mg, 0.699 mmol) and stirred at rt for 0.5 h. The reaction was then treated with saturated aqueous NaHCO$_3$ (100 ml) and extracted with 20% methanol/DCM (3×200 ml). The combined organic extracts were dried (MgSO$_4$), filtered, evaporated and chromatographed (0-20% methanol/DCM) to give the free base of the title compound as a light brown solid (66 mg, 64%).

MS (ES+) m/z 446 (MH+).

δH (CDCl$_3$, 250 MHz) 1.22-1.51 (2H, m), 1.71-1.99 (7H, m), 2.15-2.38 (2H, m) 2.45-2.82 (4H, m), 2.61-3.22 (4H, m), 3.85 (2H, s), 4.29-4.42 (1H, m) 4.50-4.61 (1H, m), 4.96-5.04 (1H, m), 6.18-6.32 (2H, m), 7.00 (1H, s), 7.47-7.59 (2H, m), 8.21 (1H, s).

The free base in DCM/MeOH 2:1 (15 ml) was treated with one equivalent of 1M HCl in diethyl ether and then evaporated to give the title monohydrochloride salt.

Example 8 (1R)-1-({4-[(6,7-Dihydro-5H-cyclopenta [c]pyridin-3-ylmethyl)amino]-1-piperidinyl}methyl)-1,2-dihydro-4H,9H-imidazo[1,2,3-ij]-1,8-naphthyridine-4,9-dione hydrochloride

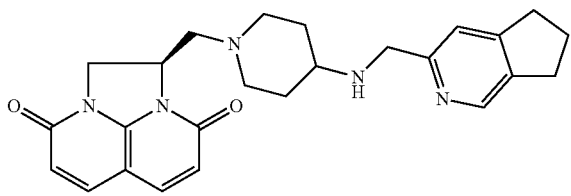 [SMILES: O=c1ccc2ccc(=O)n3c2n1C[C@H]3CN1CCC(NCc2cc3c(cn2)CCC3)CC1]

(a) Ethyl 6,7-dihydro-5H-cyclopenta[c]pyridine-3-carboxylate

A solution of 1,6-heptadiyne (1.242 ml, 10.85 mmol) and ethyl cyanoformate (1.063 ml, 10.85 mmol) in dry degassed 1,4-dioxane (100 ml) under argon at rt was treated with cyclopentadienyl-Cobalt(I)-dicarbonyl (0.293 g, 1.628 mmol) and then heated at reflux for 18 h. Reaction was then evaporated, treated with toluene (100 ml), re-evaporated, dissolved in DCM (100 ml), filtered through a short pad of Kieselguhr, eluting with DCM, organic extracts evaporated, chromatographed (0-100% DCM:40-60 Petroleum ether then 0-10% methanol/DCM) to give product as an impure brown oil (427 mg, 21%).

MS (ES+) m/z 192 (MH+).

(b) 6,7-Dihydro-5H-cyclopenta[c]pyridin-3-yl-methanol

A solution of ethyl 6,7-dihydro-5H-cyclopenta[c]pyridine-3-carboxylate (427 mg, 2.233 mmol) in (THF) (20 ml) at −78° C. under argon was treated with LiAlH$_4$ (IM in THF)(2.233 ml, 2.233 mmol) and allowed warm to rt. After 10 min at rt, water (1 ml), 2M aq NaOH (1 ml) and water (1 ml) were sequentially added and the mixture stirred at rt for 0.5 h. The mixture was then filtered through a short pad of Kieselguhr, eluting with THF (50 ml), organic extracts were then evaporated, chromatographed (0-20% methanol/DCM) to give product as an orange oil (189 mg, 57%).

MS (ES+) m/z 150 (MH+).

(c) 6,7-Dihydro-5H-cyclopenta[c]pyridine-3-carbaldehyde

A solution of 6,7-dihydro-5H-cyclopenta[c]pyridin-3-yl-methanol (189 mg, 1.267 mmol) in DCM (10 ml) at rt under argon was treated with manganese dioxide (1.101 g, 12.67 mmol) and then stirred at rt for 2 h, filtered through a thin pad of Kieselguhr, eluting with DCM (40 ml), the organic extracts were evaporated to give the crude product as a brown oil (110 mg, 59%).

MS (ES+) m/z 148 (MH+).

(d) Title Compound

A suspension of (1R)-1-[(4-amino-1-piperidinyl)methyl]-1,2-dihydro-4H,9H-imidazo[1,2,3-ij]-1,8-naphthyridine-4,9-dione dihydrochloride (82 mg, 0.220 mmol) (for a preparation see Example 5(j)) in chloroform (5 ml) and methanol (0.2 ml) at rt under argon was treated with triethylamine (92 al, 0.659 mmol) and stirred at rt for 0.25 h. The solution was then treated with 6,7-dihydro-5H-cyclopenta[c]pyridine-3-carbaldehyde (32.3 mg, 0.220 mmol) and stirred for a further 0.5 h. The solution was then treated with NaBH(OAc)$_3$ (140 mg, 0.659 mmol) and stirred at rt for 0.5 h. The reaction was then treated with saturated aqueous NaHCO$_3$ (100 ml) and extracted with 20% methanol/DCM (3×200 ml). The combined organic extracts were dried (MgSO$_4$), filtered, evaporated and chromatographed (0-20% methanol/DCM) to give the free base of the title compound as a light brown solid (39 mg, 41%).

MS (ES+) m/z 432 (MH+).

δH (CDCl$_3$, 250 MHz) 1.32-1.59 (2H, m), 1.82-2.40 (6H, m) 2.51-2.72 (3H, m), 2.82-3.18 (6H, m), 3.95 (2H, s), 4.31-4.42 (1H, m), 4.50-4.61 (1H, m), 4.92-5.08 (1H, m), 6.19-6.32 (2H, m), 7.23 (1H, s), 7.42-7.53 (2H, m), 8.38 (1H, s).

The free base in DCM/MeOH 2:1 (15 ml) was treated with one equivalent of 1M HCl in diethyl ether and then evaporated to give the title monohydrochloride salt.

Example 9 (1R)-1-({4-[(1,3-Dihydrofuro[3,4-c]pyridin-6-ylmethyl)amino]-1-piperidinyl}methyl)-1,2-dihydro-4H,9H-imidazo[1,2,3-ij]-1,8-naphthyridine-4,9-dione hydrochloride

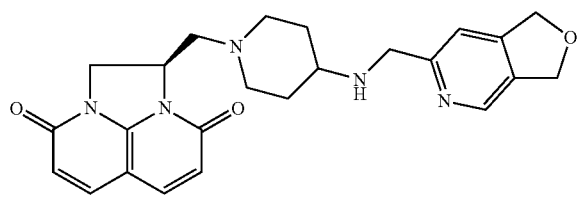 [SMILES: O=c1ccc2ccc(=O)n3c2n1C[C@H]3CN1CCC(NCc2cc3c(cn2)COC3)CC1]

(a) Ethyl 1,3-dihydrofuro[3,4-c]pyridine-6-carboxylate

A solution of di-2-propyn-1-yl ether (5.01 g, 53.2 mmol) and ethyl cyanoformate (5.21 ml, 53.2 mmol) in dry degassed 1,4-dioxane (500 ml) under argon at rt was treated with cyclopentadienyl-Cobalt(I)-dicarbonyl (1.437 g, 7.98 mmol) and then heated at reflux (heating block temp 120° C.) for 18 h. The reaction was evaporated, treated with toluene (100 ml), re-evaporated, dissolved in DCM (100 ml), filtered through a short pad of Kieselguhr, eluting with DCM, organic extracts evaporated, chromatographed (0-100% DCM:40-60 Petroleum ether then 0-10% methanol/DCM) to give product as an impure brown solid (0.871 g) and impure product as a black oil (2.684 g) which was re-chromatographed (0-10-10% methanol/DCM,) to give more material as a brown solid (1.261 g). Total product obtained was (2.132 g, 21%).

MS (ES+) m/z 194 (MH$^+$).

(b) 1,3-Dihydrofuro[3,4-c]pyridin-6-ylmethanol

A solution of ethyl 1,3-dihydrofuro[3,4-c]pyridine-6-carboxylate (0.871 g, 4.51 mmol) in THF (20 ml) at −78° C. under argon was treated with LiAlH$_4$ (1M in THF) (4.51 ml, 4.51 mmol) and allowed warm to rt. After 10 min at rt, water (1 ml), 2M aq NaOH (1 ml) and water (1 ml) were sequentially added and the mixture stirred at rt for 0.5 h. The mixture was then filtered through a short pad of Kieselguhr, eluting with THF (50 ml), organic extracts were then evaporated, chromatographed (0-20% methanol/DCM) to give product as an orange oil (66 mg, 10%).

MS (ES+) m/z 152 (MH$^+$).

(c) 1,3-Dihydrofuro[3,4-c]pyridine-6-carbaldehyde

A solution of 1,3-dihydrofuro[3,4-c]pyridin-6-ylmethanol (66 mg, 0.437 mmol) in DCM (5 ml) at rt under argon was treated with manganese dioxide (380 mg, 4.37 mmol) and then stirred at rt for 2 h, filtered through a thin pad of Kieselguhr, eluting with DCM (40 ml) and methanol (10 ml), the organic extracts were evaporated to give the crude product as a brown oil (65 mg, 100%)

MS (ES+) m/z 150 (MH$^+$).

(d) Title Compound

A suspension of (1R)-1-[(4-amino-1-piperidinyl)methyl]-1,2-dihydro-4H,9H-imidazo[1,2,3-ij]-1,8-naphthyridine-4,9-dione (121 mg, 0.324 mmol) (for a preparation see Example 5(j)) in chloroform (5 ml) and methanol (0.2 ml) at rt under argon was treated with triethylamine (0.136 ml, 0.972 mmol) and stirred at rt for 0.25 h. The solution was then treated with 1,3-dihydrofuro[3,4-c]pyridine-6-carbaldehyde (48.3 mg, 0.324 mmol) and stirred for a further 0.5 h. The solution was then treated with NaBH(OAc)$_3$ (206 mg, 0.972 mmol) and stirred at rt for 0.5 h. The reaction was then treated with saturated aqueous NaHCO$_3$ (100 ml) and extracted with 20% methanol/DCM (3×200 ml). The combined organic extracts were dried (MgSO$_4$), filtered, evaporated and chromatographed (0-20% methanol/DCM) to give the free base of the title compound as a light brown solid (37 mg, 26%).

MS (ES+) m/z 434 (MH$^+$).

δH (CDCl$_3$, 250 MHz) 1.21-1.52 (2H, m), 1.78-2.00 (2H, m), 2.15-2.40 (2H, m) 2.49-3.15 (5H, m), 3.95 (2H, s), 4.31-4.48 (1H, m) 4.50-4.62 (1H, m), 4.92-5.19 (5H, m), 6.19-6.32 (2H, m), 7.27 (1H, s), 7.41-7.54 (2H, m), 8.45 (1H, s).

The free base in DCM/MeOH 2:1 (15 ml) was treated with one equivalent 1M HCl in diethyl ether and then evaporated to give the title mono salt.

Example 10 (1R)-1-({4-[(3,4-Dihydro-2H-pyrano[2,3-c]pyridin-6-ylmethyl)amino]-1-piperidinyl}methyl)-1,2-dihydro-4H,9H-imidazo[1,2,3-ij]-1,8-naphthyridine-4,9-dione hydrochloride

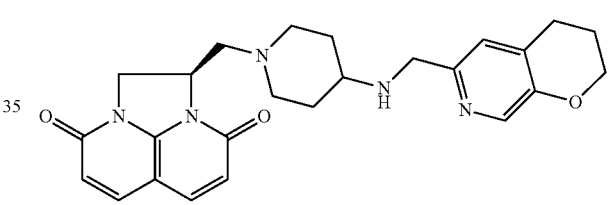

A suspension of (1R)-1-[(4-amino-1-piperidinyl)methyl]-1,2-dihydro-4H,9H-imidazo[1,2,3-ij]-1,8-naphthyridine-4,9-dione (for a preparation see Example 5(j)) (51 mg, 0.14 mmol) in chloroform:methanol (9:1, 3 ml) at rt under argon was treated with triethylamine (0.06 ml) and stirred at rt for 10 min. The solution was then treated with 1,3-dihydrofuro[3,4-c]pyridine-6-carbaldehyde (for a synthesis see WO2004058144, Example 126(e)) (21 mg, 0.133 mmol) and stirred for a further 2 h. The solution was then treated with NaBH(OAc)$_3$ (87 mg) and stirred at rt for 2 h. The reaction was then treated with saturated aqueous NaHCO$_3$ (10 ml) and extracted with 20% methanol/DCM (3×50 ml). The combined organic extracts were dried (MgSO$_4$), filtered, evaporated and chromatographed (0-20% methanol/DCM) to give the free base of the title compound as a light brown solid (20 mg, 32%)

MS (ES+) m/z 448 (MH$^+$).

δH (CDCl$_3$, 400 MHz) 1.15-1.49 (2H, m), 1.61-1.95 (2H, m), 1.99-2.09 (2H, m) 2.20-2.38 (1H, m), 2.45-2.85 (6H, m), 2.92-3.02 (1H, m), 3.05-3.15 (1H, m), 3.78 (2H, s), 4.20 (2H, t), 4.30-4.42 (1H, m), 4.52-4.61 (1H, m), 4.95-5.05 (1H, m), 6.23-6.32 (2H, m), 7.00 (1H, s), 7.47-7.50 (2H, m), 8.07 (1H, s).

The free base in DCM was treated with one equivalent 1M HCl in diethyl ether and then evaporated to give the title monohydrochloride salt.

Example 11 7-[({1-[(4,9-Dioxo-1,2-dihydro-4H,9H-imidazo[1,2,3-ij]-1,8-naphthyridin-1-yl)methyl]-4-piperidinyl}amino)methyl]-2,3-dihydro-1,4-benzodioxin-5-carbonitrile hydrochloride (2:1 mixture of R:S)

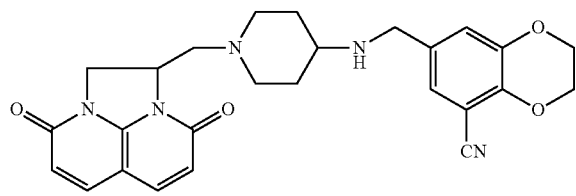 [SMILES: N#Cc1cc(CNC2CCN(CC3Cn4c(=O)ccc5ccc(=O)n3c54)CC2)cc2c1OCCO2]

(a) 1,1-Dimethylethyl (1-{(2R)-2-hydroxy-3-[7-(methyloxy)-2-oxo-3,4-dihydro-1,8-naphthyridin-1(2H)-yl]propyl}-4-piperidinyl)carbamate A mixture of 7-(methyloxy)-1-[(2S)-2-oxiranylmethyl]-3,4-dihydro-1,8-naphthyridin-2(1H)-one (made according to the general method of Example 5(f) but using (2R)-2-oxiranylmethyl 3-nitrobenzenesulfonate) (3.1 g, 13.3 mmol) and 1,1-dimethylethyl 4-piperidinylcarbamate (2.7 g, 13.3 mmol) in DMF (3 ml) was heated at 110° C. for 1 h. DMF was then evaporated. The crude product was purified by silica chromatography using a 0-10% methanol/dichloromethane gradient to provide the desired compound as a pale yellow solid, presumed R enantiomer (3.9 g; 89%; 90% purity).

MS (ES+) m/z 435 (MH$^+$).

(b) 1,1-Dimethylethyl {1-[(4,9-dioxo-1,2,8,9-tetrahydro-4H,7H-imidazo[1,2,3-ij]-1,8-naphthyridin-2-yl)methyl]-4-piperidinyl}carbamate (2:1 mixture of R:S)

A solution of 1,1-dimethylethyl (1-{(2R)-2-hydroxy-3-[7-(methyloxy)-2-oxo-3,4-dihydro-1,8-naphthyridin-1(2H)-yl]propyl}-4-piperidinyl)carbamate (3.9 g, 8.97 mmol) in chloroform (150 ml) and triethylamine (3.1 ml) under argon was treated with methanesulfonic anhydride (3.1 g, 17.94 mmol) at room temperature and then heated at reflux for 2.5 h. The solvents were evaporated and the residue dissolved in acetonitrile (150 ml) and treated with sodium iodide (6.7 g, 44.85 mmol) and heated at 80° C. After 45 minutes acetonitrile was evaporated and the residue was partitioned between water (250 ml) and 20% methanol/dichloromethane (250 ml); the layers were separated and the aqueous layer was extracted with 20% methanol/dichloromethane (4×250 ml). The combined organic extracts were dried on magnesium sulphate, filtered and evaporated. The crude was purified by silica chromatography using a 0-10% methanol/dichloromethane gradient to provide the desired compound as a bright orange foam (1.83 g; 57%, impure with triethylamine residues). The aqueous layer was evaporated and then treated with chloroform; the solid was filtered off and the chloroform was evaporated to give 2.77 g of a yellow solid. The solid was dissolved in methanol and loaded onto a SCX cartridge which was pre-wet with methanol. The cartridge was washed with methanol (50 ml) and then with 2M ammonia in methanol (50 ml). The 2M ammonia in methanol was evaporated to afford the pure product as a white solid (220 mg), presumed 2:1 mixture of R:S).

MS (ES+) m/z 403 (MH$^+$).

(c) 1,1-Dimethylethyl {1-[(4,9-dioxo-1,2-dihydro-4H,9H-imidazo[1,2,3-ij]-1,8-naphthyridin-1-yl)methyl]-4-piperidinyl}carbamate (2:1 mixture of R:S)

A mixture of 1,1-dimethylethyl {1-[(4,9-dioxo-1,2,8,9-tetrahydro-4H,7H-imidazo[1,2,3-ij]-1,8-naphthyridin-2-yl)methyl]-4-piperidinyl}carbamate (2:1 mixture of R:S) (1.83 g, 4.55 mmol) and DDQ (1.6 g, 6.83 mmol) in 1,4-dioxane (100 ml) was stirred at 60° C. under argon overnight. More DDQ (1.6 g, 6.83 mmol) was added and the reaction was stirred at 60° C. for another 1 h. The reaction was cooled to room temperature, treated with 5% aqueous solution of potassium carbonate (600 ml) and extracted with 20% methanol/dichloromethane (3×500 ml). The combined organic extracts were dried over magnesium sulphate, filtered and evaporated to afford the crude as a brown oil. LCMS showed that there was still ~8% of starting material left so the oil was combined with more starting material (220 mg) recovered from the aqueous in the previous step and was dissolved in 1,4-dioxane (100 ml), treated with 1 eq. of DDQ and heated at 60° C. for 1 h. LCMS showed that the reaction was not complete so 0.5 g of DDQ was added and the reaction was stirred at 60° C. for 0.5 h. A small work-up showed that the reaction was complete so the reaction was treated with 5% aqueous solution of potassium carbonate (500 ml) and extracted with 20% methanol/dichloromethane (2×500 ml). The combined organic extracts were dried over magnesium sulphate, filtered and evaporated to afford the product as a light brown foam (1 g, 50%).

MS (ES+) m/z 401 (MH$^+$).

(d) 1-[(4-Amino-1-piperidinyl)methyl]-1,2-dihydro-4H,9H-imidazo[1,2,3-ij]-1,8-naphthyridine-4,9-dione (2:1 mixture of R:S)

1,1-Dimethylethyl {1-[(4,9-dioxo-1,2-dihydro-4H,9H-imidazo[1,2,3-ij]-1,8-naphthyridin-1-yl)methyl]-4-piperidinyl}carbamate (2:1 mixture of R:S) (1 g, 2.5 mmol) was dissolved in chloroform (10 ml) and treated with 4M HCl in 1,4-dioxane solution (10 ml) at room temperature. A solid precipitated so some methanol was added to dissolve it. After 1 h LCMS showed that the reaction was complete so more methanol was added to dissolve all the solids, followed by toluene (~50 ml). All the solvents were evaporated under reduced pressure to afford a yellow solid. The solid was dissolved in 100 ml of methanol and stirred with Amberlyst A21 resin for 1 h. The resin was then filtered off and the methanol removed to afford 0.7 g of a brown gum. The gum was dissolved in methanol and loaded onto a SCX cartridge that was pre-wet with methanol. The cartridge was washed with methanol and then with 2M ammonia in methanol. The 2M ammonia in methanol was evaporated to afford the product as a light brown gum (0.6 g, 80%).

MS (ES+) m/z 301 (MH$^+$).

Product made by this general method was analyzed via chiral HPLC (Chiralpak AS-H (5 microns) with 90:10:0.1 acetonitrile:methanol:isopropylamine as the mobile phase.). The ratio of isomers (presumed R:S) was approximately 2:1.

(e) Title Compound

1-[(4-Amino-1-piperidinyl)methyl]-1,2-dihydro-4H,9H-imidazo[1,2,3-ij]-1,8-naphthyridine-4,9-dione (2:1 mixture of R:S) (60 mg, 0.2 mmol) and 7-formyl-2,3-dihydro-1,4- benzodioxin-5-carbonitrile (for a synthesis see WO06014580 Preparation 13 or WO2007122258 Example 31(d)) (37.8 mg, 0.2 mmol) were dissolved in dichloromethane/methanol (2/0.1 ml) at room temperature under argon and stirred at room temperature for 1 h. This was then treated with NaBH(OAc)₃ (85 mg, 0.4 mmol) and left to stir for 1 hour. A saturated solution of sodium bicarbonate (15 ml) was then added and the aqueous was extracted with 20% methanol/dichloromethane (3×35 ml). The combined organic extracts were dried on magnesium sulphate, filtered and evaporated. The crude was purified by silica chromatography using a 0-20% methanol/dichloromethane gradient to provide the free base of the title compound as a pale yellow gum (26 mg, 27%).

δH CDCl₃, (250 MHz) 1.15-1.45 (m, 2H), 1.53 (bs, 1H),1.70-1.90 (m, 2H), 2.15-2.35 (m, 1H), 2.35-2.55 (m, 1H), 2.55-2.75 (m, 2H), 2.85-3.00 (m, 2H), 3.00-3.15 (m, 1H), 3.68 (s, 2H), 4.25-4.45 (m, 5H), 4.50-4.65 (m, 1H), 4.90-5.10 (m, 1H), 6.20-6.35 (m, 2H), 7.00-7.10 (m, 2H), 7.40-7.55 (m, 2H).

MS (ES+) m/z 474 (MH⁺).

The title compound was prepared by dissolving the free base in DCM and treating it with 1 equivalent of 1M HCl in diethyl ether. This was then evaporated to dryness and dried in the vacuum desiccator in the presence of P₂O₅.

Example 12 1-[(4-{[(3-Oxo-3,4-dihydro-2H-1,4-benzothiazin-6-yl)methyl]amino}-1-piperidinyl)methyl]-1,2-dihydro-4H,9H-imidazo[1,2,3-ij]-1,8-naphthyridine-4,9-dione hydrochloride (2:1 mixture of R:S)

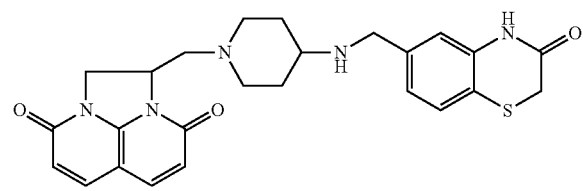 [SMILES: O=C1CSc2ccc(CNC3CCN(CC4Cn5c(=O)ccc6ccc(=O)n4c65)CC3)cc2N1]

1-[(4-Amino-1-piperidinyl)methyl]-1,2-dihydro-4H,9H-imidazo[1,2,3-ij]-1,8-naphthyridine-4,9-dione (2:1 mixture of R:S, for a preparation see Example 11(d)) (60 mg, 0.2 mmol) and 3-oxo-3,4-dihydro-2H-1,4-benzothiazine-6-carbaldehyde (for a synthesis see WO2002056882, Example 6(c)) (38.6 mg, 0.2 mmol) were dissolved in dichloromethane/methanol (2/0.1 ml) at room temperature under argon and stirred at room temperature for 1 h. This was then treated with NaBH(OAc)₃ (85 mg, 0.4 mmol) and left to stir for 1 hour. A saturated solution of sodium bicarbonate (20 ml) was then added and the aqueous was extracted with 20% methanol/dichloromethane (3×35 ml). The combined organic extracts were dried on magnesium sulphate, filtered and evaporated. The crude product was purified by silica chromatography using a 0-20% methanol/dichloromethane gradient to provide the free base of the title compound as a yellow solid (37 mg, 39%). δH CDCl₃, (250 MHz) 1.20-1.45 (m, 2H), 1.70-2.15 (m, 4H), 2.15-2.40 (m, 2H), 2.40-2.75 (m, 3H), 2.95 (d, 1H), 3.05-3.15 (m, 1H), 3.40 (s, 2H), 3.76 (s, 2H), 4.30-4.45 (m, 1H), 4.50-4.65 (m, 1H), 4.90-5.10 (m, 1H), 6.20-6.35 (m, 2H), 6.85-7.00 (m, 2H), 7.25 (d, 1H), 7.40-7.60 (m, 2H), 8.53 (bs, 1H).

MS (ES+) m/z 478 (MH⁺).

The title compound was prepared by dissolving the free base in DCM/MeOH and treating it with 1 equivalent of 1M HCl in diethyl ether. This was then evaporated to dryness and dried in the vacuum desiccator in the presence of P₂O₅ for 4 days.

Example 13A (1R)-1-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione hydrochloride

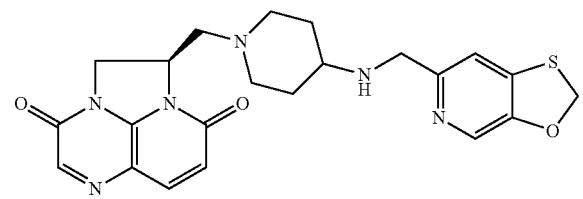 [SMILES: O=c1cnc2ccc(=O)n3c2n1C[C@H]3CN1CCC(NCc2cc3c(cn2)OCS3)CC1]

(a) 6-(Methyloxy)-3-nitro-2-pyridinamine

A solution/suspension of 2-chloro-6-(methyloxy)-3-nitropyridine (65.7 g, 348 mmol) in 2M ammonia in methanol (500 ml, 1000 mmol) and aqueous ammonia (500 ml, 348 mmol) was stirred at 65° C. for 18 h. The reaction was cooled down and the solid filtered off and washed with water (2×100 ml). The solid was dried in the vacuum oven at 40° C. overnight to afford the product as a bright yellow solid (52.14 g, 84% purity by NMR, 74%).

MS (ES+) m/z 170 (MH⁺).

(b) 6-(Methyloxy)-2,3-pyridinediamine 6-(Methyloxy)-3-nitro-2-pyridinamine (26 g, 129 mmol) was suspended in ethanol (500 ml) at room temperature under argon and then treated with palladium on carbon (15 g, 14.10 mmol) (10% paste). The reaction was stirred under 1 atm of hydrogen overnight. The reaction was filtered through a Celite pad and the pad washed with ethanol (500 ml). Ethanol was evaporated to afford the product as a purple oil (20.68 g, slightly impure).

MS (ES+) m/z 140 (MH⁺).

(c) Ethyl N-[2-amino-6-(methyloxy)-3-pyridinyl]glycinate 6-(Methyloxy)-2,3-pyridinediamine (21.7 g, estimated 87% purity, 136 mmol) was dissolved in acetonitrile (500 ml) at room temperature under argon and then treated with potassium carbonate (24.38 g, 176 mmol) and ethyl bromoacetate (18.13 ml, 163 mmol). The reaction was stirred at room temperature overnight. The acetonitrile was then removed in vacuo. The reaction was repeated using more 6-(methyloxy)-2,3-pyridinediamine (20.68 g, 87% purity, 129 mmol), in acetonitrile (500 ml), potassium carbonate (23.23 g) and ethyl bromoacetate (17.27 g) and the reaction was again stirred at room temperature overnight and the acetonitrile was then removed in vacuo. The residues were partitioned between water (1 L) and ethyl acetate (1 L) and the layers separated. The aqueous layer was extracted once more with ethyl acetate (1 L) and the combined organic extracts were dried over MgSO₄, filtered and evaporated to afford a purple oil (64 g). The oil was treated with DCM (300 ml) and the insoluble impurities filtered off. The DCM solution was loaded onto a 800 g silica column and eluted with 0-2% MeOH/DCM to afford 40.6 g of desired product as a brown solid (LCMS and NMR consistent with 75% desired product with 15% cyclized product 6-(methyloxy)-1,4-dihydropyrido[2,3-b]pyrazin-3(2H)-one and 6.4 g of cyclized product 6-(methyloxy)-1,4-dihydropyrido[2,3-b]pyrazin-3(2H)-one as a purple solid.

MS (ES+) m/z 226 (MH$^+$).

(d) 6-(Methyloxy)-1,4-dihydropyrido[2,3-b]pyrazin-3(2H)-one

Ethyl N-[2-amino-6-(methyloxy)-3-pyridinyl]glycinate (40.6 g, 135 mmol) was dissolved in tetrahydrofuran (THF) (1 L) at room temperature under argon and treated with potassium tert-butoxide (15.17 g, 135 mmol). After 2 h at room temperature saturated NH$_4$Cl (500 ml) was added and the THF evaporated. Water (500 ml) was added followed by 20% MeOH/DCM (1 L); the insoluble material was filtered off, washed with diethyl ether and dried in the vacuum oven at 40° C. overnight to afford the desired product as a yellow solid (15.3 g): LCMS and NMR consistent with product (9% of oxidized material present by NMR).

The two phases were transferred to a separating funnel and separated. The aqueous layer was extracted twice more with 20% MeOH/DCM (2×500 ml) and the combined organic extracts were dried, MgSO$_4$ filtered and evaporated to afford a brown solid which was washed with plenty of diethyl ether to afford more of the desired product as a pale green solid (7.7 g): LCMS and NMR consistent with product (20% of oxidized material present by NMR).

MS (ES+) m/z 180 (MH$^+$).

Alternative Procedure

Ethyl N-[2-amino-6-(methyloxy)-3-pyridinyl]glycinate (16.2 g, 72 mmol) was dissolved in tetrahydrofuran (500 ml) and cooled to 0° C. (ice bath cooling) under argon. This was then treated with potassium tert-butoxide (1M in THF, 80 ml, 80 mmol). After 1.5 h the reaction was treated with acetic acid (80 mmol) and evaporated to give a dark solid. This was triturated with water (200 ml), filtered and dried in vacuo (~13 g, quant.), which may be used without further purification (e) Phenylmethyl 6-(methyloxy)-3-oxo-3,4-dihydropyrido[2,3-b]pyrazine-1(2H)-carboxylate To 6-(methyloxy)-1,4-dihydropyrido[2,3-b]pyrazin-3 (2H)-one (6.35 g, 35.4 mmol) in ethyl acetate (600 ml)/sodium bicarbonate (sat. solution) (200 ml) stirred vigorously was added at room temperature benzyl chloroformate (5.31 ml, 37.2 mmol). After 45 minutes the reaction was complete. The layers were separated and the organic layer was dried on magnesium sulphate, filtered and evaporated to afford the desired product as an off-white solid (11 g, 99%).

MS (ES+) m/z 314 (MH$^+$).

(f) Phenylmethyl 6-(methyloxy)-4-[(2R)-2-oxiranylmethyl]-3-oxo-3,4-dihydropyrido[2,3-b]pyrazine-1(2H)-carboxylate Phenylmethyl 6-(methyloxy)-3-oxo-3,4-dihydropyrido[2,3-b]pyrazine-1(2H)-carboxylate (11 g, 35.1 mmol) was dissolved in DMF (300 ml) at room temperature under argon to give a yellow solution. The solution was then cooled with an ice bath and treated with sodium hydride (1.685 g, 42.1 mmol). The solution was allowed to warm to room temperature. After 20 minutes (2S)-2-oxiranylmethyl 3-nitrobenzenesulfonate (9.56 g, 36.9 mmol) was added. After 1 h all the starting material was consumed so the reaction was treated with a saturated solution of sodium bicarbonate (350 ml) and the aqueous layer was extracted with DCM (3×400 ml). The combined organic layers were dried on magnesium sulphate, filtered and evaporated to afford a light brown oil (16.93 g). The product was used as crude in the next step.

MS (ES+) m/z 370 (MH$^+$).

(g) Phenylmethyl (1S)-1-(hydroxymethyl)-3,8-dioxo-1,2,3,4-tetrahydro-5H,8H-2a,5,8a-triazaacenaphthylene-5-carboxylate Phenylmethyl 6-(methyloxy)-4-[(2R)-2-oxiranylmethyl]-3-oxo-3,4-dihydropyrido[2,3-b]pyrazine-1(2H)-carboxylate (crude, 15.93 g, estimated 32.8 mmol) was dissolved in DMF (250 ml) at room temperature and heated at 130° C. for 2 nights and at 120° C. for one night. The reaction was complete so DMF was evaporated and the residue treated with water/brine (350/50 ml) and DCM (500 ml). The layers were separated and the aqueous layer was extracted once more with DCM (500 ml). The combined organic extracts were dried on magnesium sulphate, filtered and evaporated to afford a brown oil which was dried under high vacuum over the weekend. The crude product was purified by silica chromatography using a 0-10% methanol/dichloromethane gradient to afford the desired product as a golden foam (3.6 g, 30.9%).

MS (ES+) m/z 356 (MH$^+$).

(h) (1S)-1-(Hydroxymethyl)-1,2-dihydro-3H,8H-2a,5,8a-triazaacenaphthylene-3,8-dione Phenylmethyl (1S)-1-(hydroxymethyl)-3,8-dioxo-1,2,3,4-tetrahydro-5H,8H-2a,5,8a-triazaacenaphthylene-5-carboxylate (1.6 g, 4.50 mmol) was dissolved in ethanol (100 ml) at room temperature and then treated with palladium on carbon (10% paste) (1 g, 0.940 mmol). Everything was stirred at room temperature under 1 atm of hydrogen for 3 hours. The reaction was then filtered through a Celite pad and the impurities washed with more ethanol. The product was then eluted with DMF (400 ml) and the DMF evaporated to afford a brown solid (780 mg). The solid was then suspended in 30% MeOH/DCM (150 ml) and stirred with manganese dioxide (1.174 g, 13.51 mmol) at room temperature for 5 h and then filtered through a pad of Celite which was washed with 20% methanol/dichloromethane (100 ml). The solvents were evaporated to afford the desired compound as a brown solid (750 mg, 76%).

MS (ES+) m/z 220 (MH$^+$).

(i) [(1S)-3,8-Dioxo-1,2-dihydro-3H,8H-2a,5,8a-triazaacenaphthylen-1-yl]methyl methanesulfonate (1S)-1-(Hydroxymethyl)-1,2-dihydro-3H,8H-2a,5,8a-triazaacenaphthylene-3,8-dione (750 mg, 3.42 mmol) was suspended in dry DCM (100 ml) at room temperature under argon and then treated with triethylamine (0.572 ml, 4.11 mmol). The mixture was then cooled using an ice-water bath. Methanesulfonyl chloride (0.293 ml, 3.76 mmol) was then added and the reaction was allowed to warm up to room temperature. After 50 minutes there was no starting material left so the mixture was washed with saturated NaHCO$_3$ (100 ml). The aqueous layer was extracted with 20% MeOH/

DCM (2×100 ml); the combined organic extracts were dried on magnesium sulphate, filtered and evaporated to afford the product as a brown foam (1.05 g, 90% purity by LCMS).

MS (ES+) m/z 297.9 (MH+).

(j) 1,1-Dimethylethyl (1-{[(1R)-3,8-dioxo-1,2-dihydro-3H,8H-2a,5,8a-triazaacenaphthylen-1-yl]methyl}-4-piperidinyl)carbamate A solution of [(1S)-3,8-dioxo-1,2-dihydro-3H,8H-2a,5,8a-triazaacenaphthylen-1-yl]methyl methanesulfonate (1.05 g, 3.53 mmol) in dry acetonitrile (50 ml) at room temperature under argon was treated with pyridine (0.343 ml, 4.24 mmol), followed by 1,1-dimethylethyl 4-piperidinylcarbamate (0.884 g, 4.24 mmol). The mixture was heated at 70° C. for 1.5 h and then at 90° C. for 3 h. LCMS showed ~25% of product. So 0.5 eq of pyridine and 0.5 eq of 1,1-dimethylethyl 4-piperidinylcarbamate were added and the reaction was heated at 90° C. overnight and then stirred at room temperature for 2 days.

The reaction was complete. The solvent was evaporated and the residue partitioned between sat NaHCO$_3$ and 20% methanol/dichloromethane (100 ml/100 ml). The layers were separated and the aqueous layer was extracted with 20% methanol/dichloromethane again (2×100 ml). The combined organic extracts were dried on magnesium sulphate, filtered and evaporated to afford 1.7 g of crude which was purified by silica chromatography using a 0-5% methanol/dichloromethane gradient to afford the product as a yellow solid (0.57 g, 40.2%).

MS (ES+) m/z 402 (MH+).

(k) (1R)-1-[(4-Amino-1-piperidinyl)methyl]-1,2-dihydro-3H,8H-2a,5,8a-triazaacenaphthylene-3,8-dione dihydrochloride A solution of 1,1-dimethylethyl (1-{[(1R)-3,8-dioxo-1,2-dihydro-3H,8H-2a,5,8a-triazaacenaphthylen-1-yl]methyl}-4-piperidinyl)carbamate (0.57 g, 1.420 mmol) in chloroform (7 ml) at room temperature was treated with 4M HCl in 1,4-dioxane (7 ml). A solid precipitated out and the mixture was stirred at room temperature. After 0.5 h some methanol was added to dissolve most of the solid, followed by toluene and all the solvents were removed to afford the product as a yellow solid (0.53 g, 100%).

MS (ES+) m/z 302 (MH+).

(l) Title Compound

A suspension of (1R)-1-[(4-amino-1-piperidinyl)methyl]-1,2-dihydro-3H, 8H-2a,5,8a-triazaacenaphthylene-3,8-dione dihydrochloride (165 mg, 0.441 mmol) in chloroform (10 ml) and methanol (0.4 ml) at room temperature under argon was treated with triethylamine (0.184 ml, 1.323 mmol) and stirred for 0.25 h (the suspension turned into a solution). [1,3]Oxathiolo[5,4-c]pyridine-6-carbaldehyde (for a synthesis see WO2004058144 Example 61) (73.7 mg, 0.441 mmol) was then added and the reaction was stirred at room temperature for 0.5 h. Sodium triacetoxyborohydride (280 mg, 1.323 mmol) was then added and the reaction was stirred at room temperature. After 1.5 h LCMS showed that there was still some imine present in the mixture so 1 eq of sodium triacetoxyborohydride was added. After 1 h saturated NaHCO$_3$ (50 ml) was added followed by 20% methanol/dichloromethane (80 ml) and the aqueous layer was extracted and then separated from the organic layer. The aqueous layer was extracted again twice with 20% methanol/dichloromethane (2×80 ml). The combined organic extracts were dried on magnesium sulphate, filtered and evaporated to afford 215 mg of crude product which was purified by silica chromatography using a 0-20% methanol/dichloromethane gradient to afford the free base of the title compound as a yellow solid (185 mg, 93%).

δH CDCl$_3$, (250 MHz) 1.20-1.45 (m, 2H), 1.75-2.75 (m, 8H), 2.94 (d, 1H), 3.00-3.15 (m, 1H), 3.81 (s, 2H), 4.30-4.45 (m, 1H), 4.50-4.65 (m, 1H), 4.90-5.10 (m, 1H), 5.74 (s, 2H), 6.34 (d, 1H), 7.19 (s, 1H), 7.77 (d, 1H), 7.87 (s, 1H), 7.99 (s, 1H).

MS (ES+) m/z 453 (MH+).

The title compound was prepared by dissolving the free base in methanol/dichloromethane and treating it with 1 equivalent of 1M HCl in diethyl ether.

This was then evaporated to dryness and dried in the vacuum desiccator in the presence of P$_2$O$_5$.

Example 13B (1R)-1-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione benzoate (1R)-1-({4-[([1,3]Oxathiolo[5,4-c]pyridin-6-ylmethyl)amino]-1-piperidinyl}methyl)-1,2-dihydro-3H, 8H-2a,5,8a-triazaacenaphthylene-3,8-dione hydrochloride (45 mg, 0.092 mmol) was purified using an AD-H column with CH$_3$CN:CH$_3$OH:0.1% isopropylamine. The major peak was collected and the solvent was removed. The benzoate salt was made by dissolving the compound in MeOH and adding one equivalent of the benzoic acid. The solution stirred for 1 hour, the solvent was removed to give the product.

Example 13C (1R)-1-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione fumarate (1R)-1-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione hydrochloride (49 mg, 0.100 mmol) was dissolved in MeOH 10 mL and loaded onto a SCX cartridge 2 g (pre-wet with methanol). The crude was adsorbed onto the cartridge and then the cartridge was washed with methanol (15 mL). The product was eluted using 2M NH$_3$ in methanol (15 mL); the fraction containing the product was evaporated to afford free amine product (41.5 mg, 92% recovery). LCMS and NMR consistent with product. The free amine was dissolved in a small amount of DCM/MeOH, treated with 1 eq of fumaric acid (10.6 mg) and stirred for 10 minutes. Solvents were removed and the solid dried in the desiccator (P$_2$O$_5$) overnight to afford the product as a white solid (51 mg, LCMS and NMR consistent with product).

Example 14 (1R)-1-({4-[(2,3-Dihydro[1,4]oxathiino[2,3-c]pyridin-7-ylmethyl)amino]-1-piperidinyl}methyl)-1,2-dihydro-3H,8H-2a,5,8a-triazaacenaphthylene-3,8-dione hydrochloride

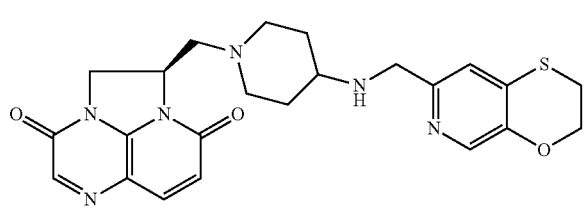

A suspension of (1R)-1-[(4-amino-1-piperidinyl)methyl]-1,2-dihydro-3H,8H-2a,5,8a-triazaacenaphthylene-3,8-dione dihydrochloride (160 mg, 0.428 mmol) (for a preparation see Example 13(k) or 15(d)) in chloroform (10 ml) and methanol (0.400 ml) under argon at room temperature was treated with triethylamine (0.179 ml, 1.283 mmol) and stirred for 0.25 h at room temperature (everything went into solution). 2,3-Dihydro[1,4]oxathiino[2,3-c]pyridine-7-carbaldehyde (for a synthesis see WO2004058144, Example 60) (77 mg, 0.428 mmol) was then added and the reaction was stirred at room temperature for 0.5 h. Sodium triacetoxyborohydride (272 mg, 1.283 mmol) was then added and the reaction was stirred at room temperature. After 1.5 h there was still some imine present by LCMS so 1 equivalent of sodium triacetoxyborohydride was added. After 1 h sat NaHCO$_3$ (50 ml) was added followed by 20% methanol/dichloromethane (80 ml) and the aqueous was extracted and then separated from the organic layer. The aqueous layer was extracted again twice with 20% methanol/dichloromethane (2×80 ml). The combined organic extracts were dried on MgSO$_4$, filtered and evaporated to afford 215 mg of crude product which was purified by silica chromatography using a 0-20% methanol/dichloromethane gradient to afford the free base of the title compound as yellow foam (179 mg, 90%).

δH CDCl$_3$, (250 MHz) 1.20-1.50 (m, 2H), 1.85 (t, 2H), 1.95-2.40 (m, 3H), 2.45-2.75 (m, 3H), 2.94 (d, 1H), 3.05-3.20 (m, 3H), 3.69 (s, 2H), 4.30-4.50 (m, 3H), 4.50-4.65 (m, 1H), 4.90-5.10 (m, 1H), 6.33, (d, 1H), 6.99 (s, 1H), 7.67 (d, 1H), 7.86 (s, 1H), 8.01 (s, 1H).

MS (ES+) m/z 467 (MH$^+$).

The title compound was prepared by dissolving the free base in DCM/MeOH and treating it with 1 equivalent of 1M HCl in diethyl ether. This was then evaporated to dryness and dried in the vacuum desiccator in the presence of P$_2$O$_5$.

Example 15 (1R)-1-({4-[(2,3-Dihydro[1,4]dioxino[2,3-c]pyridin-7-ylmethyl)amino]-1-piperidinyl}methyl)-1,2-dihydro-3H,8H-2a,5,8a-triazaacenaphthylene-3,8-dione dihydrochloride

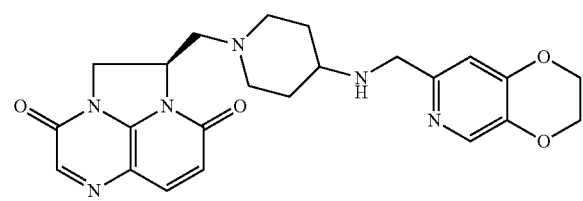 [SMILES: O=c1cnc2ccc(=O)n3c2n1C[C@H]3CN1CCC(NCc2cc3c(cn2)OCCO3)CC1]

(a) Phenylmethyl (1S)-1-{[(methylsulfonyl)oxy]methyl}-3,8-dioxo-1,2,3,4-tetrahydro-5H,8H-2a,5,8a-triazaacenaphthylene-5-carboxylate Phenylmethyl (1S)-1-(hydroxymethyl)-3,8-dioxo-1,2,3,4-tetrahydro-5H,8H-2a,5,8a-triazaacenaphthylene-5-carboxylate (242 mg, 0.681 mmol) (for a preparation see Example 13(g)) was dissolved in DCM (10 ml) at room temperature under argon and then treated with triethylamine (0.114 ml, 0.817 mmol). The mixture was then cooled using an ice-water bath. Methanesulfonyl chloride (0.058 ml, 0.749 mmol) was then added and the reaction was allowed to warm up to room temperature. After 1 h the mixture was washed with sat NaHCO$_3$ (10 ml). The aqueous layer was extracted with DCM (2×50 ml) and the combined organic extracts dried on MgSO$_4$, filtered and evaporated to afford the product as a yellow foam (232 mg, 95% purity by LCMS, 74.7%).

MS (ES+) m/z 434 (MH$^+$).

(b) Phenylmethyl (1R)-1-{[4-({[(1,1-dimethylethyl)oxy]carbonyl}amino)-1-piperidinyl]methyl}-3,8-dioxo-1,2,3,4-tetrahydro-5H, 8H-2a,5,8a-triazaacenaphthylene-5-carboxylate Phenylmethyl (1S)-1-{[(methylsulfonyl)oxy]methyl}-3,8-dioxo-1,2,3,4-tetrahydro-5H,8H-2a,5,8a-triazaacenaphthylene-5-carboxylate (232 mg, 0.508 mmol) was dissolved in dry acetonitrile (10 ml) at room temperature under argon and treated with pyridine (0.049 ml, 0.610 mmol). 1,1-Dimethylethyl 4-piperidinylcarbamate (127 mg, 0.610 mmol) was then added and the reaction was heated at 70° C. overnight. Then 0.049 ml of pyridine and 127 mg of 1,1-dimethylethyl 4-piperidinylcarbamate were added to the reaction and the temperature was increased to 80° C. for 8 h and then the reaction was stirred at room temperature overnight. The solvent was evaporated and the residue partitioned between sat NaHCO$_3$ and DCM (50/50 ml). The layers were separated and the aqueous layer was extracted with DCM again (2×50 ml). The combined organic extracts were dried (MgSO$_4$) filtered and evaporated to afford 280 mg of crude product which was purified by silica chromatography using a 0-5% methanol/dichloromethane gradient to afford the product as a yellow gum (130 mg, 47.6%).

MS (ES+) m/z 538 (MH$^+$).

(c) 1,1-Dimethylethyl (1-{[(1R)-3,8-dioxo-1,2-dihydro-3H,8H-2a,5,8a-triazaacenaphthylen-1-yl]methyl}-4-piperidinyl)carbamate Phenylmethyl (1R)-1-{[4-({[(1,1-dimethylethyl)oxy]carbonyl}amino)-1-piperidinyl]methyl}-3,8-dioxo-1,2,3,4-tetrahydro-5H, 8H-2a,5,8a-triazaacenaphthylene-5-carboxylate (130 mg, 0.242 mmol) was dissolved in ethanol (10 ml) at room temperature and then treated with palladium on carbon (10% paste) (100 mg, 0.094 mmol). Everything was stirred at room temperature under 1 atm of hydrogen for 3 hours. The reaction was then filtered through a Celite pad and washed with more ethanol (50 ml). The ethanol was evaporated to afford a yellow gum (79 mg) which was dissolved in DCM (~10 ml) and stirred with manganese dioxide (63.1 mg, 0.725 mmol) at room temperature overnight. Then 1.5 equivalents more of manganese dioxide were added (32 mg) and reaction was stirred at room temperature for 3 h. There was still starting material present by LCMS so 2 equivalents of manganese dioxide were added. The reaction was stirred at room temperature for 2 h then filtered through a Celite pad. The Celite pad was washed with DCM and the solvents were evaporated to afford the product as a brown solid (76 mg, 78%).

MS (ES+) m/z 402 (MH$^+$).

(d) (1R)-1-[(4-Amino-1-piperidinyl)methyl]-1,2-dihydro-3H,8H-2a,5,8a-triazaacenaphthylene-3,8-dione dihydrochloride A solution of 1,1-dimethylethyl (1-{[(1R)-3,8-dioxo-1,2-dihydro-3H,8H-2a,5,8a-triazaacenaphthylen-1-yl]methyl}-4-piperidinyl)carbamate (76 mg, 0.189 mmol) in chloroform (2 ml) at room temperature was treated with 4M HCl in 1,4-dioxane (2 ml). A solid precipitated out and the mixture was stirred room temperature. After 0.5 h the reaction was complete so some methanol was added to dissolve most of the solid, followed by toluene and all the solvents were removed to afford the product as a dark yellow solid (70.9 mg, 99%).

MS (ES+) m/z 302 (MH$^+$).

(e) Title Compound

A suspension of (1R)-1-[(4-amino-1-piperidinyl)methyl]-1,2-dihydro-3H, 8H-2a,5,8a-triazaacenaphthylene-3,8-dione dihydrochloride (70 mg, 0.187 mmol) in chloroform (5 ml) and methanol (0.2 ml) at room temperature under argon was treated with triethylamine (0.078 ml, 0.561 mmol) and stirred for 0.25 h. Everything went into solution; 2,3-dihydro[1,4]dioxino[2,3-c]pyridine-7-carbaldehyde (for a synthesis see WO2004058144 Example 2(c) or WO03/087098 Example 19(d))) (30.9 mg, 0.187 mmol) was then added and the reaction was stirred at room temperature for 0.5 h. Sodium triacetoxyborohydride (119 mg, 0.561 mmol) was then added and the reaction was stirred at room temperature. After 1.5 h 1 eq more of sodium triacetoxyborohydride was added. After 1 h sat NaHCO$_3$ (50 ml) was added followed by 20% MeOH/DCM (50 ml) and the aqueous layer was extracted and then separated from the organic layer. The aqueous layer was extracted again twice with 20% MeOH/DCM (2×50 ml). The combined organic extracts were dried on MgSO$_4$, filtered and evaporated to afford 90 mg of crude product which was purified by silica chromatography using a 0-20% methanol/dichloromethane gradient to afford the free base of the title compound as a pale yellow gum (60 mg, 71%).

δH CDCl$_3$, (250 MHz) 1.25-1.50 (m, 2H), 1.86 (t, 2H), 2.10-2.75 (m, 6H), 2.93 (d, 1H), 3.00-3.15 (m, 1H), 3.79 (s, 2H), 4.20-4.45 (m, 5H), 4.50-4.65 (m, 1H), 4.90-5.10 (m, 1H), 6.33 (d, 1H), 6.82 (s, 1H), 7.76 (d, 1H), 7.86 (s, 1H), 8.11 (s, 1H).

MS (ES+) m/z 451 (MH$^+$).

The title compound was prepared by dissolving the free base in DCM/MeOH and treating it with 2 equivalents of 1M HCl in diethyl ether. This was then evaporated to dryness and dried in the vacuum desiccator in the presence of P$_2$O$_5$.

Example 16A (2R)-2-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione hydrochloride

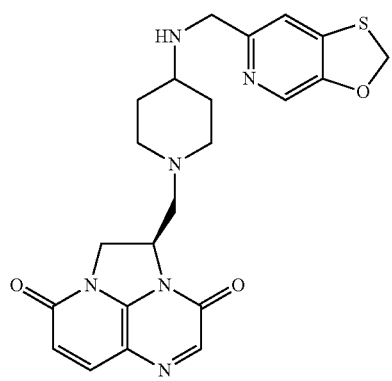 [SMILES: O=c1ccc2ncc(=O)n3c2n1C[C@H]3CN1CCC(NCc2cc3c(cn2)OCS3)CC1]

(a) 2-{[6-(Methyloxy)-3-nitro-2-pyridinyl]amino}-1,3-propanediol

6-Methoxy-2-chloro-3-nitropyridine (36.94 g, 195.9 mmol) and 2-aminopropane-1.3-diol (35.65 g, 391.3 mmol, 2 eq.) were stirred in ethanol (500 ml) at reflux under argon for 3 hours. The mixture was allowed to cool to room temperature and left overnight. The solvent was partially removed under reduced pressure (to ca. 150 ml) and the resulting bright yellow slurry was poured into ice-water (1.5 L) with vigorous stirring. The mixture was stirred for 1 hour then filtered with suction while cold. The solid was washed with ice-cold water (200 ml) and air-dried. to give the title compound as a bright yellow solid (45.03 g, 94%). LCMS showed desired product (93%) plus 7% starting material. The product was used without further purification.

MS (ES+) m/z 244 (MH$^+$)

(b) N-(2,2-Dimethyl-1,3-dioxan-5-yl)-6-(methyloxy)-3-nitro-2-pyridinamine

2-{[6-(Methyloxy)-3-nitro-2-pyridinyl]amino}-1,3-propanediol (53.93 g, 228.7 mmol) was stirred in 2,2-dimethoxypropane (900 ml) under argon and p-toluenesulphonic acid monohydrate (1.00 g) was added. The mixture was stirred at room temperature overnight. This was diluted with dichloromethane (1 L) and the resulting solution was treated with saturated aqueous sodium hydrogen carbonate (20 ml) and solid sodium hydrogen carbonate (20 g) with vigorous stirring (effervescence). The mixture was vigorously stirred for 20 minutes, then the remaining water was absorbed by addition of anhydrous sodium sulphate. The mixture was filtered with suction and the solids were washed with DCM (500 ml). The combined filtrate plus washings were evaporated under reduced pressure to give a yellow solid which was stirred with petroleum ether (40-60°) over the weekend. The solid was isolated by filtration with suction, washed with petroleum ether (40-60) and air-dried to give the title compound as a bright yellow solid 57.83 g, 92%).

MS (ES+) m/z 284 (MH$^+$).

(c) N$^2$-(2,2-Dimethyl-1,3-dioxan-5-yl)-6-(methyloxy)-2,3-pyridinediamine

N-(2,2-Dimethyl-1,3-dioxan-5-yl)-6-(methyloxy)-3-nitro-2-pyridinamine (35.00 g, 123.6 mmol) was divided into 2 aliquots, each of which was taken up in 1,4-dioxane (500 ml) and hydrogenated over 10% Pd on carbon (paste, 1:1 w:w with water, 4.00 g) under 1 atm. hydrogen pressure, at room temperature overnight. The mixtures were filtered with suction though Celite, using an argon blanket and taking care to minimise contact of the product with air. The solution was evaporated under reduced pressure to give the title compound as a deep purple oil. This was used immediately in the next step.

MS (ES+) m/z 254 (MH$^+$).

(d) Ethyl N-[2-[(2,2-dimethyl-1,3-dioxan-5-yl)amino]-6-(methyloxy)-3-pyridinyl]glycinate Crude N$^2$-(2,2-dimethyl-1,3-dioxan-5-yl)-6-(methyloxy)-2,3-pyridinediamine prepared in Example 16A(c) (assumed 123.6 mmol) was dissolved in anhydrous DMF (500 ml) under argon and anhydrous potassium carbonate (37.56 g, 2.2 eq.) was added, followed by ethyl bromoacetate (12.31 ml, 0.9 eq.). The mixture was stirred at room temperature overnight. The solvent was removed under reduced pressure and the resulting reddish-brown slurry was partitioned between DCM (1.2 L) and water (300 ml). The organic phase was separated and washed with water (300 ml), dried over sodium sulphate, filtered and evaporated under reduced pressure to give a dark red oil, this was taken up in a minimum of DCM and purified by column chromatography on silica (eluted with 5%-60% ethyl acetate in petroleum ether (40-600)). Appropriate fractions were combined and evaporated under reduced pressure to give the title compound as a dark orange oil (35.42 g, 84%).

MS (ES+) m/z 340 (MH$^+$)

(e) 4-(2,2-Dimethyl-1,3-dioxan-5-yl)-6-(methyloxy)-1,4-dihydropyrido[2,3-b]pyrazin-3(2H)-one Ethyl N-[2-[(2,2-dimethyl-1,3-dioxan-5-yl)amino]-6-(methyloxy)-3-pyridinyl]glycinate (35.42 g, 104.4 mmol) was dissolved in dry THF (500 ml) and the solution was added dropwise over 2 hours to a cooled (0° C.) suspension of sodium hydride (4.173 g of 60% w:w dispersion in oil, 1.00 eq.) in dry THF (500 ml) under argon. During the addition the colour of the suspension changed from orange to green. The mixture was stirred at 0° C. for a further 15 minutes, then allowed to warm to room temperature and stirred at rt for 1 hour. The mixture was cooled to 0° C. and saturated ammonium chloride (15 ml) was added cautiously with vigorous stirring (effervescence observed). After effervescence had ceased, the mixture was allowed to warm to room temperature and stirred for 4 hours then diluted with ethyl acetate (500 ml) and filtered with suction. The solids were washed with ethyl acetate (300 ml) and the combined filtrate plus washings were evaporated under reduced pressure to give a dark brown solid. This was stirred with petroleum ether (40-60°) (500 ml) plus ethyl acetate (20 ml) for 2 h and filtered with suction to give a lighter brown solid which was washed with petroleum ether (40-60°) (100 ml) and air-dried to afford the title compound as an amorphous tan solid (25.37 g, 82.8%).

MS (ES+) m/z 316 (MNa$^+$).

(f) 4-(2,2-Dimethyl-1,3-dioxan-5-yl)-6-(methyloxy)pyrido[2,3-b]pyrazin-3(4H)-one 4-(2,2-Dimethyl-1,3-dioxan-5-yl)-6-(methyloxy)-1,4-dihydropyrido[2,3-b]pyrazin-3(2H)-one (25.37 g) and activated manganese dioxide (120 g, ~15 eq.) were stirred in DCM (500 ml) at room temperature for 2 hours then overnight. The mixture was filtered with suction and the solids were washed with DCM (2×100 ml). The combined filtrate plus washings were evaporated under reduced pressure to give a brown foam; this was purified by column chromatography on silica (eluting with 0%-100% ethyl acetate in petroleum ether (40-600)). Appropriate fractions were combined and evaporated under reduced pressure to give the title compound as a light tan solid (17.40 g, 69%).

MS (ES+) m/z 314 (MNa$^+$).

(g) 4-[2-Hydroxy-1-(hydroxymethyl)ethyl]-6-(methyloxy)pyrido[2,3-b]pyrazin-3(4H)-one 4-(2,2-Dimethyl-1,3-dioxan-5-yl)-6-(methyloxy)pyrido[2,3-b]pyrazin-3(4H)-one (17.40 g, 59.7 mmol) was dissolved in tetrahydrofuran (THF) (220 ml) to give a dark yellow solution. 1M HCl aq. (200 ml) was added (transient blue and green colours appeared in the solution) and the now light yellow solution was stirred at room temperature for 1 hour. The mixture was concentrated to ca.300 ml on a rotary evaporator using a cold water bath (some solid was precipitated during this procedure) then was stirred vigorously while solid sodium hydrogen carbonate was added in portions (caution: effervescence) until the mixture was ca. pH 8. The resulting yellow solid was collected by filtration with suction, washed with water (2×20 ml) and air-dried to give the title compound as an amorphous yellow solid (13.805 g, 91%).

MS (ES+) m/z 252 (MH$^+$).

(h) (3,8-Dioxo-1,2,5a,8b-tetrahydro-3H,8H-2a,5,8a-triazaacenaphthylen-2-yl)methyl methanesulfonate In a 1 L round-bottomed flask was placed 4-[2-hydroxy-1-(hydroxymethyl)ethyl]-6-(methyloxy)pyrido[2,3-b]pyrazin-3(4H)-one (11.330 g, 45.1 mmol). Anhydrous chloroform (280 ml) was added, followed by triethylamine (31.4 ml, 225 mmol), and methanesulfonic anhydride (31.4 g, 180 mmol) to give a dark yellow-brown solution. During addition of the methanesulphonic anhydride, an exotherm occurred which was sufficient to cause the solvent to boil. The mixture was stirred vigorously at reflux under argon for 4.5 hours. The mixture was allowed to cool to room temperature, diluted with DCM to ca. 600 ml, and washed with water (200 ml). The organic phase was separated, and the aqueous phase was extracted with DCM (2×200 ml). The combined organic extracts were dried over anhydrous sodium sulphate, filtered, and evaporated under reduced pressure to give crude mesylate as a dark brown oil. This was left overnight under 40-60° petroleum ether (200 ml) plus DCM (50 ml). The resulting solid was isolated by filtration with suction, washed with 4:1 petrol:DCM (2×50 ml) and air-dried to give the title compound as a brown amorphous solid (6.950 g, 52%)

MS (ES+) m/z 332 (MNa$^+$), 298 (MH$^+$).

(i) 1,1-Dimethylethyl {1-[(3,8-dioxo-1,2-dihydro-3H,8H-2a,5,8a-triazaacenaphthylen-2-yl)methyl]-4-piperidinyl}carbamate Crude (3,8-dioxo-1,2,5a,8b-tetrahydro-3H,8H-2a,5,8a-triazaacenaphthylen-2-yl)methyl methanesulfonate (6.950 g, 23.38 mmol) was dissolved in dry acetonitrile (200 ml) and the mixture was treated with pyridine (7.55 ml, 94.0 mmol) followed by 1,1-dimethylethyl 4-piperidinylcarbamate (10.30 g, 51.4 mmol). The mixture was stirred at reflux under argon for 3 h then at 50° C. over the weekend. The mixture was then stirred at 90° C. for 2 hours, then the volatiles were removed under reduced pressure and the residue was partitioned between DCM (600 ml) and water (100 ml). The organic phase was separated and the aqueous phase was extracted with DCM (2×200 ml). The combined organic extracts were washed with water (2×100 ml) dried over anhydrous sodium sulphate, filtered and evaporated under reduced pressure to give a dark tan solid; this was taken up in a minimum of 5% MeOH in DCM and chromatographed on silica, eluting with 0-10% MeOH in DCM. Appropriate fractions were combined and evaporated under reduced pressure to give the title compound as an amorphous pale tan solid (5.444 g, 56.8%).

MS (ES+) m/z 424 (MNa$^+$), 402 (MH$^+$).

(j) 2-[(4-Amino-1-piperidinyl)methyl]-1,2-dihydro-3H,8H-2a,5,8a-triazaacenaphthylene-3,8-dione (Racemic and Enantiomer 1 and 2 synthesis)

Method A (Racemic Synthesis)

1,1-Dimethylethyl {1-[(3,8-dioxo-1,2-dihydro-3H,8H-2a,5,8a-triazaacenaphthylen-2-yl)methyl]-4-piperidinyl} carbamate (1.630 g, 4.06 mmol) was suspended in DCM (30 ml) and 4M HCl in 1,4-dioxane (15 ml) was added to give a bright yellow suspension (and gas evolution). The bright yellow mixture was allowed to stand at room temperature for 1 hour. LCMS showed no starting material remaining. The solvents were removed under reduced pressure and the residue was dried under reduced pressure overnight to give the dihydrochloride salt of the title compound as an amorphous tan solid (1.760 g (>theoretical yield for the dihydrochloride owing to the presence of residual solvent).

A portion of the crude dihydrochloride (0.513 g) was dissolved in methanol (4 ml) plus water (1 ml) and applied to an SCX column (10 g) (preconditioned with 2 column volumes of methanol). The column was then eluted, under gravity, using (i) methanol (2×50 ml), (ii) 0.5M ammonia in methanol (3×50 ml fractions). Appropriate fractions were combined and evaporated under reduced pressure to give the crude title compound as a tan amorphous solid (410 mg), which contained methanol-insoluble material not apparent by LCMS (possibly ammonium chloride). The product was shaken with methanol (30 ml) and the suspension was filtered. The solid was washed with methanol (20 ml) and the combined filtrate and washings were evaporated under reduced pressure to give the title compound (360 mg, 87%).
MS (ES+) m/z 302 (MH$^+$).

Method B 1,1-Dimethylethyl {1-[(3,8-dioxo-1,2-dihydro-3H,8H-2a,5,8a-triazaacenaphthylen-2-yl)methyl]-4-piperidinyl}carbamate (9.735 g, 24.25 mmol) was suspended in DCM (90 ml) and 4M HCl in 1,4-dioxane (45 ml) was added to give a bright yellow suspension (and gas evolution). The bright yellow mixture was stirred at room temperature for 1 hour. The solvents were removed under reduced pressure to give the crude dihydrochloride as a bright yellow amorphous solid (10.420 g) containing residual solvent)

The racemic dihydrochloride (10.4 g) was resolved into its two enantiomers by preparative chiral HPLC using a Chiralpak AD (20 microns) preparative column with 50:50:0.1 acetonitrile:methanol:isopropylamine as the mobile phase in three batches. The alpha value was 3.1 and baseline resolution was observed for all 3 runs. There was no overlap fraction and both enantiomers (as the free bases) were isolated in >99.8 ee each. (2R)-2-[(4-Amino-1-piperidinyl)methyl]-1,2-dihydro-3H,8H-2a,5,8a-triazaacenaphthylene-3,8-dione (first component eluted): (3.30 g, light beige solid, chiral
HPLC: 100% ee).
MS (ES+) m/z 302 (MH$^+$).
Optical rotation: alpha D=−120° (C=1.00, methanol, 21.8° C.).
(2S)-2-[(4-Amino-1-piperidinyl)methyl]-1,2-dihydro-3H,8H-2a,5,8a-triazaacenaphthylene-3,8-dione (second component eluted): (3.30 g, light beige solid, chiral HPLC: 99.8% ee).
MS (ES+) m/z 302 (MH$^+$).
Optical rotation: alpha D=+1220 (C=1.00, methanol, 21.8° C.).

(k) Title Compound (2R)-2-[(4-Amino-1-piperidinyl)methyl]-1,2-dihydro-3H, 8H-2a,5,8a-triazaacenaphthylene-3,8-dione (100 mg, 0.332 mmol) was stirred with [1,3]oxathiolo[5,4-c]pyridine-6-carbaldehyde (for a synthesis see WO2004058144

Example 61) (45 mg, 0.811 eq.) in chloroform:methanol (9:1, v:v, 5 ml) at room temperature for 2 hours; the mixture was then treated with sodium triacetoxyborohydride (211 mg, 3.0 eq.) with vigorous stirring at room temperature for 30 mins. The mixture was quenched by addition of saturated aqueous sodium hydrogen carbonate (1 ml). DCM (10 ml) was added and vigorous stirring was continued for 10 mins, followed by separation of the phases (hydrophobic frit). The organic phase was evaporated under reduced pressure and the crude product was purified by column chromatography on silica (eluting with 0-12% (2M NH$_3$ in MeOH) in DCM). Appropriate fractions were combined and evaporated under reduced pressure and dried on the vacuum line over the weekend to give the free base of the title compound as a pale yellow foam (70 mg, 44.3%)

MS (ES+) m/z 453 (MH$^+$).
$^1$H NMR (CDCl$_3$) 8.00 (1H, s); 7.82 (1H, s); 7.77 (1H, d, J=9.7 Hz); 7.18 (1H, s); 6.39 (1H, d, J=9.7 Hz); 5.73 (2H, s); 5.03 (1H, m); 4.55 (1H, dd, J=12.5 Hz, 4.6 Hz); 4.38 (1H, dd, J=12.5 Hz, 9.2 Hz); 3.80 (2H, s); 3.13 (1H, dd, J=12.9 Hz, 3.5 Hz); 2.93 (1H, m); 2.70 (1H, dd, J=12.9 Hz, 9.0 Hz); 2.67 (1H, m); 2.50 (1H, m); 2.33 (1H, dt, J=11.4 Hz, 2.6 Hz); 2.25 (1H, dt, J=11.4 Hz, 2.6 Hz); 1.85 (3H, m); 1.36 (2H, m).

Treatment of the above free base (70 mg) in DCM (1 ml) with one equivalent of 1M HCl in diethyl ether gave, after removal of solvents under reduced pressure, the title compound as a pale tan amorphous solid (75 mg).
MS (ES+) m/z 453 (MH$^+$).

Example 17A (2S)-2-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione hydrochloride

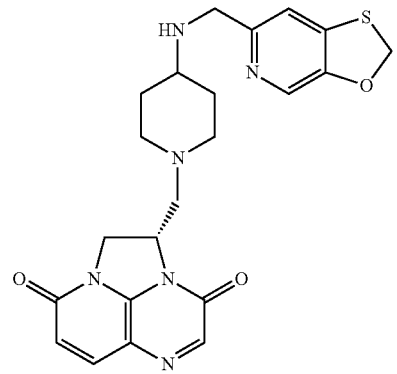 [SMILES: O=c1ccc2ncc(=O)n3c2n1C[C@@H]3CN1CCC(NCc2cc3c(cn2)OCS3)CC1]

(2S)-2-[(4-Amino-1-piperidinyl)methyl]-1,2-dihydro-3H,8H-2a,5,8a-triazaacenaphthylene-3,8-dione (for a preparation see Example 16A(j) (100 mg, 0.332 mmol) was stirred with [1,3]oxathiolo[5,4-c]pyridine-6-carbaldehyde (for a synthesis see WO2004058144 Example 61) (45 mg, 0.811 eq.) in chloroform:methanol (9:1, v:v, 5 ml) at room temperature for 2 hours; the mixture was then treated with sodium triacetoxyborohydride (211 mg, 3.0 eq.) with vigorous stirring at room temperature for 30 mins. The mixture was quenched by addition of saturated aqueous sodium hydrogen carbonate (1 ml). DCM (10 ml) was added and vigorous stirring was continued for 10 mins, followed by separation of the phases (hydrophobic frit). The organic phase was evaporated under reduced pressure and the crude product was purified by column chromatography on silica (2M $NH_3$ in MeOH) in DCM. Appropriate fractions were combined and evaporated under reduced pressure and dried on the vacuum line over the weekend to give the free base of the title compound as a pale yellow foam (91 mg, 61%).

MS (ES+) m/z 453 ($MH^+$).

$^1$H NMR ($CDCl_3$) (identical to that of (2R) enantiomer, Example 16A) 8.00 (1H, s); 7.82 (1H, s); 7.77 (1H, d, J=9.7 Hz); 7.18 (1H, s); 6.39 (1H, d, J=9.7 Hz); 5.73 (2H, s); 5.03 (1H, m); 4.55 (1H, dd, J=12.5 Hz, 4.6 Hz); 4.38 (1H, dd, J=12.5 Hz, 9.2 Hz); 3.80 (2H, s); 3.13 (1H, dd, J=12.9 Hz, 3.5 Hz); 2.93 (1H, m); 2.70 (1H, dd, J=12.9 Hz, 9.0 Hz); 2.67 (1H, m); 2.50 (1H, m); 2.33 (1H, dt, J=11.4 Hz, 2.6 Hz); 2.25 (1H, dt, J=11.4 Hz, 2.6 Hz); 1.85 (3H, m); 1.36 (2H, m).

Treatment of the above free base in DCM (1 ml) with one equivalent of 1M HCl in diethyl ether gave, after removal of solvents under reduced pressure, the title compound as an amorphous yellow solid (95 mg).

MS (ES+) m/z 453 ($MH^+$).

Example 18 2-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione hydrochloride

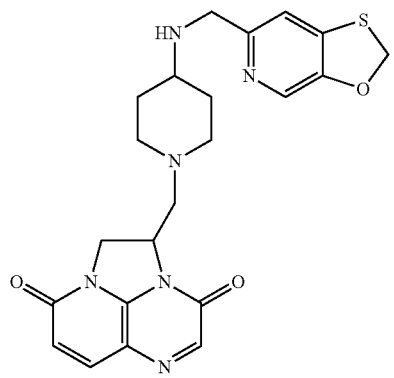 [SMILES: O=c1ccc2ncc(=O)n3c2n1CC3CN1CCC(NCc2cc3c(cn2)OCS3)CC1]

Racemic 2-[(4-amino-1-piperidinyl)methyl]-1,2-dihydro-3H,8H-2a,5,8a-triazaacenaphthylene-3,8-dione (for a preparation see Example 16A(j)) (400 mg, 1.327 mmol) was stirred with [1,3]oxathiolo[5,4-c]pyridine-6-carbaldehyde (for a synthesis see WO2004058144 Example 61) (200 mg, 0.9 eq.) in chloroform:methanol (9:1, v:v, 15 ml) at room temperature for 30 mins; the mixture was then treated with sodium triacetoxyborohydride (844 mg, 3.0 eq.) with vigorous stirring at room temperature for 30 mins. The reaction was quenched by addition of saturated aqueous sodium hydrogen carbonate (5 ml) and the mixture was stirred at room temperature for 5 mins. The organic phase was separated, dried over anhydrous $Na_2SO_4$ and evaporated under reduced pressure. The crude product was purified by column chromatography on silica (eluting with 0-12% (2M ammonia in methanol) in DCM, appropriate fractions were combined and evaporated under reduced pressure to give the free base of the (racemic) title compound as a pale yellow foam (290 mg, 46.8%).

MS (ES+) m/z 453 ($MH^+$).

$^1$H NMR ($CDCl_3$) (identical to those of the homochiral samples (Example 16A and 17A) except for the position of the N<u>H</u>) 8.00 (1H, s); 7.82 (1H, s); 7.77 (1H, d, J=9.7 Hz); 7.18 (1H, s); 6.39 (1H, d, J=9.7 Hz); 5.73 (2H, s); 5.03 (1H, m); 4.55 (1H, dd, J=12.5 Hz, 4.6 Hz); 4.38 (1H, dd, J=12.5 Hz, 9.2 Hz); 3.80 (2H, s); 3.13 (1H, dd, J=12.9 Hz, 3.5 Hz); 2.93 (1H, m); 2.70 (1H, dd, J=12.9 Hz, 9.0 Hz); 2.67 (1H, m); 2.50 (1H, m); 2.33 (1H, dt, J=11.4 Hz, 2.6 Hz); 2.25 (1H, dt, J=11.4 Hz, 2.6 Hz); 1.85 (2H, m); (NH under HOD peak at 1.70); 1.36 (2H, m).

The free base (290 mg) was dissolved in DCM (5 ml) and treated with one equivalent of 1M HCl in diethyl ether. Evaporation of the solvents under reduced pressure gave the title compound as a pale yellow amorphous solid (281 mg).

MS (ES+) m/z 453 ($MH^+$)

Example 16B (2R)-2-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione benzoate and Example 17B (2S)-2-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione benzoate Racemic 2-({4-[([1,3]oxathiolo[5,4-c]pyridin-6-ylmethyl)amino]-1-piperidinyl}methyl)-1,2-dihydro-3H, 8H-2a,5,8a-triazaacenaphthylene-3,8-dione hydrochloride, 200 mg, was resolved into its two enantiomers by preparative chiral HPLC (using a 21×250 mm Chiralpak IA, (5 microns) preparative column) with 1:1 acetonitrile (containing 0.1% isopropylamine) and acetonitrile (containing 0.1% TFA) as the mobile phase.

(2R)-2-({4-[([1,3]Oxathiolo[5,4-c]pyridin-6-ylmethyl)amino]-1-piperidinyl}methyl)-1,2-dihydro-3H,8H-2a,5,8a-triazaacenaphthylene-3,8-dione (first component eluted): (81 mg)

Optical rotation: {alpha}D at 23.9° C.=−85.58° (C=0.798 in MeOH)

MS (ES+) m/z 302 ($MH^+$).

The free base was dissolved in methanol and treated with benzoic acid (1 equivalent). Evaporation of the solvents under reduced pressure gave the product (Example 16B) as the benzoate salt.

(2S)-2-({4-[([1,3]Oxathiolo[5,4-c]pyridin-6-ylmethyl)amino]-1-piperidinyl}methyl)-1,2-dihydro-3H, 8H-2a,5,8a-triazaacenaphthylene-3,8-dione (second component eluted): (76 mg)

Optical rotation: {alpha}D at 23.9° C.=+84.90 (C=0.798 in MeOH)

MS (ES+) m/z 302 ($MH^+$).

The free base was dissolved in methanol and treated with benzoic acid (1 equivalent). Evaporation of the solvents under reduced pressure gave the product (Example 17B) as the benzoate salt.

Example 19A (2R)-2-({4-[(2,3-Dihydro[1,4]oxathiino[2,3-c]pyridin-7-ylmethyl)amino]-1-piperidinyl}methyl)-1,2-dihydro-3H,8H-2a,5,8a-triazaacenaphthylene-3,8-dione hydrochloride

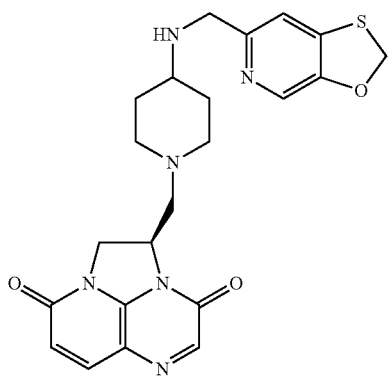 [SMILES: O=c1ccc2ncc(=O)n3c2n1C[C@H]3CN1CCC(NCc2cc3c(cn2)OCS3)CC1]

(2R)-2-[(4-Amino-1-piperidinyl)methyl]-1,2-dihydro-3H,8H-2a,5,8a-triazaacenaphthylene-3,8-dione (for a preparation see Example 16A(j)) (600 mg, 1.991 mmol), 2,3-dihydro[1,4]oxathiino[2,3-c]pyridine-7-carbaldehyde (for a synthesis see WO2004058144, Example 60) (325 mg, 0.900 eq.) and 20 µL acetic acid were stirred in chloroform:methanol (9:1, v:v, 30 ml) at room temperature for 2 hours; the mixture was then treated with sodium triacetoxyborohydride (1.266 g, 3.0 eq.) with vigorous stirring at room temperature for 30 mins. The mixture was quenched by addition of saturated aqueous sodium hydrogen carbonate (6 ml). DCM (60 ml) was added and vigorous stirring was continued for 10 mins, followed by separation of the phases (hydrophobic frit). The organic phase was evaporated under reduced pressure and the crude product was purified by column chromatography on silica (eluting with 0-12% (2M $NH_3$ in MeOH) in DCM)

Appropriate fractions were combined and evaporated under reduced pressure and dried under vacuum overnight to give the free base of the title compound as a pale yellow amorphous solid (658 mg).

MS (ES+) m/z 467 (MH+).

$^1$H NMR (CDCl$_3$, 400 MHz) 1.25-1.40 (2H, m), 1.80-1.90 (2H, m), 2.20-2.30 (1H, m), 2.30-2.40 (1H, m), 2.45-2.55 (1H, m), 2.65-2.75 (2H, m), 2.90-2.95 (1H, m), 3.10-3.20 (3H, m), 3.75 (2H, s), 4.35-4.45 (3H, m), 4.50-4.60 (1H, dd), 5.00-5.10 (1H, m), 6.40 (1H, d), 7.00 (1H, s), 7.75 (1H, d), 7.85 (1H, s), 8.05 (1H, s).

The free base (650 mg, 1.393 mmol) was suspended in dry DCM (10 ml) and a 1M solution of hydrogen chloride in diethyl ether (1393 µL, 1.000 eq.) was added. The system was kept sealed and shaken for 1 minute then the solvents were removed under reduced pressure and the residue was dried under vacuum to give the title compound as an amorphous yellow solid (682 mg).

Example 20 2-({4-[(2,3-Dihydro[1,4]oxathiino[2,3-c]pyridin-7-ylmethyl)amino]-1-piperidinyl}methyl)-1,2-dihydro-3H,8H-2a,5,8a-triazaacenaphthylene-3,8-dione hydrochloride Example 19B (2R)-2-({4-[(2,3-Dihydro[1,4]oxathiino[2,3-c]pyridin-7-ylmethyl)amino]-1-piperidinyl}methyl)-1,2-dihydro-3H,8H-2a,5,8a-triazaacenaphthylene-3,8-dione trifluoroacetate and Example 21 (2S)-2-({4-[(2,3-Dihydro[1,4]oxathiino[2,3-c]pyridin-7-ylmethyl)amino]-1-piperidinyl}methyl)-1,2-dihydro-3H,8H-2a,5,8a-triazaacenaphthylene-3,8-dione

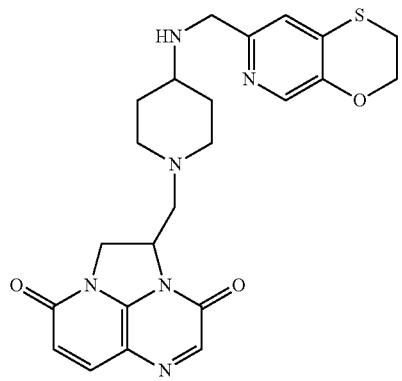

Racemic 2-[(4-amino-1-piperidinyl)methyl]-1,2-dihydro-3H,8H-2a,5,8a-triazaacenaphthylene-3,8-dione (for a preparation see Example 16A(j)) (360 mg, 1.195 mmol) was stirred with 2,3-dihydro[1,4]oxathiino[2,3-c]pyridine-7-carbaldehyde (for a synthesis see WO2004058144, Example 60) (195 mg, 0.9 eq.) in chloroform:methanol (9:1, v:v, 15 ml) at room temperature for 30 mins; the mixture was then treated with sodium triacetoxyborohydride (760 mg, 3.0 eq.) with vigorous stirring at room temperature for 30 mins. The reaction was quenched by addition of saturated aqueous sodium hydrogen carbonate (5 ml) and the mixture was stirred at room temperature for 5 mins. The organic phase was separated, dried over anhydrous $Na_2SO_4$ and evaporated under reduced pressure. The crude product was purified by column chromatography on silica (eluting with 0-12% (2M ammonia in methanol) in DCM, appropriate fractions were combined and evaporated under reduced pressure to give the free base of the title compound as a pale yellow foam (235 mg, 42%).

NMR and LC-MS identical to product of Example 19A.

The free base (225 mg) was dissolved in DCM (5 ml) and treated with one equivalent of 1M HCl in diethyl ether. Evaporation of the solvents under reduced pressure gave the title compound (Example 20) as a pale yellow amorphous solid (224 mg).

MS (ES+) m/z 467 (MH+).

The title racemic hydrochloride (Example 20), 80 mg, was resolved into its two enantiomers by preparative chiral HPLC (using a 21×250 mm Chiralpak IA, (5 microns) preparative column) with 2:2:1 methanol:acetonitrile:t-butanol (containing 0.1% isopropylamine) as the mobile phase.

(2R)-2-({4-[(2,3-Dihydro[1,4]oxathiino[2,3-c]pyridin-7-ylmethyl)amino]-1-piperidinyl}methyl)-1,2-dihydro-3H, 8H-2a,5,8a-triazaacenaphthylene-3,8-dione (first component eluted): (31 mg) MS (ES+) m/z 467 (MH+).

The 2R material was of 98.7% purity; further purification was effected by reverse-phase HPLC on a Kromasil 5 micron C-18 column (21 mm×250 mm) eluted with 9:1 water (+0.1% TFA) and acetonitrile (+0.1% TFA) (3 runs) to give the di-trifluoroacetate salt (Example 19B).

(2S)-2-({4-[(2,3-Dihydro[1,4]oxathiino[2,3-c]pyridin-7-ylmethyl)amino]-1-piperidinyl}methyl)-1,2-dihydro-3H, 8H-2a,5,8a-triazaacenaphthylene-3,8-dione (second component eluted): (32 mg) (Example 21). The stereochemistry of this compound was determined by small molecule x-ray crystallography. MS (ES+) m/z 467 (MH+).

Example 22 2-({4-[(2,3-Dihydro[1,4]dioxino[2,3-c]pyridin-7-ylmethyl)amino]-1-piperidinyl}methyl)-1, 2-dihydro-3H,8H-2a,5,8a-triazaacenaphthylene-3,8-dione hydrochloride

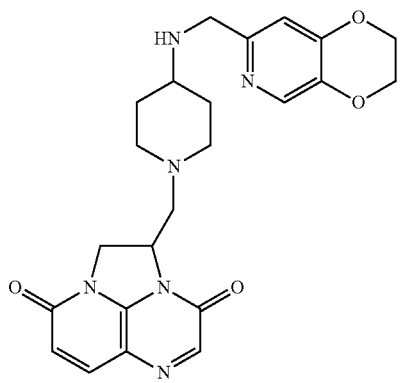 [SMILES: O=c1ccc2ncc(=O)n3c2n1CC3CN1CCC(NCc2cc3c(cn2)OCCO3)CC1]

Racemic 2-[(4-amino-1-piperidinyl)methyl]-1,2-dihydro-3H,8H-2a,5,8a-triazaacenaphthylene-3,8-dione (for a preparation see Example 16A(j)) (50 mg, 0.166 mmol) was stirred in 9:1 v:v chloroform:methanol (2 ml) with 2,3-dihydro[1,4]dioxino[2,3-c]pyridine-7-carbaldehyde (for a synthesis see WO2004058144 Example 2(c) or WO03/087098 Example 19(d)) (28 mg, 1.0 equivalent) at room temperature for 30 minutes, then the mixture was treated with sodium triacetoxyborohydride (105 mg, 3.0 equivalents) with vigorous stirring. After a further 25 minutes stirring, the reaction was quenched by addition of saturated aqueous sodium hydrogen carbonate (2 ml), diluted with dichloromethane and stirred vigorously at room temperature for 20 minutes. The organic phase was separated (hydrophobic frit) and evaporated under reduced pressure to give an orange gum; this was purified by column chromatography on silica (eluting with 0-12% (2M $NH_3$ in MeOH) in DCM).

Appropriate fractions were combined and evaporated under reduced pressure to give the free base of the title compound as a cream amorphous solid (30 mg, 40%).

MS (ES+) m/z 451 (MH+).

$^1$H NMR (CD$_3$OD) □ 7.98 (1H, s); 7.88 (1H, d, J=9.7 Hz); 7.77 (1H, s); 6.94 (1H, s); 6.37 (1H, d, J=9.7 Hz); 5.12 (1H, m); 4.43 (2H, m); 4.35 (2H, m); 4.29 (2H, m); 3.73 (2H, s); 3.07 (1H, m); 3.03 (1H, m); 2.83 (1H, dd, J=13.2 Hz, 8.3 Hz); 2.70 (1H, m); 2.44 (1H, m); 2.26 (1H, dt, J=11.6 Hz, 2.4 Hz); 2.18 (1H, dt, J=11.6 Hz, 2.4 Hz); 1.85 (2H, m); 1.33 (2H, m).

The free base was dissolved in DCM (1 ml) and treated with a 1M solution of hydrogen chloride in diethyl ether (67 □□L, 1.0 equivalent); the vessel was sealed and kept at room temperature for 5 minutes then the solvents were removed under reduced pressure to give the title compound (20 mg; some product lost due to splashing on evaporation of solvents).

MS (ES+) m/z 451 (MH+).

Example 23 (1R)-1-({4-[(2,3-Dihydro[1,4]oxathiino[2,3-c]pyridin-7-ylmethyl)amino]-4-methyl-1-piperidinyl}methyl)-1,2-dihydro-4H,9H-imidazo[1, 2,3-ij]-1,8-naphthyridine-4,9-dione hydrochloride

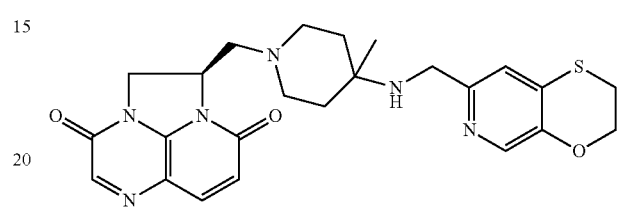

(a) 1,1-Dimethylethyl 4-methyl-4-({[(phenylmethyl)oxy]carbonyl}amino)-1-piperidinecarboxylate A solution of 1-{[(1,1-dimethylethyl)oxy]carbonyl}-4-methyl-4-piperidinecarboxylic acid (12.092 g, 49.7 mmol) in toluene (300 ml) was treated with triethylamine (13.85 ml, 99 mmol) and then diphenylphosphoryl azide (21.42 ml, 99 mmol), heated to 90° C. for 2 h (bubbling observed) before treatment with benzyl alcohol (10.34 ml, 99 mmol). The reaction was then heated at 90° C. for a further 18 h, then cooled, treated with saturated aqueous sodium bicarbonate (500 ml), the organic extracts were separated and the aqueous extracted with diethyl ether (200 ml), the combined organic extracts were dried (MgSO$_4$), filtered, evaporated, columned (0-50% ethyl acetate:40-60 petroleum ether, Rf=0.4 in 4:1 ethyl acetate:40-60 petroleum ether) to give product as a clear oil (15.473 g, 89%).

(b) Phenylmethyl (4-methyl-4-piperidinyl)carbamate

A solution of 1,1-dimethylethyl 4-methyl-4-({[(phenylmethyl)oxy]carbonyl}amino)-1-piperidinecarboxylate (15.473 g, 44.4 mmol) in DCM (50 ml) under argon at rt, was treated with trifluoroacetic acid (50 ml, 649 mmol) and stirred at rt for 0.5 h. The reaction mixture was then evaporated, dissolved in water (200 ml), washed with diethyl ether (3×200 ml). The aqueous phase was then basified with solid potassium carbonate, extracted with 20% methanol/DCM (3×200 ml), these organic extracts were then dried (MgSO$_4$), filtered and evaporated to give the product as a yellow oil (6.327 g, 57%).

MS (ES+) m/z 249 (MH+).

(c) Phenylmethyl (1-{[(2R)-4,9-dioxo-1,2,8,9-tetrahydro-4H,7H-imidazo[1,2,3-ij]-1,8-naphthyridin-2-yl]methyl}-4-methyl-4-piperidinyl)carbamate A solution of (1S)-1-(hydroxymethyl)-1,2,5,6-tetrahydro-4H,9H-imidazo[1,2,3-ij]-1,8-naphthyridine-4,9-dione (for a preparation see Example 5A(g)) (1.494 g, 6.78 mmol) in DCM (50 ml) at 0° C. under argon was treated with triethylamine (1.7 ml, 12.20 mmol) and then methanesulfonyl chloride (0.800 ml, 10.27 mmol) and then allowed to warm to rt and stirred at rt for 1 h. The reaction mixture was then treated with saturated aqueous bicarbonate (200 ml) and the mixture was extracted with DCM (3×200 ml). The combined organic solvents were then dried (MgSO$_4$), filtered, evaporated to give the crude mesylate (2.082 g, 6.987 mmol, 103% crude yield). The mesylate was dissolved in dry acetonitrile (30 ml) and then treated with pyridine (1.097 ml, 13.57 mmol) and a solution of phenylmethyl (4-methyl-4-piperidinyl)carbamate (3.164 g, 12.74 mmol) in dry acetonitrile (20 ml) and heated at reflux (heating block 95° C.) for 6 h. The reaction mixture was then evaporated, treated with saturated aqueous NaHCO$_3$ (200 ml) and the mixture was extracted with DCM (3×200 ml). The combined organic solvents were then dried (MgSO$_4$), filtered, evaporated to give the crude product as an orange solid which was then chromatographed (0-10% methanol/DCM, Rf=0.5 in 10% methanol/DCM) to give product as a yellow solid (1.848 g, 61%).

MS (ES+) m/z 451 (MH$^+$).

(d) (1R)-1-[(4-Amino-4-methyl-1-piperidinyl)methyl]-1,2,5,6-tetrahydro-4H,9H-imidazo[1,2,3-ij]-1,8-naphthyridine-4,9-dione A solution of phenylmethyl (1-{[(2R)-4,9-dioxo-1,2,8,9-tetrahydro-4H,7H-imidazo[1,2,3-ij]-1,8-naphthyridin-2-yl]methyl}-4-methyl-4-piperidinyl)carbamate (1.848 g, 4.10 mmol) in ethanol at rt under argon was treated with palladium on carbon (10% paste) (0.462 g, 4.34 mmol) (20% w/w) and stirred under 1 atmosphere of hydrogen for 2 h, reaction mixture was filtered through a thin pad of Kieselguhr eluting with ethanol (100 ml). The filtrate was treated with palladium on carbon (10% paste) (0.462 g, 4.34 mmol) and and stirred under 1 atm of hydrogen for 18 h. The reaction mixture was filtered through a thin pad of Kieselguhr eluting with ethanol (500 ml) and the filtrate was then evaporated to give the product as a yellow solid (1.294 g, 100%).

MS (ES+) m/z 317 (MH$^+$).

(e) (1R)-1-[(4-Isocyanato-4-methyl-1-piperidinyl)methyl]-1,2,5,6-tetrahydro-4H,9H-imidazo[1,2,3-ij]-1,8-naphthyridine-4,9-dione A solution of (1R)-1-[(4-amino-4-methyl-1-piperidinyl)methyl]-1,2,5,6-tetrahydro-4H,9H-imidazo[1,2,3-ij]-1,8-naphthyridine-4,9-dione (1.294 g, 4.09 mmol) in DCM (30 ml) under argon at rt was treated with triethylamine (0.684 ml, 4.91 mmol), then di-tert-butyl dicarbonate (1.045 ml, 4.50 mmol) and finally 4-dimethylaminopyridine (0.050 g, 0.409 mmol) and stirred at rt for 1 h. The reaction mixture was treated with aq sodium bicarbonate (100 ml) and extracted with DCM (3×200 ml). The combined organic fractions were dried (MgSO$_4$), filtered and evaporated to give the crude product as a yellow solid which was then chromatographed (0-10% methanol/DCM, Rf=0.5 in 10% methanol/DCM) to give the product as a white solid (561 mg, 40%).

MS (ES+) m/z 343 (MH$^+$).

(f) (1R)-1-[(4-Amino-4-methyl-1-piperidinyl)methyl]-1,2,5,6-tetrahydro-4H,9H-imidazo[1,2,3-ij]-1,8-naphthyridine-4,9-dione A solution of (1R)-1-[(4-isocyanato-4-methyl-1-piperidinyl)methyl]-1,2,5,6-tetrahydro-4H,9H-imidazo[1,2,3-ij]-1,8-naphthyridine-4,9-dione (561 mg, 1.638 mmol) in THF (10 ml) and water (10.00 ml) at rt was treated with sodium hydroxide (5 ml, 10.00 mmol), and stirred at rt for 1 h. Reaction was then treated with concentrated HCl (5 ml, 12M) and stirred at rt for 18 h, then evaporated. The resultant solid was treated with methanol (20 ml) and then the solvent was decanted from the solid and evaporated to give the product as an impure green solid (687 mg, 108%).

MS (ES+) m/z 317 (MH$^+$).

(g) N-(1-{[(2R)-4,9-Dioxo-1,2,8,9-tetrahydro-4H,7H-imidazo[1,2,3-ij]-1,8-naphthyridin-2-yl]methyl}-4-methyl-4-piperidinyl)-2,2,2-trifluoroacetamide A solution of (1R)-1-[(4-amino-4-methyl-1-piperidinyl)methyl]-1,2,5,6-tetrahydro-4H,9H-imidazo[1,2,3-ij]-1,8-naphthyridine-4,9-dione (687 mg, 1.765 mmol) in DCM (20 ml) and triethylamine (1.476 ml, 10.59 mmol) at 0° C. under argon was treated with trifluoroacetic anhydride (0.299 ml, 2.118 mmol) and stirred at rt for 1 h. The reaction was treated with saturated sodium bicarbonate (50 ml) and extracted with DCM (3×100 ml). The combined organic solvents were then dried (MgSO$_4$), filtered, evaporated to give the crude product as an orange solid which was then chromatographed (0-10% methanol/DCM, Rf=0.4 in 10% methanol/DCM) to give product as an impure yellow solid (375 mg, 52%).

MS (ES+) m/z 413 (MH$^+$).

(h) N-(1-{[(1R)-4,9-Dioxo-1,2-dihydro-4H,9H-imidazo[1,2,3-ij]-1,8-naphthyridin-1-yl]methyl}-4-methyl-4-piperidinyl)-2,2,2-trifluoroacetamide A solution of N-(1-{[(2R)-4,9-dioxo-1,2,8,9-tetrahydro-4H,7H-imidazo[1,2,3-ij]-1,8-naphthyridin-2-yl]methyl}-4-methyl-4-piperidinyl)-2,2,2-trifluoroacetamide (375 mg, 0.909 mmol) in 1,4-dioxane (20 ml) at rt was treated with DDQ (248 mg, 1.091 mmol) and then heated at 80° C. for 1 h. The reaction was then cooled to rt. The reaction mixture was treated with saturated aqueous K$_2$CO$_3$ (5%, 100 ml), then with DCM (100 ml) and the mixture filtered through Kieselguhr. The organic fraction was separated and the aqueous layer extracted with DCM (2×100 ml). The combined organic solvents were then dried (MgSO$_4$), filtered and evaporated to give the crude product as a yellow oil.

Chromatography on silica (0-10% methanol:DCM, Rf=0.4 in 10% MeOH/DCM) gave the product as a clear oil (171 mg, 46%).

MS (ES+) m/z 411 (MH$^+$).

(i) (1R)-1-[(4-Amino-4-methyl-1-piperidinyl)methyl]-1,2-dihydro-4H,9H-imidazo[1,2,3-ij]-1,8-naphthyridine-4,9-dione N-(1-{[(1R)-4,9-Dioxo-1,2-dihydro-4H,9H-imidazo[1,2,3-ij]-1,8-naphthyridin-1-yl]methyl}-4-methyl-4-piperidinyl)-2,2,2-trifluoroacetamide (171 mg, 0.417 mmol) was treated with a 7% solution of potassium carbonate (450 mg in 2 ml water/5 ml methanol) and stirred at rt for 2 h, and then at 70° C. for 18 h then evaporated and dissolved in 5% MeOH/DCM (100 ml), filtered and purified by SCX (5 g, eluting with MeOH and then 0.5M NH$_3$/MeOH and then 2M NH$_3$/MeOH). Fractions containing product were then evaporated to give product as a pink solid (60 mg, 46%)

MS (ES+) m/z 315 (MH$^+$).

(j) Title Compound

A suspension of (1R)-1-[(4-amino-4-methyl-1-piperidinyl)methyl]-1,2-dihydro-4H,9H-imidazo[1,2,3-ij]-1,8- naphthyridine-4,9-dione (34 mg, 0.108 mmol) in chloroform (2 ml) and methanol (0.1 ml) at rt under argon was treated with 2,3-dihydro[1,4]oxathiino[2,3-c]pyridine-7-carbaldehyde (19.60 mg, 0.108 mmol) (for a synthesis see WO2004058144, Example 60) and stirred for 2 h. The solution was then treated with sodium triacetoxyborohydride (68.8 mg, 0.324 mmol) and stirred at rt for 0.5 h. The reaction was then treated with saturated aqueous NaHCO$_3$ (20 ml) and extracted with 20% methanol/DCM (3×100 ml). The combined organic extracts were dried (MgSO$_4$), filtered, evaporated and chromatographed (0-20% methanol/DCM, Rf=0.4 in 15% methanol/DCM) to give the free base of the title compound as a light brown solid (32 mg, 0.067 mmol, 62%).

MS (ES+) m/z 517 (MH$^+$).

δH (CDCl$_3$, 250 MHz) 1.14 (3H, s), 1.42-1.70 (4H, m), 2.30-2.45 (1H, m), 2.50-2.82 (4H, m), 3.05-3.22 (3H, m), 3.68 (2H, s), 4.28-4.48 (3H, m) 4.51-4.63 (1H, m), 4.96-5.11 (1H, m), 6.20-6.35 (2H, m), 7.04 (1H, s), 7.46-7.51 (2H, m), 8.00 (1H, s).

The free base in DCM/MeOH 2:1 (10 ml) was treated with 1M HCl in diethyl ether and then evaporated to give the title mono-hydrochloride salt as a white solid (34 mg)

Example 24 (1R)-1-({4-Methyl-4-[([1,3]oxathiolo [5,4-c]pyridin-6-ylmethyl)amino]-1-piperidinyl}methyl)-1,2-dihydro-4H,9H-imidazo[1,2,3-ij]-1,8-naphthyridine-4,9-dione hydrochloride

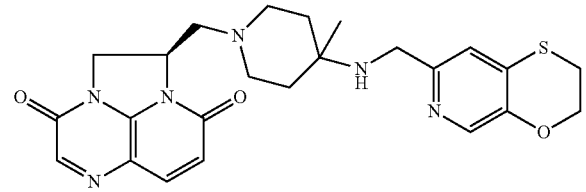 [SMILES: CC1(NCc2cc3c(cn2)OCCS3)CCN(C[C@@H]2Cn3c(=O)cnc4ccc(=O)n2c43)CC1]

A suspension of (1R)-1-[(4-amino-4-methyl-1-piperidinyl)methyl]-1,2-dihydro-4H,9H-imidazo[1,2,3-ij]-1,8-naphthyridine-4,9-dione (26 mg, 0.083 mmol) (for a preparation see Example 23(i)) in chloroform (2 ml) and methanol (0.1 ml) at rt under argon was treated with [1,3]oxathiolo [5,4-c]pyridine-6-carbaldehyde (13.83 mg, 0.083 mmol) (for a synthesis see WO2004058144 Example 61) and stirred at rt for 2 h. The solution was then treated with sodium triacetoxyborohydride (52.6 mg, 0.248 mmol) and stirred at rt for 0.5 h. The reaction was then treated with saturated aqueous NaHCO$_3$ (10 ml) and extracted with 20% methanol/DCM (3×50 ml). The combined organic fractions were dried (MgSO$_4$), filtered, evaporated and chromatographed (0-20% methanol/DCM, Rf=0.3 in 15% methanol/DCM) to give the free base of the title compound as a yellow solid (29 mg, 75%).

MS (ES+) m/z 466 (MH$^+$).

δH (CDCl$_3$, 250 MHz) 1.14 (3H, s), 1.40-1.71 (4H, m), 2.30-2.46 (1H, m), 2.51-2.82 (4H, m), 3.08-3.22 (1H, m), 3.73 (2H, s), 4.28-4.42 (1H, m) 4.51-4.65 (1H, m), 4.92-5.09 (1H, m), 5.72 (2H, s), 6.20-6.34 (2H, m), 7.25 (1H, s), 7.50-7.51 (2H, m), 7.98 (1H, s).

The free base in DCM/MeOH 2:1 (5 ml) was treated with 1M HCl in diethyl ether and then evaporated to give the title mono-hydrochloride salt.

Example 25 (2R)-2-({4-[(2,1,3-Benzothiadiazol-5-ylmethyl)amino]-1-piperidinyl}methyl)-1,2-dihydro-3H,8H-2a,5,8a-triazaacenaphthylene-3,8-dione hydrochloride

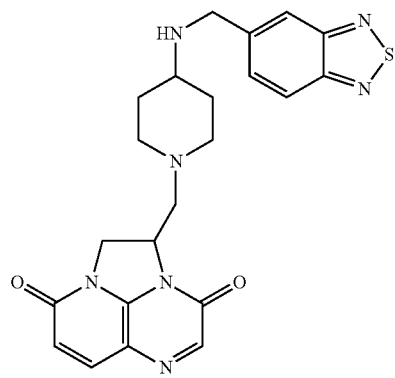 [SMILES: O=c1ccc2ncc(=O)n3c2n1CC3CN1CCC(NCc2ccc3nsnc3c2)CC1]

(2R)-2-[(4-Amino-1-piperidinyl)methyl]-1,2-dihydro-3H,8H-2a,5,8a-triazaacenaphthylene-3,8-dione (50 mg, 0.166 mmol) (for a preparation see Example 16(j)) and 2,1,3-benzothiadiazole-5-carbaldehyde (25 mg, 0.918 eq.) were stirred in 9:1 v:v chloroform:methanol (1 ml) for 2.5 hours. Sodium triacetoxyborohydride (105 mg, 3.000 eq.) was then added in one portion and the mixture was stirred vigorously at room temperature for 30 min. Saturated aqueous sodium hydrogen carbonate (0.5 ml) was then added, followed by dichloromethane (10 ml) and the mixture was stirred vigorously at room temperature for 10 min and the phases were separated (hydrophobic frit). The organic phase was evaporated under reduced pressure and the crude product was purified by column chromatography on silica (eluted with 0-12% (2M NH$_3$ in MeOH) in DCM). Appropriate fractions were combined and evaporated under reduced pressure to give the free base of the title compound as a yellow solid (41 mg).

MS (ES+) m/z 450 (MH$^+$).

$^1$H NMR (CDCl$_3$): □ 7.95 (1H, d, J=9.0 Hz); 7.90 (1H, s); 7.83 (1H, s); 7.77 (1H, d, J=9.7 Hz); 7.61 (1H, dd, J=9.2 Hz, 1.8 Hz); 6.39 (1H, d, J=9.7 Hz); 5.03 (1H, m); 4.56 (1H, dd, J=12.5 Hz, 4.6 Hz); 4.39 (1H, dd, J=12.5 Hz, 9.2 Hz); 3.98 (2H, s); 3.14 (1H, dd, J=13.2 Hz, 3.5 Hz); 2.94 (1H, broad m); 2.69 (2H, m); 2.56 (1H, m); 2.34 (1H, dt, J=11.4 Hz, 2.6 Hz); 2.25 (1H, dt, J=11.4 Hz, 2.6 Hz); 1.89 (2H, m); (NH under HOD peak at 1.48); 1.37 (2H, m).

The free base (35 mg, 0.078 mmol) was dissolved in DCM (1 ml) and hydrogen chloride (1.0M) in diethyl ether (78 L, 1.0 eq.) was added. The system was sealed and shaken at room temperature for 1 minute, then the solvents were removed under reduced pressure to give the title compound as a yellow solid (38 mg).

MS (ES+) m/z 450 (MH$^+$).

Example 26 (2R)-2-[(4-{[(7-Fluoro-2,3-dihydro-1,4-benzodioxin-6-yl)methyl]amino}-1-piperidinyl)methyl]-1,2-dihydro-3H,8H-2a,5,8a-triazaacenaphthylene-3,8-dione hydrochloride

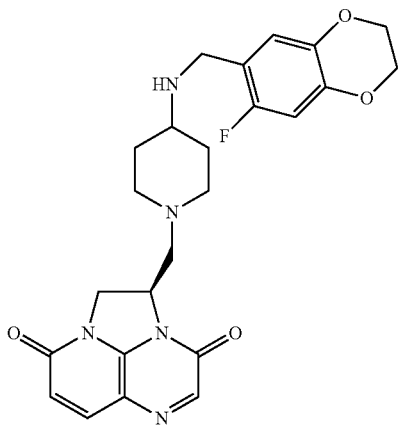 [SMILES: O=c1ccc2ncc(=O)n3c2n1C[C@H]3CN1CCC(NCc2cc3c(cc2F)OCCO3)CC1]

(2R)-2-[(4-Amino-1-piperidinyl)methyl]-1,2-dihydro-3H,8H-2a,5,8a-triazaacenaphthylene-3,8-dione (50 mg, 0.166 mmol) (for a preparation see Example 16(j)) and 7-fluoro-2,3-dihydro-benzo[1,4]dioxin-6-carboxaldehyde (28 mg, 0.926 eq.) (for a synthesis see WO2002056882, Example 23(a)) were stirred in 9:1 v:v chloroform:methanol (1 ml) for 2.5 hours. Sodium triacetoxyborohydride (105 mg, 3.000 eq.) was then added in one portion and the mixture was stirred vigorously at room temperature for 30 min. Saturated aqueous sodium hydrogen carbonate (0.5 ml) was then added, followed by dichloromethane (10 ml) and the mixture was stirred vigorously at room temperature for 10 min and the phases were separated (hydrophobic frit). The organic phase was evaporated under reduced pressure and the crude product was purified by column chromatography on silica (eluted with 0-12% (2M $NH_3$ in MeOH) in DCM. Appropriate fractions were combined and evaporated under reduced pressure to give the free base of the title compound as a white solid (48 mg).

MS (ES+) m/z 468 (MH$^+$).

$^1$H NMR (CDCl$_3$): ☐ 7.82 (1H, s); 7.76 (1H, d, J=9.7 Hz); 6.79 (1H, d, J=7.2 Hz); 6.57 (1H, d, J=10.5 Hz); 6.38 (1H, d, J=9.7 Hz); 5.03 (1H, m); 4.54 (1H, dd, J=12.5 Hz, 4.4 Hz); 4.38 (1H, dd, J=12.5 Hz, 9.4 Hz); 4.23 (4H, m); 3.71 (2H, s); 3.12 (1H, dd, J=12.9 Hz, 3.3 Hz); 2.92 (1H, m); 2.68 (2H, m); 2.68 (2H, m); 2.47 (1H, m); 2.33 (1H, dt, J=11.4 Hz, 2.6 Hz); 2.24 (1H, dt, J=11.4 Hz, 2.6 Hz); 1.83 (2H, m); (NH under HOD peak at 1.50); 1.33 (2H, m).

The free base (48 mg, 0.103 mmol) was dissolved in DCM (1 ml) and hydrogen chloride (1.0M) in diethyl ether (103 L, 1.0 eq.) was added. The system was sealed and shaken at room temperature for 1 minute, then the solvents were removed under reduced pressure to give the title compound as a yellow solid (55 mg)

MS (ES+) m/z 468 (MH$^+$).

Example 27 (2R)-2-({4-[(3,4-Dihydro-2H-[1,4]oxathiepino[2,3-c]pyridin-8-ylmethyl)amino]-1-piperidinyl}methyl)-1,2-dihydro-3H,8H-2a,5,8a-triazaacenaphthylene-3,8-dione hydrochloride

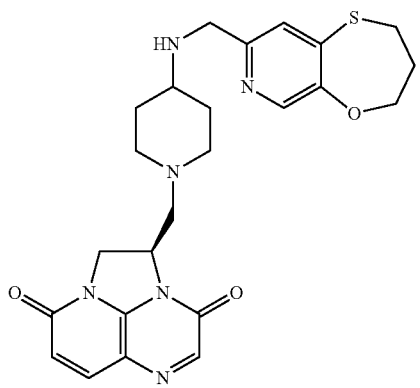 [SMILES: O=c1ccc2ncc(=O)n3c2n1C[C@H]3CN1CCC(NCc2cc3c(cn2)OCCCS3)CC1]

(2R)-2-[(4-Amino-1-piperidinyl)methyl]-1,2-dihydro-3H,8H-2a,5,8a-triazaacenaphthylene-3,8-dione (50 mg, 0.166 mmol) (for a preparation see Example 16(j)) and 3,4-dihydro-2H-[1,4]oxathiepino[2,3-c]pyridine-8-carbaldehyde (29 mg, 0.895 eq.) (may be prepared analogously to the synthesis of 2,3-dihydro[1,4]oxathiino[2,3-c]pyridine-7-carbaldehyde (WO2004058144, Example 60) but replacing dibromoethane with dibromopropane) were stirred in 9:1 v:v chloroform:methanol (1 ml) for 2.5 hours. Sodium triacetoxyborohydride (105 mg, 3.000 eq.) was then added in one portion and the mixture was stirred vigorously at room temperature for 30 minutes. Saturated aqueous sodium hydrogen carbonate (0.5 ml) was then added, followed by dichloromethane (10 ml) and the mixture was stirred vigorously at room temperature for 10 min and the phases were separated (hydrophobic frit). The organic phase was evaporated under reduced pressure and the crude product was purified by column chromatography on silica (eluted with 0-12% (2M $NH_3$ in MeOH) in DCM). Appropriate fractions were combined and evaporated under reduced pressure to give the free base of the title compound as a pale yellow solid (65 mg).

MS (ES+) m/z 481 (MH$^+$).

$^1$H NMR (CDCl$_3$): ☐ 8.12 (1H, s); 7.82 (1H, s); 7.76 (1H, d, J=9.7 Hz); 7.17 (1H, s); 6.38 (1H, d, J=9.7 Hz); 5.03 (1H, m); 4.55 (1H, dd, J=12.5 Hz, 4.5 Hz); 4.37 (3H, m); 3.79 (2H, s); 3.13 (3H, m); 2.94 (1H, m); 2.69 (2H, m); 2.52 (1H, m); 2.30 (4H, m); 1.86 (3H, m); 1.37 (2H, m).

The free base (60 mg, 0.125 mmol) was suspended in dry DCM (1 ml) and a 1M solution of hydrogen chloride in diethyl ether (125 μL, 1.000 eq.) was added. The system was kept sealed and shaken for 1 minute then the solvents were removed under reduced pressure and the residue was dried on the vacuum line to give the title compound as an amorphous yellow solid (64 mg).

MS (ES+) m/z 481 (MH$^+$).

Example 28 (2R)-2-({4-[([1,3]Oxathiolo[4,5-c]pyridin-6-ylmethyl)amino]-1-piperidinyl}methyl)-1,2-dihydro-3H,8H-2a,5,8a-triazaacenaphthylene-3,8-dione hydrochloride

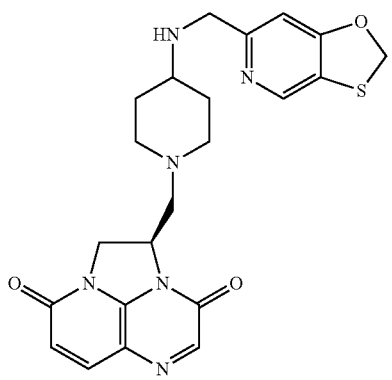 [SMILES: O=c1ccc2ncc(=O)n3c2n1C[C@H]3CN1CCC(NCc2cc3c(cn2)SCO3)CC1]

(a) [1,3]Oxathiolo[4,5-c]pyridine-6-carbaldehyde

The title compound was prepared by: (i) treatment of [5-({[4-(methyloxy)phenyl]methyl}oxy)-4-oxo-1,4-dihydro-2-pyridinyl]methyl acetate (for a synthesis see WO2004058144, Example 60(c)) with triphenylphospine, diisopropylazodicarboxylate and benzyl alcohol to give {5-({[4-(methyloxy)phenyl]methyl}oxy)-4-[(phenylmethyl) oxy]-2-pyridinyl}methyl acetate; (ii) treatment of {5-({[4-(methyloxy)phenyl]methyl}oxy)-4-[(phenylmethyl)oxy]-2-pyridinyl}methyl acetate with trifluoroacetic acid and triethylsilane to give {5-hydroxy-4-[(phenylmethyl)oxy]-2-pyridinyl}methyl acetate trifluoroacetate; (iii) treatment of {5-hydroxy-4-[(phenylmethyl)oxy]-2-pyridinyl}methyl acetate trifluoroacetate with 1,1,1-trifluoro-N-phenyl-N-[(trifluoromethyl)sulfonyl]methanesulfonamide and triethylamine to give (4-[(phenylmethyl)oxy]-5-{[(trifluoromethyl)sulfonyl]oxy}-2-pyridinyl)methyl acetate; (iv) treatment of (4-[(phenylmethyl)oxy]-5-{[(trifluoromethyl) sulfonyl]oxy}-2-pyridinyl)methyl acetate with (R)-(+)-2,2 bis(diphenylphosphino)-1,1-binaphthyl, palladium acetate and sodium 2-methyl-2-propanethiolate to give {5-[(1,1-dimethylethyl)thio]-4-[(phenylmethyl)oxy]-2-pyridinyl}methyl acetate; (v) treatment of {5-[(1,1-dimethylethyl)thio]-4-[(phenylmethyl)oxy]-2-pyridinyl}methyl acetate with palladium on carbon under 1 atmosphere of hydrogen to give {5-[(1,1-dimethylethyl)thio]-4-oxo-1,4-dihydro-2-pyridinyl}methyl acetate; (vi) treatment of {5-[(1,1-dimethylethyl)thio]-4-oxo-1,4-dihydro-2-pyridinyl}methyl acetate with concentrated hydrochloric acid to give 2-(hydroxymethyl)-5-mercapto-4(1H)-pyridinone; (vii) treatment of 2-(hydroxymethyl)-5-mercapto-4(1H)-pyridinone with potassium carbonate and dibromomethane to give [1,3]oxathiolo[4,5-c]pyridin-6-ylmethanol and (viii) treatment of [1,3]oxathiolo[4,5-c]pyridin-6-ylmethanol with manganese dioxide to give the title compound.

(b) Title Compound (2R)-2-[(4-Amino-1-piperidinyl)methyl]-1,2-dihydro-3H,8H-2a,5,8a-triazaacenaphthylene-3,8-dione (50 mg, 0.166 mmol) (for a preparation see Example 16(j)) and [1,3]oxathiolo[4,5-c]pyridine-6-carbaldehyde (25 mg, 0.901 eq.) were stirred in 9:1 v:v chloroform:methanol (1 ml) for 2.5 hours. Sodium triacetoxyborohydride (105 mg, 3.000 eq.) was then added in one portion and the mixture was stirred vigorously at room temperature for 30 min. Saturated aqueous sodium hydrogen carbonate (0.5 ML) was then added, followed by dichloromethane (10 ml) and the mixture was stirred vigorously at room temperature for 10 min and the phases were separated (hydrophobic frit). The organic phase was evaporated under reduced pressure and the crude product was purified by column chromatography on silica (eluted with 0-12% (2M $NH_3$ in MeOH) in DCM). Appropriate fractions were combined and evaporated under reduced pressure to give the free base of the title compound as a pale yellow amorphous solid (48 mg).

$^1$H NMR (CDCl$_3$) ☐ 8.22 (1H, s); 7.82 (1H, s); 7.76 (1H, d, J=9.7 Hz); 6.80 (1H, s); 6.38 (1H, d, J=9.7 Hz); 5.77 (2H, s); 5.03 (1H, m); 4.55 (1H, dd, J=12.5 Hz, 4.6 Hz); 4.38 (1H, dd, J=12.5 Hz, 9.4 Hz); 3.81 (2H, s); 3.13 (1H, dd, J=13.0 Hz, 3.5 Hz); 2.93 (1H, m); 2.68 (2H, m); 2.49 (1H, m); 2.33 (1H, dt, J=11.4 Hz, 2.6 Hz); 2.24 (1H, dt, J=11.4 Hz, 2.6 Hz); 1.84 (3H, m); (NH under HOD peak at 1.66); 1.34 (2H, m).

MS (ES+) m/z 453 (MH$^+$).

The free base of the title compound (48 mg, 0.106 mmol) was suspended in dry DCM (1 ml) and a 1M solution of hydrogen chloride in diethyl ether (106 μL, 1.000 eq.) was added. The system was kept sealed and shaken for 1 minute then the solvents were removed under reduced pressure and the residue was dried on the vacuum line to give the title compound as an amorphous yellow solid (48 mg).

MS (ES+) m/z 453 (MH$^+$).

Example 29 (2R)-2-[(4-{[(3-Oxo-3,4-dihydro-2H-pyrido[3,2-b][1,4]thiazin-6-yl)methyl]amino}-1-piperidinyl)methyl]-1,2-dihydro-3H,8H-2a,5,8a-triazaacenaphthylene-3,8-dione hydrochloride

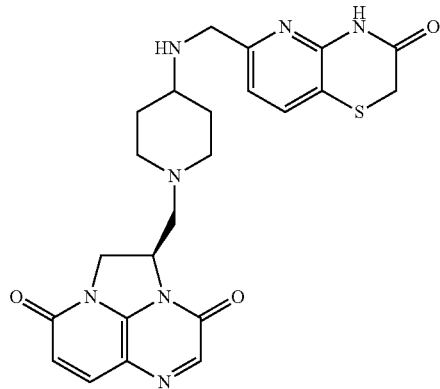 [SMILES: O=C1CSc2ccc(CNC3CCN(C[C@@H]4Cn5c(=O)ccc6ncc(=O)n4c65)CC3)nc2N1]

(2R)-2-[(4-Amino-1-piperidinyl)methyl]-1,2-dihydro-3H,8H-2a,5,8a-triazaacenaphthylene-3,8-dione (50 mg, 0.166 mmol) (for a preparation see Example 16(j)) and 3-oxo-3,4-dihydro-2H-pyrido[3,2-b][1,4]thiazine-6-carboxaldehyde (29 mg, 0.90 eq.) (for a synthesis see WO2003087098, Example 301(d)) were stirred in 9:1 chloroform:methanol (1 ml) at room temperature for 3 hours, then sodium triacetoxyborohydride (105 mg, 3.00 eq.) was added. The mixture was stirred at room temperature for a further 30 minutes, then saturated aqueous sodium hydrogen carbonate (0.5 ml) was added, and the organic phase was diluted with DCM (10 ml). The mixture was stirred vigorously for 10 minutes, then the organic phase was separated (hydrophobic frit) and evaporated under reduced pressure. The residue was taken up in DCM (ca. 3 ml)+1 drop MeOH and purified by column chromatography on silica (eluted with 0-12% (2M $NH_3$ in MeOH) in DCM). Appropriate fractions were combined and evaporated to give the free base of the title compound as a yellow amorphous solid.

$^1$H NMR (CDCl$_3$) □ 8.58 (1H, broad s); 7.83 (1H, s); 7.77 (1H, d, J=9.7 Hz); 7.57 (1H, d, J=7.8 Hz); 6.97 (1H, d, J=7.8 Hz); 6.38 (1H, d, J=9.7 Hz); 5.04 (1H, m); 4.55 (1H, dd, J=12.5 Hz, 4.5 Hz); 4.38 (1H, dd, J=12.5 Hz, 9.3 Hz); 3.82 (2H, s); 3.47 (2H, s): 3.14 (1H, dd, J=13.0 Hz, 3.5 Hz); 2.94 (1H, m); 2.69 (2H, m); 2.51 (1H, m); 2.33 (1H, dt, J=11.4 Hz, 2.4 Hz); 2.25 (1H, dt, J=11.4 Hz, 2.4 Hz); (NH under HOD peak at 2.06); 1.85 (2H, m); 1.37 (2H, m).

MS (ES+) m/z 480 (MH$^+$).

The free base of the title compound (43 mg, 0.090 mmol) was dissolved in DCM (2 ml) and a 1M solution of hydrogen chloride in diethyl ether was added. The system was kept sealed and shaken for 1 minute then the solvents were removed under reduced pressure and the residue was dried on the vacuum line to give the title compound as an amorphous yellow solid (38 mg).

MS (ES+) m/z 480 (MH$^+$).

The solvents were removed and the solid dried in the desiccator (P$_2$O$_5$) overnight to afford the product as a white solid (51 mg, LCMS and NMR consistent with product).

Example 30 (1R)-1-({4-[(2,3-Dihydro-1,4-benzodioxin-6-ylmethyl)amino]-1-piperidinyl}methyl)-1,2-dihydro-4H,9H-imidazo[1,2,3-ij]-1,8-naphthyridine-4,9-dione hydrochloride

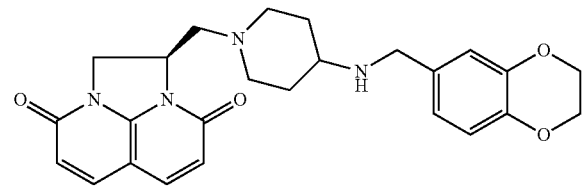

A suspension of (1R)-1-[(4-amino-1-piperidinyl)methyl]-1,2-dihydro-4H,9H-imidazo[1,2,3-ij]-1,8-naphthyridine-4,9-dione dihydrochloride (for a preparation see Example 5A(j)) (60 mg, 0.161 mmol) in chloroform (2 ml) and methanol (0.100 ml) at rt under argon was treated with triethylamine (0.067 ml, 0.482 mmol) and stirred at rt for 15 h. The solution was then treated with 2,3-dihydro-1,4-benzodioxin-6-carbaldehyde (commercially available) (23.75 mg, 0.145 mmol) and stirred for a further 30 min. The solution was then treated with sodium triacetoxyborohydride (102 mg, 0.482 mmol) and stirred at rt for 30 min, LC-MS after 30 min showed some starting material present, more sodium triacetoxyborohydride (19 mg) was added, the reaction was stirred for 15 min. This was then treated with saturated aqueous NaHCO$_3$ (10 ml) and extracted with 20% methanol/DCM (3×25 ml). The combined organic extracts were dried (MgSO$_4$), filtered, evaporated and chromatographed (0-20% methanol/DCM) to give the title compound as the free base (48 mg, 67%) as a yellow gum.

$^1$H NMR δH CDCl$_3$, (250 MHz) 1.28-1.51 (m, 2H), 1.75-1.99 (m, 2H), 2.13-2.38 (m, 2H), 2.41-2.80 (m, 3H), 2.90-3.15 (m, 2H), 3.75 (s, 2H), 4.22 (s, 4H), 4.31-4.42 (m, 1H), 4.51-4.62 (m, 1H), 4.90-5.08 (m, 1H), 6.20-6.32 (m, 2H), 6.81 (m, 2H), 6.84 (m, 1H), 7.42-7.53 (m, 2H).

MS (ES+) m/z 449 (MH$^+$).

The free base of the title compound was dissolved in a small amount of DCM, treated with one equivalent of 1M HCl in diethyl ether and then evaporated to give the title compound as the mono-HCl salt (44 mg, 53%). LCMS was consistent with product.

Example 31 (1R)-1-[(4-{[(8-Fluoro-2,3-dihydro-1,4-benzodioxin-6-yl)methyl]amino}-1-piperidinyl)methyl]-1,2-dihydro-4H,9H-imidazo[1,2,3-ij]-1,8-naphthyridine-4,9-dione hydrochloride

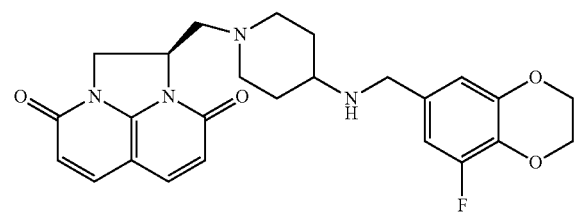 [SMILES: O=c1ccc2ccc(=O)n3c2n1C[C@H]3CN1CCC(NCc2cc(F)c3c(c2)OCCO3)CC1]

A suspension of (1R)-1-({4-[(1,2,3-benzothiadiazol-5-ylmethyl)amino]-1-piperidinyl}methyl)-1,2-dihydro-4H,9H-imidazo[1,2,3-ij]-1,8-naphthyridine-4,9-dione dihydrochoride (for a preparation see Example 5A(j)) (50 mg, 0.134 mmol) in chloroform (2 ml) and methanol (0.100 ml) at rt under argon was treated with triethylamine (0.056 ml, 0.402 mmol) and stirred at rt for 15 min. The solution was then treated with 8-fluoro-2,3-dihydro-1,4-benzodioxin-6-carbaldehyde (for a synthesis see WO2007122258, Example 8(b)) (21.96 mg, 0.121 mmol) and stirred for a further 30 min. The solution was treated with sodium triacetoxyborohydride (85 mg, 0.402 mmol) and stirred at rt for 30 min, LCMS after 30 min showed there was still starting material and the imine of the product. So more sodium triacetoxyborohydride (40 mg) was added, the reaction was stirred for a further 30 min. LCMS after this time showed that the reaction was complete. The reaction was then treated with saturated aqueous NaHCO$_3$ (10 ml) and extracted with 20% methanol/DCM (3×25 ml). The combined organic fractions were dried (MgSO$_4$), filtered, evaporated and chromatographed (0-20% methanol/DCM) to give the free base of the title compound (6 mg, 9.6%) as a pale yellow solid and some crude product (15 mg, 24%) as an impure pale yellow solid which was purified using an SCX column to give more identical title compound, free base.

$^1$H NMR δH CDCl$_3$, (250 MHz) 1.15-1.50 (m, 2H), 1.70-2.10 (m, 2H), 2.15-2.39 (m, 2H), 2.41-2.58 (m, 1H), 2.60-2.74 (2H, m), 2.85-3.11 (m, 1H), 3.11-3.15 (m, 1H), 3.69 (s, 2H), 4.22-4.45 (m, 5H), 4.50-4.62 (m, 1H), 4.90-5.09 (m, 1H), 6.20-6.35 (m, 2H), 6.60-6.72 (m, 2H), 7.41-7.52 (m, 2H).

MS (ES+) m/z 467 (MH$^+$).

The free base of the title compound was then treated with one equivalent of 1M HCl in diethyl ether to give the title compound as the mono hydrochloride salt (16.7 mg, 27.5%). LCMS was consistent with product.

Example 32 (1R)-1-[(4-{[(7-Chloro-3-oxo-3,4-di-hydro-2H-pyrido[3,2-b][1,4]oxazin-6-yl)methyl]amino}-1-piperidinyl)methyl]-1,2-dihydro-4H,9H-imidazo[1,2,3-ij]-1,8-naphthyridine-4,9-dione dihydrochloride

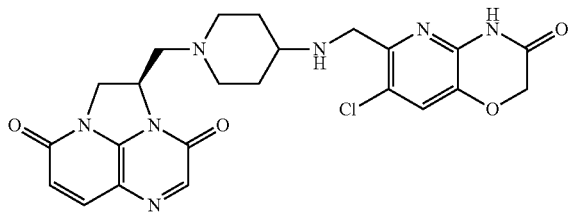 [SMILES: O=C1COc2cc(Cl)c(CNC3CCN(C[C@@H]4Cn5c(=O)ccc6ncc(=O)n4c65)CC3)nc2N1]

In a 10 mL round-bottomed flask (1R)-1-[(4-amino-1-piperidinyl)methyl]-1,2-dihydro-4H,9H-imidazo[1,2,3-ij]-1,8-naphthyridine-4,9-dione (for a preparation see Example 5A(j) (80 mg, 0.266 mmol), 7-chloro-3-oxo-3,4-dihydro-2H-pyrido[3,2-b][1,4]oxazine-6-carbaldehyde (for a synthesis see WO2003064421, Example 15(c)) (62.3 mg, 0.293 mmol), and sodium bicarbonate (100 mg, 1.190 mmol) in DCM (4 ml) and methanol (1 ml) were combined to give a brown solution. Sodium sulfate (200 mg, 1.408 mmol) was added and the reaction was allowed to stir at rt overnight. After 15 h sodium triacetoxyborohydride (113 mg, 0.533 mmol) was added and the reaction was allowed to stir at 25° C. under nitrogen for 4 h. The reaction mixture was adsorbed onto silica and purified using 0-10% MeOH/DCM (1% NH$_4$OH). The LCMS and 1H NMR of the product were consistent with the title compound as the free base.

$^1$H NMR δH D-4 MeOH, (400 MHz) 1.24-1.45 (m, 2H), 1.79-1.96 (m, 2H), 2.22-2.31 (m, 2H), 2.46-2.53 (m, 1H), 2.59-2.68 (m, 1H), 2.87-3.09 (m, 4H), 3.89 (s, 2H), 4.42-4.51 (m, 2H), 4.69 (s, 2H), 5.07-5.15 (m, 1H), 6.26-6.35 (m, 2H), 7.39 (s, 1H), 7.75-7.81 (m, 2H),

MS (ES+) m/z 497/499 (MH$^+$).

The free base of the title compound was taken up in 10% MeOH/DCM and treated with 1N HCl to form title compound as the diHCl salt (55 mg, 36.2%)

Example 33 (1R)-1-[(4-{[(4-Chloro-7-oxo-6,7-di-hydro-1H-pyrimido[5,4-b][1,4]oxazin-2-yl)methyl]amino}-1-piperidinyl)methyl]-1,2-dihydro-4H,9H-imidazo[1,2,3-ij]-1,8-naphthyridine-4,9-dione

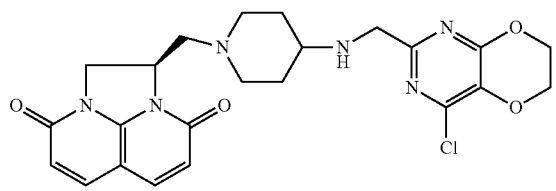 [SMILES: O=c1ccc2ccc(=O)n3c2n1C[C@H]3CN1CCC(NCc2nc(Cl)c3c(n2)OCCO3)CC1]

In a 10 mL round-bottomed flask were combined (1R)-1-[(4-amino-1-piperidinyl)methyl]-1,2-dihydro-4H,9H-imidazo[1,2,3-ij]-1,8-naphthyridine-4,9-dione (for a preparation see Example 5A(j)) (60 mg, 0.178 mmol), 4-chloro-7-oxo-6,7-dihydro-1H-pyrimido[5,4-b][1,4]oxazine-2-carbaldehyde (for a synthesis see WO2008009700, Example 124(g)) (38 mg, 0.178 mmol), and sodium bicarbonate (150 mg, 1.78 mmol) in DCM (5 ml) and methanol (1 ml) to give a brown solution. Sodium sulfate (200 mg, 1.408 mmol) was added and the reaction was allowed to stir at rt overnight. After 15 h sodium triacetoxyborohydride (113 mg, 0.533 mmol) was added and the reaction was allowed to stir at 25° C. under nitrogen for 4 h. The reaction mixture was adsorbed onto silica and purified using 0-20% MeOH/DCM (1% NH$_4$OH) to give the title compound (4 mg orange solid, 4.51%).

$^1$H NMR δH CDCl$_3$, (250 MHz) 1.28-1.51 (m, 2H), 1.75-1.99 (m, 2H), 2.13-2.38 (m, 2H), 2.41-2.80 (m, 3H), 2.90-3.15 (m, 2H), 3.75 (s, 2H), 4.31-4.42 (m, 1H), 4.51-4.62 (m, 1H), 4.8 (s, 2H), 4.90-5.08 (m, 1H), 6.25-6.32 (m, 2H), 7.51-7.53 (m, 2H),

MS (ES+) m/z 498/500 (MH$^+$).

Example 34 (1R)-1-[(4-{[(7-Oxo-6,7-dihydro-1H-pyrimido[5,4-b][1,4]thiazin-2-yl)methyl]amino}-1-piperidinyl)methyl]-1,2-dihydro-4H,9H-imidazo[1,2,3-ij]-1,8-naphthyridine-4,9-dione dihydrochloride

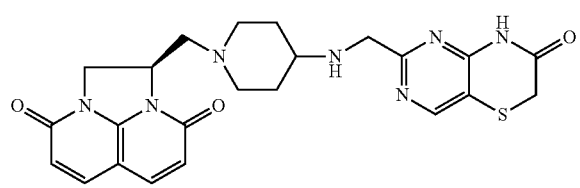 [SMILES: O=C1CSc2cnc(CNC3CCN(C[C@@H]4Cn5c(=O)ccc6ccc(=O)n4c65)CC3)nc2N1]

(a) Ethyl [(2,4-dioxo-1,2,3,4-tetrahydro-5-pyrimidinyl)thio]acetate

A solution of 5-bromo-2,4(1H,3H)-pyrimidinedione (15 g, 79 mmol) and ethyl mercaptoacetate (8.58 ml, 79 mmol) in DMF (200 mL) was treated with tetrabutylammonium hydrogen sulfate (6.67 g, 19.64 mmol) and potassium carbonate (23.88 g, 173 mmol) and stirred at ambient temperature overnight. The solution was filtered and concentrated under reduced pressure to yield crude title compound as a yellow oil which foams up under reduced pressure.

MS (ES+) m/z 231.1 (MH$^+$).

(b) Ethyl [(2,4-dichloro-5-pyrimidinyl)thio]acetate A suspension of ethyl [(2,4-dioxo-1,2,3,4-tetrahydro-5-pyrimidinyl)thio]acetate (crude material) (18.19 g, 79 mmol) in phosphorus oxychloride (100 ml, 1073 mmol) was treated with dimethyl aniline (2.500 ml, 19.72 mmol), and the reaction was heated to reflux and stirred for 2 hours. The solution was allowed to cool to room temperature and poured slowly onto ice to quench the excess phosphorus oxychloride. Once quenched, the aqueous layer was extracted with CH$_2$Cl$_2$ (3×). The organic layers were combined, dried over Na$_2$SO$_4$, filtered, and concentrated under reduced pressure. The crude material was chromatographed using a gradient of 0-50% EtOAc/Hexanes. The product was isolated as a dark yellow oil. 1H NMR (400 MHz, chloroform-d) ppm 1.22 (t, J=7.07 Hz, 3H) 3.71 (s, 2H) 4.15 (d, J=7.33 Hz, 1H) 8.53 (s, 1H)

(c) Ethyl [(4-amino-2-chloro-5-pyrimidinyl)thio]acetate

A solution of ethyl [(2,4-dichloro-5-pyrimidinyl)thio]acetate (2.0 g, 7.49 mmol) in DMF (75 ml) was treated with ammonia in isopropanol (7.49 ml, 14.97 mmol) in a pressure tube. The tube was capped, and the reaction was stirred at ambient temperature.

Upon completion, the solution was concentrated under reduced pressure and pumped on to remove any residual DMF. The crude material was chromatographed using a gradient of 0-10% acetone/chloroform. The product contained a small amount of cyclized material (which is the product of the next step). The product was isolated as a light yellow solid.

MS (ES+) m/z 248.0 (MH$^+$).

(d) 2-Chloro-1H-pyrimido[5,4-b][1,4]thiazin-7(6H)-one

A suspension of ethyl [(4-amino-2-chloro-5-pyrimidinyl)thio]acetate (0.786 g, 3.17 mmol) in ethanol (50 ml) was heated to 70° C. Cesium carbonate (1.034 g, 3.17 mmol) was added and the solution was heated for a further 5 minutes. A white solid precipitated out of solution almost immediately. The solution was concentrated under reduced pressure. The residue was dissolved in water and brought to pH=5 with 1N HCl. The aqueous layer was extracted with $CH_2Cl_2$ (2×). The organic layers were combined, dried over $Na_2SO_4$, filtered, and concentrated under reduced pressure to yield a light yellow solid.

MS (ES+) m/z 202.0 (MH$^+$).

(e) 2-Ethenyl-1H-pyrimido[5,4-b][1,4]thiazin-7(6H)-one

2-Chloro-1H-pyrimido[5,4-b][1,4]thiazin-7(6H)-one (0.639 g, 3.17 mmol) was treated with tributylvinyl tin (1.388 ml, 4.76 mmol), and tetrakis(triphenylphosphine)palladium(0) (0.293 g, 0.254 mmol) in 1,4-dioxane (4 ml) and toluene (4 mL) in a microwave vial. The reaction was heated in the microwave at 140° C. for 20 minutes. The solution was diluted with EtOAc and washed with saturated $NaHCO_3$ solution. The aqueous layer was extracted with EtOAc (2×). The organic solution were combined, dried over $Na_2SO_4$, filtered, and concentrated under reduced pressure. The crude material was chromatographed using a gradient of 0-60% $CH_2Cl_2/(CH_2Cl_2/MeOH/NH_4OH)$ (90:10:1). The product was isolated as a mixture of the desired product and triphenylphosphine. Pure material was obtained by triturating and washing with diethyl ether. The product was isolated as an orange solid.

MS (ES+) m/z 194.0 (MH$^+$).

(f) 7-Oxo-6,7-dihydro-1H-pyrimido[5,4-b][1,4]thiazine-2-carbaldehyde A solution of 2-ethenyl-1H-pyrimido[5,4-b][1,4]thiazin-7(6H)-one (0.262 g, 1.356 mmol) in methanol/DCM was cooled to −78° C. and treated with ozone until the solution turned blue. The solution was stirred at −78° C. for an additional 5 minutes. Dimethyl sulfide (5.0 ml, 67.6 mmol) was added and the solution was allowed to warm to room temperature and stir overnight. The solution was concentrated onto silical gel and the crude material was chromatographed using a gradient of 0-100% $CH_2Cl_2/(CH_2Cl_2/MeOH/NH_4OH)$ (90:10:1). The product was isolated as a light yellow solid.

MS (ES+) m/z 195.9 (MH$^+$).

(g) Title Compound

A suspension of (1R)-1-[(4-amino-1-piperidinyl)methyl]-1,2-dihydro-4H,9H-imidazo[1,2,3-ij]-1,8-naphthyridine-4,9-dione (for a preparation see Example 5A(j)) (0.060 g, 0.179 mmol) in 1:1 $CH_2Cl_2$/MeOH (10 mL) was treated with 7-oxo-6,7-dihydro-1H-pyrimido[5,4-b][1,4]thiazine-2-carbaldehyde (0.035 g, 0.179 mmol) and sodium bicarbonate (0.151 g, 1.793 mmol). Excess $Na_2SO_4$ was added and the reaction stirred at room temperature for 18 hours. Sodium triacetoxyborohydride (0.114 g, 0.538 mmol) was added and the reaction stirred at room temperature for 1 hour. The solution was concentrated onto silica gel and the crude material was chromatographed using a gradient of 0-100% $CH_2Cl_2/(CH_2Cl_2/MeOH/NH_4OH)$ (90:10:1). The free base of the title compound was isolated as a yellow solid (0.027 g).

MS (ES+) m/z 480.1 (MH$^+$).

1H NMR (400 MHz, CHLOROFORM-d) ppm 1.62 (d, J=2.53 Hz, 1H) 1.61 (br. s., 1H) 1.90-2.09 (m, 3H) 2.20-2.42 (m, 2H) 2.59-2.78 (m, 2H) 3.14 (dd, J=12.88, 3.03 Hz, 2H) 3.53 (s, 2H) 4.05-4.14 (m, 2H) 4.41 (dd, J=12.38, 9.35 Hz, 1H) 4.57 (dd, J=12.63, 4.04 Hz, 1H) 5.04 (dd, J=7.96, 4.42 Hz, 1H) 5.32 (s, 1H) 6.28 (dd, J=16.29, 9.22 Hz, 2H) 7.49 (d, J=3.28 Hz, 1H) 7.50-7.57 (m, 1H).

The title di-HCl salt was formed by dissolving the free base in $CH_2Cl_2$ and adding 0.113 mL 1N HCl/ether.

Example 35 (1R)-1-({4-[(1,2,3-Benzothiadiazol-5-ylmethyl)amino]-1-piperidinyl}methyl)-1,2-dihydro-4H,9H-imidazo[1,2,3-ij]-1,8-naphthyridine-4,9-dione hydrochloride

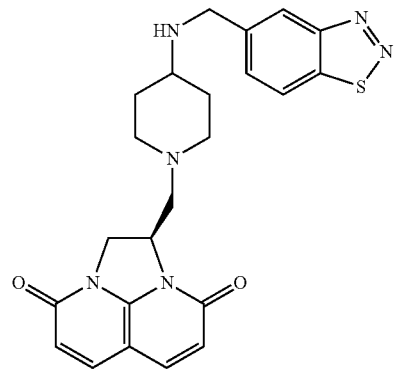 [SMILES: O=c1ccc2ccc(=O)n3c2n1C[C@H]3CN1CCC(NCc2ccc3snnc3c2)CC1]

A suspension of (1R)-1-({4-[(1,2,3-benzothiadiazol-5-ylmethyl)amino]-1-piperidinyl}methyl)-1,2-dihydro-4H,9H-imidazo[1,2,3-ij]-1,8-naphthyridine-4,9-dione dihydrochoride (for a preparation see Example 5A(j)) (60 mg, 0.161 mmol) in chloroform (2 ml) and methanol (0.100 ml) at rt under nitrogen was treated with triethylamine (0.067 ml, 0.482 mmol) and stirred at rt for 15 h. The solution was then treated with 1,2,3-benzothiadiazole-5-carbaldehyde (for a synthesis see WO0208224 Example 20(a)) (23.75 mg, 0.145 mmol) and stirred for a further 30 min. The solution was then treated with sodium triacetoxyborohydride (102 mg, 0.482 mmol) and stirred at rt for 45 min, LC-MS after 45 min showed reaction complete. This was then treated with saturated aqueous $NaHCO_3$ (10 ml) and extracted with 20% methanol/DCM (3×25 ml). The combined organic extracts were dried ($MgSO_4$), filtered, evaporated and chromatographed (0-5% methanol/DCM 5% methanol/DCM) to give the free base of the title compound (26 mg, 36%) as a pale yellow solid.

$^1$H NMR δH CDCl$_3$, (400 MHz) 1.30-1.49 (m, 2H), 1.80-1.98 (m, 2H), 2.21-2.39 (m, 2H), 2.51-2.61 (m, 1H), 2.61-2.75 (m, 2H), 2.90-3.02 (m, 1H), 3.05-3.19 (m, 1H), 4.04 (s, 2H), 4.31-4.42 (m, 1H), 4.51-4.61 (m, 1H), 4.92-5.05 (m, 1H), 6.20-6.31 (m, 2H), 7.45-7.53 (2H, m), 7.71 (d, 1H). 8.11 (d, 1H), 8.56 (s, 1H)

MS (ES+) m/z 449 (MH+).

The free base of the title compound was dissolved in a small amount of DCM, treated with one equivalent of 1M HCl in diethyl ether and then evaporated to give the title compound as the mono-HCl salt (16.2 mg, 20.8%). LCMS consistent with product.

Example 36 (1R)-1-({4-[(2,3-Dihydro-1-benzofuran-5-ylmethyl)amino]-1-piperidinyl}methyl)-1,2-dihydro-4H,9H-imidazo[1,2,3-ij]-1,8-naphthyridine-4,9-dione hydrochloride

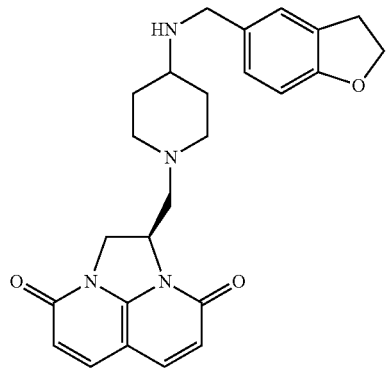 [SMILES: O=c1ccc2ccc(=O)n3c2n1C[C@H]3CN1CCC(NCc2ccc3c(c2)CCO3)CC1]

A suspension of (1R)-1-({4-[(1,2,3-benzothiadiazol-5-ylmethyl)amino]-1-piperidinyl}methyl)-1,2-dihydro-4H,9H-imidazo[1,2,3-ij]-1,8-naphthyridine-4,9-dione dihydrochoride (for a preparation see Example 5A(j)) (60 mg, 0.161 mmol) in chloroform (2 ml) and methanol (0.100 ml) at rt under nitrogen was treated with triethylamine (0.067 ml, 0.482 mmol) and stirred at rt for 15 min. The solution was then treated with 2,3-dihydro-1-benzofuran-5-carbaldehyde (commercially available) (0.020 ml, 0.161 mmol) and stirred for a further 30 min. The solution was then treated with sodium triacetoxyborohydride (102 mg, 0.482 mmol) and stirred at rt for 45 min. This was then treated with saturated aqueous NaHCO₃ (10 ml) and extracted with 20% methanol/DCM (3×25 ml). The combined organic fractions were dried (NaSO₄), filtered, evaporated and chromatographed (5-25% methanol/DCM) to give the free base of the title compound (24 mg, 34.5%) as a white solid.

¹H NMR δH CDCl₃, (400 MHz) 1.22-1.49 (m, 2H), 1.79-2.10 (m, 2H), 2.21-2.40 (m, 2H), 2.45-2.58 (m, 1H), 2.61-2.72 (m, 2H), 2.90-3.01 (m, 1H), 3.05-3.15 (m, 1H), 3.21 (t, 2H), 3.72 (s, 2H), 4.32-4.42 (m, 1H), 4.51-4.62 (m, 3H), 4.95-5.05 (m, 1H), 6.22-6.33 (m, 2H), 6.72 (d, 1H), 7.14 (d, 1H), 7.19 (s, 1H), 7.45-7.52 (2H, m),

MS (ES+) m/z 433 (MH+).

The free base of the title compound was dissolved in a small amount of DCM, treated with one equivalent of 1M HCl in diethyl ether and then evaporated to give the title compound as the mono-HCl salt (22.7 mg, 28.6%). LCMS consistent with product.

Example 37 (1R)-1-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride

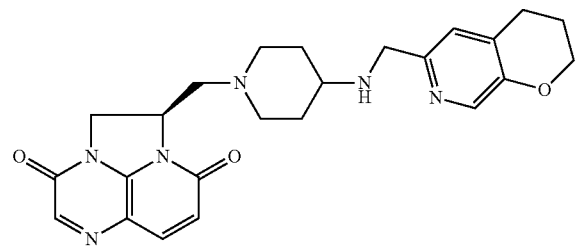 [SMILES: O=c1cnc2ccc(=O)n3c2n1C[C@H]3CN1CCC(NCc2cc3c(cn2)OCCC3)CC1]

A suspension of (1R)-1-[(4-amino-1-piperidinyl)methyl]-1,2-dihydro-3H,8H-2a,5,8a-triazaacenaphthylene-3,8-dione dihydrochloride (for a preparation see Example 13(k) or 15(d)) (50 mg, 0.100 mmol) in chloroform (4 ml) and methanol (0.200 ml) at room temperature under nitrogen was treated with triethylamine (0.042 ml, 0.301 mmol) and stirred for 0.25 h (the suspension turned into a solution). 3,4-Dihydro-2H-pyrano[2,3-c]pyridine-6-carbaldehyde (for a synthesis see WO2004058144, Example 126(e)) (16.35 mg, 0.100 mmol) was then added and the reaction was stirred at room temperature for 0.5 h. Sodium triacetoxyborohydride (67.1 mg, 0.301 mmol) was then added and the reaction was stirred at room temperature. After 3 h there was still some starting material so 30 mg of sodium triacetoxyborohydride were added. After 1 h a saturated aqueous solution of sodium bicarbonate (25 mL) was added followed by 20% methanol/DCM (25 mL) and the aqueous layer was extracted and then separated from the organic layer. The aqueous layer was extracted again twice with 20% methanol/DCM (2×25 mL). The combined organic layers were dried on sodium sulphate, filtered and evaporated to afford 60 mg of crude product. The crude product was purified by silica chromatography (0-20% MeOH/DCM) to afford the free base of the title compound as a yellow solid (39 mg, 87%).

¹H NMR δH CDCl₃, (400 MHz) 1.25-1.45 (m, 2H), 1.78-2.08 (m, 4H), 2.22-2.38 (m, 2H), 2.45-2.60 (m, 1H), 2.62 (d, 1H), 2.67-2.80 (m, 3H), 2.93 (d, 1H), 3.05-3.14 (m, 1H), 3.78 (s, 2H), 4.15-4.25 (m, 2H), 4.30-4.45 (m, 1H), 4.50-4.60 (m, 1H), 4.95-5.05 (m, 1H), 6.33 (d, 1H), 6.96 (s, 1H), 7.75 (s, 1H), 7.87 (s, 1H), 8.07 (s, 1H).

MS (ES+) m/z 449 (MH+).

The free base of the title compound was dissolved in a small amount of methanol/DCM and treated with 1 eq of 1M hydrochloric acid in diethyl ether. The solvents were removed and the solid was dried in the desiccator (in the presence of P₂O₅) over the weekend to afford the title compound as the mono-HCl salt as a yellow solid (40.6 mg, 79%). LCMS was consistent with product.

Example 38 (1R)-1-({4-[(2,3-Dihydrofuro[2,3-c]pyridin-5-ylmethyl)amino]-1-piperidinyl}methyl)-1,2-dihydro-3H,8H-2a,5,8a-triazaacenaphthylene-3,8-dione hydrochloride

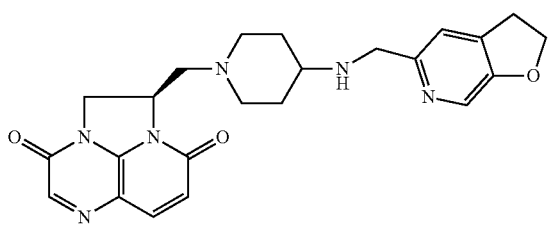 [SMILES: O=c1cnc2ccc(=O)n3c2n1C[C@H]3CN1CCC(NCc2cc3c(cn2)OCC3)CC1]

A suspension of (1R)-1-[(4-amino-1-piperidinyl)methyl]-1,2-dihydro-3H,8H-2a,5,8a-triazaacenaphthylene-3,8-dione dihydrochloride (for a preparation see Example 13(k) or 15(d)) (50 mg, 0.100 mmol) in chloroform (20 ml) and methanol (0.800 ml) at room temperature under nitrogen was treated with triethylamine (0.042 ml, 0.301 mmol) and stirred for 0.25 h (the suspension turned into a solution). 2,3-Dihydrofuro[2,3-c]pyridine-5-carbaldehyde (for a synthesis see WO2007122258, Example 43(f)(14.94 mg, 0.100 mmol) was then added and the reaction was stirred at room temperature for 0.5 h. Sodium triacetoxyborohydride (67.1 mg, 0.301 mmol) was then added and the reaction was stirred at room temperature. After 3 h there was still some starting material so 30 mg of sodium triacetoxyborohydride were added. After 1 h a saturated aqueous solution of sodium bicarbonate (25 mL) was added followed by 20% methanol/DCM (25 mL) and the aqueous layer was extracted and then separated from the organic layer. The aqueous layer was extracted again twice with 20% methanol/DCM (2×25 mL). The combined organic extracts were dried on sodium sulphate, filtered and evaporated to afford 50 mg of crude product. The crude product was purified by silica chromatography (0-20% methanol/DCM) to afford the free base of the title compound as a yellow solid (31 mg, 71.2%).

$^1$H NMR δH CDCl$_3$, (250 MHz) 1.25-1.43 (m, 2H), 1.81-2.00 (m, 2H), 2.22-2.35 (m, 2H), 2.49-2.54 (m, 1H), 2.66 (d, 1H), 2.71-2.74 (m, 1H), 2.92 (d, 1H), 3.07-3.12 (m, 1H), 3.19-3.24 (m, 2H), 3.82 (s, 2H), 4.37-4.42 (m, 1H), 4.56-4.62 (m, 3H), 4.96-5.06 (m, 1H), 6.33 (d, 1H), 7.18 (s, 1H), 7.76 (d, 1H), 7.86 (s, 1H), 8.06 (s, 1H).

MS (ES+) m/z 435 (MH$^+$).

The free base of the title compound was dissolved in a small amount of methanol/DCM and treated with 1 eq of 1M hydrochloric acid in diethyl ether. The solvents were removed and the solid was dried in the desiccator (in the presence of P$_2$O$_5$) over the weekend to afford the title compound as the mono-HCl salt as an orange solid (33.5 mg, 67.4%). LCMS was consistent with product.

Example 39 (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride

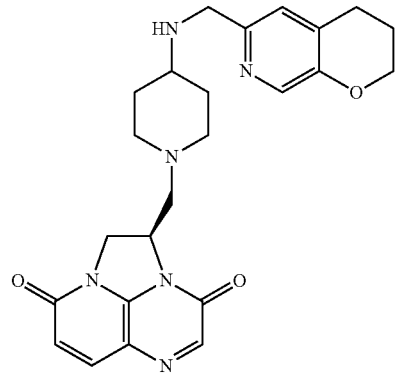 [SMILES: O=c1ccc2ncc(=O)n3c2n1C[C@H]3CN1CCC(NCc2cc3c(cn2)OCCC3)CC1]

A suspension of (2R)-2-[(4-amino-1-piperidinyl)methyl]-1,2-dihydro-3H, 8H-2a,5,8a-triazaacenaphthylene-3,8-dione (for a preparation see Example 16A(j)) (60 mg, 0.199 mmol) and 3,4-dihydro-2H-pyrano[2,3-c]pyridine-6-carbaldehyde (for a synthesis see WO2004058144, Example 126 (e)) (29.2 mg, 0.179 mmol) in chloroform (2 ml) and methanol (0.061 ml) at rt under nitrogen was treated with sodium triacetoxyborohydride (127 mg, 0.597 mmol) and stirred at rt for 30 min. The reaction was then treated with saturated aqueous NaHCO$_3$ (10 ml) and extracted with 20% methanol/DCM (3×20 ml). The combined organic extracts were dried (MgSO$_4$), filtered, evaporated and purified using silica chromatography (0-20% MeOH/DCM) to give the free base of the title compound as a light brown solid $^1$H NMR δH CDCl$_3$, (400 MHz) 1.28-1.40 (m, 2H), 1.78-1.86 (m, 2H), 1.96-2.01 (m, 2H), 2.14-2.34 (m, 2H), 2.45-2.52 (m, 1H), 2.62-2.74 (m, 4H), 2.91 (m, 1H), 3.07-3.11 (m, 1H), 3.74 (s, 2H), 4.16-4.18 (m, 2H), 4.32-4.37 (m, 1H), 4.48-4.52 (m, 1H), 4.97-5.03 (m, 1H), 6.34 (d, 1H), 6.93 (s, 1H), 7.72 (d, 1H), 7.77 (s, 1H), 8.03 (s, 1H), MS (ES+) m/z 449 (MH$^+$).

The free base of the title compound in a small amount of DCM was treated with one equivalent of 1M HCl in diethyl ether (0.17 ml), evaporated and dried in a dessicator overnight to give the title compound as the mono-HCl salt (57.3 mg, 56.4% yield). LCMS consistent with product.

Example 40 (2R)-2-({4-[(2,3-Dihydro-1,4-benzodioxin-6-ylmethyl)amino]-1-piperidinyl}methyl)-1,2-dihydro-3H,8H-2a,5,8a-triazaacenaphthylene-3,8-dione hydrochloride

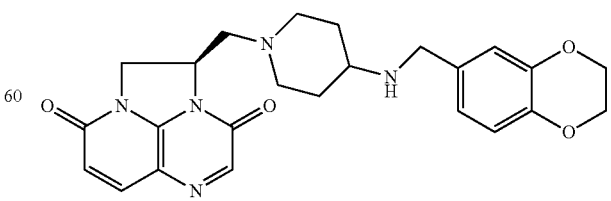

A suspension of (2R)-2-[(4-amino-1-piperidinyl)methyl]-1,2-dihydro-3H, 8H-2a,5,8a-triazaacenaphthylene-3,8-dione (for a preparation see Example 16A(j)) (60 mg, 0.199 mmol) and 2,3-dihydro-1,4-benzodioxin-6-carbaldehyde (commercially available) (29.4 mg, 0.179 mmol) in chloroform (2 ml) and methanol (0.100 ml) at rt under nitrogen was treated with sodium triacetoxyborohydride (127 mg, 0.597 mmol) and stirred for 90 min, LC-MS after 90 min showed reaction complete. This was treated with saturated aqueous NaHCO₃ (10 ml) and extracted with 20% methanol/DCM (3×25 ml). The combined organic extracts were dried (MgSO₄), filtered, evaporated and chromatographed (0-20% methanol/DCM) to give the free base of the title compound (46.8 mg, 58.4%) as a yellow gum.

¹H NMR δH CDCl₃, (400 MHz) 1.20-1.41 (m, 2H), 1.73-1.91 (m, 2H), 2.09-2.38 (m, 2H), 2.42-2.55 (m, 1H), 2.61-2.72 (m, 2H), 2.85-2.95 (m, 1H), 3.05-3.15 (m, 1H), 3.68 (s, 2H), 4.32 (m, 4H). 4.32-4.42 (m, 1H), 4.49-4.59 (m, 1H), 4.95-5.06 (m, 1H), 6.39 (d, 1H), 6.71-6.85 (m, 3H), 7.75 (d, 1H), 7.81 s, 1H).

MS (ES+) m/z 450 (MH⁺).

The free base of the title compound was dissolved in a small amount of DCM, treated with one equivalent of 1M HCl in diethyl ether and then evaporated to give the title compound as the mono-HCl salt (43.8 mg, 53.4%). LCMS consistent with product.

Example 41 (2R)-2-[(4-{[(8-Fluoro-2,3-dihydro-1,4-benzodioxin-6-yl)methyl]amino}-1-piperidinyl)methyl]-1,2-dihydro-3H,8H-2a,5,8a-triazaacenaphthylene-3,8-dione hydrochloride

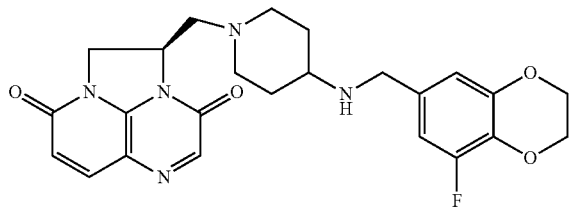 [SMILES: O=c1ccc2ncc(=O)n3c2n1C[C@H]3CN1CCC(NCc2cc(F)c3c(c2)OCCO3)CC1]

A suspension of (2R)-2-[(4-amino-1-piperidinyl)methyl]-1,2-dihydro-3H, 8H-2a,5,8a-triazaacenaphthylene-3,8-dione (for a preparation see Example 16A(j)) (58.5 mg, 0.194 mmol) and 8-fluoro-2,3-dihydro-1,4-benzodioxin-6-carbaldehyde (for a synthesis see WO2007122258, Example 8(b)) (31.8 mg, 0.175 mmol) in chloroform (2 ml) and methanol (0.100 ml) at room temperature under nitrogen was stirred for 0.5 h. This was then treated with sodium triacetoxyborohydride (123 mg, 0.582 mmol) and stirred for 90 min. This was then treated with saturated aqueous NaHCO₃ (10 ml) and extracted with 20% methanol/DCM (3×25 ml). The combined organic extracts were dried (NaSO₄), filtered, evaporated and purified using silica chromatography (0-20% methanol/DCM) to give the free base of the title compound as a yellow gum (44.9 mg, 49.5%).

¹H NMR δH CDCl₃, (400 MHz) 1.24-1.55 (m, 2H), 1.78-1.85 (m, 2H), 2.21-2.36 (m, 2H), 2.44-2.51 (m, 1H), 2.64-2.73 (m, 2H), 2.92 (d, 1H), 3.10-3.14 (m, 1H), 3.65 (s, 2H), 4.26-4.30 (m, 4H), 4.35-4.40 (m, 1H), 4.52-4.56 (m, 1H), 4.99-5.05 (m, 1H), 6.38 (d, 1H), 6.62-6.67 (m, 2H), 7.76 (d, 1H), 7.81 (s, 1H),

MS (ES+) m/z 468 (MH⁺).

The free base of the title compound was dissolved in a small amount of DCM, treated with one equivalent of 1M HCl in diethyl ether and then evaporated and dried in a desiccator overnight to give the title compound as the mono-HCl salt (30.1 mg, 29.2%).

LCMS consistent with product.

Example 42 7-{[(1-{[(2R)-3,8-Dioxo-1,2-dihydro-3H,8H-2a,5,8a-triazaacenaphthylen-2-yl]methyl}-4-piperidinyl)amino]methyl}-2,3-dihydro-1,4-benzodioxin-5-carbonitrile hydrochloride

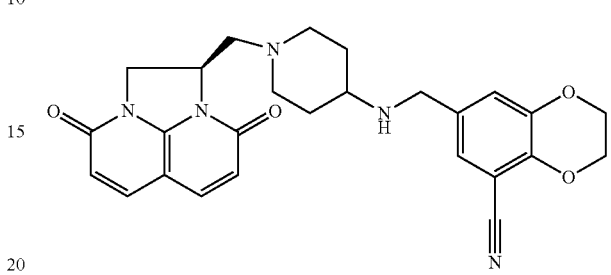

A suspension of (2R)-2-[(4-amino-1-piperidinyl)methyl]-1,2-dihydro-3H, 8H-2a,5,8a-triazaacenaphthylene-3,8-dione (for a preparation see Example 16A(j)) (60 mg, 0.199 mmol) and 7-formyl-2,3-dihydro-1,4-benzodioxin-5-carbonitrile (for a synthesis see WO06014580 Preparation 13 or WO2007122258, Example 31(d)) (37.7 mg, 0.199 mmol) in chloroform (2 ml) and methanol (0.100 ml) at room temperature under nitrogen was treated with sodium triacetoxyborohydride (127 mg, 0.597 mmol) and stirred for 90 min. This was then treated with saturated aqueous NaHCO₃(10 ml) and extracted with 20% methanol/DCM (3×25 ml). The combined organic extracts were dried (NaSO₄), filtered, evaporated and purified using silica chromatography (0-20% methanol/DCM) to give the free base of the title compound as a yellow gum (40 mg, 42.3%).

¹H NMR δH CDCl₃, (400 MHz) 1.24-156 (m, 2H), 1.79-1.86 (m, 2H), 2.21-2.36 (m, 2H), 2.43-2.50 (m, 1H), 2.65-2.72 (m, 2H), 2.93 (d, 1H), 3.12-3.16 (m, 1H), 3.68 (s, 2H), 4.29-4.41 (m, 5H), 4.53-4.57 (m, 1H), 5.00-5.06 (m, 1H), 6.39 (d, 1H), 7.06-7.09 (m, 2H), 7.77 (d, 1H), 7.83 (s, 1H),

MS (ES+) m/z 475 (MH⁺).

The free base of the title compound was dissolved in a small amount of DCM, treated with one equivalent of 1M HCl in diethyl ether, evaporated and dried in a dessicator overnight to give the title compound as the mono-HCl salt (45 mg, 42%) as a pale yellow solid. LCMS consistent with product.

Example 43 (2R)-2-({4-[(2,3-Dihydrofuro[2,3-c]pyridin-5-ylmethyl)amino]-1-piperidinyl}methyl)-1,2-dihydro-3H,8H-2a,5,8a-triazaacenaphthylene-3,8-dione hydrochloride

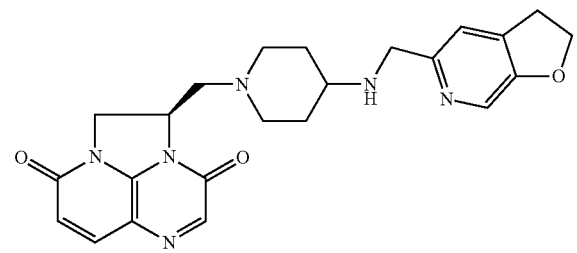 [SMILES: O=c1ccc2ncc(=O)n3c2n1C[C@H]3CN1CCC(NCc2cc3c(cn2)OCC3)CC1]

A suspension of (2R)-2-[(4-amino-1-piperidinyl)methyl]-1,2-dihydro-3H,8H-2a,5,8a-triazaacenaphthylene-3,8-dione (for a preparation see Example 16A(j)) (70 mg, 0.232 mmol) and 2,3-dihydrofuro[2,3-c]pyridine-5-carbaldehyde (for a synthesis see WO2007122258, Example 43(f) (34.6 mg, 0.232 mmol) in chloroform (5 ml) and methanol (0.250 ml) at room temperature under nitrogen was stirred for 0.5 h (the suspension turned into a solution). Sodium triacetoxyborohydride (155 mg, 0.697 mmol) was then added and the reaction was stirred at room temperature. After 3 h there was no starting material left so a saturated aqueous solution of sodium bicarbonate (25 mL) was added followed by 20% methanol/DCM (25 mL) and the aqueous layer was extracted and then separated from the organic layer. The aqueous layer was extracted again twice with 20% methanol/DCM (2×25 mL). The combined organic extracts were dried on sodium sulphate, filtered and evaporated to afford 90 mg of crude product. The crude product was purified by silica chromatography (0-20% MeOH/DCM) to afford the free base of the title compound as a pale yellow solid (77 mg, 76%).

$^1$H NMR δH CDCl$_3$, (400 MHz) 1.28-1.48 (m, 2H), 1.81-1.89 (m, 2H), 2.21-2.36 (m, 2H), 2.43-2.55 (m, 1H), 2.64-2.72 (m, 2H), 2.93 (d, 1H), 3.10-3.14 (m, 1H), 3.19-3.23 (m, 2H), 3.81 (s, 2H), 4.34-4.40 (m, 1H), 4.52-4.61 (m, 3H), 4.95-5.08 (m, 1H), 6.37 (d, 1H), 7.17 (s, 1H), 7.76 (d, 1H), 7.81 (s, 1H), 8.06 (s, 1H).

MS (ES+) m/z 435 (MH$^+$).

The free base of the title compound was dissolved in a small amount of methanol/DCM and treated with 1 eq of 1M hydrochloric acid in diethyl ether. The solvents were removed and the solid was dried in the desiccator (in the presence of P$_2$O$_5$) over the weekend to afford the title compound as the mono-HCl salt as an off-white solid (78.9 mg, 68.5%). LCMS was consistent with product.

Example 44 (1R)-1-({4-[(2,3-Dihydro-1,4-benzodioxin-6-ylmethyl)amino]-1-piperidinyl}methyl)-1,2-dihydro-3H,8H-2a,5,8a-triazaacenaphthylene-3,8-dione hydrochloride

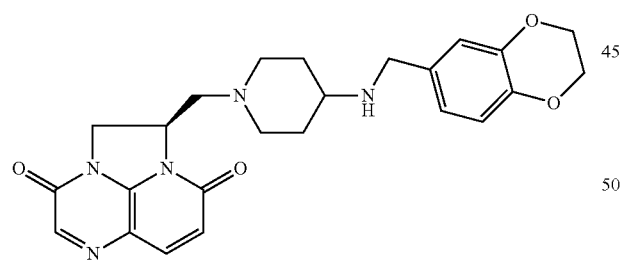

A suspension of (1R)-1-[(4-amino-1-piperidinyl)methyl]-1,2-dihydro-3H,8H-2a,5,8a-triazaacenaphthylene-3,8-dione dihydrochloride (for a preparation see Example 13(k) or 15(d)) (50 mg, 0.100 mmol) in chloroform (4 ml) and methanol (0.200 ml) at room temperature under nitrogen was treated with triethylamine (0.042 ml, 0.301 mmol) and stirred for 0.25 h (the suspension turned into a solution). 2,3-Dihydro-1,4-benzodioxin-6-carbaldehyde (commercially available) (16.45 mg, 0.100 mmol) was then added and the reaction was stirred at room temperature for 0.5 h. Sodium triacetoxyborohydride (67.1 mg, 0.301 mmol) was then added and the reaction was stirred at room temperature. After 3 h 40 mg more of sodium triacetoxyborohydride was added. After 1 h 30 mg more of sodium triacetoxyborohydride was added. After 1 h saturated NaHCO$_3$ (25 mL) was added followed by 20% MeOH/DCM (25 mL) and the aqueous layer was separated from the organic layer. The aqueous layer was extracted again twice with 20% MeOH/DCM (2×25 mL). The combined organic extracts were dried NaSO$_4$, filtered and evaporated to afford the crude product. The crude product was purified by chromatography on silica (0-20% MeOH/DCM) to give 27 mg of the free base of the title compound (59.9% total yield).

$^1$H NMR δH CDCl$_3$, (400 MHz) 1.21-1.42 (m, 2H), 1.70-1.92 (m, 2H), 2.21-2.36 (m, 2H), 2.41-2.55 (m, 1H), 2.58-2.78 (m, 2H), 2.88-2.98 (m, 1H), 3.05-3.14 (m, 1H), 3.68 (s, 2H), 4.25 (s, 4H), 4.43-4.52 (m, 1H), 4.51-4.62 (m, 1H), 4.98-5.06 (m, 1H), 6.34 (d, 1H), 6.75-6.84 (m, 3H), 7.76 (d, 1H), 7.87 (s, 1H).

MS (ES+) m/z 450 (MH$^+$).

The free base of the title compound was dissolved in a small amount of MeOH/DCM and treated with 1 eq of a 1M solution of HCl in Et$_2$O. The solvents were removed and the solid dried in the desiccator (P$_2$O$_5$) overnight to afford the title compound as the mono-HCl salt (26 mg, 0.051 mmol, 50.7% yield) as a yellow solid.

Example 45 (1R)-1-({4-[([1,2,5]Thiadiazolo[3,4-b]pyridin-6-ylmethyl)amino]-1-piperidinyl}methyl)-1,2-dihydro-4H,9H-imidazo[1,2,3-ij]-1,8-naphthyridine-4,9-dione hydrochloride

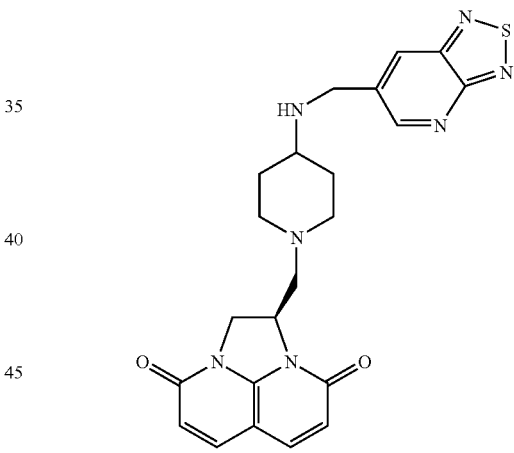

To (1R)-1-[(4-amino-1-piperidinyl}methyl)-1,2-dihydro-4H,9H-imidazo[1,2,3-ij]-1,8-naphthyridine-4,9-dione dihydrochoride (for a preparation see Example 5A(j) (60 mg, 0.161 mmol) was added chloroform (3 ml), methanol (0.3 ml) and triethylamine (0.067 ml, 0.482 mmol). The reaction was stirred under a nitrogen atmosphere for 30 mins, then [1,2,5]thiadiazolo[3,4-b]pyridine-6-carbaldehyde (for a preparation see Example 49(b)) (25.2 mg, 0.153 mmol) was added. The reaction was stirred for a further 2 hrs then sodium triacetoxyborohydride (102 mg, 0.482 mmol) was added and stirring continued for 16 hours. Further sodium triacetoxyborohydride (102 mg, 0.482 mmol) was added and stirred for 30 mins. Further sodium triacetoxyborohydride (102 mg, 0.482 mmol) was added and stirring continued for 2 hours. The reaction was partitioned between sat. NaHCO$_3$ and 20% MeOH in DCM. The aqueous was further extracted with 20% MeOH in DCM and the combined organic extracts passed thought a hydrophobic frit and concentrated to give a reddish brown solid (~65 mg). This was purified by silica chromatography eluting with 0-20% MeOH in DCM to give the free base of the title compound as a pale tan gum (18 mg).

$^1$H NMR δH CD$_3$OD 400 MHz 1.30 (m, 1H), 1.42 (m, 1H), 1.88 (br d, 1H), 1.98 (br d, 1H), 2.28 (q, 2H), 2.63 (m, 2H), 2.89 (dd, 1H), 3.01 (dd, 1H), 3.06 (br d, 1H), 4.08 (s, 2H), 4.45 (m, 2H), 5.10 (m, 1H), 6.28 (dd, 2H), 7.76 (d, 2H), 8.41 (br d, 1H), 9.08 (br d, 1H)

MS (ES+) m/z 450 (MH$^+$).

The free base of the title compound was dissolved in 2:1 DCM:MeOH (1 ml) and HCl (1M in diethyl ether) (0.040 ml, 0.04 mmol) was added. The solvent was evaporated to give a pale brown solid (22 mg, 28%).

Example 46 (1R)-1-[(4-{[(4-Fluoro-1H-benzimidazol-2-yl)methyl]amino}-1-piperidinyl)methyl]-1,2-dihydro-4H,9H-imidazo[1,2,3-ij]-1,8-naphthyridine-4,9-dione dihydrochloride

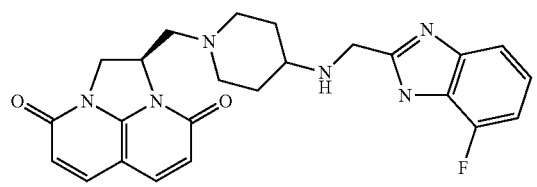 [SMILES: O=c1ccc2ccc(=O)n3c2n1C[C@H]3CN1CCC(NCc2nc3cccc(F)c3[nH]2)CC1]

To a 10 mL round-bottomed flask were added (1R)-1-[(4-amino-1-piperidinyl)methyl]-1,2-dihydro-4H,9H-imidazo[1,2,3-ij]-1,8-naphthyridine-4,9-dione (for a preparation see Example 5A(j)) (80 mg, 0.238 mmol), 4-fluoro-1H-benzimidazole-2-carbaldehyde (for a synthesis see WO2003087098, Example 320) (42.9 mg, 0.261 mmol), and sodium bicarbonate (100 mg, 1.190 mmol) in DCM (4 ml) and methanol (1 ml) to give a brown suspension. Sodium sulfate (200 mg, 1.408 mmol) was added and the reaction was stirred at rt overnight. After 15 h sodium triacetoxyborohydride (101 mg, 0.475 mmol) was added and the reaction was stirred at 25° C. under nitrogen for 4 h. The reaction mixture was adsorbed onto silica and purified using 0-10% MeOH/DCM (1% NH$_4$OH) to give the free base of the title compound. The LCMS and 1H NMR were consistent with the desired product.

$^1$H NMR δH D-4 MeOH, (400 MHz) 1.35-1.55 (m, 2H), 1.90-1.96 (m, 2H), 2.30-2.41 (m, 2H), 2.71-2.81 (m, 2H), 2.91-2.99 (m, 1H), 3.05-3.15 (m, 1H), 4.20 (s, 2H), 4.41-4.50 (m, 2H), 4.69 (s, 2H), 5.10-5.20 (m, 1H), 6.25-6.36 (m, 2H), 6.91-7.05 (m, 1H), 7.16-7.25 (m, 1H), 7.31-7.39 (m, 1H), 7.75-7.81 (m, 2H),

MS (ES+) m/z 449 (MH$^+$).

The free base of the title compound was taken up in 10% MeOH/DCM and treated with 1N HCl to form the title compound as the diHCl salt (17 mg, 0.033 mmol, 13.73% yield).

Example 47 (1R)-1-[((2S)-2-{[([1,3]Oxathiolo[5,4-c]pyridin-6-ylmethyl)amino]methyl}-4-morpholinyl)methyl]-1,2-dihydro-4H,9H-imidazo[1,2,3-ij]-1,8-naphthyridine-4,9-dione dihydrochloride

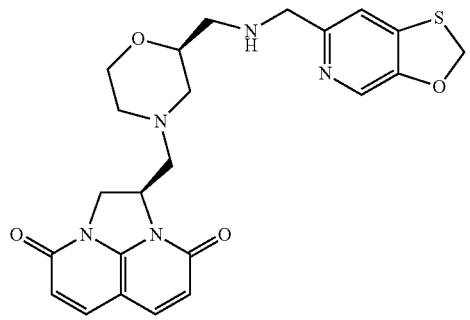 [SMILES: O=c1ccc2ccc(=O)n3c2n1C[C@H]3CN1CCO[C@@H](CNCc2cc3c(cn2)OCS3)C1]

(a) 1,1-Dimethylethyl [((2S)-4-{[(2R)-4,9-dioxo-1,2,8,9-tetrahydro-4H,7H-imidazo[1,2,3-ij]-1,8-naphthyridin-2-yl]methyl}-2-morpholinyl)methyl]carbamate In a 100 mL round-bottomed flask were (1S)-1-(hydroxymethyl)-1,2,5,6-tetrahydro-4H,9H-imidazo[1,2,3-ij]-1,8-naphthyridine-4,9-dione (for a preparation see Example 5A(g)) (450 mg, 2.043 mmol) and triethylamine (0.342 ml, 2.452 mmol) in DCM (20 ml) at 0° C. to give a orange solution. Methane sulfonylchloride (0.174 ml, 2.248 mmol) was added and the reaction was allowed to warm to rt and stirred for 1 h. LCMS indicated that the methanesulfonate had formed. The reaction mixture was diluted with DCM (100 mL) and washed with 2×25 mL of a saturated aqueous NaHCO$_3$ solution. The organic phase was separated and dried over Na$_2$SO$_4$. The solution was concentrated under vacuum, and taken up in acetonitrile (20.00 ml). Pyridine (0.500 ml) was added followed by 1,1-dimethylethyl [(2R)-2-morpholinylmethyl]carbamate (for a synthesis see WO2008009700 Example 89(e)) (884 mg, 4.09 mmol), and the reaction was heated to 75° C. The reaction was stirred for 5 h at which time LCMS indicated a complete reaction. The reaction was cooled to rt and concentrated under vacuum. The reaction mixture was diluted with DCM (100 mL) and washed with 25 mL of a saturated aqueous NaHCO$_3$ solution. The organic phase was separated and dried over Na$_2$SO$_4$. The resulting residue was purified on silica 0-10% MeOH/DCM and the title compound (805 mg, 1.539 mmol, 75% yield) was isolated as a red oil.

MS (ES+) m/z 419 (MH$^+$).

(b) 1,1-Dimethylethyl [((2S)-4-{[(1R)-4,9-dioxo-1,2-dihydro-4H,9H-imidazo[1,2,3-ij]-1,8-naphthyridin-1-yl]methyl}-2-morpholinyl)methyl]carbamate To a 50 mL round-bottomed flask was added 1,1-dimethylethyl [((2S)-4-{[(2R)-4,9-dioxo-1,2,8,9-tetrahydro-4H,7H-imidazo[1,2,3-ij]-1,8-naphthyridin-2-yl]methyl}-2-morpholinyl)methyl]carbamate (805 mg, 1.924 mmol) in 1,4-dioxane (10 ml) at rt under nitrogen to give a orange solution. DDQ (655 mg, 2.89 mmol) was added and the reaction became very dark. The reaction was heated to 90° C. on an oil bath and stirred for 30 min.

The reaction was cooled to rt, 200 mL of a 5% aqueous K$_2$CO$_3$ solution was added and the reaction was extracted with DCM (3×200 mL). The combined organic layers were washed with saturated aqueous NaCl solution; the organic layer was separated and dried over Na$_2$SO$_4$, and concentrated to give the crude product. The crude product was added to a silica gel column and was eluted with 0-20% MeOH/CHCl$_3$ to give the title compound (830 mg, 1.794 mmol, 93% yield) as a red oil.

MS (ES+) m/z 417 (MH$^+$).

(c) (1R)-1-{[(2S)-2-(Aminomethyl)-4-morpholinyl]methyl}-1,2-dihydro-4H,9H-imidazo[1,2,3-ij]-1,8-naphthyridine-4,9-dione(HCl)

To a 50 mL round-bottomed flask was added 1,1-dimethylethyl [((2S)-4-{[(1R)-4,9-dioxo-1,2-dihydro-4H,9H-imidazo[1,2,3-ij]-1,8-naphthyridin-1-yl]methyl}-2-morpholinyl)methyl]carbamate (830 mg, 1.993 mmol) in DCM (10 ml) to give a brown solution. 4N HCl in dioxane (2.491 ml, 9.96 mmol) was added and the reaction mixture stirred at rt. After 30 min the solution became cloudy so 2 mL of methanol was added and the reaction was stirred for another 30 min. The reaction was concentrated under vacuum to give the desired product as an HCl salt (520 mg, 1.474 mmol, 74.0% yield) as a brown solid which was used without further purification.

(d) Title Compound

To a 10 mL round-bottomed flask were added (1R)-1-{[(2S)-2-(aminomethyl)-4-morpholinyl]methyl}-1,2-dihydro-4H,9H-imidazo[1,2,3-ij]-1,8-naphthyridine-4,9-dione(HCl) (85 mg, 0.241 mmol), [1,3]oxathiolo[5,4-c]pyridine-6-carbaldehyde (40.3 mg, 0.241 mmol) (for a synthesis see WO2004058144 Example 61), and NaHCO$_3$ (60.7 mg, 0.723 mmol) in DCM (4 ml) and methanol (1 ml) to give a yellow suspension. The reaction was stirred overnight and sodium triacetoxyborohydride (102 mg, 0.482 mmol) was added. The reaction was stirred for 4 h, then filtered through celite and the pad washed with 10% MeOH/DCM. Chromatography on silica eluting with 0-10% MeOH/CHCl$_3$(1% NH$_4$OH) gave the free base of the title compound in which the LCMS, $^1$H NMR were consistent.

$^1$H NMR δH D-4 MeOH, (400 MHz) 2.02-2.13 (m, 1H), 2.34-2.49 (m, 2H), 2.60-2.78 (m, 2H), 2.85-3.08 (m, 2H), 3.40-3.68 (m, 2H), 3.72-3.89 (m, 1H), 4.40-4.51 (m, 2H), 4.89 (s, 2H), 5.10-5.20 (m, 1H), 5.80-5.89 (m, 2H), 6.23-6.38 (m, 2H), 7.72-7.82 (m, 2H), 7.90-7.96 (m, 2H),

MS (ES+) m/z 468 (MH$^+$).

The free base of the title compound was taken up in 10% MeOH/DCM and treated with 500 uL 1N HCl in ether. The solution was concentrated under vacuum to give the title compound as the diHCl salt (49 mg, 0.091 mmol, 37.6% yield) as a tan solid.

Example 48 (1R)-1-{[(2S)-2-({[(7-Chloro-3-oxo-3,4-dihydro-2H-pyrido[3,2-b][1,4]oxazin-6-yl)methyl]amino}methyl)-4-morpholinyl]methyl}-1,2-dihydro-4H,9H-imidazo[1,2,3-]-1,8-naphthyridine-4,9-dione dihydrochloride

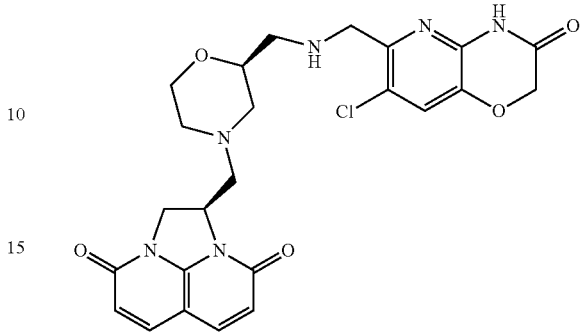

To a 10 mL round-bottomed flask were added (1R)-1-{[(2S)-2-(aminomethyl)-4-morpholinyl]methyl}-1,2-dihydro-4H,9H-imidazo[1,2,3-ij]-1,8-naphthyridine-4,9-dione(HCl) (for a preparation see Example 47(c)) (85 mg, 0.241 mmol), 7-chloro-3-oxo-3,4-dihydro-2H-1,4-benzoxazine-6-carbaldehyde (51.0 mg, 0.241 mmol) (for a synthesis see WO2003064421, Example 15(c)), and NaHCO$_3$ (60.7 mg, 0.723 mmol) in DCM (4 ml) and methanol (1 ml) to give a yellow suspension. Na$_2$SO$_4$ (171 mg, 1.205 mmol) was added, the reaction was stirred overnight, and sodium triacetoxyborohydride (102 mg, 0.482 mmol) was added. The reaction was stirred for 4 h, filtered through celite, and the pad washed with 10% MeOH/DCM. Chromatography on silica eluting with 0-10% MeOH/CHCl$_3$ (1% NH$_4$OH) gave the free base of the title compound in which the LCMS, 1H NMR were consistent with desired product.

$^1$H NMR δH D-4 MeOH, (400 MHz) 2.05-2.13 (m, 1H), 2.32-2.49 (m, 2H), 2.59-2.80 (m, 2H), 2.88-3.07 (m, 3H), 3.42 (s, 2H), 3.40-3.49 (m, 1H), 3.58-3.67 (m, 1H), 3.72-3.96 (m, 3H), 4.42-4.51 (m, 2H), 4.68 (s, 2H), 5.10-5.18 (m, 1H), 6.22-6.35 (m, 2H), 7.39 (s, 1H) 7.72-7.80 (m, 2H).

MS (ES+) m/z 513/515 (MH$^+$).

The free base of the title compound was taken up in 10% MeOH/DCM and treated with 500 uL 1N HCl in ether. The solution was concentrated under vacuum to give the title compound as the diHCl salt (61 mg, 0.104 mmol, 43.2% yield) as a pale yellow solid.

Example 49 (2R)-2-({4-[([1,2,5]Thiadiazolo[3,4-b]pyridin-6-ylmethyl)amino]-1-piperidinyl}methyl)-1,2-dihydro-3H,8H-2a,5,8a-triazaacenaphthylene-3,8-dione

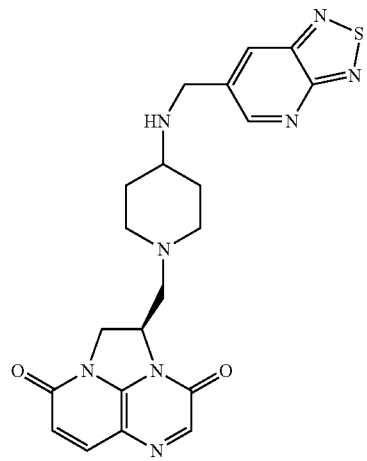 [SMILES: O=c1ccc2ncc(=O)n3c2n1C[C@H]3CN1CCC(NCc2cnc3nsnc3c2)CC1]

(a) 6-[(E)-2-Phenylethenyl][1,2,5]thiadiazolo[3,4-b]pyridine

To 6-bromo[1,2,5]thiadiazolo[3,4-b]pyridine (for a preparation see Indian Journal of Chemistry, Section B: Organic Chemistry Including Medicinal Chemistry (1979), 17B(1), 13-16) (1.9 g, 8.79 mmol), [(E)-2-phenylethenyl]boronic acid (1.561 g, 10.55 mmol) and tetrakistriphenylphosphine palladium(0) (0.508 g, 0.440 mmol) was added 1,4-dioxane (38 ml) and then potassium carbonate (1.276 g, 9.23 mmol) in water (19 ml). The reaction was then stirred at reflux for 1.5 hours. The cooled reaction was partitioned between chloroform and water. The phases were separated with a hydrophobic frit and the organic extracts concentrated to give a black solid/gum (~2.4 g). This crude material was purified by chromatography on silica eluting with 20-50% EtOAc in cyclohexane to give the product as a yellow/brown solid (0.88 g).

$^1$H NMR δH D6-DMSO 400 MHz 7.36 (t, 1H), 7.45 (t, 2H), 7.55 (d, 1H), 7.70 (d, 2H), 7.78 (d, 1H), 8.3 (s, 1H), 9.51 (s, 1H)

MS (ES+) m/z 240 (MH$^+$).

(b) [1,2,5]Thiadiazolo[3,4-b]pyridine-6-carbaldehyde

To 6-[(E)-2-phenylethenyl][1,2,5]thiadiazolo[3,4-b]pyridine (0.88 g, 3.68 mmol) was added acetone (30 ml), N-methyl-morpholine-N-oxide, 50 wt. % in water (1.525 ml, 7.35 mmol) and then osmium tetroxide in water (0.225 ml, 0.037 mmol). The reaction was then stirred for 20 hours. To the pale brown solution was added sodium periodate (3.15 g, 14.71 mmol) and stirring continued for 45 mins. The solvent was reduced by rotary evaporation and the remainder partitioned between chloroform and water. The aqueous was further extracted with chloroform and the combined organic extracts passed through a hydrophobic frit and concentrated to give brown/black solid (0.6 g). A portion of this material (0.575 g) was purified by chromatography on silica eluting with 20% EtOAc in cyclohexane to a pale yellow solid (160 mg).

$^1$H NMR δH D6-DMSO 400 MHz 9.18 (s, 1H), 9.49 (s, 1H), 10.30 (s, 1H)

(c) Title Compound

To (2R)-2-[(4-aminocyclohexyl)methyl]-1,2-dihydro-3H,8H-2a,5,8a-triazaacenaphthylene-3,8-dione dihydrochloride (for a preparation see Example 16A(j)) (100 mg, 0.333 mmol) was added chloroform (3 ml), methanol (0.300 ml) and triethylamine (0.139 ml, 0.999 mmol). The mixture was stirred for 20 mins then [1,2,5]thiadiazolo[3,4-b]pyridine-6-carbaldehyde (52.2 mg, 0.316 mmol) was added. The reaction was stirred overnight then sodium triacetoxyborohydride (212 mg, 0.999 mmol) was added and stirring continued for 1 hour. Further sodium triacetoxyborohydride (212 mg, 0.999 mmol) was added and the reaction stirred for 1 hour. The reaction was partitioned between sat. NaHCO$_3$ and 20% MeOH in chloroform. The aqueous was further extracted with 20% MeOH in chloroform and the combined organic extracts were passed through a hydrophobic frit and concentrated. This crude material (~110 mg) was purified by chromatography eluting with 0-20% MeOH in DCM to furnish product (46 mg, 27%). This was freeze dried from 1,4-dioxane to give the title compound as a pale brown solid (45 mg, 25%)).

$^1$H NMR δH CDCl$_3$ 400 MHz 1.38 (m, 2H), 1.91 (t, 2H), 2.25 (dt, 1H), 2.35 (dt, 1H), 2.58 (m, 1H), 2.71 (m, 2H), 2.96 (br d, 1H), 3.16 (dd, 1H), 4.06 (s, 2H), 4.40 (dd, 1H), 4.56 (dd, 1H), 5.04 (m, 1H), 6.40 (d, 1H), 7.78 (d, 1H), 7.83 (s, 1H), 8.26 (s, 1H)

MS (ES+) m/z 451 (MH$^+$).

Example 50 (1R)-1-({4-[(3,4-Dihydro-2H-chromen-7-ylmethyl)amino]-1-piperidinyl}methyl)-1,2-dihydro-4H,9H-imidazo[1,2,3-ij]-1,8-naphthyridine-4,9-dione hydrochloride

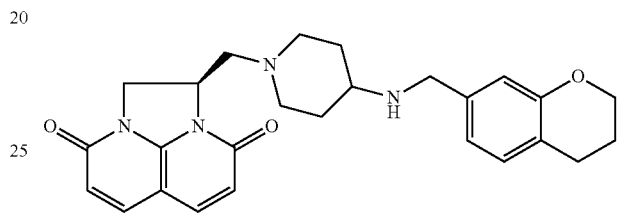

A solution of (1R)-1-[(4-amino-1-piperidinyl)methyl]-1,2-dihydro-4H,9H-imidazo[1,2,3-ij]-1,8-naphthyridine-4,9-dione dihydrochloride (for a preparation see example 5A(j)) (188 mg, 0.503 mmol) and triethylamine (0.175 ml, 1.256 mmol) in chloroform (4.5 ml) and methanol (0.5 ml) at rt was stirred at rt for 15 min then 3,4-dihydro-2H-chromene-7-carbaldehyde (for a synthesis see WO2007067511 Example 19 (chromane-7-carbaldehyde)) (68 mg, 0.419 mmol) in chloroform (2 ml) was added dropwise at rt. The reaction mixture was stirred at rt for 1 h then sodium triacetoxyborohydride (444 mg, 2.096 mmol) was added in one portion and the reaction mixture was stirred at rt overnight. LCMS showed a mixture of product, some residual aldehyde. Additional sodium triacetoxyborohydride (267 mg, 1.258 mmol) was added and the reaction stirred at rt for 6 h. The reaction was quenched with NaHCO$_3$ (aq) (20 ml) and extracted with 20% MeOH/DCM (3×30 ml). The combined organic layers were dried over MgSO$_4$, filtered, evaporated and chromatographed (0-50% MeOH/DCM) to deliver the free base of the title compound as a pale yellow clear oil (49 mg, 0.11 mmol, 26%).

$^1$H NMR δH CDCl$_3$, (400 MHz) 1.28-1.42 (m, 2H), 1.78-1.87 (m, 2H), 1.97-2.01 (m, 2H), 2.17-2.31 (m, 2H), 2.47-2.55 (m, 1H), 2.62-2.68 (m, 2H), 2.74-2.77 (m, 2H), 2.95 (d, 1H), 3.07 (dd, 1H) 3.71 (m, 2H), 4.17 (t, 2H), 4.35 (dd, 1H), 4.56 (dd, 1H), 4.96-5.02 (m, 1H), 6.23-6.31 (m, 2H), 6.72 (s, 1H), 6.77 (dd, 1H), 6.98 (d, 1H), 7.47-7.50 (m, 2H).

MS (ES+) m/z 447 (MH$^+$).

The free base of the title compound in 2 ml DCM was treated with one equivalent of 1M HCl in diethyl ether and then evaporated to give the title compound as the mono-HCl salt as a pale orange powder (51 mg, 25%). LCMS was consistent with product.

Example 51 (1R)-1-({4-[(2,3-Dihydro-1-benzofuran-6-ylmethyl)amino]-1-piperidinyl}methyl)-1,2-dihydro-4H,9H-imidazo[1,2,3-ij]-1,8-naphthyridine-4,9-dione hydrochloride

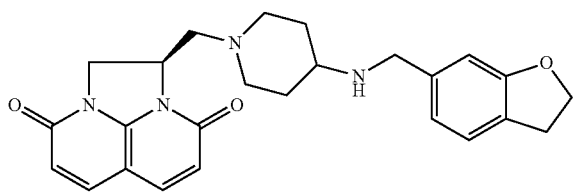 [SMILES: O=c1ccc2ccc(=O)n3c2n1C[C@H]3CN1CCC(NCc2ccc3c(c2)OCC3)CC1]

(a) 2,3-Dihydro-1-benzofuran-6-carbaldehyde

To a solution of 6-bromo-2,3-dihydro-1-benzofuran (190 mg, 0.955 mmol) in THF (4 ml) at −78° C. was added n-BuLi (1.313 ml, 2.100 mmol). The reaction mixture was stirred at −78° C. for 45 min then a solution of DMF (1.109 ml, 1.6 M in hexanes, 14.32 mmol) in THF (2 ml) was added dropwise and the reaction was stirred at −78° C. for 10 min then warmed to rt and stirred for 1 h. LCMS showed no starting material remaining. The reaction was stirred at rt for a further 2.5 h. The reaction mixture was poured cautiously into 2 M HCl (50 ml) and extracted with ethyl acetate (3×50 ml). The combined organic extracts were washed with brine (50 ml), dried over MgSO$_4$, filtered, evaporated and chromatographed (eluting 0-100% EtOAc/Hexane). The relevant fractions were combined and evaporated to deliver the product as a clear, colourless oil (44 mg, 0.297 mmol, 31%).

$^1$H NMR δH CDCl$_3$, (400 MHz) 3.28 (t, 2H), 4.64 (t, 2H), 7.26 (s, 1H), 7.33-7.39 (m, 2H), 9.91 (s, 1H).

(b) Title Compound

A solution of (1R)-1-[(4-amino-1-piperidinyl)methyl]-1,2-dihydro-4H,9H-imidazo[1,2,3-ij]-1,8-naphthyridine-4,9-dione dihydrochloride (for a preparation see Example 5A(j)) (133 mg, 0.356 mmol) and triethylamine (0.124 ml, 0.891 mmol) in chloroform (4.5 ml) and methanol (0.5 ml) at rt was stirred at rt for 15 min then 2,3-dihydro-1-benzofuran-6-carbaldehyde (44 mg, 0.297 mmol) in chloroform (2 ml) was added dropwise at rt. The reaction mixture was stirred at rt overnight. The reaction was quenched with NaHCO$_3$ (aq) (20 ml), extracted with 20% MeOH/DCM (3×30 ml). The combined organic layers were dried over MgSO$_4$, filtered, evaporated and chromatographed (0-50% MeOH/DCM). The relevant fractions were combined and evaporated to deliver the free base of the title compound as a pale yellow clear oil (18 mg, 0.04 mmol, 26%).

$^1$H NMR δH CDCl$_3$, (400 MHz) 1.40-1.53 (m, 2H), 1.85-1.92 (m, 2H), 2.16-2.30 (m, 2H), 2.54-2.68 (m, 3H), 2.98 (d, 1H), 3.08 (dd, 1H), 3.16 (t, 2H), 3.78 (s, 2H), 4.33-4.38 (m, 1H), 4.52-4.57 (m, 3H), 4.96-5.02 (m, 1H), 6.24 (d, 1H), 6.29 (d, 1H), 6.79 (s, 1H), 6.84 (d, 1H), 7.13 (d, 1H), 7.47-7.50 (m, 2H).

MS (ES+) m/z 433 (MH$^+$).

The free base of the title compound in 2 ml DCM was treated dropwise with 1 M HCl in diethyl ether (0.04 ml, 0.04 mmol) to give the title compound as the mono-HCl salt as an orange powder (20 mg, 14%).

Example 52 (1R)-1-({4-[(3,4-Dihydro-2H-chromen-6-ylmethyl)amino]-1-piperidinyl}methyl)-1,2-dihydro-4H,9H-imidazo[1,2,3-ij]-1,8-naphthyridine-4,9-dione hydrochloride

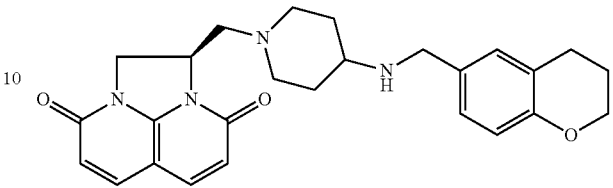

A solution of (1R)-1-[(4-amino-1-piperidinyl)methyl]-1,2-dihydro-4H,9H-imidazo[1,2,3-ij]-1,8-naphthyridine-4,9-dione dihydrochloride (for a preparation see Example 5A(j)) (12 mg, 0.032 mmol) and triethylamine (0.139 ml, 0.999 mmol) in DCM (4.5 ml) and methanol (0.5 ml) at rt was stirred for 5 min. 3,4-Dihydro-2H-chromene-6-carbaldehyde (commercially available) (45 mg, 0.277 mmol) was added and the resulting solution was stirred overnight for 18 h. LCMS showed that aldehyde remained and no amine remained. Additional (1R)-1-[(4-amino-1-piperidinyl)methyl]-1,2-dihydro-4H,9H-imidazo[1,2,3-ij]-1,8-naphthyridine-4,9-dione (120 mg, 0.321 mmol) and additional triethylamine (0.138 ml, 0.999 mmol) were added and the resulting mixture stirred for 1 h. Additional sodium triacetoxyborohydride (294 mg, 1.387 mmol) was added and resulting solution was stirred for 60 h. The reaction was diluted with DCM (10 ml) and sodium bicarbonate solution (10 ml) and stirred at rt for 10 mins and extracted with methanol:DCM (20%, 3×150 ml). The combined organic extracts were dried (MgSO$_4$), filtered, evaporated and chromatographed (0-50% methanol:DCM). The column waste was concentrated to afford a brown oil that was re-chromatographed (0-50% methanol:DCM). The relevant fractions were combined to afford the free base of the title compound as a white solid (27 mg, 0.06 mmol, 22%).

$^1$H NMR δH CDCl$_3$, (400 MHz) 1.76-1.86 (m, 2H), 1.91-1.97 (m, 2H), 2.04-2.06 (mm, 2H), 2.15 (t, 1H), 2.24 (t, 1H), 2.62 (dd, 1H), 2.75-2.81 (m, 4H), 3.06-3.14 (m, 2H), 3.85 (s, 2H), 4.12 (t, 2H), 4.40 (dd, 1H), 4.51 (dd, 1H), 4.96-5.02 (m, 1H), 6.22-6.29 (m, 2H), 6.77 (d, 1H), 7.25-7.27 (m, 2H), 7.47-7.50 (m, 2H).

MS (ES+) m/z 447 (MH$^+$).

The free base of the title compound in chloroform (5 ml) and methanol (3 ml) was treated dropwise with hydrochloric acid in ether (IM, 0.06 ml, 0.06 mmol) to give the title compound as the mono-HCl salt as a white solid (6 mg, 4%).

Example 53 (2R)-2-[(4-{[(5-Fluoro-2,3-dihydro-1,4-benzodioxin-6-yl)methyl]amino}-1-piperidinyl)methyl]-1,2-dihydro-3H,8H-2a,5,8a-triazaacenaphthylene-3,8-dione hydrochloride

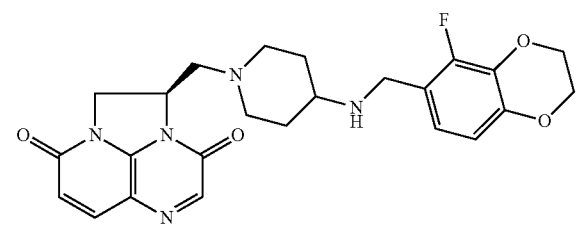 [SMILES: O=c1ccc2ncc(=O)n3c2n1C[C@H]3CN1CCC(NCc2ccc3c(c2F)OCCO3)CC1]

(a) 5-Fluoro-2,3-dihydro-1,4-benzodioxin

A solution of 3-fluoro-1,2-benzenediol (5.278 g, 41.2 mmol) in DMF (50 ml) was treated with potassium carbonate (17.08 g, 124 mmol) and 1,2-dibromoethane (3.91 ml, 45.3 mmol) and stirred at rt for 72 h. The reaction was treated with water (200 ml) and extracted 3×200 ml (EtOAc). The combined organic extracts were washed with water (200 ml), brine (200 ml), dried (MgSO$_4$), evaporated and chromatographed (0-20% EtOAc-Cyclohexane) to give product as a clear oil. (2.437 g, 38%).

$^1$H NMR δH CDCl$_3$, (400 MHz) 4.22-4.39 (m, 4H), 6.60-6.82 (m, 3H).

(b) 6-Bromo-5-fluoro-2,3-dihydro-1,4-benzodioxin solution of 5-fluoro-2,3-dihydro-1,4-benzodioxin (0.335 g, 2.173 mmol) in methanol (10 ml) at 0° C. was treated with bromine (0.134 ml, 2.61 mmol) and allowed warm to rt over 10 min and stirred at rt for 18 h. Reaction was then treated with saturated aqueous sodium metabisulfate (100 ml), extracted 3×100 ml (DCM), the combined organic extracts dried (MgSO$_4$), filtered, evaporated, chromatographed (0-50% EtOAC:Cyclohexane) to give product as a clear oil, which solidified in the freezer to give a white solid (351 mg, 59%).

$^1$H NMR δH CDCl$_3$, (400 MHz) 4.20-4.39 (m, 4H), 6.52-6.65 (m, 1H), 6.91-7.05 (m, 1H).

(c) 5-Fluoro-2,3-dihydro-1,4-benzodioxin-6-carbaldehyde

A solution of 6-bromo-5-fluoro-2,3-dihydro-1,4-benzodioxin (146 mg, 0.627 mmol) in THF (5 ml) at −78° C. was treated with n-BuLi (0.551 ml, 1.378 mmol) under a nitrogen atmosphere and stirred at −78° C. for 15 min before treatment with a solution of DMF (0.243 ml, 3.13 mmol) in THF)(2.00 ml). The reaction was stirred for 10 min at −78° C. and then the reaction was allowed warm to rt over 10 min and stirred at rt for 0.5 h. Reaction was treated with 2M HCl (20 ml) and extracted with ethyl acetate (3×100 ml). The organic extracts were evaporated, dried (MgSO$_4$), filtered, evaporated, chromatographed (0-100% EtOAC:Cyclohexane) to give product as a white solid (25 mg, 22%).

MS (ES+) m/z 183 (MH$^+$).

(d) Title Compound

A suspension of (2R)-2-[(4-amino-1-piperidinyl)methyl]-1,2-dihydro-3H, 8H-2a,5,8a-triazaacenaphthylene-3,8-dione dihydrochloride (for a preparation see Example 16A(j), amine was converted into dihydrochloride after chiral hplc purification) (51.3 mg, 0.137 mmol) in chloroform (5 ml) and methanol (0.1 ml) at rt under argon was treated with triethylamine (0.057 ml, 0.411 mmol) and stirred at rt for 0.25 h. The solution was then treated with 5-fluoro-2,3-dihydro-1,4-benzodioxin-6-carbaldehyde (24.95 mg, 0.137 mmol) and stirred for a further 0.5 h. The solution was then treated with sodium triacetoxyborohydride (174 mg, 0.822 mmol) and stirred at rt for 2 h, more sodium triacetoxyborohydride (174 mg, 0.137 mmol) was added, reaction stirred for a further 1 h, the reaction was then treated with saturated aqueous NaHCO$_3$ (20 ml) and extracted with 20% methanol/DCM (3×20 ml). The combined organic extracts were dried (MgSO$_4$) and chromatographed (0-20% methanol:DCM) to give the free base of the title compound as a white solid (29 mg, 0.062 mmol, 45%).

$^1$H NMR δH CDCl$_3$, (400 MHz) 1.20-1.46 (m, 2H), 1.73-1.95 (m, 2H), 2.15-2.39 (m, 2H), 2.41-2.55 (m, 1H), 2.61-2.75 (m, 2H), 2.88-3.00 (m, 1H), 3.10-3.20 (m, 1H), 3.78 (s, 2H), 4.22-4.42 (m, 5H). 4.51-4.60 (m, 1H), 4.95-5.09 (m, 1H), 6.38 (d, 1H), 6.62 (m, 1H), 6.71-6.80 (m, 1H), 7.76 (d, 1H), 7.81 (s, 1H)

MS (ES+) m/z 468 (MH$^+$).

The free base of the title compound (29 mg) in DCM/MeOH 2:1 (5 ml) was treated with 1M HCl in diethyl ether 62 ul) and then evaporated to give the title compound as the mono-HCl salt (31 mg, 0.062 mmol) as a yellow solid.

Example 54 (1R)-1-{[(2S)-2-({[(7-fluoro-2,3-dihydro-1,4-benzodioxin-6-yl)methyl]amino}methyl)-4-morpholinyl]methyl}-1,2-dihydro-4H,9H-imidazo[1,2,3-ij]-1,8-naphthyridine-4,9-dione dihydrochloride

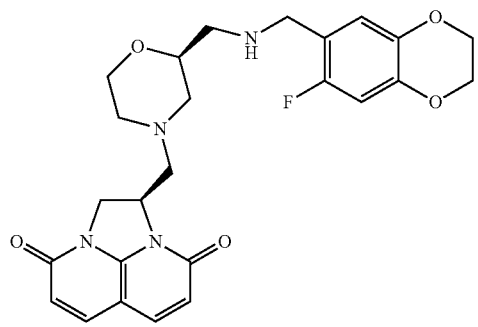 [SMILES: O=c1ccc2ccc(=O)n3c2n1C[C@H]3CN1CCO[C@@H](CNCc2cc3c(cc2F)OCCO3)C1]

To a 10 mL round-bottomed flask were added (1R)-1-{[(2S)-2-(aminomethyl)-4-morpholinyl]methyl}-1,2-dihydro-4H,9H-imidazo[1,2,3-ij]-1,8-naphthyridine-4,9-dione(HCl) (85 mg, 0.241 mmol) (for a preparation see Example 47(c)), 7-fluoro-2,3-dihydro-1,4-benzodioxin-6-carbaldehyde (48.3 mg, 0.265 mmol) (for a synthesis see WO2002056882, Example 23(a)), and NaHCO$_3$ (60.7 mg, 0.723 mmol) in DCM (4 ml) and methanol (1 ml) to give a yellow suspension. Sodium sulfate (171 mg, 1.205 mmol) was added, the reaction was stirred overnight at which point sodium triacetoxyborohydride (102 mg, 0.482 mmol) was added. The reaction was stirred for 4 h at which point LCMS showed the reaction to be complete. The reaction mixture was diluted with 10% MeOH in DCM (20 mL), filtered, adsorbed onto silica and purified by chromatography on silica eluting with 0-10% MeOH/CHCl$_3$ (1% NH$_4$OH) to give the free base of the title compound in which the LCMS, $^1$H NMR were consistent with the desired product.

$^1$H NMR δH D-4 MeOH, (400 MHz) 2.03-2.10 (m, 1H), 2.33-2.49 (m, 2H), 2.51-2.68 (m, 2H), 2.83-2.95 (m, 2H), 2.99-3.07 (m, 1H), 3.39 (s, 2H), 3.41-3.50 (m, 1H), 3.55-3.63 (m, 1H), 3.68-3.80 (m, 3H), 4.42-4.51 (m, 2H), 4.79 (s, 2H), 5.08-5.18 (m, 1H), 6.22-6.32 (m, 2H), 6.58-6.62, (m, 1H), 6.81-6.88 (m, 1H), 7.73-7.80 (m, 2H).

MS (ES+) m/z 483 (MH$^+$).

The free base of the title compound was diluted in 5% MeOH/CHCl$_3$ and treated with 1N HCl in ether 100 uL and concentrated to give the title compound as the diHCl salt (55 mg, 0.099 mmol, 41.1% yield) as a pale yellow solid.

Example 55 (1R)-1-[((3S)-3-{[([1,3]Oxathiolo[5,4-c]pyridin-6-ylmethyl)amino]methyl}-1-pyrrolidinyl)methyl]-1,2-dihydro-4H,9H-imidazo[1,2,3-ij]-1,8-naphthyridine-4,9-dione dihydrochloride

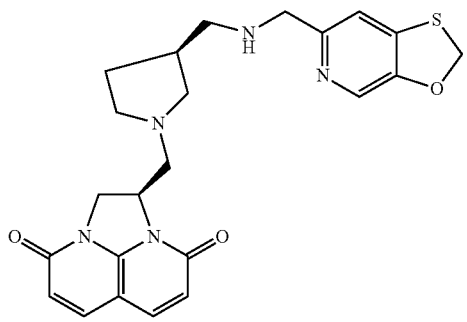 [SMILES: O=c1ccc2ccc(=O)n3c2n1C[C@H]3CN1CC[C@@H](CNCc2cc3c(cn2)OCS3)C1]

(a) 1,1-Dimethylethyl (3S)-3-{[(trifluoroacetyl)amino]methyl}-1-pyrrolidinecarboxylate To a 100 mL round-bottomed flask was added 1,1-dimethylethyl (3S)-3-(aminomethyl)-1-pyrrolidinecarboxylate (commercially available) (750 mg, 3.74 mmol) in (DCM) (20 ml) to give a colorless solution. Triethylamine (1.044 ml, 7.49 mmol) was added and the reaction was cooled to 0° C. Trifluoroaceticanhydride (0.635 ml, 4.49 mmol) was added and the reaction was allowed to warm to rt while stirring for 14 h. The solution was diluted with 100 mL DCM and washed with saturated aqueous solution of NaHCO₃, and a saturated aqueous solution of NaCl. The organic layer was separated, dried over Na₂SO₄, filtered and concentrated. The residue was subjected to chromatography on silica to give the product (0.990 g, 3.34 mmol, 89% yield) as a pale yellow oil.

MS (ES+) m/z 297 (MH$^+$).

(b) 2,2,2-Trifluoro-N-[(3R)-3-pyrrolidinylmethyl]acetamide hydrochloride

To a 100 mL round-bottomed flask was added 1,1-dimethylethyl (3S)-3-{[(trifluoroacetyl)amino]methyl}-1-pyrrolidinecarboxylate (830 mg, 2.80 mmol) in DCM (25 ml) at 25° C. to give a colorless solution. 4N HCl (3.50 ml, 14.01 mmol) in dioxane was added and the reaction was allowed to stir o/n. The reaction was concentrated under vacuum to give the desired compound as colorless oil which was used in the next reaction without further purification. Isolated 2,2,2-trifluoro-N-[(3R)-3-pyrrolidinylmethyl]acetamide (550 mg, 2.364 mmol, 84% yield).

MS (ES+) m/z 197 (MH$^+$).

(c) N-[((3S)-1-{[(2R)-4,9-dioxo-1,2,8,9-tetrahydro-4H,7H-imidazo[1,2,3-ij]-1,8-naphthyridin-2-yl]methyl}-3-pyrrolidinyl)methyl]-2,2,2-trifluoroacetamide To a 100 mL round-bottomed flask was added (1S)-1-(hydroxymethyl)-1,2,5,6-tetrahydro-4H,9H-imidazo[1,2,3-ij]-1,8-naphthyridine-4,9-dione HCl (for a preparation see Example 47(c)) (350 mg, 1.589 mmol), triethylamine (0.266 ml, 1.907 mmol) in DCM (20 ml) 0° C. to give a orange solution. Methane sulfonylchloride (0.135 ml, 1.748 mmol) was added and the reaction was allowed to warm to rt and stir for 1 h. LCMS indicated that the methanesulfonate had formed. The reaction was diluted with DCM (100 mL) and washed with 2×25 mL of a saturated aqueous NaHCO₃ solution. The organic phase was separated and dried over Na₂SO₄. The solution was concentrated under vacuum, diluted with acetonitrile (20.00 ml) and pyridine (0.500 ml) was added. 2,2,2-trifluoro-N-[(3R)-3-pyrrolidinylmethyl]acetamide (550 mg, 2.364 mmol) was added and the reaction was heated to 80° C. and stirred for 25 h. LCMS indicated a complete reaction. The reaction was cooled to rt and concentrated under vacuum. The reaction mixture was diluted with DCM (100 mL) and washed with 25 mL of a saturated NaHCO₃ solution. The organic phase was separated and dried over Na₂SO₄. The crude product was purified on silica eluting with 0-15% MeOH/DCM to give product (240 mg, 0.602 mmol, 37.9% yield) as a pale yellow oil.

MS (ES+) m/z 399 (MH$^+$).

(d) N-[((3S)-1-{[(1R)-4,9-dioxo-1,2-dihydro-4H,9H-imidazo[1,2,3-ij]-1,8-naphthyridin-1-yl]methyl}-3-pyrrolidinyl)methyl]-2,2,2-trifluoroacetamide To a 25 mL round-bottomed flask was added N-[((3S)-1-{[(2R)-4,9-dioxo-1,2,8,9-tetrahydro-4H,7H-imidazo[1,2,3-ij]-1,8-naphthyridin-2-yl]methyl}-3-pyrrolidinyl)methyl]-2,2,2-trifluoroacetamide (240 mg, 0.602 mmol) in 1,4-dioxane (5 ml) at rt under nitrogen to give a orange solution. DDQ (205 mg, 0.904 mmol) was added and the reaction became very dark. The reaction was heated to 80° C. on an oil bath and stirred for 10 h. The reaction was cooled to rt. 5% Aqueous K₂CO₃ (20 mL) was added and the reaction was extracted with DCM (3×100 mL). The combined organic layers were washed with a saturated aqueous NaCl solution and the organic phase was dried over Na₂SO₄, filtered and concentrated to give the crude product. The crude product was added to a silica gel column and was eluted with 0-20% MeOH/CHCl₃ to give product (85 mg, 0.214 mmol, 35.6% yield) as an orange solid.

MS (ES+) m/z 397 (MH$^+$).

(e) (1R)-1-{[(3S)-3-(aminomethyl)-1-pyrrolidinyl]methyl}-1,2-dihydro-4H,9H-imidazo[1,2,3-ij]-1,8-naphthyridine-4,9-dione To a 25 mL round-bottomed flask was added N-[((3S)-1-{[(1R)-4,9-dioxo-1,2-dihydro-4H,9H-imidazo[1,2,3-ij]-1,8-naphthyridin-1-yl]methyl}-3-pyrrolidinyl)methyl]-2,2,2-trifluoroacetamide (85 mg, 0.214 mmol) in methanol (9 ml) and water (1.00 ml) to give a yellow solution. Potassium carbonate (59.3 mg, 0.429 mmol) was added and the reaction was stirred overnight. LCMS indicated a complete reaction. The reaction was diluted with 20% MeOH/DCM (100 mL), dried over Na₂SO₄, filtered and concentrated to give the product (60 mg, 0.200 mmol, 93% yield) as an orange solid.

MS (ES+) m/z 301 (MH$^+$).

(f) Title Compound

To a 10 mL round-bottomed flask were added (1R)-1-{[(3S)-3-(aminomethyl)-1-pyrrolidinyl]methyl}-1,2-dihydro-4H,9H-imidazo[1,2,3-ij]-1,8-naphthyridine-4,9-dione (60 mg, 0.200 mmol), [1,3]oxathiolo[5,4-c]pyridine-6-carbaldehyde (33.4 mg, 0.200 mmol) (for a synthesis see WO2004058144 Example 61), and sodium sulfate (250 mg, 1.760 mmol) in DCM (4 ml) and methanol (1.00 ml) to give an orange suspension. The reaction was stirred overnight under nitrogen. Sodium triacetoxyborohydride (85 mg, 0.400 mmol) was added and the reaction was stirred for 3 h. The reaction mixture was diluted with 10% MeOH/DCM (20 mL), filtered, adsorbed onto silica and then purified by silica chromatography eluting with 0-10% MeOH/DCM (1% NH$_4$OH) to give the free base of the title compound as a yellow oil. LCMS/NMR consistent with the desired product.

$^1$H NMR δH D-4 MeOH, (400 MHz) 1.34-1.43 (m, 1H), 1.85-1.96 (m, 1H), 2.15-2.30 (m, 2H), 2.38-2.51 (m, 3H), 2.68-2.75 (m, 1H), 2.04-3.17 (m, 2H), 3.41-3.50 (m, 1H), 3.69 (s, 2H), 4.42-4.51 (m, 2H), 5.08-5.18 (m, 1H), 5.83 (s, 2H), 6.26-6.32 (m, 2H), 7.33 (s, 1H), 7.73-7.78 (m, 2H), 7.94 (s, 1H).

MS (ES+) m/z 452 (MH$^+$).

The free base of the title compound was diluted with 10% MeOH/CHCl$_3$, 100 uL of 1N HCl in ether was added and the mixture concentrated under vacuum to give the title compound as the dihydrochloride salt (47 mg, 0.090 mmol, 44.9% yield) as a tan solid.

Example 56 7-{[(1-{[(1R)-3,8-Dioxo-1,2-dihydro-3H,8H-2a,5,8a-triazaacenaphthylen-1-yl]methyl}-4-piperidinyl)amino]methyl}-2,3-dihydro-1,4-benzodioxin-5-carbonitrile hydrochloride

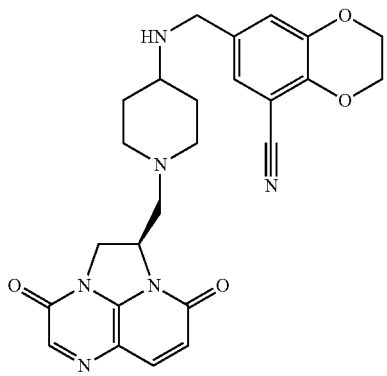 [SMILES: N#Cc1cc(CNC2CCN(C[C@@H]3Cn4c(=O)cnc5ccc(=O)n3c54)CC2)cc2c1OCCO2]

A suspension of (1R)-1-[(4-amino-1-piperidinyl)methyl]-1,2-dihydro-3H, 8H-2a,5,8a-triazaacenaphthylene-3,8-dione dihydrochloride (for a preparation see Example 13(k) or 15(d)) (50 mg, 0.100 mmol) in chloroform (4 ml) and methanol (0.121 ml) at rt under nitrogen was treated with triethylamine (0.587 ml, 4.21 mmol) and stirred for 15 min (the suspension turned into a solution). 7-Formyl-2,3-dihydro-1,4-benzodioxin-5-carbonitrile (for a synthesis see WO06014580 Preparation 13 or WO2007122258, Example 31(d)) ((18.95 mg, 0.100 mmol) was then added and the reaction was stirred for 30 min. Sodium triacetoxyborohydride (63.7 mg, 0.301 mmol) was then added and the reaction was stirred for 1 h. LC-MS after 1 h showed some imine intermediate so more sodium triacetoxyborohydride (63.7 mg, 0.301 mmol) was added and the reaction stirred for 2 h. LCMS after this time still showed imine intermediate, More sodium triacetoxyborohydride (63.7 mg, 0.301 mmol) was added and the reaction left stirring overnight (16 h), LCMS after this time showed no starting material. Saturated NaHCO$_3$ (10 mL) was added followed by 20% MeOH/DCM (20 ml) and the aqueous phase was extracted and then separated from the organic layer. The aqueous phase was extracted again with 20% MeOH/DCM (2×20 ml). The combined organic extracts were dried (NaSO$_4$), filtered and evaporated to give crude product. The crude product was purified on a silica column (0-20% MeOH/DCM) to give the free base of the title compound (33 mg, 69.4%).

$^1$H NMR δH CDCl$_3$, (400 MHz) 1.15-1.41 (m, 2H), 1.72-1.91 (m, 2H), 2.19-2.39 (m, 2H), 2.40-2.52 (m, 1H), 2.53-2.78 (m, 2H), 2.89-2.98 (m, 1H), 3.02-3.14 (m, 1H), 3.68 (s, 2H), 4.22-4.49 (m, 5H), 4.51-4.62 (m, 1H), 4.98-5.08 (m, 1H), 6.32 (d, 1H), 7.06 (m, 2H), 7.78 (d, 1H), 7.88 (s, 1H).

MS (ES+) m/z 475 (MH$^+$).

The free base of the title compound was dissolved in a small amount of DCM and treated with one equivalent of 1M HCl in diethyl ether. This gave the title compound as the mono HCl salt (33 mg, 65%).

Example 57 (1R)-1-[(4-{[(7-Fluoro-2,3-dihydro-1,4-benzodioxin-6-yl)methyl]amino}-1-piperidinyl)methyl]-1,2-dihydro-3H,8H-2a,5,8a-triazaacenaphthylene-3,8-dione hydrochloride

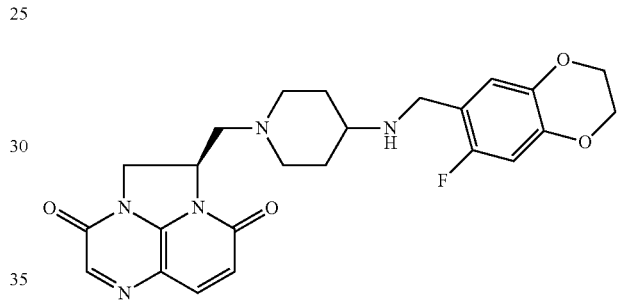

A suspension of (1R)-1-[(4-amino-1-piperidinyl)methyl]-1,2-dihydro-3H, 8H-2a,5,8a-triazaacenaphthylene-3,8-dione dihydrochloride (for a preparation see Example 13(k)) or 15(d) (50 mg, 0.100 mmol) in chloroform (3 ml) and methanol (0.150 ml) at room temperature under nitrogen was treated with triethylamine (0.042 ml, 0.301 mmol) and stirred for 0.25 h (the suspension turned into a solution). 7-Fluoro-2,3-dihydro-1,4-benzodioxin-6-carbaldehyde (for a synthesis see WO2002056882, Example 23(a)) (18.25 mg, 0.100 mmol) was then added and the reaction was stirred at room temperature for 0.5 h. Sodium triacetoxyborohydride (67.1 mg, 0.301 mmol) was then added and the reaction was stirred at room temperature. After 1 h more sodium triacetoxyborohydride (67.1 mg, 0.301 mmol) was added and the reaction stirred at rt overnight. More sodium triacetoxyborohydride (67.1 mg, 0.301 mmol) was then added and the reaction stirred at rt. After 1 h no starting material remained. Saturated NaHCO$_3$ (30 mL) was added followed by 20% MeOH/DCM (30 mL) and the aqueous phase was extracted and then separated from the organic layer. The aqueous phase was extracted again twice with 20% MeOH/DCM (2×30 mL). The combined organic extracts were dried NaSO$_4$, filtered and evaporated to afford the crude product. The crude product was purified by chromatography on silica (0-20% MeOH/DCM) to afford 35 mg of the free base of the title compound as a yellow solid (74.7%).

$^1$H NMR δH CDCl$_3$, (400 MHz) 1.21-1.41 (m, 2H), 1.76-1.92 (m, 2H), 2.10-2.39 (m, 2H), 2.41-2.52 (m, 1H), 2.61-2.79 (m, 2H), 2.86-2.98 (m, 1H), 3.05-3.14 (m, 1H), 3.72 (s, 2H), 4.18-4.29 (m, 4H), 4.38-4.43 (m, 1H), 4.51-

4.62 (m, 1H), 4.94-5.05 (m, 1H), 6.33 (d, 1H), 6.58 (d, 1H), 6.80 (1H, d), 7.77 (d, 1H), 7.86 (s, 1H).

MS (ES+) m/z 468 (MH+).

The free base of the title compound was dissolved in a small amount of DCM/MeOH and treated with 1 eq of a 1M solution of HCl in Et2O. The solvents were removed and the solid dried in the desiccator (P2O5) to afford the title compound as the hydrochloride salt as a dark yellow solid (36 mg).

Example 58 (1R)-1-[(4-{[(8-Fluoro-2,3-dihydro-1,4-benzodioxin-6-yl)methyl]amino}-1-piperidinyl)methyl]-1,2-dihydro-3H,8H-2a,5,8a-triazaacenaphthylene-3,8-dione hydrochloride

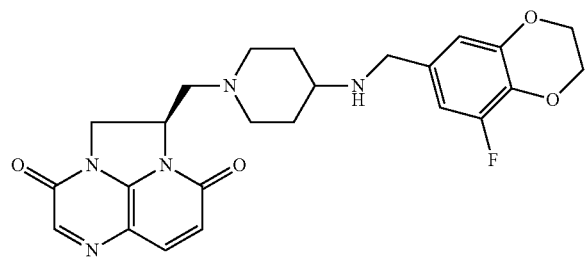 [SMILES: O=c1cnc2ccc(=O)n3c2n1C[C@H]3CN1CCC(NCc2cc(F)c3c(c2)OCCO3)CC1]

A suspension of (1R)-1-[(4-amino-1-piperidinyl)methyl]-1,2-dihydro-3H, 8H-2a,5,8a-triazaacenaphthylene-3,8-dione dihydrochloride (for a preparation see Example 13(k) or 15(d)) (50 mg, 0.100 mmol) in chloroform (25 ml) and methanol (1.250 ml) at room temperature under nitrogen was treated with triethylamine (0.042 ml, 0.301 mmol) and stirred for 0.25 h (the suspension turned into a solution). 8-Fluoro-2,3-dihydro-1,4-benzodioxin-6-carbaldehyde (for a synthesis see WO2007122258, Example 8(b))(19.62 mg, 0.100 mmol) was then added and the reaction was stirred at room temperature for 0.5 h. Sodium triacetoxyborohydride (67.1 mg, 0.301 mmol) was then added and the reaction was stirred at room temperature. After 1 h still starting material so sodium triacetoxyborohydride (67.1 mg, 0.301 mmol) was added and the reaction stirred at rt overnight. Still starting material so sodium triacetoxyborohydride (67.1 mg, 0.301 mmol) was added and the reaction stirred at rt for 1 h. Saturated NaHCO3 (30 mL) was added followed by 20% MeOH/DCM (30 mL) and the aqueous phase was extracted and then separated from the organic layer. The aqueous phase was extracted again twice with 20% MeOH/DCM (2×30 mL). The combined organic extracts were dried NaSO4, filtered and evaporated to afford the crude product. The crude product was purified by chromatography on silica (0-20% MeOH/DCM) to afford 26 mg of the free base of the title compound as a yellow solid.

$^1$H NMR δH CDCl3, (400 MHz) 1.20-1.41 (m, 2H), 1.72-1.89 (m, 2H), 2.09-2.35 (m, 2H), 2.42-2.52 (m, 1H), 2.55-2.78 (m, 2H), 2.85-2.99 (m, 1H), 3.08-3.15 (m, 1H), 3.63 (s, 2H), 4.22-4.48 (m, 5H), 4.51-4.63 (m, 1H), 4.95-5.06 (m, 1H), 6.32 (d, 1H), 6.61-6.72 (m, 2H), 7.75 (d, 1H), 7.89 (s, 1H).

MS (ES+) m/z 468 (MH+).

The free base of the title compound was dissolved in a small amount of DCM/MeOH and treated with 1 eq of a 1M solution of HCl in Et2O. The solvents were removed and the solid dried in the desiccator (P2O5) overnight to afford the title compound as the hydrochloride salt as a yellow solid (26.6 mg, consistent with product).

Example 59 (1R)-1-[(4-{[(2-Oxo-2H-chromen-7-yl)methyl]amino}-1-piperidinyl)methyl]-1,2-dihydro-4H,9H-imidazo[1,2,3-ij]-1,8-naphthyridine-4,9-dione

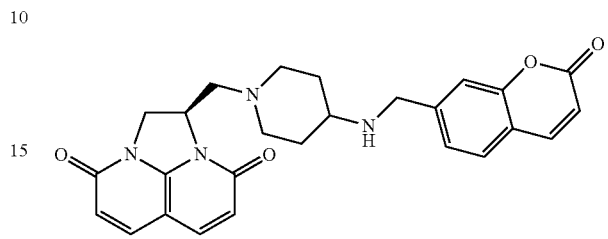

To a 10 mL round-bottomed flask were added (1R)-1-[(4-amino-1-piperidinyl)methyl]-1,2-dihydro-4H,9H-imidazo[1,2,3-ij]-1,8-naphthyridine-4,9-dione dihydrochloride (for a preparation see Example 5A(j)) (80 mg, 0.266 mmol), 2-oxo-2H-chromene-7-carbaldehyde (for a synthesis see WO2008009700 Example 224) (46.4 mg, 0.266 mmol), and NaHCO3 (100 mg, 1.190 mmol) in dichloromethane (DCM) (4 ml) and methanol (1 ml) to give a brown solution. Sodium sulfate (200 mg, 1.408 mmol) was added and the reaction was allowed to stir at rt overnight. After 15 h sodium triacetoxyborohydride (113 mg, 0.533 mmol) was added and the reaction was allowed to stir at 25° C. under nitrogen for 4 h. The reaction mixture was adsorbed onto silica and purified using 0-10% MeOH/DCM (1% NH4OH) to give the title compound as a free base (30 mg, 0.064 mmol, 24.07% yield) as a tan solid. LCMS & 1H NMR consistant with desired product.

$^1$H NMR δH D-4 MeOH, (400 MHz) 1.20-1.39 (m, 2H), 1.72-1.89 (m, 2H), 1.90-2.09 (m, 1H), 2.13-2.31 (m, 2H), 2.39-2.50 (m, 1H), 2.56-2.70 (m, 2H), 2.90-3.10 (m, 2H), 3.83 (s, 2H), 4.32-4.58 (m, 2H), 4.98-5.18 (m, 1H), 6.20-6.39 (m, 3H), 7.19-7.28 (m, 2H), 7.39-7.51 (m, 3H), 7.62-7.71 (m, 1H).

MS (ES+) m/z 459 (MH+).

Example 60 (1R)-1-[(4-{[(2-oxo-2H-chromen-7-yl)methyl]amino}-1-piperidinyl)methyl]-1,2-dihydro-4H,9H-imidazo[1,2,3-ij]-1,8-naphthyridine-4,9-dione

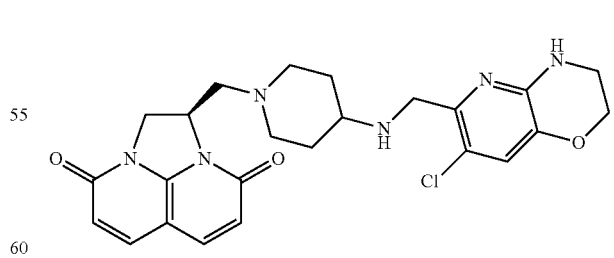

To a 10 mL round-bottomed flask were added (1R)-1-[(4-amino-1-piperidinyl)methyl]-1,2-dihydro-4H,9H-imidazo[1,2,3-ij]-1,8-naphthyridine-4,9-dione dihydrochloride (for a preparation see Example 5A(j)) (45 mg, 0.134 mmol), 7-chloro-3,4-dihydro-2H-pyrido[3,2-b][1,4]oxazine-6-carbaldehyde (prepared by (1) reduction of 7-chloro-3-oxo-3,4- dihydro-2H-pyrido[3,2-b][1,4]oxazine-6-carbaldehyde (for a synthesis see WO2003064421 Example 15(c)) with LiAlH₄ to give (7-chloro-3,4-dihydro-2H-pyrido[3,2-b][1,4]oxazin-6-yl)methanol and then (2) oxidation with MnO₂) (29.2 mg, 0.147 mmol), and NaHCO₃ (100 mg, 1.190 mmol) in dichloromethane (DCM) (4 ml) and methanol (1 ml) to give a brown suspension. Sodium sulfate (200 mg, 1.408 mmol) was added and the reaction was stirred at rt overnight. After 15 h sodium triacetoxyborohydride (56.6 mg, 0.267 mmol) was added and the reaction was stirred at 25° C. under nitrogen for 4 h. The reaction mixture was adsorbed onto silica and purified using 0-10% MeOH/DCM (1% NH₄OH) to give the title compound as a free base (9.4 mg, 0.019 mmol, 14.57% yield).

¹H NMR δH D-4 MeOH, (400 MHz) 1.49-1.70 (m, 2H), 2.00-2.17 (m, 2H), 2.28-2.49 (m, 2H), 2.72-2.81 (m, 1H), 2.89-2.94 (m, 1H), 3.05-3.20 (m, 3H), 3.38 (s, 2H), 3.50-3.58 (m, 1H), 4.18 (s, 2H) 4.20-4.24 (m, 2H), 4.43-4.50 (m, 2H), 5.08-5.18 (m, 1H), 6.28-6.35 (m, 2H), 7.06 (s, 1H), 7.78-7.83 (m, 2H).

MS (ES+) m/z 483/485 (MH⁺).

Example 61 (1R)-1-[(4-{[(2-oxo-2H-chromen-7-yl)methyl]amino}-1-piperidinyl)methyl]-1,2-dihydro-4H,9H-imidazo[1,2,3-ij]-1,8-naphthyridine-4,9-dione

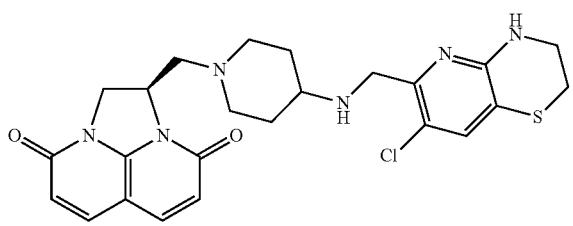 [SMILES: O=c1ccc2ccc(=O)n3c2n1C[C@H]3CN1CCC(NCc2nc3c(cc2Cl)SCCN3)CC1]

To a 10 mL round-bottomed flask were added (1R)-1-[(4-amino-1-piperidinyl)methyl]-1,2-dihydro-4H,9H-imidazo[1,2,3-ij]-1,8-naphthyridine-4,9-dione dihydrochloride (for a preparation see Example 5A(j)) (75 mg, 0.223 mmol), 7-chloro-3,4-dihydro-2H-pyrido[3,2-b][1,4]thiazine-6-carbaldehyde (prepared by (1) reduction of 7-chloro-3-oxo-3,4-dihydro-2H-pyrido[3,2-b][1,4]thiazine-6-carbaldehyde (for a synthesis see WO2003087098 Example 306(e)) with LiAlH₄ to give (7-chloro-3,4-dihydro-2H-pyrido[3,2-b][1,4]thiazin-6-yl)methanol and then (2) oxidation with MnO₂)) (47.8 mg, 0.223 mmol), and NaHCO₃ (100 mg, 1.190 mmol) in DCM (4 ml) and methanol (1 ml) to give a brown suspension. Sodium sulfate (200 mg, 1.408 mmol) was added and the reaction was allowed to stir at rt overnight. After 15 h sodium triacetoxyborohydride (94 mg, 0.445 mmol) was added and the reaction was allowed to stir at 25° C. under nitrogen for 4 h. The reaction mixture was adsorbed onto silica and purified using 0-10% MeOH/DCM (1% NH₄OH) to give the title compound as a free base (45 mg, 0.090 mmol, 40.5% yield). LCMS & 1H NMR were consistent with the desired product.

¹H NMR δH D-4 MeOH, (400 MHz) 1.20-1.45 (m, 2H), 1.65-1.92 (m, 2H), 2.19-2.39 (m, 2H), 2.42-2.71 (m, 2H), 2.82-3.10 (m, 5H), 3.65-3.80 (m, 4H), 4.40-4.50 (m, 2H), 5.05-5.20 (m, 1H), 6.25-6.35 (m, 2H), 7.22 (s, 1H), 7.72-7.83 (m, 2H).

MS (ES+) m/z 483/485 (MH⁺).

Example 62 (1R)-1-({4-[(3,4-dihydro-2H-pyrido[3,2-b][1,4]thiazin-6-ylmethyl)amino]-1-piperidinyl}methyl)-1,2-dihydro-4H,9H-imidazo[1,2,3-ij]-1,8-naphthyridine-4,9-dione

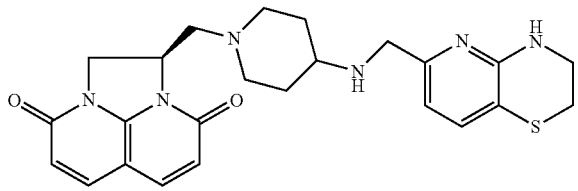 [SMILES: O=c1ccc2ccc(=O)n3c2n1C[C@H]3CN1CCC(NCc2ccc3c(n2)NCCS3)CC1]

A suspension of (1R)-1-[(4-amino-1-piperidinyl)methyl]-1,2-dihydro-4H,9H-imidazo[1,2,3-ij]-1,8-naphthyridine-4,9-dione dihydrochloride (for a preparation see Example 5A(j)) (0.075 g, 0.201 mmol) in dichloromethane (5 ml) and methanol (1 ml) at rt under argon was treated with 3,4-dihydro-2H-pyrido[3,2-b][1,4]thiazine-6-carbaldehyde (prepared by (1) reduction of 3-oxo-3,4-dihydro-2H-pyrido[3,2-b][1,4]thiazine-6-carboxaldehyde (for a synthesis see WO2003087098, Example 301(d)) with LiAlH₄ to give 3,4-dihydro-2H-pyrido[3,2-b][1,4]thiazin-6-ylmethanol and then (2) oxidation with MnO₂)) (0.036 g, 0.201 mmol), sodium bicarbonate (0.150 g, 1.786 mmol) and sodium sulfate (0.300 g, 2.112 mmol) and stirred at rt for 5 h. The solution was then treated with sodium triacetoxyborohydride (0.128 g, 0.603 mmol) and stirred over weekend for 65 hours. The solution was evaporated, taken up in CH₃OH, adsorbed onto silica gel and chromatographed on silica (0-15% CH₃OH in DCM (with 1% NH₄OH)) to give the title compound as the free base (59 mg, 63%) as a beige solid.

¹H NMR DMSO-D6, (400 MHz) 1.02-1.27 (m, 2H), 1.61-1.78 (m, 2H), 1.81-1.96 (s, 1H), 2.01-2.19 (m, 2H), 2.28-2.38 (m, 1H), 2.67-2.79 (m, 1H), 2.82-2.98 (m, 4H), 3.50 (s, 2H), 3.55-3.61 (m, 2H), 4.21-4.34 (m, 2H), 4.91-4.99 (m, 1H), 6.10-6.19 (m, 2H), 6.48-6.52 (d, 1H), 6.69-6.75 (s, 1H), 7.12-7.19 (d, 1H), 7.71-7.82 (d, 2H)

MS (ES+) m/z 465 (MH⁺).

Example 63 1-[(4-{[(3-Oxo-3,4-dihydro-2H-1,4-benzothiazin-6-yl)methyl]amino}-1-piperidinyl)methyl]-1,2-dihydro-4H,9H-imidazo[1,2,3-ij]-1,8-naphthyridine-4,9-dione hydrochloride (2:1 mixture of R:S)

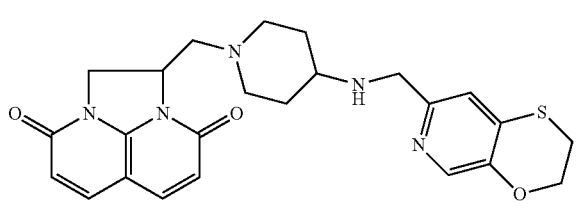 [SMILES: O=c1ccc2ccc(=O)n3c2n1CC3CN1CCC(NCc2cc3c(cn2)OCCS3)CC1]

The title compound was prepared from 1-[(4-amino-1-piperidinyl)methyl]-1,2-dihydro-4H,9H-imidazo[1,2,3-ij]-1,8-naphthyridine-4,9-dione (2:1 mixture of R:S, for a preparation see Example 11(d)) and 2,3-dihydro[1,4]oxathiino[2,3-c]pyridine-7-carbaldehyde (for a synthesis see WO2004058144, Example 60) according to the general method of Example 12.

¹H NMR, LC-MS and mono-hydrochloride salt formation as for Example 6A.

Example 64 1-({4-[([1,3]oxathiolo[5,4-c]pyridin-6-ylmethyl)amino]-1-piperidinyl}methyl)-1,2-dihydro-4H,9H-imidazo[1,2,3-ij]-1,8-naphthyridine-4,9-dione (2:1 Mixture of S:R)

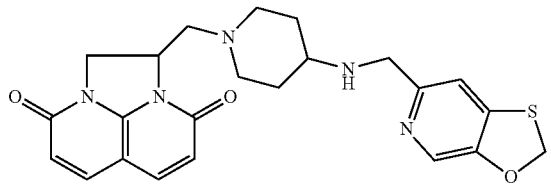 [SMILES: O=c1ccc2ccc(=O)n3c2n1CC3CN1CCC(NCc2cc3c(cn2)OCS3)CC1]

The title compound was prepared from 1-[(4-amino-1-piperidinyl)methyl]-1,2-dihydro-4H,9H-imidazo[1,2,3-ij]-1,8-naphthyridine-4,9-dione (2:1 mixture of S:R prepared analogously to Example 11(a-d)) but using 7-(methyloxy)-1-[(2R)-2-oxiranylmethyl]-3,4-dihydro-1,8-naphthyridin-2(1H)-one (for a synthesis see example 5(f)) and 2,3-dihydro[1,4]oxathiino[2,3-c]pyridine-7-carbaldehyde (for a synthesis see WO2004058144, Example 60) according to the general method of Example 12.

$^1$H NMR, LC-MS and mono-hydrochloride salt formation as for Example 6A.

TABLE 1

| | | Made using the specified starting materials according to the method of Example 5(k) | |
|---|---|---|---|
| Ex # | Salt form | Structure | Starting materials (for a preparation see referenced examples) |
| 65 | di-HCl MS (ES+) m/z 432(MH$^+$) | | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 1H-imidazo[4,5-b]pyridine-2-carbaldehyde (commercial) |
| 66 | Free base MS (ES+) m/z 431(MH$^+$) | | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 1H-pyrrolo[2,3-b]pyridine-2-carbaldehyde (commercial) |
| 67 | di-HCl MS (ES+) m/z 480(MH$^+$) | | (1R)-1-[(4-Amino-1-piperidinyl) methyl]-1,2-dihydro-4H,9H-imidazo[1,2,3-ij]-1,8-naphthyridine-4,9-dione dihydrochloride (Example 5A(j)) 8-Fluoro-3-oxo-3,4-dihydro-2H-1,4-benzoxazine-6-carbaldehyde (for a synthesis see WO2006014580 Preparation 15) |
| 68 | di-HCl MS (ES+) m/z 466(MH$^+$) | | (1R)-1-[(4-Amino-1-piperidinyl) methyl]-1,2-dihydro-4H,9H-imidazo[1,2,3-ij]-1,8-naphthyridine-4,9-dione dihydrochloride (Example 5A(j)) 8-fluoro-3,4-dihydro-2H-1,4-benzoxazine-6-carbaldehyde Prepared by (1) reduction of 8-fluoro-3-oxo-3,4-dihydro-2H-1,4-benzoxazine-6-carbaldehyde (for a synthesis see WO2006014580 Preparation 15) with LiAlH$_4$ to give (8-fluoro-3,4-dihydro-2H-1,4-benzoxazin-6-yl)methanol and then (2) oxidation with MnO$_2$)) |

TABLE 1-continued

Made using the specified starting materials according to the method of Example 5(k)

| Ex # | Salt form | Structure | Starting materials (for a preparation see referenced examples) |
|---|---|---|---|
| 69 | Free base MS (ES+) m/z 484(MH+) | 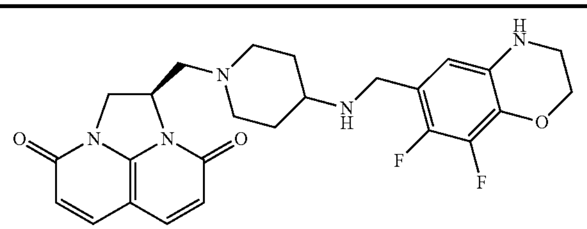 | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 7,8-Difluoro-3,4-dihydro-2H-1,4-benzoxazine-6-carbaldehyde Prepared by (1) reduction of methyl 7,8-difluoro-3-oxo-3,4-dihydro-2H-1,4-benzoxazine-6-carboxylate with LiAlH$_4$ to give (7,8-difluoro-3,4-dihydro-2H-1,4-benzoxazin-6-yl)methanol and then (2) oxidation with MnO$_2$)) |
| 70 | Free base MS (ES+) m/z 513/515(MH+) | 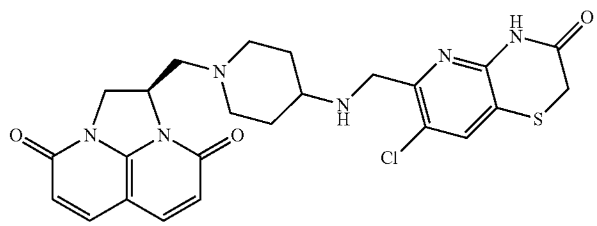 [SMILES: O=C1CSc2cc(Cl)c(CNC3CCN(C[C@@H]4Cn5c(=O)ccc6ccc(=O)n4c65)CC3)nc2N1] | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 7-Chloro-3-oxo-3,4-dihydro-2H-pyrido[3,2-b][1,4]thiazine-6-carbaldehyde (for a synthesis see WO03087098 Ex306(e)) |
| 71 | Mono-HCl MS (ES+) m/z 453(MH+) | 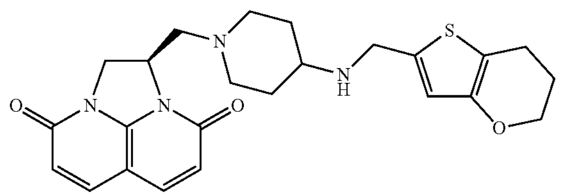 [SMILES: O=c1ccc2ccc(=O)n3c2n1C[C@H]3CN1CCC(NCc2cc3c(s2)CCCO3)CC1] | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 6,7-Dihydro-5H-thieno[3,2-b]pyran-2-carbaldehyde (for a synthesis see WO02007122258 Example 88(c)) |
| 72 | Mono-HCl MS (ES+) m/z 454(MH+) | 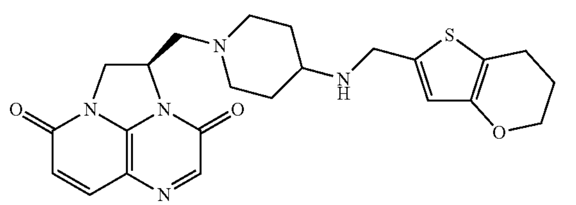 [SMILES: O=c1ccc2ncc(=O)n3c2n1C[C@H]3CN1CCC(NCc2cc3c(s2)CCCO3)CC1] | (2R)-2-[(4-Amino-1-piperidinyl)methyl]-1,2-dihydro-3H,8H-2a,5,8a-triazaacenaphthylene-3,8-dione (Example 16A(j) method B) 6,7-Dihydro-5H-thieno[3,2-b]pyran-2-carbaldehyde (for a synthesis see WO2007122258 Example 88(c)) |
| 73 | Mono-HCl MS (ES+) m/z 454(MH+) | 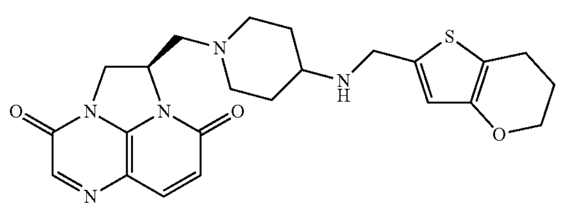 [SMILES: O=c1cnc2ccc(=O)n3c2n1C[C@H]3CN1CCC(NCc2cc3c(s2)CCCO3)CC1] | (1R)-1-[(4-Amino-1-piperidinyl)methyl]-1,2-dihydro-3H,8H-2a,5,8a-triazaacenaphthylene-3,8-dione dihydrochloride (Example 13A(k) or 15(d)) 6,7-Dihydro-5H-thieno[3,2-b]pyran-2-carbaldehyde (for a synthesis see WO2007122258 Example 88(c)) |
| 74 | Di-HCl MS (ES+) m/z 448(MH+) | 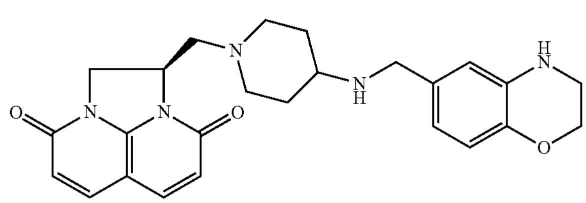 [SMILES: O=c1ccc2ccc(=O)n3c2n1C[C@H]3CN1CCC(NCc2ccc3c(c2)NCCO3)CC1] | (1R)-1-[(4-Amino-1-piperidinyl)methyl]-1,2-dihydro-4H,9H-imidazo[1,2,3-ij]-1,8-naphthyridine-4,9-dione dihydrochloride (commercial) |

TABLE 1-continued

Made using the specified starting materials according to the method of Example 5(k)

| Ex # | Salt form | Structure | Starting materials (for a preparation see referenced examples) |
|---|---|---|---|
| 75 | Di-HCl MS (ES+) m/z 492(MH+) | 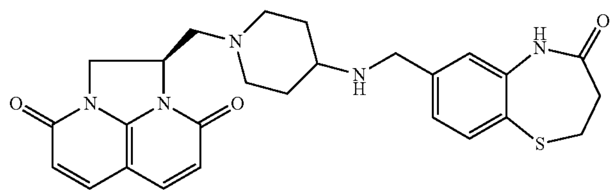 [SMILES: O=C1CCSc2ccc(CNC3CCN(C[C@@H]4Cn5c(=O)ccc6ccc(=O)n4c65)CC3)cc2N1] | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 4-Oxo-2,3,4,5-tetrahydro-1,5-benzothiazepine-7-carbaldehyde (for a synthesis see WO2004058144 Example 128(e) |
| 76 | Di-HCl MS (ES+) m/z 463(MH+) | 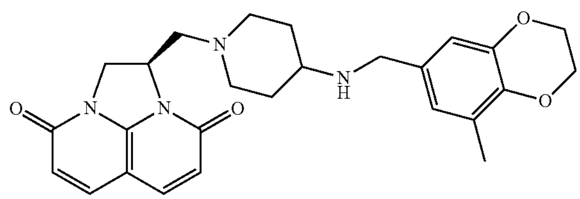 [SMILES: Cc1cc(CNC2CCN(C[C@@H]3Cn4c(=O)ccc5ccc(=O)n3c54)CC2)cc2c1OCCO2] | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 8-Methyl-2,3-dihydro-1,4-benzodioxin-6-carbaldehyde (Prepared from 8-bromo-2,3-dihydro-1,4-benzodioxin-6-carbaldehyde (for a synthesis see WO2007122258 Example 31(c)) by palladium catalysed Stille coupling with tetramethyltin) |
| 77 | Free base MS (ES+) m/z 464(MH+) | 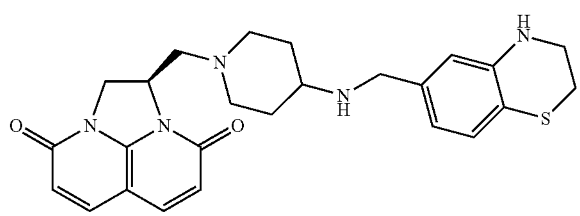 [SMILES: O=c1ccc2ccc(=O)n3c2n1C[C@H]3CN1CCC(NCc2ccc3c(c2)NCCS3)CC1] | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 3,4-Dihydro-2H-1,4-benzothiazin-6-carbaldehyde (for a synthesis see WO2003087098 Example 214) |
| 78 | Di-HCl MS (ES+) m/z 478(MH+) | 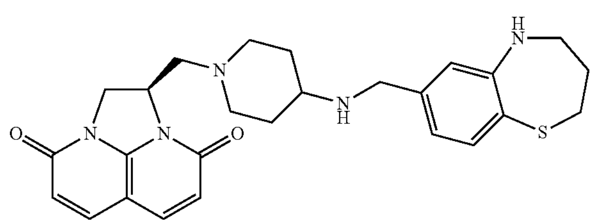 [SMILES: O=c1ccc2ccc(=O)n3c2n1C[C@H]3CN1CCC(NCc2ccc3c(c2)NCCCS3)CC1] | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 2,3,4,5-Tetrahydro-1,5-benzothiazepin-7-carbaldehyde (prepared from methyl 4-oxo-2,3,4,5-tetrahydro-1,5-benzothiazepine-7-carboxylate (for a synthesis see WO2007016610, Preparation 18(c)) by treatment with Borane-THF to give methyl 2,3,4,5-tetrahydro-1,5-benzothiazepine-7-carboxylate, then treatment of this with LiAlH$_4$ to give 2,3,4,5-tetrahydro-1,5-benzothiazepin-7-ylmethanol and finally treatment with MnO$_2$ |

TABLE 1-continued

Made using the specified starting materials according to the method of Example 5(k)

| Ex # | Salt form | Structure | Starting materials (for a preparation see referenced examples) |
|---|---|---|---|
| 79 | Di-HCl MS (ES+) m/z 466(MH+) | 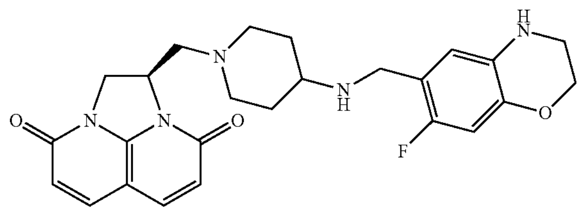 [SMILES: O=c1ccc2ccc(=O)n3c2n1C[C@H]3CN1CCC(NCc2cc3c(cc2F)OCCN3)CC1] | (1R)-1-[(4-Amino-1-piperidinyl)methyl]-1,2-dihydro-4H,9H-imidazo[1,2,3-ij]-1,8-naphthyridine-4,9-dione dihydrochloride (Example 5A(j)) 7-Fluoro-3,4-dihydro-2H-1,4-benzoxazine-6-carbaldehyde (prepared from 7-fluoro-3-oxo-3,4-dihydro-2H-1,4-benzoxazine-6-carbonitrile (for a synthesis see WO2002056882, Example 8(b)) by treatment with diisobutylaluminium hydride) |

Preparation A: 6,7-Dihydro[1,4]dioxino[2,3-c]pyridazine-3-carbaldehyde (a) 3,4,6-Trichloropyridazine This was prepared by a slight variation on the method of Kasnar et al, Nucleosides & Nucleotides (1994), 13(1-3), 459-79.

Hydrazine sulphate salt (51 g) was suspended in water (250 ml), heated to reflux and bromomaleic anhydride (90.38 g) was added dropwise. The mixture was heated at reflux for 4 hours then cooled to room temperature. The reaction was repeated with 29 g hydrazine sulphate, 53 g bromomaleic anhydride and 130 ml water. The precipitates were collected by filtration, washed with water and acetone and dried as a combined batch in vacuo to afford 4-bromo-1,2-dihydro-3,6-pyridazinedione as a white solid (113 g).

The solid in two batches was treated with phosphorus oxychloride (2×200 ml) and heated to reflux for 3.5 hours. The mixture was cooled, evaporated and azeotroped with toluene. The residue was partitioned between dichloromethane and saturated aqueous sodium bicarbonate solution and extracted with DCM twice more. The organic extracts were dried and evaporated. This residue was re-dissolved in dichloromethane, and chromatographed on silica gel (300 g) (DCM as eluent) to give a white solid (101.5 g, 87%).

(LC/MS analysis showed ca 20-30% impurity, isomers of bromo-dichloropyridazine).

MS (+ve ion electrospray) m/z 184/185/186 (MH+), trichloropyridazine.

MS (+ve ion electrospray) m/z 228/229/231 (MH+), bromo-dichloropyridazine.

(b) 2-[(3,6-Dichloro-4-pyridazinyl)oxy]ethanol

A solution of ethylene glycol (55 ml) in tetrahydrofuran (200 ml) was treated at around 0° C. (ice bath cooling) with sodium hydride (60% dispersion in oil, 5.9 g) over 40 minutes. After the addition was complete, 3,4,6-trichloropyridazine (27 g) containing isomers of bromo-dichloropyridazine as impurity was added portionwise and washed in with more dry THF (50 ml) and the mixture was stirred at 0° C. for 1 hour and then at room temperature overnight. The mixture was concentrated (to 1/3 volume) then diluted with aqueous sodium bicarbonate solution and extracted with chloroform (5×) and ethyl acetate (3×). The combined organic extracts were washed with water, dried over sodium sulphate and evaporated and the solids filtered off and washed with $CHCl_3$ (×3) and dried in a vacuum oven overnight at 40° C. affording a white solid (25.5 g, 83%), containing some bromo-derivative (10-15%).

MS (+ve ion electrospray) m/z 209/211 (MH+).

MS (+ve ion electrospray) m/z 255/7 (MH+), bromo-derivative.

(c) 3-Chloro-6,7-dihydro[1,4]dioxino[2,3-c]pyridazine

A solution of 2-[(3,6-dichloro-4-pyridazinyl)oxy]ethanol containing some bromo-derivative (15.46 g; 0.0703 mol) in dry 1,4-dioxane (1.2 L) was treated with lithium hydride (2.3 g; 0.28 mol) in portions and stirred at room temperature for 1 hour under argon, then heated at 110° C. overnight. The reaction mixture was quenched with wet 1,4-dioxane, then iced-water. The solution was evaporated to half volume, taken to pH 8 with 5M hydrochloric acid and evaporated to dryness. Water was added and the residue was extracted 5×with chloroform, dried (sodium sulphate) and evaporated to afford a white solid (12.4 g, ca.77%) (containing ca. 15% of a bromo species).

MS (+ve ion electrospray) m/z 173/5 (Cl MH+); 217/9 (Br MH+)

(d) 3-Ethenyl-6,7-dihydro[1,4]dioxino[2,3-c]pyridazine

A solution of 3-chloro-6,7-dihydro[1,4]dioxino[2,3-c]pyridazine (13.6 g, 0.079 mol) containing ca. 15% of a bromo species in dimethoxyethane (400 ml) was degassed under argon for 10 min then tetrakis(triphenylphosphine)palladium (0) (2 g), potassium carbonate (10.33 g), 2,4,6-trivinylcyclotriboroxane pyridine complex (11.32 g) and water (55 ml) were added. The mixture was heated at 95° C. for 48 hours and cooled and evaporated to dryness. The mixture was treated with aqueous sodium bicarbonate solution and extracted (5×) with DCM. Extracts were dried (sodium sulphate), evaporated and the residue chromatographed on silica gel (500 g), eluting with 0-100% ethyl acetate-hexane, affording the product (6.43 g, 50%); [also some impure fractions (1.8 g)].

MS (+ve ion electrospray) m/z 165 (MH+).

(e) Title Compound

A solution of 3-ethenyl-6,7-dihydro[1,4]dioxino[2,3-c]pyridazine (11.58 g) in 1,4-dioxane/water (600 ml/180 ml), cooled in ice, was treated with an aqueous solution of osmium tetroxide (4% w/v, 25 ml) and sodium periodate (43 g). This mixture was allowed to warm to room temperature and after 7 hours under stirring the mixture was evaporated to dryness and azeotroped with 1,4-dioxane. Silica gel, 1,4-dioxane and chloroform were added and the mixture was evaporated to dryness overnight, then added to a silica column (400 g) and chromatographed, eluting with chloroform then 0-100% ethyl acetate in hexane, to afford a white solid (7.55 g, 64%).

MS (+ve ion electrospray) m/z 167 (MH$^+$).

Biological Activity

Antimicrobial Activity Assay:

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically". The compounds were tested in serial two-fold dilutions ranging from 0.016 to 16 mcg/ml.

The minimum inhibitory concentration (MIC) was determined as the lowest concentration of compound that inhibited visible growth. A mirror reader was used to assist in determining the MIC endpoint.

Compounds were evaluated against Gram-positive organisms, selected from *Staphylococcus aureus, Streptococcus pneumoniae, Streptococcus pyogenes, Enterococcus faecalis* and *Enterococcus faecium*.

In addition, compounds were evaluated against Gram-negative organisms selected from *Haemophilus influenzae, Moraxella catarrhalis, Escherichia coli, Pseudomonas aeruginosa, Proteus mirabilis, Enterobacter cloacae, Enterobacter aerogenes, Klebsiella pneumoniae* and *Stenotrophomonas maltophilia*.

Each of the listed Examples, as identified in the present application, except Examples 71-73 and 76-79, was tested in at least one exemplified salt or free base form. Unless otherwise noted, the tested Examples had a MIC≤2 g/ml against a strain of at least one of the organisms listed above, with the exception of Example 9 which had an MIC≤4 g ml against a strain of at least one of the organisms listed above. For at least one strain of every organism listed above, at least one Example had a MIC≤2 g ml.

*Mycobacterium tuberculosis* H37Rv Inhibition Assay

The measurement of the minimum inhibitory concentration (MIC) for each tested compound was performed in 96 wells flat-bottom, polystyrene microtiter plates. Ten two-fold drug dilutions in neat DMSO starting at 400 µM were performed. Five 1 of these drug solutions were added to 95 µl of Middlebrook 7H9 medium. (Lines A-H, rows 1-10 of the plate layout). Isoniazid was used as a positive control, 8 two-fold dilution of Isoniazid starting at 160 µgml$^{-1}$ was prepared and 5 µl of this control curve was added to 95 µl of Middlebrook 7H9 (Difco catalogue Ref. 271310)+ADC medium (Becton Dickinson Catalogue Ref. 211887). (Row 11, lines A-H). Five 1 of neat DMSO were added to row 12 (growth and Blank controls).

The inoculum was standardised to approximately 1×10$^7$ cfu/ml and diluted 1 in 100 in Middlebrook 7H9+ADC medium and 0.025% Tween 80 (Sigma P4780), to produce the final inoculum of H37Rv strain (ATCC25618). One hundred µl of this inoculum was added to the entire plate but G-12 and H-12 wells (Blank controls). All plates were placed in a sealed box to prevent drying out of the peripheral wells and they were incubated at 37° C. without shaking for six days. A resazurin solution was prepared by dissolving one tablet of resazurin (Resazurin Tablets for Milk Testing; Ref 330884Y VWR International Ltd) in 30 ml sterile PBS (phosphate buffered saline). 25 µl of this solution was added to each well. Fluorescence was measured (Spectramax M5 Molecular Devices, Excitation 530 nm, Emission 590 nm) after 48 hours to determine the MIC value.

Examples 1-4, 5A, 6A, 7-9, 12, 13A, 14, 15, 16A, 17A, 19A, 20, 23-32, 34, 37-44, 46-50, 53-57, 59 and 63 were tested in the *Mycobacterium tuberculosis* H37Rv inhibition assay. Examples 2, 4, 5A, 6A, 7, 8, 12, 13A, 14, 16A, 19A, 20, 23-26, 28-32, 34, 37, 39, 40, 42, 44, 46, 49, 50, 56, 59 and 63 showed an MIC value of lower than 2.0 µg/ml. Examples 4, 5A, 7, 8, 12, 13A, 14, 16A, 19A, 25, 26, 30-32, 37, 40, 49, 50, and 56 showed an MIC value of 1.0 µg/ml or lower.

Invitro Assay

Studies were conducted to assess the in vitro activity of compounds of the present invention.

In particular, Example 39 in the present invention (i.e., identified as (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride) was tested against 30 strains of *Neisseria gonorrhoeae* collected between 2003 through 2007.

Ceftriaxone and ciprofloxacin were included as comparators. Minimum inhibitory concentrations (MICs) for Example 39 and comparators were determined by agar dilution according to Clinical and Laboratory Standards Institute (CLSI) approved methodology and guidelines (i.e., see Clinical Laboratory Standards Institute (CLSI). Approved Standard M07-A9. Methods for Dilution Antimicrobial Susceptibility Tests for Bacteria That Grow Aerobically. Ninth Edition. Wayne, Pa., 2012).

The MIC$_{90}$ (MIC which inhibits 90% of the isolates tested) for Example 39 (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride was 0.5 µg/mL against 30 isolates of *N. gonorrhoeae*.

This MIC$_{90}$ value was at least 16-fold higher than that of ceftriaxone (<0.03 g/ml) and at least 8-fold lower than ciprofloxacin (>2 µg/mL). The modal value of Example 39 (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride remained unchanged against the 9 ciprofloxacin-resistant *N. gonorrhoeae* tested.

A second study tested Example 39 (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride by CLSI agar dilution against 145 isolates of *N. gonorrhoeae*, the majority of which were collected in 2013. The MIC$_{90}$ for Example 39 (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride against all isolates tested was 0.5 µg/mL. Against a subset of 37 ciprofloxacin-nonsusceptible isolates, the MIC$_{90}$ for Example 39 (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride was 1 µg/mL.

These studies demonstrate the in vitro activity of Example 39 (2R)-2-({4-[(3,4-Dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione hydrochloride against *N. gonorrhoeae*, including ciprofloxacin-resistant strains.

In Vivo Assay Data

A mouse model of *N. gonorrhoeae* vaginal colonization was performed to evaluate the efficacy of compounds of the present invention. Two independent studies were performed by the same laboratory.

In particular, Example 39 (i.e., (2R)-2-({4-[(3,4-Dihydro-2H-pyrano[2,3-c]pyridin-6-ylmethyl)amino]-1-piperidinyl}methyl)-1,2-dihydro-3H, 8H-2a,5,8a-triazaacenaphthylene-3,8-dione hydrochloride) was tested in this model following a single oral dose or a total of two oral doses administered on the same day. Female mice were primed for colonization using estradiol; trimethoprim sulfate and streptomycin were administered to control commensals. On day 0, mice were inoculated intravaginally with *N. gonorrhoeae* MS11 (Example 39—MIC 1 µg/ml). Successful colonization was confirmed via vaginal swab culture on days 1 and 2. Single oral doses at 100 mg/kg and 200 mg/kg or a total of two oral doses at 100 mg/kg each of Example 39 were administered on day 2. Vaginal swabs for quantitative culture were collected daily through day 10 (8 days post treatment).

In one study, blood samples were collected terminally from a separate group of mice at 1, 2, 6 and 12 hours post Example 39 administration (n=3 per time point and dose) to allow for estimation of PK parameters.

Example 39 at a single oral dose of 100 or 200 mg/kg or two 100 mg/kg doses administered on the same day eliminated colonization with *N. gonorrhoeae* MS11 in 70-80%, 90-100% and 100% of mice, respectively, by the end of the study while 0-10% of mice receiving the saline vehicle demonstrated bacterial clearance. The $fAUC_{0-24}$ values for these doses were estimated to be 8, 22 and 16 µg·h/mL, respectively.

In the first study, one mouse in each of the Example 39 dose groups demonstrated initial clearance of *N. gonorrhoeae* for several consecutive days, followed by regrowth to a high number of organisms by the end of the study. Although this regrowth was not observed in the follow-up study, colonies of *N. gonorrhoeae* MS11 recovered from GSK2140944-treated mice were evaluated and did not demonstrate any change in susceptibility to GSK2140944 compared with stock cultures of the organism.

It is to be understood that the invention is not limited to the embodiments illustrated hereinabove and the right is reserved to the illustrated embodiments and all modifications coming within the scope of the following claims.

The various references to journals, patents, and other publications which are cited herein comprise the state of the art and are incorporated herein by reference as though fully set forth.

What is claimed is:

1. A method for treating *Neisseria gonorrhoeae* infection in a subject in need thereof, which comprises administering to the subject 2-({4-[(3,4-dihydro-2H-pyrano[2,3-c]pyridin-6-ylmethyl)amino]-1-piperidinyl{methyl)-1,2-dihydro-3H, 8H-2a,5,8triazaacenaphthylene-3,8-dione as shown below:

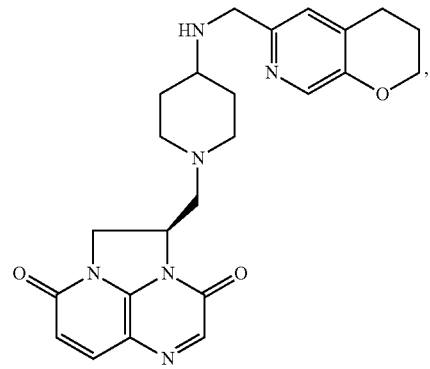

or a pharmaceutically acceptable salt thereof.

2. A method for treating *Neisseria gonorrhoeae* infection in a subject in need thereof, which comprises administering to the subject 2-({4-[(3,4-dihydro-2H-pyrano[2,3-c]pyridin-6-ylmethyl)amino]-1-piperidinyl}methyl)-1,2-dihydro-3H, 8H-2a,5,8a-triazaacenaphthylene-3,8-dione as shown below:

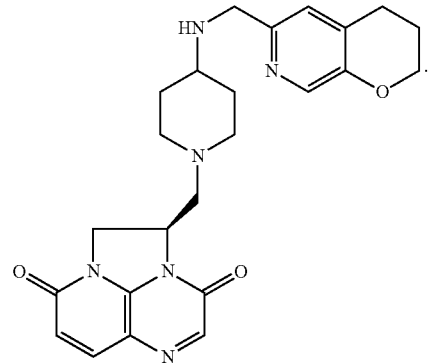 [SMILES: O=c1ccc2ncc(=O)n3c2n1C[C@H]3CN1CCC(NCc2cc3c(cn2)OCCC3)CC1]

3. A method for treating *Neisseria gonorrhoeae* infection in a subject in need thereof, which comprises administering to the subject a pharmaceutical composition comprising one or more pharmaceutically acceptable excipients and 2-({4-[(3,4-dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione as shown below:

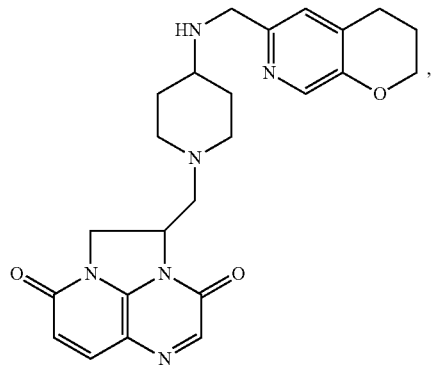 [SMILES: O=c1ccc2ncc(=O)n3c2n1CC3CN1CCC(NCc2cc3c(cn2)OCCC3)CC1]

or a pharmaceutically acceptable salt thereof.

4. A method for treating *Neisseria gonorrhoeae* infection in a subject in need thereof, which comprises administering to the subject a pharmaceutical composition comprising one or more pharmaceutically acceptable excipients and 2-({4-[(3,4-dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione as shown below:

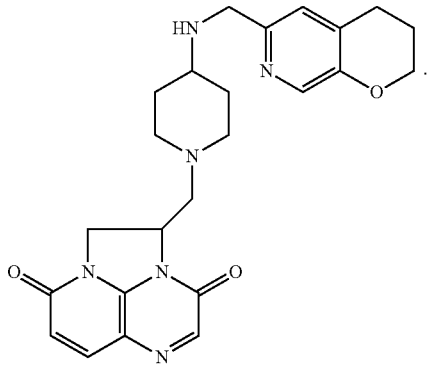 [SMILES: O=c1ccc2ncc(=O)n3c2n1CC3CN1CCC(NCc2cc3c(cn2)OCCC3)CC1]

5. A method for treating *Neisseria gonorrhoeae* infection in a subject in need thereof, which comprises administering to the subject (2R)-2-({4-[(3,4-dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione as shown below:

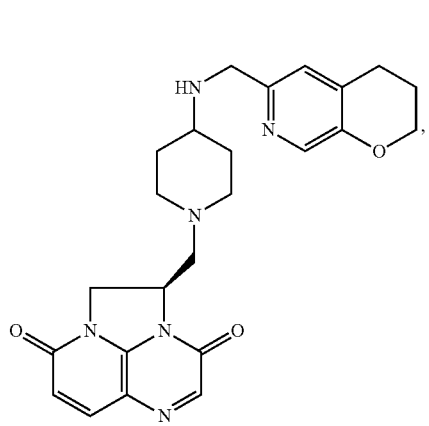 [SMILES: O=c1ccc2ncc(=O)n3c2n1C[C@H]3CN1CCC(NCc2cc3c(cn2)OCCC3)CC1]

or a pharmaceutically acceptable salt thereof.

6. The method according to claim 5, which comprises administering to the subject (2R)-2-({4-[(3,4-dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione as shown below:

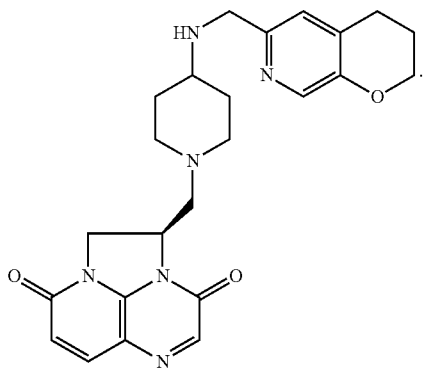 [SMILES: O=c1ccc2ncc(=O)n3c2n1C[C@H]3CN1CCC(NCc2cc3c(cn2)OCCC3)CC1]

7. The method according to claim 5, wherein the pharmaceutically acceptable salt is an acid addition salt formed from an acid selected from the group consisting of hydrochloric acid, hydrobromic acid, sulfuric acid, nitric acid, phosphoric acid, acetic acid, fumaric acid, succinic acid, maleic acid, citric acid, benzoic acid, p-toluenesulfonic acid, methanesulfonic acid, naphthalenesulfonic acid, and tartaric acid.

8. The method according to claim 5, wherein the pharmaceutically acceptable salt is an acid addition salt formed from methanesulfonic acid.

9. A method for treating *Neisseria gonorrhoeae* infection in a subject in need thereof, which comprises administering to the subject a mesylate salt of (2R)-2-({4-[(3,4-dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione as shown below:

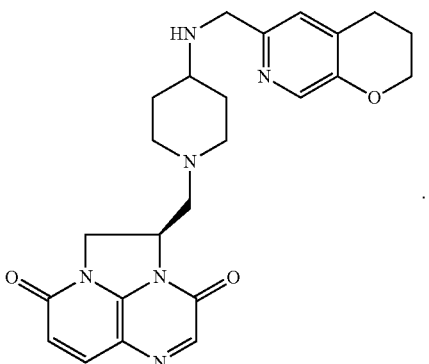

10. A method for treating *Neisseria gonorrhoeae* infection in a subject in need thereof, which comprises administering to the subject a pharmaceutical composition comprising one or more pharmaceutically acceptable excipients and (2R)-2-({4-[(3,4-dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione as shown below:

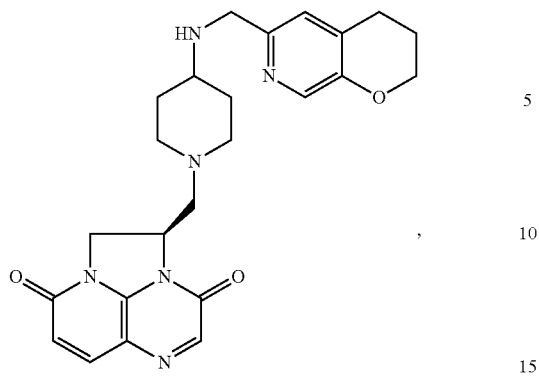

or a pharmaceutically acceptable salt thereof.

11. The method according to claim 10, wherein the pharmaceutically acceptable salt is an acid addition salt formed from an acid selected from the group consisting of hydrochloric acid, hydrobromic acid, sulfuric acid, nitric acid, phosphoric acid, acetic acid, fumaric acid, succinic acid, maleic acid, citric acid, benzoic acid, p-toluenesulfonic acid, methanesulfonic acid, naphthalenesulfonic acid, and tartaric acid.

12. The method according to claim 10, wherein the pharmaceutically acceptable salt is an acid addition salt formed from methanesulfonic acid.

* * * * *

UNITED STATES PATENT AND TRADEMARK OFFICE
CERTIFICATE OF CORRECTION

Page 1 of 2

PATENT NO. : 10,702,521 B2
APPLICATION NO. : 15/505715
DATED : July 7, 2020
INVENTOR(S) : Katherine Louisa Widdowson It is certified that error appears in the above-identified patent and that said Letters Patent is hereby corrected as shown below:

On the Title Page

Item (54) and in the Specification Column 1, Lines 1-4 the title should read "METHODS FOR TREATING NEISSERIA GONORRHOEAE INFECTION WITH 2-({4-[(3,4-DIHYDRO-2H-PYRANO[2,3-c]PYRIDIN-6-YLMETHYL)AMINO]-1-PIPERIDINYL}METHYL)-1,2-DIHYDRO-3H,8H-2a,5,8a-TRIAZAACENAPHTHYLENE-3,8-DIONE";

In the Claims

In Claim 1, at Column 141, Lines 65-67, please delete "2-({4-[(3,4-dihydro-2H-pyrano[2,3-c]pyridin-6-ylmethyl)amino]-1-piperidinyl{methyl)-1,2-dihydro-3H,8H-2a,5,8triazaacenaphthylene-3,8-dione" and insert in place thereof -- 2-({4-[(3,4-dihydro-2H-pyrano[2,3-c]pyridin-6-ylmethyl)amino]-1-piperidinyl}methyl)-1,2-dihydro-3H,8H-2a,5,8a-triazaacenaphthylene-3,8-dione --;

Signed and Sealed this
Third Day of June, 2025

Coke Morgan Stewart
*Acting Director of the United States Patent and Trademark Office*

CERTIFICATE OF CORRECTION (continued)
U.S. Pat. No. 10,702,521 B2

In Claim 1, at Column 142, Lines 1-15 and in Claim 2, at Column 142, Lines 25-39, the chemical structure " 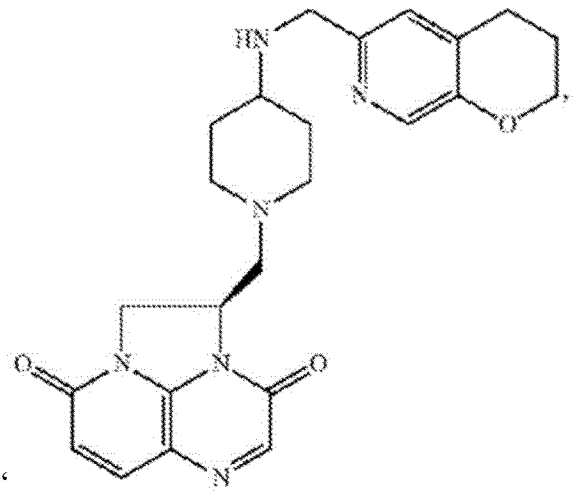 " in each occurrence should be replaced with -- 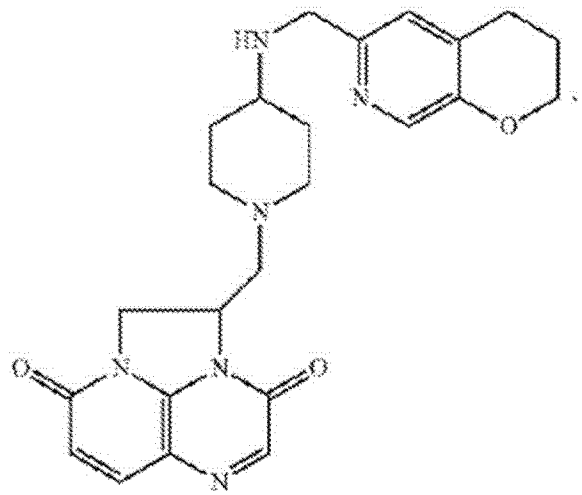 --.